US010760128B2

(12) United States Patent
Watnick et al.

(10) Patent No.: US 10,760,128 B2
(45) Date of Patent: Sep. 1, 2020

(54) PKD MUTATIONS AND EVALUATION OF SAME

(71) Applicants: Athena Diagnostics, Inc., Worcester, MA (US); The Johns Hopkins University, Baltimore, MD (US)

(72) Inventors: Terry J. Watnick, Chevy Chase, MD (US); Miguel Garcia-Gonzalez, Brion (ES); Gregory G. Germino, Chevy Chase, MD (US); Jeffery G. Jones, Wilbraham, MA (US)

(73) Assignees: ATHENA DIAGNOSTICS, INC., Worcester, MA (US); THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/289,160

(22) Filed: May 28, 2014

(65) Prior Publication Data
US 2014/0349290 A1 Nov. 27, 2014

Related U.S. Application Data

(63) Continuation of application No. 12/309,337, filed as application No. PCT/US2007/016705 on Jul. 24, 2007, now Pat. No. 8,771,946.

(60) Provisional application No. 60/832,780, filed on Jul. 24, 2006.

(51) Int. Cl.
C12Q 1/6883 (2018.01)
(52) U.S. Cl.
CPC ...... *C12Q 1/6883* (2013.01); *C12Q 2600/118* (2013.01); *C12Q 2600/156* (2013.01); *C12Q 2600/158* (2013.01)
(58) Field of Classification Search
None
See application file for complete search history.

(56) References Cited

U.S. PATENT DOCUMENTS

| 6,100,386 | A | * | 8/2000 | Carpino | C07K 14/47 435/320.1 |
|---|---|---|---|---|---|
| 6,485,960 | B1 | | 11/2002 | Harris et al. | |
| 6,656,681 | B1 | | 12/2003 | Harris et al. | |
| 6,916,619 | B2 | | 7/2005 | Jones et al. | |
| 7,083,915 | B2 | | 8/2006 | Somlo et al. | |
| 7,273,701 | B2 | | 9/2007 | Jones et al. | |
| 7,294,465 | B2 | | 11/2007 | Somlo et al. | |
| 7,553,644 | B2 | | 6/2009 | Germino et al. | |
| 2002/0061520 | A1 | | 5/2002 | Somlo et al. | |
| 2003/0008288 | A1 | * | 1/2003 | Germino et al. | 435/6 |
| 2006/0246504 | A1 | | 11/2006 | Germino et al. | |

FOREIGN PATENT DOCUMENTS

| CA | 2 461 106 A1 | 10/2004 |
|---|---|---|
| JP | 2004-313194 | 11/2004 |
| WO | WO 95/18225 | 7/1995 |
| WO | WO 96/12033 A | 4/1996 |
| WO | WO 02/06529 A | 1/2002 |
| WO | WO 2008/094194 | 8/2008 |

OTHER PUBLICATIONS

Inoue (Human Mutation 19:622-628 2002).*
GenBank dbSNP entry for rs13333553 added with build 121 on Jun. 1, 2004.*
Tabor (Nature Reviews Genetics May 2002 vol. 3 pp. 1-7).*
Watnick (Human Molecular Genetics 1997 vol. 6 No. 9 pp. 1473-1481).*
Rossetti et al., "Mutation Analysis of the Entire PKD1 Gene: Genetic and Diagnostic Implications," *Am. J. Hum. Genet.*, vol. 68, pp. 46-63 (2001).
International Preliminary Report on Patentability, PCT/US2007/016705, dated Jan. 27, 2009.
Bouba, I., et al., "Novel PKD1 Deletions and Missense Variants in a Cohort of Hellenic Polycystic Kidney Disease Families," *Eur. Journ. Hum. Genetics*, 9:677-684 (Sep. 2001).
Bresin, E., et al., "A Common Polymorphism in Exon 46 of the Human Autosomal Dominant Polycystic Kidney Disease 1 Gene (PKD1)," *Molecular and Cellular Probes*, 10:463-465 (Dec. 1996).
Garcia-Gonzales, Miguel et al., Polycystic Kidney Disease (PKD): from the Clinical Genetic Test, through in Vitro and in Vivo Analysis, and back to Humans found online at //hdl.handle.net/10347/9599 available date Jan. 7, 2014, 139 pages.
Garcia-Gonzalez, M.A., et al., "Evaluating the Clinical Utility of a Molecular Genetic Test for Polycystic Kidney Disease," *Mol. Genetics and Metabolism*, 92:160-167 (May 2007).
Juppner Functional Properties of the PTH/PTHrP receptor, Bone, vol. 17, No. 2, Supplement 39S-42S (1995).
Neophytou, P., et al. "Detection of a Novel Nonsense Mutation and an Intragenic Polymorphism in the PKD1 Gene of a Cypriot Family with Autosomal Dominant Polycystic Kidney Disease," *Human Genetics*, 98:437-442 (Jan. 1996).
Peral, B., et al., "A Stable, Nonsense Mutation Associated With a Case of Infantile Onset Polycystic Kidney Disease 1 (PKD1)," *Human Molecular Genetics*, 5:539-542 (1996, mo. not available).
Peral, B., et al., "Screening 3' Region of the Polycystic Kidney Disease 1 (PKD1) Gene Reveals Six Novel Mutations," *Am. Journ. Hum. Genetics*, 58:86-96 (Jan. 1996).
Perrichot, R.A., et al., "DGGE Screening of PKD1 Gene Reveals Novel Mutations in a Large Cohort of 146 Unrelated Patients," *Human Genetics*, 105:231-239 (Jan. 1999).
Reiterová, J., et al., "Four Novel Mutations of the PKD2 Gene in Czech Families With Autosomal Dominant Polycystic Kidney Disease," *Human Mutation*, vol. 19, No. 5, p. 573 (Feb. 2002).

(Continued)

*Primary Examiner* — Amanda Haney
(74) *Attorney, Agent, or Firm* — Foley & Lardner LLP

(57) ABSTRACT

The present invention relates to methods of detecting novel mutations in a PKD1 and/or PKD2 gene that have been determined to be associated with autosomal dominant polycystic kidney disease (ADPKD) in order to detect or predict the occurrence of ADPKD in an individual.

6 Claims, 37 Drawing Sheets
Specification includes a Sequence Listing.

(56) References Cited

OTHER PUBLICATIONS

Reynolds, D.M., et al., "Aberrant Splicing in the PKD2 Gene as a Cause for Polycystic Kidney Disease," *J. Am. Soc. Nephrol.*, 10:2342-2351 (May 1999).
Roelfsma, J.H., et al., "Mutation Detection in the Repeated Part of the PKD1 Gene," *Am. Journ. Hum. Genetics*, 61:1044-1052 (Nov. 1997).
Rossetti, S., et al., "A Complete Mutation Screen of the ADPKD Genes by DHPLC," *Kidney International*, 61:1588-1599 (2002).
Rossetti, S., et al., "Detection of Mutations in Human Genes by a New Rapid Method: Cleavage Fragment Length Polymorphism Analysis (CFLPA)," *Molecular and Cellular Probes*, 11:155-160 (Apr. 1997).
Thomas et al., Identification of Mutations in the Repeated Part of the Autosomal Dominant Polycystic Kidney Disease Type 1 Gene, PKD1, by Long Range PCR, *Am. J. Hum. Genet.*, vol. 65, pp. 39-49 (1999).
Thongnoppakhun, A., et al., "A Novel Splice-Acceptor Site Mutation (IVS13-2A>T) of Polycystic Kidney Disease 1 (PKD1) Gene Resulting in an RNA Processing Defect with a 74-Nucleotide Deletion in Exon 14 of the mRNA Transcript," *Human Mutation*, 15:115 (Jan. 2000).
Turco, A.E., et al., "A Novel Nonsense Mutation in the PKD1 Gene (C3817T) is Associated with Autosomal Dominant Polycystic Kidney Disease (ADPKD) in a Large Three-Generation Italian Family," *Human Molecular Genetics*, 4:1331-1335 (Jan. 1995).
Turco, A.E., et al., "Three Novel Mutations of the PKD1 Gene in Italian Families with Autosomal Dominant Polycystic Kidney Disease," *Human Mutation*, 10:164-167 (1997, mo. not available).
Watnick, T., et al, "Mutation Detection of PKD1 Identifies a Novel Mutation Common to Three Families with Aneurysms and/or Very-Early-Onset Disease," *Am. Journ. Hum. Genetics*, 65:1561-1571 (Dec. 1999).
Afzal AR, Florencio RN, Taylor R, et al. Novel mutations in the duplicated region of the polycystic kidney disease 1 (PKD1) gene provides supporting evidence for gene conversion. *Genet* 4(4):365-70, 2000.
Aguiari G, Savelli S, Garbo M, et al. Novel splicing and missense mutations autosomal dominant polycystic kidney disease 1 (PKD1) gene: expression in of mutated genes. *Hum Mutat* 16(5):444-5, 2000.
Bogdanova N, McCluskey M, Sikmann K, et al. Screening the 3' region of the polycystic kidney disease 1 (PKD1) gene in 41 Bulgarian and Australian kindreds reveals a prevalence of protein truncating mutations. *Hum Mutat* 16(2):166-74, 2000.

Boletta, A., Qian, F., Onuchic, L. F., et al. Polycystin-1, the gene product of PKD1, induces resistance to apoptosis and spontaneous tubulogenesis in MDCK cells. *Mol. Cell* 6, 1267-1273, 2000.
Bycroft M, Bateman A, Clarke J, et al. The structure of a PKD domain from polycystin-1: implications for polycystic kidney disease. *EMBO J.* 15;18(2):297-305, 1999.
Gabow PA. Autosomal dominant polycystic kidney disease. *N Engl J Med* 29;329(5):332-42, 1993.
Hanaoka K, Qian F, Boletta A, et al. Co-assembly of polycystin-1 and -2 produces unique cation-permeable currents. *Nature* 408, 990-994, 2000.
Inoue S, Inoue K, Utsunomiya M, et al. Mutation analysis in PKD1 of Japanese autosomal dominant polycystic kidney disease patients. *Hum Mutat* 19(6):622-8, 2002.
Peral B, Gamble V, Strong C, et al. Identification of mutations in the duplicated region of the polycystic kidney disease 1 gene (PKD1) by a novel approach. *Am J Hum Genet* 60(6):1399-410, 1997.
Perrichot R, Mercier B, Quere I, et al. Novel mutations in the duplicated region of PKD1 gene. *Eur J Hum Genet* 8(5):353-9, 2000.
Phakdeekitcharoen, et al. Thirteen novel mutations of the replicated region of PKD1 in an Asian population. *Kidney Int* 58(4):1400-12, 2000.
Qian F, Boletta A, Bhunia AK, Xu H, et al. Cleavage of polycystin-1 requires the receptor for egg jelly domain and is disrupted by human autosomal-dominant polycystic kidney disease 1-associated mutations. *Proc Natl Acad Sci U S A* 24;99(26):16981-6, 2002.
Rossetti S, Bresin E, Restagno G, et al. Autosomal dominant polycystic kidney disease (ADPKD) in an Italian family carrying a novel nonsense mutation and two missense changes in exons 44 and 45 of the PKD1 Gene. *Am J Med Genet* 16; 65(2):155-9, 1996.
Rossetti S, Chauveau D, Kubly V, et al. Association of mutation position in polycystic kidney disease 1 (PKD1) gene and development of a vascular phenotype. *Lancet* 28;361(9376):2196-201, 2003.
Torra R, Viribay M, Telleria D, et al. Seven novel mutations of the PKD2 gene in families with autosomal dominant polycystic kidney disease. *Kidney Int* 56(1):28-33, 1999.
Veldhuisen B, Saris JJ, de Haij S, et al. A spectrum of mutations in the second gene for autosomal dominant polycystic kidney disease (PKD2). *Am J Hum Genet* 61(3):547-55, 1997.
Watnick TJ, Tones VE, Gandolph MA, et al. Somatic mutation in individual liver cysts supports a two-hit model of cystogenesis in autosomal dominant polycystic kidney disease. *Mol Cell* 2(2):247-51, 1998.
Office Action issued in co-pending Canadian Patent Application No. 2,993,381, dated Oct. 25, 2018.

\* cited by examiner

```
gcactgcagc gccagcgtcc gagcgggcgg ccgagctccc ggagcggcct ggccccgagc   60
cccgagcggg cgtcgctcag cagcaggtcg cggccgcgca gccccatcca gccccgcgcc  120
cgccatgccg tccgcgggcc ccgcctgagc tgcggtctcc gcgcgcgggc gggcctgggg  180
acggcggggc catgcgcgcg ctgccctaac gatgccgccc gccgcgcccg cccgcctggc  240
gctggccctg ggcctgggcc tgtggctcgg ggcgctggcg gggggccccg ggcgcggctg  300
cgggccctgc gagccccccct gcctctgcgg cccagcgccc ggcgccgcct gccgcgtcaa  360
ctgctcgggc cgcgggctgc ggacgctcgg tcccgcgctg cgcatccccg cggacgccac  420
agcgctagac gtctcccaca acctgctccg ggcgctggac gttgggctcc tggcgaacct  480
ctcggcgctg gcagagctgg atataagcaa caacaagatt tctacgttag aagaaggaat  540
atttgctaat ttatttaatt taagtgaaat aaacctgagt gggaacccgt ttgagtgtga  600
ctgtggcctg gcgtggctgc cgcgatgggc ggaggagcag caggtgcggg tggtgcagcc  660
cgaggcagcc acgtgtgctg ggcctggctc cctggctggc cagcctctgc ttggcatccc  720
cttgctggac agtggctgtg gtgaggagta tgtcgcctgc ctccctgaca acagctcagg  780
caccgtggca gcagtgtcct tttcagctgc ccacgaaggc ctgcttcagc cagaggcctg  840
cagcgccttc tgcttctcca ccggccaggg cctcgcagcc ctctcggagc agggctggtg  900
cctgtgtggg gcggcccagc cctccagtgc ctcctttgcc tgcctgtccc tctgctccgg  960
cccccccgcca cctcctgccc ccacctgtag gggccccacc ctcctccagc acgtcttccc 1020
tgcctcccca ggggccaccc tggtggggcc ccacggacct ctggcctctg gccagctagc 1080
agccttccac atcgctgccc cgctccctgt cactgccaca cgctgggact tcggagacgg 1140
ctccgccgag gtggatgccg ctgggccggc tgcctcgcat cgctatgtgc tgcctgggcg 1200
ctatcacgtg acggccgtgc tggccctggg ggccggctca gccctgctgg ggacagacgt 1260
gcaggtggaa gcggcacctg ccgccctgga gctcgtgtgc cgtcctcgg tgcagagtga 1320
cgagagcctt gacctcagca tccagaaccg cggtggttca ggcctggagg ccgcctacag 1380
catcgtggcc ctgggcgagg agccggcccg agcggtgcac ccgctctgcc cctcggacac 1440
ggagatcttc cctggcaacg ggcactgcta ccgcctggtg gtggagaagg cggcctggct 1500
gcaggcgcag gagcagtgtc aggcctgggc cggggccgcc ctggcaatgg tggacagtcc 1560
cgccgtgcag cgcttcctgg tctcccgggt caccaggagc ctagacgtgt ggatcggctt 1620
ctcgactgtg caggggggtgg aggtgggccc agcgccgcag ggcgaggcct tcagcctgga 1680
gagctgccag aactggctgc ccggggagcc acaccagcc acagccgagc actgcgtccg 1740
gctcgggccc accgggtggt gtaacaccga cctgtgctca gcgccgcaca gctacgtctg 1800
cgagctgcag cccggaggcc cagtgcagga tgccgagaac ctcctcgtgg gagcgccag 1860
tggggacctg cagggacccc tgacgcctct ggcacagcag gacggcctct cagccccgca 1920
cgagcccgtg gaggtcatgg tattcccggg cctgcgtctg agccgtgaag ccttcctcac 1980
cacggccgaa tttgggaccc aggagctccg gcggcccgcc cagctgcggc tgcaggtgta 2040
ccggctcctc agcacagcag ggacccggga aacggcagc gagcctgaga gcaggtcccc 2100
ggacaacagg acccagctgg ccccccgcgtg catgccaggg ggacgctggt gccctggagc 2160
caacatctgc ttgccgctgg acgcctcttg ccacccccag gcctgcgcca atggctgcac 2220
gtcagggcca gggctacccg ggcccccta tgcgctatgg agagagttcc tcttctccgt 2280
tgccgcgggg cccccgcgc agtactcggt caccctccac ggccaggatg tcctcatgct 2340
ccctggtgac ctcgttggct tgcagcacga cgctggccct ggcgcctcc tgcactgctc 2400
gccggctccc ggccaccctg gtcccaggc cccgtacctc tccgccaacg cctcgtcatg 2460
gctgccccac ttgccagccc agctggaggg cacttgggcc tgccctgcct gtgccctgcg 2520
gctgcttgca gccacggaac agctcaccgt gctgctgggc ttgaggccca accctggact 2580
gcggatgcct gggcgctatg aggtccgggc agaggtgggc aatggcgtgt ccaggcacaa 2640
cctctcctgc agctttgacg tggtctcccc agtggctggg ctgcgggtca tctaccctgc 2700
ccccgcgac ggccgcctct acgtgcccac caacggctca gccttggtgc tccaggtgga 2760
ctctggtgcc aacgccacgg ccacggctcg ctggcctggg ggcagtgtca gcgcccgctt 2820
tgagaatgtc tgccctgccc tggtggccac cttcgtgccc ggctgccct gggagaccaa 2880
cgatacccctg ttctcagtgg tagcactgcc gtggctcagt gaggggagc acgtggtgga 2940
cgtggtggtg gaaaacagcg ccagccgggc caacctcagc ctgcgggtga cggcggagga 3000
gcccatctgt ggcctccgcg ccacgcccag ccccgaggcc cgtgtactgc agggagtcct 3060
agtgaggtac agcccgtggt tggaggccgg ctcggacatg gtcttccggt ggaccatcaa 3120
cgacaagcag tccctgacct tccagaacgt ggtcttcaat gtcatttatc agagcgcggc 3180
ggtcttcaag ctctcactga cggcctccaa ccacgtgagc aacgtcaccg tgaactacaa 3240
cgtaaccgtg gagcggatga acaggatgca gggtctgcag gtctccacag tgccggccgt 3300
gctgtcccccc aatgccacgc tagcactgac ggcgggcgtg ctggtggact cggccgtgga 3360
ggtggccttc ctgtggaact ttgggggatgg ggagcaggcc ctccaccagt tccagcctcc 3420
```

FIG. 1A

```
gtacaacgag tccttcccgg ttccagaccc ctcggtggcc caggtgctgg tggagcacaa 3480
tgtcatgcac acctacgctg cccaggtga gtacctcctg accgtgctgg catctaatgc 3540
cttcgagaac ctgacgcagc aggtgcctgt gagcgtgcgc gcctccctgc cctccgtggc 3600
tgtgggtgtg agtgacggcg tcctggtggc cggccggccc gtcaccttct acccgcaccc 3660
gctgccctcg cctggggtg ttctttacac gtgggacttc ggggacggct ccctgtcct 3720
gacccagagc cagccggctg ccaaccacac ctatgcctcg aggggcacct accacgtgcg 3780
cctggaggtc aacaacacgg tgagcggtgc ggcggcccag gcggatgtgc gcgtctttga 3840
ggagctccgc ggactcagcg tggacatgag cctggccgtg gagcagggcg ccccgtggt 3900
ggtcagcgcc gcggtgcaga cgggcgacaa catcacgtgg accttcgaca tggggacgg 3960
caccgtgctg tcgggcccgg aggcaacagt ggagcatgtg tacctgcggg cacagaactg 4020
cacagtgacc gtgggtgcgg ccagccccgc cggccacctg cccggagcc tgcacgtgct 4080
ggtcttcgtc ctggaggtgc tgcgcgttga accgccgcc tgcatcccca cgcagcctga 4140
cgcgcggctc acggcctacg tcaccgggaa cccggcccac tacctcttcg actggacctt 4200
cggggatggc tcctccaaca cgaccgtgcg ggggtgcccg acggtgacac acaacttcac 4260
gcggagcggc acgttccccc tggcgctggt gctgtccagc cgcgtgaaca gggcgcatta 4320
cttcaccagc atctgcgtgg agccagaggt gggcaacgtc accctgcagc cagagaggca 4380
gtttgtgcag ctcggggacg aggcctggct ggtggcatgt gcctggcccc cgttcccta 4440
ccgctacacc tgggactttg gcaccgagga agccgccccc acccgtgcca ggggccctga 4500
ggtgacgttc atctaccgag acccaggctc ctatcttgtg acagtcaccg cgtccaacaa 4560
catctctgct gccaatgact cagccctggt ggaggtgcag gagcccgtgc tggtcaccag 4620
catcaaggtc aatggctccc ttgggctgga gctgcagcag ccgtacctgt tctctgctgt 4680
gggccgtggg cgccccgcca gctacctgtg ggatctgggg gacggtgggt ggctcgaggg 4740
tccggaggtc acccacgctt acaacagcac aggtgacttc accgttaggg tggccggctg 4800
gaatgaggtg agccgcagcg aggcctggct caatgtgacg gtgaagcggc gcgtgcgggg 4860
gctcgtcgtc aatgcaagcc gcacggtggt gcccctgaat gggagcgtga gcttcagcac 4920
gtcgctggag gccggcagtg atgtgcgcta ttcctgggtg ctctgtgacc gctgcacgcc 4980
catccctggg ggtcctacca tctcttacac cttccgctcc gtgggcacct caatatcat 5040
cgtcacggct gagaacgagg tgggctccgc ccaggacagc atcttcgtct atgtcctgca 5100
gctcatagag gggctgcagg tggtgggcgg tggccgctac ttccccacca accacacggt 5160
acagctgcag gccgtggtta gggatggcac caacgtctcc tacagctgga ctgcctggag 5220
ggacaggggc ccggccctgg ccggcagcgg caaaggcttc tcgctcaccg tgctcgaggc 5280
cggcacctac catgtgcagc tgcgggccac caacatgctg ggcagcgcct gggccgactg 5340
caccatggac ttcgtggagc ctgtggggtg gctgatggtg accgcctccc cgaacccagc 5400
tgccgtcaac acaagcgtca ccctcagtgc cgagctggct ggtggcagtg gtgtcgtata 5460
cacttggtcc ttggaggagg ggctgagctg ggagacctcc gagccattta ccacccatag 5520
cttccccaca cccggcctgc acttggtcac catgacggca gggaacccgc tgggctcagc 5580
caacgccacc gtggaagtgg atgtgcaggt gcctgtgagt ggcctcagca tcagggccag 5640
cgagcccgga ggcagcttcg tggcggccgg gtcctctgtg ccctttggg ggcagctggc 5700
cacgggcacc aatgtgagct ggtgctgggc tgtgcccggc ggcagcagca gcgtggccc 5760
tcatgtcacc atggtcttcc cggatgctgg caccttctcc atccggctca tgcctccaa 5820
cgcagtcagc tgggtctcag ccacgtacaa cctcacggcg gaggagccca tcgtgggcct 5880
ggtgctgtgg gccagcagca aggtggtggc gcccgggcag ctggtccatt ttcagatcct 5940
gctggctgcc ggctcagctg tcaccttccg cctgcaggtc ggcggggcca ccccgaggt 6000
gctccccggg ccccgtttct cccacagctt ccccgcgtc ggagaccacg tggtgagcgt 6060
gcggggcaaa aaccacgtga gctgggccca ggcgcaggtg cgcatcgtgg tgctggaggc 6120
cgtgagtggg ctgcagatgc caactgctg cgagcctggc atcgccacgg cactgagag 6180
gaacttcaca gcccgcgtgc agcgcggctc tcgggtcgcc tacgcctggt acttctcgct 6240
gcagaaggtc cagggcgact cgctggtcat cctgtcgggc cgcgacgtca cctacacgcc 6300
cgtggccgcg ggctgttggg agatccaggt gcgcgccttc aacgccctgg gcagtgagaa 6360
ccgcacgctg gtgctggagg ttcaggacgc cgtccagtat gtggccctgc agagcggccc 6420
ctgcttcacc aaccgctcgg cgcagtttga ggccgccacc agcccagcc cccggcgtgt 6480
ggcctaccac tgggactttg gggatgggtc gccagggcag gacacagatg agcccaggc 6540
cgagcactcc tacctgaggc ctgggggacta ccgcgtgcag gtgaacgcct ccaacctggt 6600
gagcttcttc gtggcgcagg ccacggtgac cgtccaggtc ctggcctgcc gggagccgga 6660
ggtggacgtg gtcctgcccc tgcaggtgct gatgcggcga tcacagcgca actacttgga 6720
ggcccacgtt gacctgcgcg actgcgtcac ctaccagact gagtaccgct gggaggtgta 6780
tcgcaccgcc agctgccagc ggccggggcg cccagcgcgt gtggccctgc ccggcgtgga 6840
```

FIG. 1B

```
cgtgagccgg cctcggctgg tgctgccgcg gctggcgctg cctgtggggc actactgctt 6900
tgtgtttgtc gtgtcatttg gggacacgcc actgacacag agcatccagg ccaatgtgac 6960
ggtggccccc gagcgcctgg tgcccatcat tgagggtggc tcataccgcg tgtggtcaga 7020
cacacgggac ctggtgctgg atgggagcga gtcctacgac cccaacctgg aggacggcga 7080
ccagacgccg ctcagtttcc actgggcctg tgtggcttcg acacagaggg aggctggcgg 7140
gtgtgcgctg aactttgggc cccgcgggag cagcacggtc accattccac gggagcggct 7200
ggcggctggc gtggagtaca ccttcagcct gaccgtgtgg aaggccggcc gcaaggagga 7260
ggccaccaac cagacggtgc tgatccggag tggccgggtg cccattgtgt ccttggagtg 7320
tgtgtcctgc aaggcacagg ccgtgtacga agtgagccgc agctcctacg tgtacttgga 7380
gggccgctgc ctcaattgca gcagcggctc caagcgaggg cggtgggctg cacgtacgtt 7440
cagcaacaag acgctggtgc tggatgagac caccacatcc acgggcagtg caggcatgcg 7500
actggtgctg cggcggggcg tgctgcggga cggcgaggga tacaccttca cgctcacggt 7560
gctgggccgc tctggcgagg aggagggctg cgcctccatc cgcctgtccc caaccgccc 7620
gccgctgggg ggctcttgcc gcctcttccc actgggcgct gtgcacgccc tcaccaccaa 7680
ggtgcacttc gaatgcacgg gctggcatga cgcggaggat gctggcgccc cgctggtgta 7740
cgccctgctg ctgcggcgct gtcgccaggg ccactgcgag gagttctgtg tctacaaggg 7800
cagcctctcc agctacggag ccgtgctgcc cccgggtttc aggccacact cgaggtggg 7860
cctggccgtg gtggtgcagg accagctggg agccgctgtg gtcgccctca caggtctttt 7920
ggccatcacc ctcccagagc ccaacggcag cgcaacgggg ctcacagtct ggctgcacgg 7980
gctcaccgct agtgtgctcc cagggctgct gcggcaggcc gatccccagc acgtcatcga 8040
gtactcgttg gccctggtca ccgtgctgaa cgagtacgag cgggccctgg acgtggcggc 8100
agagcccaag cacgagcggc agcaccgagc ccagatacgc aagaacatca cggagactct 8160
ggtgtccctg agggtccaca ctgtggatga catccagcag atcgctgctg cgctggccca 8220
gtgcatgggg cccagcaggg agctcgtatg ccgctcgtgc ctgaagcaga cgctgcacaa 8280
gctggaggcc atgatgctca tcctgcaggc agagaccacc gcgggcaccg tgacgcccac 8340
cgccatcgga gacagcatcc tcaacatcac aggagacctc atccacctgg ccagctcgga 8400
cgtgcgggca ccacagccct cagagctggg agccgagtca ccatctcgga tggtggcgtc 8460
ccaggcctac aacctgacct ctgccctcat gcgcatcctc atgcgctccc gcgtgctcaa 8520
cgaggagccc ctgacgctgg cgggcgagga gatcgtggcc cagggcaagc gctcggaccc 8580
gcggagcctg ctgtgctatg gcggcgcccc agggcctggc tgccacttct ccatccccga 8640
ggctttcagc ggggccctgg ccaacctcag tgacgtggtg cagctcatct ttctggtgga 8700
ctccaatccc tttccctttg gctatatcag caactacacc gtctccacca aggtggcctc 8760
gatggcattc cagacacagg ccggcgccca gatccccatc gagcggctgg cctcagagcg 8820
cgccatcacc gtgaaggtgc ccaacaactc ggactgggct gccggggcc accgcagctc 8880
cgccaactcc gccaactccg ttgtggtcca gccccaggcc tccgtcggtg ctgtggtcac 8940
cctggacagc agcaaccctg cggccgggct gcatctgcag ctcaactata cgctgctgga 9000
cggccactac ctgtctgagg aacctgagcc ctacctggca gtctacctac actcggagcc 9060
ccggcccaat gagcacaact gctcggctag caggaggatc cgcccagagt cactccaggg 9120
tgctgaccac cggccctaca ccttcttcat ttccccgggg agcagagacc cagcggggag 9180
ttaccatctg aacctctcca gccacttccg ctggtcggcg ctgcaggtgt ccgtgggcct 9240
gtacacgtcc ctgtgccagt acttcagcga ggaggacatg tgtggcgga cagagggct 9300
gctgccctg gaggagacct cgccccgcca ggccgtctgc ctcacccgcc acctcaccgc 9360
cttcggcgcc agcctcttcg tgccccaag ccatgtccgc tttgtgtttc ctgagccgac 9420
agcggatgta aactacatcg tcatgctgac atgtgctgtg tgcctggtga cctacatggt 9480
catggccgcc atcctgcaca agctggacca gttggatgcc agccggggcc gcgccatccc 9540
tttctgtggg cagcggggcc gcttcaagta cgagatcctc gtcaagacag gctgggccg 9600
gggctcaggt accacggccc acgtgggcat catgctgtat ggggtggaca gccggagcgg 9660
ccaccggcac ctggacggcg acagagcctt ccaccgcaac agcctggaca tcttccggat 9720
cgccaccccg cacagcctgg gtagcgtgtg aagatccga gtgtggcacg acaacaaagg 9780
gctcagccct gcctggttcc tgcagcacgt catcgtcagg acctgcaga cggcacgcag 9840
cgccttcttc ctggtcaatg actggctttc ggtggagacg gaggccaacg ggggcctggt 9900
ggagaaggag gtgctggccg cgagcgacgc agccctttg cgcttccggc gcctgctggt 9960
ggctgagctg cagcgtggct tctttgacaa gcacatctgg ctctccatat gggaccggcc 10020
gcctcgtagc cgtttcactc gcatccagag ggccacctgc tgcgttctcc tcatctgcct 10080
cttcctgggc gccaacgccg tgtggtacgg ggctgttggc gactctgcct acagcacggg 10140
gcatgtgtcc aggctgagcc cgctgagcgt cgacacagtc gctgttggcc tggtgtccag 10200
cgtggttgtc tatcccgtct acctggccat ccttttttctc ttccggatgt cccggagcaa 10260
```

FIG. 1C

```
ggtggctggg agcccgagcc ccacacctgc cgggcagcag gtgctggaca tcgacagctg 10320
cctggactcg tccgtgctgg acagctcctt cctcacgttc tcaggcctcc acgctgaggc 10380
ctttgttgga cagatgaaga gtgacttgtt tctggatgat tctaagagtc tggtgtgctg 10440
gccctccggc gagggaacgc tcagttggcc ggacctgctc agtgacccgt ccattgtggg 10500
tagcaatctg cggcagctgg cacggggcca ggcgggccat gggctggcc cagaggagga 10560
cggcttctcc ctggccagcc cctactcgcc tgccaaatcc ttctcagcat cagatgaaga 10620
cctgatccag caggtccttg ccgaggggt cagcagccca gccctaccc aagacaccca 10680
catggaaacg gacctgctca gcagcctgtc cagcactcct ggggagaaga cagagacgct 10740
ggcgctgcag aggctggggg agctgggcc acccagccca ggcctgaact gggaacagcc 10800
ccaggcagcg aggctgtcca ggacaggact ggtggagggt ctgcggaagc gcctgctgcc 10860
ggcctggtgt gcctcctgg cccacgggct cagcctgctc ctggtggctg tggctgtggc 10920
tgtctcaggg tgggtgggtg cgagcttccc cccggggcgtg agtgttgcgt ggctcctgtc 10980
cagcagcgcc agcttcctgg cctcattcct cggctgggag ccactgaagg tcttgctgga 11040
agccctgtac ttctcactgg tggccaagcg gctgcaccg gatgaagatg acaccctggt 11100
agagagcccg gctgtgacgc ctgtgagcgc acgtgtgccc cgcgtacggc caccccacgg 11160
ctttgcactc ttcctggcca aggaagaagc ccgcaaggtc aagaggctac atggcatgct 11220
gcggagcctc ctggtgtaca tgcttttct gctggtgacc ctgctggcca gctatgggga 11280
tgcctcatgc catgggcacg cctaccgtct gcaaagcgcc atcaagcagg agctgcacag 11340
ccgggccttc ctggccatca cgcggtctga ggagctctgg ccatggatgg cccacgtgct 11400
gctgccctac gtccacggga accagtccag cccagagctg gggccccac ggctgcggca 11460
ggtgcggctg caggaagcac tctacccaga ccctcccggc cccagggtcc acacgtgctc 11520
ggccgcagga ggcttcagca ccagcgatta cgacgttggc tgggagagtc ctcacaatgg 11580
ctcggggacg tgggcctatt cagcgccgga tctgctgggg gcatggtcct ggggctcctg 11640
tgccgtgtat gacagcgggg gctacgtgca ggagctgggc ctgagcctgg aggagagccg 11700
cgaccggctg cgcttcctgc agctgcacaa ctggctggac aacaggagcc gcgctgtgtt 11760
cctggagctc acgcgctaca gcccggccgt ggggctgcac gccgccgtca cgctgcgcct 11820
cgagttcccg gcggccggcc gcgccctggc cgccctcagc gtccgcccct ttgcgctgcg 11880
ccgcctcagc gcgggcctct cgctgcctct gctcacctcg gtgtgcctgc tgctgttcgc 11940
cgtgcacttc gccgtggccg aggcccgtac ttggcacagg gaagggcgct ggcgcgtgct 12000
gcggctcgga gcctgggcgc ggtggctgct ggtggcgctg acggcggcca cggcactggt 12060
acgcctcgcc cagctgggtg ccgctgaccg ccagtggacc cgtttcgtgc gcggccgccc 12120
gcgccgcttc actagcttcg accaggtggc gcagctgagc tccgcagccc gtggcctggc 12180
ggcctcgctg ctcttcctgc ttttggtcaa ggctgcccag cagctacgct cgtgcgcca 12240
gtggtccgtc tttggcaaga cattatgccg agctctgcca gagctcctgg gggtcacctt 12300
gggcctggtg gtgctcgggg tagcctacgc ccagctggcc atcctgctcg tgtcttcctg 12360
tgtggactcc ctctggagcg tggcccaggc cctgttggtg ctgtgccctg ggactgggct 12420
ctctaccctg tgtcctgccg agtcctggca cctgtcaccc ctgctgtgtg tggggctctg 12480
ggcactgcgg ctgtggggcg ccctacggct gggggctgtt attctccgct ggcgctacca 12540
cgccttgcgt ggagagctgt accggccggc ctgggagccc caggactacg agatggtgga 12600
gttgttcctg cgcaggctgc gcctctggat gggcctcagc aaggtcaagg agttccgcca 12660
caaagtccgc tttgaaggga tggagccgct gccctctcgc tcctccaggg gctccaaggt 12720
atccccggat gtgcccccac ccagcgctgg ctccgatgcc tcgcacccct ccacctcctc 12780
cagccagctg gatgggctga gcgtgagcct gggccggctg ggacaaggt gtgagcctga 12840
gccctcccgc ctccaagccg tgttcgaggc cctgctcacc cagtttgacc gactcaacca 12900
ggccacagag gacgtctacc agctggagca gcagctgcac agcctgcaag ccgcaggag 12960
cagccgggcg cccgccggat cttcccgtgg cccatccccg ggcctgcggc cagcactgcc 13020
cagccgcctt gcccgggcca gtcggggtgt ggacctggcc actggcccca gcaggacacc 13080
ccttcgggcc aagaacaagg tccaccccag cagcacttag tcctccttcc tggcgggggt 13140
gggccgtgga gtcggagtgg acaccgctca gtattacttt ctgccgctgt caaggccgag 13200
ggccaggcag aatggctgca cgtaggttcc ccagagagca ggcaggggca tctgtctgtc 13260
tgtgggcttc agcactttaa agaggctgtg tggccaacca ggacccaggg tcccctcccc 13320
agctcccttg ggaaggacac agcagtattg gacggttct agcctctgag atgctaattt 13380
atttccccga gtcctcaggt acagcgggct gtgccggcc ccaccccctg ggcagatgtc 13440
ccccactgct aaggctgctg gcttcaggga gggttagcct gcaccgccgc caccctgccc 13500
ctaagttatt acctctccag ttcctaccgt actccctgca ccgtctcact gtgtgtctcg 13560
tgtcagtaat ttatatggtg ttaaaatgtg tatattttg tatgtcacta ttttcactag 13620
gcctgagggg cctgcgccca gagctggcct cccccaacac ctgctgcgct tggtaggtgt 13680
```

FIG. 1D

```
ggtggcgtta tggcagcccg gctgctgctt ggatgcgagc ttggccttgg gccggtgctg 13740
ggggcacagc tgtctgccag gcactctcat cacccccagag gccttgtcat cctcccttgc 13800
cccaggccag gtagcaagag agcagcgccc aggcctgctg gcatcaggtc tgggcaagta 13860
gcaggactag gcatgtcaga ggacccccagg gtggttagag gaaaagactc ctcctggggg 13920
ctggctccca gggtggagga aggtgactgt gtgtgtgtgt gtgtgcgcgc gcgacgcgcg 13980
agtgtgctgt atggcccagg cagcctcaag gccctcggag ctggctgtgc ctgcttctgt 14040
gtaccacttc tgtgggcatg gccgcttcta gagcctcgac acccccccaa ccccccgcacc 14100
aagcagacaa agtcaataaa agagctgtct gactgc                          14136
```

FIG. 1E

```
ggctcctgag gcgcacagcg ccgagcgcgg cgccgcgcac ccgcgcgccg gacgccagtg   60
accgcgatgg tgaactccag tcgcgtgcag cctcagcagc ccggggacgc caagcggccg  120
cccgcgcccc gcgcgccgga cccgggccgg ctgatggctg gctgcgcggc cgtgggcgcc  180
agcctcgccg ccccgggccg cctctgcgag cagcggggcc tggagatcga gatgcagcgc  240
atccggcagg cggccgcgcg ggaccccccg gccggagccg cggcctcccc ttctcctccg  300
ctctcgtcgt gctcccggca ggcgtggagc cgcgataacc ccggcttcga ggccgaggag  360
gaggaggagg aggtggaagg ggaagaaggc ggaatggtgg tggagatgga cgtagagtgg  420
cgcccgggca gccggaggtc ggccgcctcc tcggccgtga gctccgtggg cgcgcggagc  480
cggggcttg ggggctacca cggcgcgggc caccgagcg ggaggcggcg ccggcgagag  540
gaccagggcc cgccgtgccc cagcccagtc ggcggcgggg acccgctgca tcgccacctc  600
ccctggaag ggcagccgcc ccgagtggcc tgggcggaga ggctggttcg cgggctgcga  660
ggtgtaagag cgcgcgaccc gcagcggcag atgcacgaac cagaacggcc ggcgccgggng  720
gcttcttaaa taaaatgata tcttttcttt tcttcattat tattttaaag gtctctgggg  780
aacaagactc atggaggaaa gcagcactaa ccgagagaaa taccttaaaa gtgttttacg  840
ggaactggtc atatacctcc tttttctcat agtcttgtgc atctgtaagt agaatatttc  900
cttgcactaa tgggaaagtt ttgaaacgat gtgaatttgt ccaaaatgtt tatccacagg  960
aacaatccct ttgtgaaggc tgctggtatg tggatgtgtg ccggttccct tggggcgttc 1020
atttggatct ttctgtgttc cagtgaccta cggcatgatg agctccaatg tgtactacta 1080
cacccggatg atgtcacagc tcttcctaga caccccgtg tccaaaacgg agaaaactaa 1140
ctttaaaact ctgtcttcca tggaagactt ctggaaggta tttggaaata acttttgaaag 1200
tacctctcta tcacaagcca atgcttggtt atgcaacgat gcaggcaggg caaagcagcg 1260
gcatgagctt gaacttnnnn agatgttnnc tttcttttag ttcacagaag gctccttatt 1320
ggatgggctg tactggaaga tgcagcccag caaccagact gaagctgaca accgaagttt 1380
catcttctat gagaacctgc tgttagggt tccacgaata cggcaactcc gagtcagaaa 1440
tggatcctgc tctatcccc aggacttgag agatgaaatt aaagagtgct atgatgtcta 1500
ctctgtcagt agtgaagata gggctccctt tgggccccga aatggaaccg cgtaagtgtc 1560
tgtgactcat tggcactcgg tgatattcat ccttgtaatt gcctcaagtg ttccactgat 1620
tgtaactgtt tgttttngg ttttgttttt aatcagttgg atctacacaa gtgaaaaga 1680
cttgaatggt agtagccact ggggaatcat tgcaacttat agtggagctg ctattatct 1740
ggatttgtca agaacaagag aggaaacagc tgcacaagtt gctagcctca agaaaaatgt 1800
ctggctggac cgaggaacca gggcaacttt tattgacttc tcagtgtaca acgccaacat 1860
taacctgttc tgtgtggtca ggtgtgtgac tgaggacatg catccctcct atttctgtgt 1920
ggttgtacat acatcctatt ctagggttac ccagaaaaac cttttntgc aggttgttat 1980
tgttttaatt gttcttattt acatgcaggt tattggttga attcccagca acaggtggtg 2040
tgattccatc ttggcaattt cagcctttaa agctgatccg atatgtcaca acttttgatt 2100
tcttcctggc agcctgtgag attatctttt gtttctttat cttttactat gtggtggaag 2160
agatattgga aattcgcatt cacaaactac actatttcag gagtttctgg aattgtctgg 2220
atgttgtgat cgttgtggta ggtccganca ncancaccaa atttcctatt ctattctaca 2280
agnatgttaa caattaatac attggtgaag aaaatatac tagtcatatt aaggtaagtt 2340
tcatatttct aaaacactgt aataaaatat aaatattttg cttttcagct gtcagtggta 2400
gctataggaa ttaacatata cagaacatca aatgtggagg tgctactaca gtttctgaa 2460
gatcaaaata cttttcccaa ctttgagcat ctggcatatt ggcagataca gttcaacaat 2520
atagctgctg tcacagtatt ttttgtctgg attaaggtaa tttataaatt tcatgttcta 2580
cattnnaaat aatattttct ttaaaaaaaa tgagttccac aaaancatgc gaaacaatgt 2640
tttattatac acagtcacac catttggttt atccattcat ctattgatgt cttctctctc 2700
ttacagctct tcaaattcat caatttttaac aggaccatga gccagctctc gacaaccatg 2760
tctcgatgtg ccaaagacct gttcggcttt gctattatgt tcttcattat tttcctagcg 2820
tatgctcagt tggcatacct tgtctttggc actcaggtcg atgacttcag tactttccaa 2880
gagtgtatgt aagtatatat gaaattaaga agaaaatttt agtcagagta gncactgttg 2940
cgtggacant ctttggtttt gtattgtggt gntttgtntt attttatag cttcactcaa 3000
ttccgtatca ttttgggcga tatcaacttt gcagagattg aggaagctaa tcgagttttg 3060
ggaccaattt atttcactac atttgtgttc tttatgttct tcattctttt ggtatgtaca 3120
tttatattta tagtggaggt tcaatttaaa cttcgtaaat ccttgtcttc tcttttttga 3180
ttgataattc caaattatgt ttcttccttt aattttgcc ctcctttcat ttacaaacag 3240
aatatgtttt tggctatcat caatgatact tactctgaag tgaaatctga cttggcacag 3300
cagaaagctg aaatggaact ctcagatctt atcagaaagg taggaaaaac cttaattctc 3360
aaaaattctt ctgtttctga cataaaatga gcattgtttc acccanattt tagaatacnc 3420
```

FIG. 2A

```
taaaccaagt cttttatttt ttctctctct gatagggcta ccataaagct ttggtcaaac 3480
taaaactgaa aaaaaatacc gtggatgaca tttcagagag tctgcggcaa ggaggaggca 3540
agttaaactt tgacgaactt cgacaagatc tcaaagggtg agaatcatgc ttcctgaggt 3600
tctnaaaaat tcctgcttct aaagataaat tcctggtgat aagagtattt ctagcccaag 3660
ggctcatggg aacanaggat gaatgttatc tgtatcctct ctctaatttc aggaagggcc 3720
atactgatgc agagattgag gcaatattca caaagtacga ccaagatgga gaccaagaac 3780
tgaccgaaca tgaacatcag cagatgagag acgacttgga gaaagagagg gtgggtctgg 3840
tttaggagna accggatttg atttggtacc tacaacacca cacttctgtg gggtctcagt 3900
gttctgctcc tcactcagtg accccttgtt cttcaggagg acctggattt ggatcacagt 3960
tctttaccac gtcccatgag cagccgaagt ttcctcgaa gcctggatga ctctgaggag 4020
gatgacgatg aagatagcgg acatagctcc agaaggaggg gaagcatttc tagtggcgtt 4080
tcttacgaag agtttcaagt gtaagtataa aggaattggc agaatttgcg tngacaattt 4140
gtccctctgt actgtgtttt ccttgcagcc tggtgagacg agtggaccgg atggagcatt 4200
ccatcggcag catagtgtcc aagattacg ccgtgatcgt gaagctagag attatggagc 4260
gagccaaact gaagaggagg gaggtgctgg gaaggctgtt ggatggggtg gccgaggtca 4320
gtagtcatga gctgaanaca ccgctgctga gcatggtgtt attaatnnna atatatgttg 4380
ctgacagttg tatttnaagt attnactgac ccccaacacc agtttctttt tcccttttta 4440
ggatgaaagg ctgggtcgtg acagtgaaat ccatagggaa cagatggaac ggctagtacg 4500
tgaagagttg gaacgctggg aatccgatga tgcagcttcc cagatcagtc atggtttagg 4560
cacgccagtg ggactaaatg gtcaacctcg ccccagaagc tcccgcccat cttcctccca 4620
atctacagaa ggcatggaag gtgcaggtgg aaatgggagt tctaatgtcc acgtatgata 4680
tgtgtgtttc agtatgtgtg tttctaataa gtgaggaagt ggctgtcctg aattgctgta 4740
acaagcacac tatttatatg ccctgaccac cataggatgc tagtctttgt gaccgattgc 4800
taatcttctg cactttaatt tatttatat aaactttacc catggttcaa agattttttt 4860
ttcttttttct catataagaa atctaggtgt aaatattgag tacagaaaaa aaatcttcat 4920
gatgtgtatt gagcggtacg cccagttgcc accatgactg agtcttctca gttgacaatg 4980
aagtagcctt ttaaagctag aaaactgtca aagggcttct gagtttcatt tccagtcaca 5040
aaaatcagta ttgttatttt ttccaagag tgtgaaggaa aatggggcaa ttccttttcca 5100
ctctggcata gttcatgagc ttaatacata gctttctttt aagaaggag ccttttttttt 5160
caactagctt cctggggtaa acttttctaa aagataaaat gggaaggaac tccaaactat 5220
gatagaatct gtgtgaatgg ttaagatgaa tgttaaatac tatgcttttt tgtaagttga 5280
tcgtatctga tgtctgtggg actaactgta tcacttaatt tttacttat tttggctcta 5340
atttgaataa gctgagtaaa accaccaaag atcagttata ggataaaatg gcatctctaa 5400
ccataacaca ggagaattgg aaggagccct aagttgtcac tcagtttaat ttctttttaat 5460
ggttagttta gcctaaagat ttatctgcat attcttttc ccatgtggct ctactcattt 5520
gcaactgaat ttaatgttat aactcatcta gtgagaccaa cttactaaat ttttagtatg 5580
cactgaaagt ttttatccaa caattatgtt catttaagc aaaattttaa gaaagttttg 5640
aaattcataa agcatttggt tttaaactat tttaagaata tagtactcgg tcaggtatgn 5700
nncacgcctg taatcccagc actttgggag gccgaaacag gcgaatcact tgagcccagg 5760
agttcaagac caacatgggc aatgtggcga aactccatct ctacaaaaaa tgcaaaaata 5820
aaaaatatag tactcaagta ttcttgatcc tgtgtttcaa aactagaatt tgtaatgcaa 5880
atggagctca gtctaataaa aagaggttt tggtattaaa agttcataca ttagacagta 5940
tcagccaaaa tttgagttag caacactgtt ttctttacga gagggtctca cccaaattta 6000
tggggagaaa tctatttctc aaaaaaaaa aatcttcttt tacagaaatg ttgagtaagg 6060
tgacattttg agcgctaata agcaaaagag catgcagtgc tgttgaataa ccctcacttg 6120
gagaaccaag agaatcctgt cgtttaatgc tatatttaa tttcacaagt tgttcattta 6180
actggtagaa tgtcagtcca atctccaatg agaacatgag caaatagacc tttccaggtt 6240
gaaagtgaaa catactgggt ttctgtaagt ttttcctcat ggcttcatct ctatctttac 6300
tttctcttga atatgctaca caaagttctt tattactaca tactaaagtt tgcattccag 6360
ggatattgac tgtacatatt tatgtatatg taccatgttg ttacatgtaa acaaacttca 6420
atttgaagtg cagctattat gtggtatcca tgtgtatcga ccatgtgcca tatatcaatt 6480
atggtcacta gaaagtctct ttatgatact ttttattgta ctgtttttca tttcacttgc 6540
aaaatttgc agaattcctc ctttctaccc ataaattaca tataatttt cttctttagt 6600
catggagaac nccccccat catctcancc ctattancctt tcccatgtgt actggtatta 6660
ttaaaagac atttacatac gcaagttttt cactgacaan caagaatgtt attaatgtgt 6720
aatactgagc acntttactt cttaataaa                                  6749
```

FIG. 2B

| Codon Number | | Sequence |
|---|---|---|
| 1 | ☐ | EXON 1<br>212 atgccgccgccgcgcccgcccgcctggcgctggccctgggcctg<br>M P P A A P A R L A L A L G L |
| 16 | ☐ | 257 ggcctgtggctcggggcgctggcggggggccccgggcgcggctgc<br>G L W L G A L A G G P G R G C |
| 31 | ☐ | 302 gggccctgcgagcccccctgcctctgcggcccagcgcccggcgcc<br>G P C E P P C L C G P A P G A |
| 46 | | 347 gcctgccgcgtcaactgctcgggccgcgggctgcggacgctcggt<br>A C R V N C S G R G L R T L G |
| 61 | | EXON 2<br>392 cccgcgctgcgcatccccgcggacgccacagcgctagacgtctcc<br>P A L R I P A D A T A L D V S |
| 76 | | 437 cacaacctgctccgggcgctggacgttgggctcctggcgaacctc<br>H N L L R A L D V G L L A N L |
| 91 | | EXON 3<br>482 tcggcgctggcagagctggatataagcaacaacaagatttctacc<br>S A L A E L D I S N N K I S T |
| 106 | | EXON 4<br>527 ttagaagaaggaatatttgctaatttatttaatttaagtgaaata<br>L E E G I F A N L F N L S E I |
| 121 | | 572 aacctgagtggaaacccgtttgagtgtgactgtggcctggcgtgg<br>N L S G N P F E C D C G L A W |
| 136 | | 617 ctgccgcgatgggcggaggagcagcaggtgcgggtggtgcagccc<br>L P R W A E E Q Q V R V V Q P |
| 151 | | 662 gaggcagccacgtgtgctgggcctggctccctggctggccagcct<br>E A A T C A G P G S L A G Q P |
| 166 | | EXON 5-A<br>707 ctgcttggcatcccttgctggacagtggctgtgtgaggagtat<br>L L G I P L L D S G C G E Y |
| 181 | | 752 gtggcctgcctccctgacaacagctcaggcaccgtggcagcagtg<br>V A C L P D N S S G T V A A V |

*FIG. 3A*

```
196  797 tcctttcagctgcccacgaaggcctgcttcagccagaggcctgc
        S  F  S  A  A  H  E  G  L  L  Q  P  E  A  C 211  842 agcgccttctgcttctccaccggccagggcctcgcagccctctcg
        S  A  F  C  F  S  T  G  Q  G  L  A  A  L  S
                                       → 5-B
226  887 gagcagggctggtgcctgtgtgggcggcccagccctccagtgcc
        E  Q  G  W  C  L  C  G  A  A  Q  P  S  S  A
                                  ← 5-A
241  932 tcctttgcctgcctgtccctctgctccggcccccgccacctcct
        S  F  A  C  L  S  L  C  S  G  P  P  P  P  P 256  977 gcccccacctgtaggggccccaccctcctccagcacgtcttccct
        A  P  T  C  R  G  P  T  L  L  Q  H  V  F  P 271 1022 gcctcccaggggccaccctggtggggccccacggacctctggcc
        A  S  P  G  A  T  L  V  G  P  H  G  P  L  A 286 1067 tctggccagctagcagccttccacatcgctgccccgctccctgtc
        S  G  Q  L  A  A  F  H  I  A  A  P  L  P  V
                                          → 5-C
301 1112 actgccacacgctgggacttcggagacggctccgccgaggtggat
        T  A  T  R  W  D  F  G  D  G  S  A  E  V  D
                                          ← 5-B
316 1157 gccgctgggccggctgcctcgcatcgctatgtgctgcctgggcgc
        A  A  G  P  A  A  S  H  R  Y  V  L  P  G  R 331 1202 tatcacgtgacggccgtgctggccctgggggccggctcagccctg
        Y  H  V  T  A  V  L  A  L  G  A  G  S  A  L 346 1247 ctggggacagacgtgcaggtggaagcggcacctgccgccctggag
        L  G  T  D  V  Q  V  E  A  A  P  A  A  L  E 361 1292 ctcgtgtgcccgtcctcggtgcagagtgacgagagccttgacctc
        L  V  C  P  S  S  V  Q  S  D  E  S  L  D  L 376 1337 agcatccagaaccgcggtggttcaggcctggaggccgcctacagc
        S  I  Q  N  R  G  G  S  G  L  E  A  A  Y  S
                                              EXON 6
391 1382 atcgtggccctgggcgaggagccggcccgagaggtgcacccgctc
        I  V  A  L  G  E  E  P  A  R  A  V  H  P  L
```

*FIG. 3B*

```
406   1427 tgccccctcggacacggagatcttccctggcaacgggcactgctac
           C  P  S  D  T  E  I  F  P  G  N  G  H  C  Y 421   1472 cggctggtggtggagaaggcggcctggctgcaggcgcaggagcag
           R  L  V  V  E  K  A  A  W  L  Q  A  Q  E  Q 436   1517 tgtcaggcctgggccggggccgccctggcaatggtggacagtccc
           C  Q  A  W  A  G  A  A  L  A  M  V  D  S  P
                                                    EXON 7
451   1562 gccgtgcagcgcttcctggtctcccgggtcaccaggagcctagac
           A  V  Q  R  F  L  V  S  R  V  T  R  S  L  D 466   1607 gtgtggatcggcttctcgactgtgcaggggggtggaggtgggccca
           V  W  I  G  F  S  T  V  Q  G  V  E  V  G  P 481   1652 gcgccgcagggcgaggccttcagcctggagagctgccagaactgg
           A  P  Q  G  E  A  F  S  L  E  S  C  Q  N  W 496   1697 ctgcccggggagccacacccagccacagccgagcactgcgtccgg
           L  P  G  E  P  H  P  A  T  A  E  H  C  V  R 511   1742 ctggggcccaccgggtggtgtaacaccgacctgtgctcagcgcc
           L  G  P  T  G  W  C  N  T  D  L  C  S  A  P
                                            EXON 8
526   1787 cacagctacgtctgcgagctgcagcccggagcccagtgcaggat
           H  S  Y  V  C  E  L  Q  P  G  P  V  Q  D 541   1832 gccgagaacctcctcgtgggagcgcccagtggggacctgcaggga
           A  E  N  L  L  V  G  A  P  S  G  D  L  Q  G 556   1877 ccctgacgcctctggcacagcaggacggcctctcagccccgcac
           P  L  T  P  L  A  Q  Q  D  G  L  S  A  P  H
                   EXON 9
571   1922 gagcccgtggaggtcatggtattccccgggctgcgtctgagccgt
           E  P  V  E  V  M  V  F  P  G  L  R  L  S  R 586   1967 gaagccttcctcaccacggccgaatttgggacccaggagctccgg
           E  A  F  L  T  T  A  E  F  G  T  Q  E  L  R 601   2012 cggccccgccagctgcggctgcaggtgtaccggctcctcagcaca
           R  P  A  Q  L  R  L  Q  V  Y  R  L  L  S  T
           EXON 10
616   2057 gcagggaccccggagaacggcagcgagcctgagagcaggtccccg
           A  G  T  P  E  N  G  S  E  P  E  S  R  S  P
```

*FIG. 3C*

```
631  2102 gacaacaggacccagctggccccccgcgtgcatgccaggggggacgc
          D  N  R  T  Q  L  A  P  A  C  M  P  G  G  R 646  2147 tggtgccctggagccaacatctgcttgccgctggacgcctcttgg
          W  C  P  G  A  N  I  C  L  P  L  D  A  S  C 661  2192 cacccccaggcctgcgccaatggctgcacgtcagggccagggcta
          H  P  Q  A  C  A  N  G  C  T  S  G  P  G  L 676  2237 cccggggcccctatgcgctatggagagagttcctcttctccgtt
          P  G  A  P  Y  A  L  W  R  E  F  L  F  S  V EXON 11-A
691  2282 gccgcggggccccccgcgcagtactcgtcaccctccacggccag
          A  A  G  P  P  A  Q  Y  S  V  T  L  H  G  Q 706  2327 gatgtcctcatgctccctggtgacctcgttggcttgcagcacgac
          D  V  L  M  L  P  G  D  L  V  G  L  Q  H  D 721  2372 gctggccctggcgccctcctgcactgctcgccggctcccggccac
          A  G  P  G  A  L  L  H  C  S  P  A  P  G  H 736  2417 cctggtccccaggccccgtacctctccgccaacgcctcgtcatgg
          P  G  P  Q  A  P  Y  L  S  A  N  A  S  S  W
                                              → 11-B
751  2462 ctgccccacttgccagcccagctggagggcacttgggcctgccct
          L  P  H  L  P  A  Q  L  E  G  T  W  A  C  P 766  2507 gcctgtgccctgcggctgcttgcagccacggaacagctcaccgtg
          A  C  A  L  R  L  L  A  A  T  E  Q  L  T  V
          ← 11-A
781  2552 ctgctgggcttgaggcccaaccctggactgcggatgcctgggcgc
          L  L  G  L  R  P  N  P  G  L  R  M  P  G  R 796  2597 tatgaggtccgggcagaggtgggcaatggcgtgtccaggcacaac
          Y  E  V  R  A  E  V  G  N  G  V  S  R  H  N 811  2642 ctctcctgcagctttgacgtggtctccccagtggctgggctgcgg
          L  S  C  S  F  D  V  V  S  P  V  A  G  L  R 826  2687 gtcatctaccctgcccccccgcgacggccgcctctacgtgcccacc
          V  I  Y  P  A  P  R  D  G  R  L  Y  V  P  T 841  2732 aacggctcagccttggtgctccaggtggactctggtgccaacgcc
          N  G  S  A  L  V  L  Q  V  D  S  G  A  N  A
```

*FIG. 3D*

```
                2777  acggccacggctcgctggcctgggggcagtgtcagcgccgcttt
          856         T   A  T  A  R  W  P  G  G  S  V  S  A  R  F
                                                                    → 11-C 2822  gagaatgtctgccctgccctggtggccaccttcgtgcccggctgc
          871         E  N  V  C  P  A  L  V  A  T  F  V  P  G  C 2867  ccctgggagaccaacgataccctgttctcagtggtagcactgccg
          886         P  W  E  T  N  D  T  L  F  S  V  V  A  L  P
                                                        ← 11-B 2912  tggctcagtgagggggagcacgtggtggacgtggtggtggaaaac
          901         W  L  S  E  G  E  H  V  V  D  V  V  V  E  N 2957  agcgccagccggggccaacctcagcctgcgggtgacggcggaggag
          916         S  A  S  R  A  N  L  S  L  R  V  T  A  E  E 3002  cccatctgtggcctccgcgccacgccagccccgaggcccgtgta
          931         P  I  C  G  L  R  A  T  P  S  P  E  A  R  V
                                              EXON 12
                3047  ctgcagggagtcctagt|aggtacagccccgtggtggaggccggc
          946         L  Q  G  V  L  V  R  Y  S  P  V  V  E  A  G 3092  tcggacatggtcttccggtggaccatcaacgacaagcagtccctg
          961         S  D  M  V  F  R  W  T  I  N  D  K  Q  S  L 3137  accttccagaacgtggtcttcaatgtcatttatcagagcgcggcg
          976         T  F  Q  N  V  V  F  N  V  I  Y  Q  S  A  A
                                         EXON 13
                3182  gtcttcaagctctca|ctgacggcctccaaccacgtgagcaacgtc
          991         V  F  K  L  S  L  T  A  S  N  H  V  S  N  V 3227  accgtgaactacaacgtaaccgtggagcggatgaacaggatgcag
         1006         T  V  N  Y  N  V  T  V  E  R  M  N  R  M  Q 3272  ggtctgcaggtctccacagtgccggccgtgctgtcccccaatgcc
         1021         G  L  Q  V  S  T  V  P  A  V  L  S  P  N  A 3317  acgctagcactgacggcgggcgtgctggtggactcggccgtggag
         1036         T  L  A  L  T  A  G  V  L  V  D  S  A  V  E
                                      EXON 14
                3362  gtggccttcct|gtggaactttggggatggggagcaggccctccac
         1051         V  A  F  L  W  N  F  G  D  G  E  Q  A  L  H 3407  cagttccagcctccgtacaacgagtccttcccggttccagacccc
         1066         Q  F  Q  P  P  Y  N  E  S  F  P  V  P  D  P
```

*FIG. 3E*

```
1081   3452  tcggtggcccaggtgctggtggagcacaatgtcatgcacacctac
              S   V   A   Q   V   L   V   E   H   N   V   M   H   T   Y
                             EXON 15-A 1096   3497  gctgcccaggtgagtacctcctgaccgtgctggcatctaatgcc
              A   A   P   G   E   Y   L   L   T   V   L   A   S   N   A 1111   3542  ttcgagaacctgacgcagcaggtgcctgtgagcgtgcgcgcctcc
              F   E   N   L   T   Q   Q   V   P   V   S   V   R   A   S 1126   3587  ctgccctccgtggctgtgggtgtgagtgacggcgtcctggtggcc
              L   P   S   V   A   V   G   V   S   D   G   V   L   V   A
                                                              →  15-B 1141   3632  ggccggcccgtcaccttctaccogcacccgctgcctcgcctggg
              G   R   P   V   T   F   Y   P   H   P   L   P   S   P   G 1156   3677  ggtgttctttacacgtgggacttcggggacggctcccctgtcctg
              G   V   L   Y   T   W   D   F   G   D   G   S   P   V   L
        ←        15-A 1171   3722  acccagagccagccggctgccaaccacacctatgcctcgagggc
              T   Q   S   Q   P   A   A   N   H   T   Y   A   S   R   G 1186   3767  acctaccacgtgcgcctggaggtcaacaacacggtgagcggtgcg
              T   Y   H   V   R   L   E   V   N   N   T   V   S   G   A 1201   3812  gcggcccaggcggatgtgcgcgtctttgaggagctccgcggactc
              A   A   Q   A   D   V   R   V   F   E   E   L   R   G   L
                                                          15-C 1216   3857  agcgtggacatgagcctggccgtggagcagggcgcccccgtggtg
              S   V   D   M   S   L   A   V   E   Q   G   A   P   V   V
                                     ←  15-B 1231   3902  gtcagcgccgcggtgcagacgggcgacaacatcacgtggaccttc
              V   S   A   A   V   Q   T   G   D   N   I   T   W   T   F 1246   3947  gacatggggacggcaccgtgctgtcgggccggaggcaacagtg
              D   M   G   D   G   T   V   L   S   G   P   E   A   T   V 1261   3992  gagcatgtgtacctgcggcacagaactgcacagtgaccgtgggt
              E   H   V   Y   L   R   Q   N   C   T   V   T   V   G 1276   4037  gcggccagccccgccggccacctggcccggagcctgcacgtgctg
              A   A   S   P   A   G   H   L   A   R   S   L   H   V   L
                      →  15-D 1291   4082  gtcttcgtcctggaggtgctgcgcgttgaacccgccgcctgcatc
              V   F   V   L   E   V   L   R   V   E   P   A   A   C   I
              ←        15-C
```

*FIG. 3F*

```
       4127 ccacgcagcctgacgcgcggtcacggcctacgtcacgggaac
1306         P  T  Q  P  D  A  R  L  T  A  Y  V  T  G  N 4172 ccggcccactacctcttcgactggaccttcggggatggctcctcc
1321         P  A  H  Y  L  P  D  W  T  F  G  D  G  S  S 4217 aacacgaccgtgcggggggtgcccgacggtgacacacaacttcacg
1336         N  T  T  V  R  G  C  P  T  V  T  H  N  F  T
                                                     →  15-E 4262 cggagcggcacgttccccctggcgctggtgctgtccagccgcgtg
1351         R  S  G  T  F  P  L  A  L  V  L  S  S  R  V
                                                  ←  15-D 4307 aacagggcgcattacttcaccagcatctgcgtggagccagaggtg
1366         N  R  A  H  Y  F  T  S  I  C  V  E  P  E  V 4352 ggcaacgtcaccctgcagccagagaggcagtttgtgcagctcggg
1381         G  N  V  T  L  Q  P  E  R  Q  F  V  Q  L  G 4397 gacgaggcctggctggtggcatgtgcctggcccccgttcccctac
1396         D  E  A  W  L  V  A  C  A  W  P  P  F  P  Y 4442 cgctacacctgggactttggcaccgaggaagccgcccccacccgt
1411         R  Y  T  W  D  F  G  T  E  E  A  A  P  T  R
                                                  →  15-F 4487 gccaggggccctgaggtgacgttcatctaccgagacccaggctcc
1426         A  R  G  P  E  V  T  F  I  Y  R  D  P  G  S
                                                  ←  15-E 4532 tatcttgtgacagtcaccgcgtccaacaacatctctgctgccaat
1441         Y  L  V  T  V  T  A  S  N  N  I  S  A  A  N 4577 gactcagccctggtggaggtgcaggagcccgtgctggtcaccagc
1456         D  S  A  L  V  E  V  Q  E  P  V  L  V  T  S 4622 atcaaggtcaatggctcccttgggctggagctgcagcagccgtac
1471         I  K  V  N  G  S  L  G  L  E  L  Q  Q  P  Y
                                                  →  15-G 4667 ctgttctctgctgtgggccgtgggcgccccgccagctacctgtgg
1486         L  F  S  A  V  G  R  G  R  P  A  S  Y  L  W 4712 gatctgggggacggtgggtggctcgagggtccggaggtcacccac
1501         D  L  G  D  G  G  W  L  E  G  P  E  V  T  H
                                                  ←  15-F 4757 gcttacaacagcacaggtgacttcaccgttagggtggccggctgg
1516         A  Y  N  S  T  G  D  F  T  V  R  V  A  G  W
```

*FIG. 3G*

```
1531      4802  aatgaggtgagccgcagcgaggcctggctcaatgtgacggtgaag
                 N  E  V  S  R  S  E  A  W  L  N  V  T  V  K
                                    → 15-H 1546      4847  cggcgcgtgcggggcctcgtcgtcaatgcaagccgcacggtggtg
                 R  R  V  R  G  L  V  V  N  A  S  R  T  V  V
                                    ←
                                          15-G 1561      4892  cccctgaatgggagcgtgagcttcagcacgtcgctggaggccggc
                 P  L  N  G  S  V  S  F  S  T  S  L  E  A  G 1576      4937  agtgatgtgcgctattcctgggtgctctgtgaccgctgcacgccg
                 S  D  V  R  Y  S  W  V  L  C  D  R  C  T  P 1591      4982  atcctgggggtcctaccatctcttacaccttccgctccgtgggc
                 I  P  G  G  P  T  I  S  Y  T  F  R  S  V  G
                                                       → 15-I 1606      5027  accttcaatatcatcgtcacggctgagaacgaggtgggctccgcc
                 T  F  N  I  I  V  T  A  E  N  E  V  G  S  A 1621      5072  caggacagcatcttcgtctatgtcctgcagctcatagaggggctg
                 Q  D  S  I  F  V  Y  V  L  Q  L  I  E  G  L
             ←       15-H 1636      5117  caggtggtgggcggtggccgctacttccccaccaaccacacggta
                 Q  V  V  G  G  R  Y  F  P  T  N  H  T  V 1651      5162  cagctgcaggccgtggttagggatggcaccaacgtctcctacagc
                 Q  L  Q  A  V  V  R  D  G  T  N  V  S  Y  S
                                                    → 15-J 1666      5207  tggactgcctggagggacaggggcccggccctggccggcagcggc
                 W  T  A  W  R  D  R  G  P  A  L  A  G  S  G 1681      5252  aaaggcttctcgctcaccgtgctcgaggccggcacctaccatgtg
                 K  G  F  S  L  T  V  L  E  A  G  T  Y  H  V
                                        ←  15-J 1696      5297  cagctgcgggccaccaacatgctgggcagcgcctgggccgactgc
                 Q  L  R  A  T  N  M  L  G  S  A  W  A  D  C 1711      5342  accatggacttcgtggagcctgtggggtggctgatggtgaccgcc
                 T  M  D  F  V  E  P  V  G  W  L  M  V  T  A 1726      5387  tccccgaacccagctgccgtcaacacaagcgtcaccctcagtgcc
                 S  P  N  P  A  A  V  N  T  S  V  T  L  S  A 1741      5432  gagctggctggtggcagtggtgtcgtatacacttggtccttggag
                 E  L  A  G  G  S  G  V  V  Y  T  W  S  L  E
```

*FIG. 3H*

```
                                                    →  15-K
        5477  gagggggctgagctgggagacctccgagccatttaccacccatagc
1756          E  G  L  S  W  E  T  S  E  P  P  T  T  H  S 5522  ttccccacaccggcctgcacttggtcaccatgacggcagggaac
1771          F  P  T  P  G  L  H  L  V  T  M  T  A  G  N 5567  ccgctgggctcagccaacgccaccgtggaagtggatgtgcaggtg
1786          P  L  G  S  A  N  A  T  V  E  V  D  V  Q  V 5612  cctgtgagtggcctcagcatcagggccagcgagcccggaggcagc
1801          P  V  S  G  L  S  I  R  A  S  E  P  G  G  S 5657  ttcgtggcggccgggtcctctgtgcccttttgggggcagctggca
1816          F  V  A  A  G  S  S  V  P  F  W  G  Q  L  A
                                              ←  15-J 5702  acgggcaccaatgtgagctggtgctgggctgtgcccggcggcagc
1831          T  G  T  N  V  S  W  C  W  A  V  P  G  G  S 5747  agcaagcgtggccctcatgtcaccatggtcttcccggatgctggc
1846          S  K  R  G  P  H  V  T  M  V  F  P  D  A  G 5792  accttctccatccggctcaatgcctccaacgcagtcagctgggtc
1861          T  F  S  I  R  L  N  A  S  N  A  V  S  W  V 5837  tcagccacgtacaacctcacggcggaggagcccatcgtgggcctg
1876          S  A  T  Y  N  L  T  A  E  E  P  I  V  G  L
                      →  15-L 5882  gtgctgtgggccagcagcaaggtggtggcgcccgggcagctggtc
1891          V  L  W  A  S  S  K  V  V  A  P  G  Q  L  V
                                  ←  15-K 5927  cattttcagatcctgctggctgccgggtcagctgtcaccttccgc
1906          H  F  Q  I  L  L  A  A  G  S  A  V  T  F  R 5972  ctgcaggtcggcggggccaaccccgaggtgctccccgggccccgt
1921          L  Q  V  G  G  A  N  P  E  V  L  P  G  P  R 6017  ttctcccacagcttccccgcgtcggagaccacgtggtgagcgtg
1936          F  S  H  S  F  P  R  V  G  D  H  V  V  S  V 6062  cggggcaaaaaccacgtgagctgggcccaggcgcaggtgcgcatc
1951          R  G  K  N  H  V  S  W  A  Q  A  Q  V  R  I 6107  gtggtgctggaggccgtgagtgggctgcagatgcccaactgctgc
1968          V  V  L  E  A  V  S  G  L  Q  M  P  N  C  C
```

*FIG. 3I*

```
                6152 gagcctggcatcgccacgggcactgagaggaacttcacagccgc
1981                  E  P  G  I  A  T  G  T  E  R  N  F  T  A  R 6197 gtgcagcgcggctctcgggtcgcctacgcctggtacttctcgctg
1996                  V  Q  R  G  S  R  V  A  Y  A  W  Y  F  S  L
                         → 15-M 6242 cagaaggtccaggcgactcgctggtcatcctgtcgggccgcgac
2011                  Q  K  V  Q  G  D  S  L  V  I  L  S  G  R  D 6287 gtcacctacacgcccgtggccgcgggcctgttggagatccaggtg
2026                  V  T  Y  T  P  V  A  A  G  L  L  E  I  Q  V
                                              ← 15-L 6332 cgcgccttcaacgccctgggcagtgagaaccgcacgctggtgctg
2041                  R  A  F  N  A  L  G  S  E  N  R  T  L  V  L 6377 gaggttcaggacgccgtccagtatgtggccctgcagagcggccc
2056                  E  V  Q  D  A  V  Q  Y  V  A  L  Q  S  G  P 6422 tgcttcaccaaccgctcggcgcagtttgaggccgccaccagccc
2071                  C  F  T  N  R  S  A  Q  F  E  A  A  T  S  P 6467 agccccggcgtgtggcctaccactgggactttggggatgggtcg
2086                  S  P  R  R  V  A  Y  H  W  D  F  G  D  G  S 6512 ccagggcaggacacagatgagcccagggccgagcactcctacctg
2101                  P  G  Q  D  T  D  E  P  R  A  E  H  S  Y  L 6557 aggcctggggactaccgcgtgcaggtgaacgcctccaacctggtg
2116                  R  P  G  D  Y  R  V  Q  V  N  A  S  N  L  V 6602 agcttcttcgtggcgcaggccacggtgaccgtccaggtgctggc
2131                  S  F  F  V  A  Q  A  T  V  T  V  Q  V  L  A 6647 tgccgggagccggaggtggacgtggtcctgcccctgcaggtgctg
2146                  C  R  E  P  E  V  D  V  V  L  P  L  Q  V  L
                                              → 15-N 6692 atgcggcgatcacagcgcaactacttggaggcccacgttgacctg
2161                  M  R  R  S  Q  R  N  Y  L  E  A  H  V  D  L 6737 cgcgactgcgtcacctaccagactgagtaccgctgggaggtgtat
2176                  R  D  C  V  T  Y  Q  T  E  Y  R  W  E  V  Y 6782 cgcaccgccagctgccagcggccgggcgcccagcgcgtgtggcc
2191                  R  T  A  S  C  Q  R  P  G  R  P  A  R  V  A
```

*FIG. 3J*

```
                                    15-M
            6827  ctgcccggcgtggacgtgagccggcctcggctggtgctgccgcgg
   2206            L  P  G  V  D  V  S  R  P  R  L  V  L  P  R 6872  ctggcgctgcctgtggggcactactgctttgtgtttgtcgtgtca
   2221            L  A  L  P  V  G  H  Y  C  F  V  F  V  V  S 6917  tttggggacacgccactgacacagagcatccaggccaatgtgacg
   2236            F  G  D  T  P  L  T  Q  S  I  Q  A  N  V  T 6962  gtggcccccgagcgcctggtgcccatcattgagggtggctcatac
   2251            V  A  P  E  R  L  V  P  I  I  E  G  G  S  Y 7007  cgcgtgtggtcagacacacgggacctggtgctggatgggagcgag
   2266            R  V  W  S  D  T  R  D  L  V  L  D  G  S  E 7052  tcctacgaccccaacctggaggacggcgaccagacgccgctcagt
   2281            S  Y  D  P  N  L  E  D  G  D  Q  T  P  L  S
                                                              EXON 16
            7097  ttccactgggcctgtgtggcttcgacacag agggaggctggcggg
   2296            F  H  W  A  C  V  A  S  T  Q  R  E  A  G  G 7142  tgtgcgctgaactttgggccccgcgggagcagcacggtcaccatt
   2311            C  A  L  N  F  G  P  R  G  S  S  T  V  T  I 7187  ccacgggagcggctggcggctggcgtggagtacaccttcagcctg
   2326            P  R  E  R  L  A  A  G  V  E  Y  T  F  S  L 7232  acgtgtggaaggccggccgcaaggaggaggccaccaaccagacc
   2341            T  V  W  K  A  G  R  K  E  E  A  T  N  Q  T
                  EXON 17
            7277  gtgctgatccggagtggccgggtgcccattgtgtccttggagtgt
   2356            V  L  I  R  S  G  R  V  P  I  V  S  L  E  C 7322  gtgtcctgcaaggcacaggccgtgtacgaagtgagccgcagctcc
   2371            V  S  C  K  A  Q  A  V  Y  E  V  S  R  S  S 7367  tacgtgtacttggagggccgctgcctcaattgcagcagcggctcc
   2386            Y  V  Y  L  E  G  R  C  L  N  C  S  S  G  S
                                   EXON 18
            7412  aagcgagggcggtgggctgcacgtacgttcagcaacaagacgctg
   2401            K  R  G  R  W  A  A  R  T  F  S  N  K  T  L 7457  gtgctggatgagaccaccacatccacgggcagtgcaggcatgcga
   2416            V  L  D  E  T  T  T  S  T  G  S  A  G  M  R
```

*FIG. 3K*

| | | |
|---|---|---|
| 2431 | 7502 | ctggtgctgcggcggggcgtgctgcgggacggcgagggatacacc |
| | | L V L R R G V L R D G E G Y T |
| 2446 | 7547 | ctcacggtcacggtgctgggccgctctggcgaggaggagggctgc |
| | | F T L T V L G R S G E E E G C |
| 2461 | 7592 | gcctccatccgcctgtccccaaccgcccgcctggggggctct |
| | | A S I R L S P N R P P L G S |
| 2476 | 7637 | tgccgcctcttcccactgggcgctgtgcacgcctcaccaccaag |
| | | C R L F P L G A V H A L T T K |
| 2491 | 7682 | gtgcacttcgaatgcacgggctggcatgacgcggaggatgctggc |
| | | V H F E C T G W H D A E D A G |
| 2506 | 7727 | gccccgctggtgtacgccctgctgctgcggcgctgtcgccagggc |
| | | A P L V Y A L L L R R C R Q G |
| 2521 | 7772 | cactgcgaggagttctgtgtctacaagggcagcctctccagctac |
| | | H C E E F C V Y K G S L S S Y |
| 2536 | 7817 | ggagccgtgctgcccccggggtttcaggccacacttcgaggtgggc |
| | | G A V L P P G F R P H F E V G |
| 2551 | 7862 | ctggccgtggtggtgcaggaccagctgggagccgctgtggtcgcc |
| | | L A V V V Q D Q L G A A V V A |
| 2566 | 7907 | ctcaacaggtctttggccatcaccctcccagagcccaacggcagc |
| | | L N R S L A I T L P E P N G S |
| 2581 | 7952 | gcaacggggctcacagtctggctgcacgggctcaccgctagtgtg |
| | | A T G L T V W L H G L T A S V |
| 2596 | 7997 | ctcccagggctgctgcggcaggcgatccccagcacgtcatcgag |
| | | L P G L L R Q A D P Q H V I E |
| 2611 | 8042 | tactcgttggccctggtcaccgtgctgaacgagtacgagcgggcc |
| | | Y S L A L V T V L N E Y E R A |
| 2626 | 8087 | ctggacgtggcggcagagcccaagcacgagcggcagcaccgagcc |
| | | L D V A A E P K H E R Q H R A |
| 2641 | 8132 | cagatacgcaagaacatcacggagactctggtgtccctgagggtc |
| | | Q I R K N I T E T L V S L R V |

FIG. 3L

| | | |
|---|---|---|
| 2656 | 8177 | cacactgtggatgacatccagcagatcgctgctgcgctggcccag |
| | | H T V D D I Q Q I A A A L A Q |
| | | EXON 22 |
| 2671 | 8222 | tgcatggggcccagcagggagctcgtatgcgctcgtgcctgaag |
| | | C M G P S R E L V C R S C L K |
| 2686 | 8267 | cagacgctgcacaagctggaggccatgatgctcatcctgcaggca |
| | | Q T L H K L E A M M L I L Q A |
| 2701 | 8312 | gagaccaccgcgggcaccgtgacgcccaccgccatcggagacagc |
| | | E T T A G T V T P T A I G D S |
| | | EXON 23-A |
| 2716 | 8357 | atcctcaacatcacagagacctcatccacctggccagctggac |
| | | I L N I T G D L I H L A S S D |
| 2731 | 8402 | gtgcgggcaccacagccctcagagctgggagccgagtcaccatct |
| | | V R A P Q P S E L G A E S P S |
| 2746 | 8447 | cggatggtggcgtcccaggcctacaacctgacctctgccctcatg |
| | | R M V A S Q A Y N L T S A L M |
| 2791 | 8492 | cgcatcctcatgcgctcccgcgtgctcaacgaggagcccctgacg |
| | | R I L M R S R V L N E E P L T |
| | | → 23-B |
| 2776 | 8537 | ctggcgggcgaggagatcgtggcccagggcaagcgctcggacccg |
| | | L A G E E I V A Q G K R S D P |
| 2761 | 8582 | cggagcctgctgtgctatggcggcgccccagggcctggctgccac |
| | | R S L L C Y G G A P G P G C H |
| 2806 | 8627 | ttctccatccccgaggctttcagcggggcccctggccaacctcagt |
| | | F S I P E A F S G A L A N L S |
| | | → 23-C |
| 2821 | 8672 | gacgtggtgcagctcatctttctggtggactccaatccctttccc |
| | | D V V Q L I F L V D S N P F P |
| | | 23-A ← 23-B |
| 2836 | 8717 | tttggctatatcagcaactacaccgtctccaccaaggtggcctcg |
| | | F G Y I S N Y T V S T K V A S |
| 2851 | 8762 | atggcattccagacacaggccggcgcccagatccccatcgagcgg |
| | | M A F Q T Q A G A Q I P I E R |
| 2866 | 8807 | ctggcctcagagcgcgccatcaccgtgaaggtgcccaacaactcg |
| | | L A S E R A I T V K V P N N S |

*FIG. 3M*

| | | |
|---|---|---|
| 2881 | 8852 | gactgggctgcccggggccaccgcagtccgccaactccgccaac |
| | | D W A A R G H R S S A N S A N |
| 2896 | 8897 | tccgttgtggtccagccccaggcctccgtcggtgctgtggtcacc |
| | | S V V V Q P Q A S V G A V V T |
| 2911 | 8942 | ctggacagcagcaaccctgcggccgggctgcatctgcagctcaac |
| | | L D S S N P A A G L H L Q L N |
| | | EXON 24 |
| 2926 | 8987 | tatacgctgctggacgccactacctgtctgaggaacctgagccc |
| | | Y T L L D H Y L S E E P E P |
| 2941 | 9032 | tacctggcagtctacctacactcggagcccggcccaatgagcgc |
| | | Y L A V Y L H S E P R P N E R |
| 2956 | 9077 | aactgctcggctagcaggaggatccgcccagagtcactccaggt |
| | | N C S A S R R I R P E S L Q G |
| | | EXON 25 |
| 2971 | 9122 | gctgaccaccggccctacaccttcttcatttccccgggcagcaga |
| | | A D H R P Y T F F I S P G S R |
| 2986 | 9167 | gacccagcggggagttaccatctgaacctctccagccacttccgc |
| | | D P A G S Y H L N L S S H F R |
| 3001 | 9212 | tggtcggcgctgcaggtgtccgtgggcctgtacacgtccctgtgc |
| | | W S A L Q V S V G L Y T S L C |
| 3016 | 9257 | cagtacttcagcgaggaggacatggtgtggcggacagaggggctg |
| | | Q Y F S E E D M V W R T E G L |
| 3031 | 9302 | ctgcccctggaggagacctcgccccgccaggccgtctgcctcacc |
| | | L P L E E T S P R Q A V C L T |
| 3046 | 9347 | cgccacctcaccgccttcggcgccagcctcttcgtgcccccaagc |
| | | R H L T A F G A S L F V P P S |
| | | EXON 26 |
| 3061 | 9392 | catgtccgctttgtgttcctgagccgacagcggatgtaaactac |
| | | H V R F V F P E P T A D V N Y |
| 3076 | 9437 | atcgtcatgctgacatgtgctgtgtgcctggtgacctacatggtc |
| | | I V M L T C A V C L V T Y M V |
| 3091 | 9482 | atggccgccatcctgcacaagctggaccagttggatgccagccgg |
| | | M A A I L H K L D Q L D A S R |

FIG. 3N

```
3106  9527 ggccgcgccatcccttctgtgggcagcggggccgcttcaagtac
           G  R  A  I  P  F  C  G  Q  R  G  R  F  K  Y
                                                    EXON 27
3121  9572 gagatcctcgtcaagacaggctggggcggggctcac gtaccacg
           E  I  L  V  K  T  G  W  G  R  G  S   G  T  T 3136  9617 gcccacgtgggcatcatgctgtatggggtggacagccggagcggg
           A  H  V  G  I  M  L  Y  G  V  D  S  R  S  G 3151  9662 caccggcacctggacggcgacagagccttccaccgcaacagcctg
           H  R  H  L  D  G  D  R  A  F  H  R  N  S  L 3166  9707 gacatcttccggatcgccacccccgcacagcctgggtagcgtgtgg
           D  I  F  R  I  A  T  P  H  S  L  G  S  V  W
                                          EXON 28
3181  9752 aagatccgagtgtggcacgacaacaaag gctcagccctgcctgg
           K  I  R  V  W  H  D  N  K   G  L  S  P  A  W 3196  9797 ttcctgcagcacgtcatcgtcagggacctgcagacggcacgcagc
           F  L  Q  H  V  I  V  R  D  L  Q  T  A  R  S 3211  9842 gccttcttcctggtcaatgactggctttcggtggagacggaggcc
           A  F  F  L  V  N  D  W  L  S  V  E  T  E  A
                                                    EXON 29
3226  9887 aacgggggcctggtggagaaggaggtgctggccgcg cgacgca
           N  G  L  V  E  K  E  V  L  A  A   S  D  A 3241  9932 gccctttttgcgcttccggcgcctgctggtggctgagctgcagcgt
           A  L  L  R  F  R  R  L  L  V  A  E  L  Q  R 3256  9977 ggcttctttgacaagcacatctggctctccatatgggaccggccg
           G  F  F  D  K  H  I  W  L  S  I  W  D  R  P 3271 10022 cctcgtagccgtttcactcgcatccagagggccacctgctgcgtt
           P  R  S  R  F  T  R  I  Q  R  A  T  C  C  V 3286 10067 ctcctcatctgcctcttcctgggcgccaacgccgtgtggtacggg
           L  L  I  C  L  F  L  G  A  N  A  V  W  Y  G
                                    EXON 30
3301 10112 gctgttggcgactctgcctacag cacggggcatgtgtccaggctg
           A  V  G  D  S  A  Y  S  T  G  R  V  S  R  L 3316 10157 agcccgctgagcgtcgacacagtcgctgttggcctggtgtccagc
           S  P  L  S  V  D  T  V  A  V  G  L  V  S  S
```

*FIG. 30*

```
3331  10202 gtggttgtctatcccgtctacctggccatccttttctcttccgg
            V  V  V  Y  P  V  Y  L  A  I  L  F  L  F  R
                                    EXON 31
3346  10247 atgtcccggagcaagtggctgggagcccgagccccacacctgcc
            M  S  R  S  K  V  A  G  S  P  S  P  T  P  A
3361  10292 gggcagcaggtgctggacatcgacagctgcctggactcgtccgtg
            G  Q  Q  V  L  D  I  D  S  C  L  D  S  S  V
                                                    EXON 32
3376  10337 ctggacagctccttcctcacgttctcaggcctccacgctgaggcc
            L  D  S  S  F  L  T  F  S  G  L  H  A  E  A
3391  10382 tttgttggacagatgaagagtgacttgtttctggatgattctaag
            F  V  G  Q  M  K  S  D  L  F  L  D  D  S  K
            EXON 33
3406  10427 agtctggtgtgctggccctccggcgagggaacgctcagttggccg
            S  L  V  C  W  P  S  G  E  G  T  L  S  W  P
3421  10472 gacctgctcagtgacccgtccattgtgggtagcaatctgcggcag
            D  L  L  S  D  P  S  I  V  G  S  N  L  R  Q
3436  10517 ctggcacgggggccaggcgggccatgggctgggcccagaggaggac
            L  A  R  G  Q  A  G  H  G  L  G  P  E  E  D
3451  10562 ggcttctccctggccagcccctactcgcctgccaaatccttctca
            G  F  S  L  A  S  P  Y  S  P  A  K  S  F  S
                         EXON 34
3466  10607 gcatcagatgaagacctgatccagcaggtccttgccgaggggtc
            A  S  D  E  D  L  I  Q  Q  V  L  A  E  G  V
3481  10652 agcagcccagccccctacccaagacacccacatggaaacggacctg
            S  S  P  A  P  T  Q  D  T  H  M  E  T  D  L
                              EXON 35
3496  10697 ctcagcagcctgtccagcactcctggggagaagacagagacgctg
            L  S  S  L  S  S  T  P  G  E  K  T  E  T  L
3511  10742 gcgctgcagaggctgggggagctggggccacccagcccaggcctg
            A  L  Q  R  L  G  E  L  G  P  P  S  P  G  L
                                                    EXON 36
3526  10787 aactgggaacagccccaggcagcgaggctgtccaggacaggactg
            N  W  E  Q  P  Q  A  A  R  L  S  R  T  G  L
3541  10832 gtggagggtctgcggaagcgcctgctgccggcctggtgtgcctcc
            V  E  G  L  R  K  R  L  L  P  A  W  C  A  S
```

*FIG. 3P*

```
3556  10877 ctggcccacgggctcagcctgctcctggtggctgtggctgtggct
            L   A  H  G  L  S  L  L  L  V  A  V  A  V  A 3571  10922 gtctcagggtgggtgggtgcagcttccccccggggcgtgagtgtt
            V   S  G  W  V  G  A  S  F  P  P  G  V  S  V 3586  10967 gcgtggctcctgtccagcagcgccagcttcctggcctcattcctc
            A   W  L  L  S  S  S  A  S  F  L  A  S  F  L
                                          EXON 37
3601  11012 ggctgggagccactgaag gtcttgctggaagccctgtacttctca
            G   W  E  P  L  K   V  L  L  E  A  L  Y  F  S 3616  11057 ctggtggccaagcggctgcaccccgatgaagatgacaccctggta
            L   V  A  K  R  L  H  P  D  E  D  D  T  L  V 3631  11102 gagagcccggctgtgacgcctgtgagcgcacgtgtgccccgcgta
            E   S  P  A  V  T  P  V  S  A  R  V  P  R  V 3646  11147 cggccagcccacgggctttgcactcttcctggccaaggaagaagcc
            R   P  P  H  G  F  A  L  F  L  A  K  E  E  A
                                                 EXON 38
3661  11192 cgcaaggtcaagagggctacatggcatgctgcgg agcctcctggtg
            R   K  V  K  R  L  H  G  M  L  R   S  L  L  V 3676  11237 tacatgcttttcctgctggtgaccctgctggccagctatggggat
            Y   M  L  F  L  L  V  T  L  L  A  S  Y  G  D 3691  11282 gcctcatgccatgggcacgcctaccgtctgcaaagcgccatcaag
            A   S  C  H  G  H  A  Y  R  L  Q  S  A  I  K
                                                    EXON 39
3706  11327 caggagctgcacagccgggccttcctggccatcacgcc gtctgag
            Q   E  L  H  S  R  A  F  L  A  I  T  P   S  E 3721  11372 gagctctggccatggatggcccacgtgctgctgccctacgtccac
            E   L  W  P  W  M  A  H  V  L  L  P  Y  V  H 3736  11417 gggaaccagtccagcccagagctggggcccccacggctgcggcag
            G   N  Q  S  S  P  E  L  G  P  P  R  L  R  Q
                          EXON 40
3751  11462 gtgcggctgcaggaag cactctacccagaccctcccggccccagg
            V   R  L  Q  E   A  L  Y  P  D  P  P  G  P  R 3766  11507 gtccacacgtgctcggccgcaggaggcttcagcaccagcgattac
            V   H  T  C  S  A  A  G  G  F  S  T  S  D  Y
```

FIG. 3Q

```
3781  11552 gacgttggctgggagagtcctcacaatggctcggggacgtggagcc
            D   V   G   W   E   S   P   H   N   G   S   G   T   W   A
                                              [EXON 41]
3796  11597 tattcagcgccggatctgctgggggcatggtcctgggggctcctg
            Y   S   A   P   D   L   L   G   A   W   S   W   G   S   C 3811  11642 gccgtgtatgacagcgggggctacgtacaggagctgggcctgagc
            A   V   Y   D   S   G   G   Y   V   Q   E   L   G   L   S 3826  11687 ctggaggagagccgcgaccggctgcgcttcctgcagctgcacaac
            L   E   E   S   R   D   R   L   R   F   L   Q   L   H   N
                                [EXON 42]
3841  11732 tggctggacaacaggagccgcgctgtgttcctggagctcacgcgc
            W   L   D   N   R   S   R   A   V   F   L   E   L   T   R 3856  11777 tacagcccggccgtgggactgcacgccgccgtcacgctgcgcctc
            Y   S   P   A   V   G   L   H   A   A   V   T   L   R   L 3871  11822 gagttcccggcggccggccgcgccctggccgccctcagcgtccgc
            E   F   P   A   A   G   R   A   L   A   A   L   S   V   R 3886  11867 cccttttgcgctgcgccgcctcagcgcggggctctcgctgcctctg
            P   F   A   L   R   R   L   S   A   G   L   S   L   P   L
                                [EXON 43]
3901  11912 ctcacctcggtgtgcctgctgctgttcgccgtgcacttcgccgtg
            L   T   S   V   C   L   L   L   F   A   V   H   F   A   V 3916  11957 gccgaggcccgtacttggcacagggaagggcgctggcgcgtgctg
            A   E   A   R   T   W   H   R   E   G   R   W   R   V   L 3931  12002 cggctcggagcctgggcgcggtggctgctggtggcgctgacggcg
            R   L   G   A   W   A   R   W   L   L   V   A   L   T   A 3946  12047 gccacggcactggtacgcctcgcccagctgggtgccgctgaccgc
            A   T   A   L   V   R   L   A   Q   L   G   A   A   D   R 3961  12092 cagtggacccgtttcgtgcgcggccgcccgcgccgcttcactagc
            Q   W   T   R   F   V   R   G   R   P   R   R   F   T   S 3976  12137 ttcgaccaggtggcgcagctgagctccgcagcccgtggcctggca
            F   D   Q   V   A   Q   L   S   S   A   A   R   G   L   A
                                                    [EXON 44]
3991  12182 gcctcgctgctgcttcctgctttttggtcaaggctgcccagcagcta
            A   S   L   L   F   L   L   V   K   A   A   Q   Q   L
```

*FIG. 3R*

```
4006    12227  cgcttcgtgcgccagtggtcgtcttggcaagacattatgccga
               R  F  V  R  Q  W  S  V  F  G  K  T  L  C  R 4021    12272  gctctgccagagctcctgggggtcaccttgggcctcctcctgctc
               A  L  P  E  L  L  G  V  T  L  G  L  V  V  L EXON 45
4036    12317  ggggtagcctacgcccagctggccatcctcctcgtgtcttcctgt
               G  V  A  Y  A  Q  L  A  I  L  L  V  S  S  C 4051    12362  gtggactccctctggagcgtggcccaggccctgttggtgctgtgc
               V  D  S  L  W  S  V  A  Q  A  L  L  V  L  C 4066    12407  cctggactgggctctctaccctgtgtcctgccgagtcctggcac
               P  G  T  G  L  S  T  L  C  P  A  E  S  W  H 4081    12452  ctgtcacccctgctgtgtgtggggctctgggcactgcggctgtgg
               L  S  P  L  L  C  V  G  L  W  A  L  R  L  W 4096    12497  ggcgccctacggctgggggctgttattctccgctggcgctaccac
               G  A  L  R  L  G  A  V  I  L  R  W  R  Y  H 4111    12542  gccttgcgtggagagctgtaccggccggcctgggagccccaggac
               A  L  R  G  E  L  Y  R  P  A  W  E  P  Q  D 4126    12587  tacgagatggtggagttgttcctgcgcaggctgcgcctctggatg
               Y  E  M  V  E  L  F  L  R  R  L  R  L  W  M EXON 46
4141    12632  ggcctcagcaaggtcaaggagttccgccacaaagtccgctttgaa
               G  L  S  K  V  K  E  F  R  H  K  V  R  F  E 4156    12677  gggatggagccgctgccctctcgctcctccaggggctccaaggta
               G  M  E  P  L  P  S  R  S  S  R  G  S  K  V 4171    12722  tccccggatgtgccccacccagcgctggtccgatgcctcgcac
               S  P  D  V  P  P  P  S  A  G  S  D  A  S  H 4186    12767  ccctccacctcctccagccagctggatgggctgagcgtgagcctg
               P  S  T  S  S  S  Q  L  D  G  L  S  V  S  L 4201    12812  ggccggctggggacaaggtgtgagcctgagccctccgcctccaa
               G  R  L  G  T  R  C  E  P  E  P  S  R  L  Q 4216    12857  gccgtgttcgaggccctgctcacccagtttgaccgactcaaccag
               A  V  F  E  A  L  L  T  Q  F  D  R  L  N  Q
```

*FIG. 3S*

| | 12902 | gccacagaggacgtctaccagctggagcagcagctgcacagcctg |
|---|---|---|
| 4231 | | A T E D V Y Q L E Q Q L H S L |

| | 12947 | caaggccgcaggagcagccgggcgcccgccggatcttcccgtggc |
|---|---|---|
| 4246 | | Q G R R S S R A P A G S S R G |

| | 12992 | ccatccccggcctgcggccagcactgcccagccgccttgcccgg |
|---|---|---|
| 4261 | | P S P G L R P A L P S R L A R |

| | 13037 | gccagtcggggtgtggacctggccactggccccagcaggacaccc |
|---|---|---|
| 4276 | | A S R G V D L A T G P S R T P |

| | 13082 | cttcgggccaagaacaaggtccaccccagcagcacttag | 13120 | (SEQ ID NO. 2) |
|---|---|---|---|---|
| 4291 | | L R A K N K V H P S S T * | | (SEQ ID NO. 3) |

FIG. 3T

| CODON NUMBER | | |
|---|---|---|
| | 67 | EXON 1-A |
| 1 | | atggtgaactccagtcgcgtgcagcctcagcagcccggggacgcc |
| | | M V N S S R V Q P Q Q P G D A |
| 16 | 112 | aagcggccgccgcgcccccgcgcgccggaccccggggccggctgatg |
| | | K R P P A P R A P D P G R L M |
| 31 | 157 | gctggctgcggcggccgtgggcgccagcctcgccgccccggggcgg |
| | | A G C A A V G A S L A A P G G |
| 46 | 202 | ctctgcgagcagcgggggcctggagatcgagatgcagcgcatccgg |
| | | L C E Q R G L E I E M Q R I R |
| 61 | 247 | caggcggccgcgcgggaccccccggccggagccgcggcctcccct | (1-B) |
| | | Q A A A R D P P A G A A A S P |
| 76 | 292 | tctcctccgctctcgtcgtgctcccggcaggcgtggagccgcgat | (1-A) |
| | | S P P L S S C S R Q A W S R D |
| 91 | 337 | aaccccggcttcgaggccgaggaggaggaggaggaggtggaaggg |
| | | N P G F E A E E E E E E V E G |
| 106 | 382 | gaagaaggcggaatggtggtggagatggacgtagagtggcgccc |
| | | E E G G M V V E M D V E W R P |
| 121 | 427 | ggcagccggaggtcggccgcctcctcggccgtgagctccgtgggc |
| | | G S R R S A A S S A V S S V G |
| 136 | 472 | gcgcggagccgggggcttgggggctaccacggcgcggggccaccc | (1-C) |
| | | A R S R G L G G Y H G A G H P |
| 151 | 517 | agcgggaggcggcgccggcgagaggaccagggcccgccgtgcccg |
| | | S G R R R R R E D Q G P P C P |
| 166 | 562 | agcccagtcggcggcggggacccgctgcatcgccacctcccctg | (1-B) |
| | | S P V G G G D P L H R H L P L |
| 181 | 607 | gaaggcagccgccccgagtggcctggggcggagaggctggttcgc |
| | | E G Q P P R V A W A E R L V R |
| 196 | 652 | gggctgccaggtctctggggaacaagactcatggaggaaagcagc | EXON 2 |
| | | G L P G L W G T R L M E E S S |
| 211 | 697 | actaaccgagagaaatccttaaaagtgttttacgggaactggtc |
| | | T N R E K Y L K S V L R E L V |
| | 742 | acatacctcctttttctcatagtcttgtgcatct gacctacggc | EXON 3 |

*FIG. 4A*

```
226           T Y L L F L I V L C I L T Y Q 787 atgatgagctccaatgtgtactactacacccggatgatgtcacag
241           M M S S N V Y Y Y T R M M S Q 832 ctcttcctagacaccccgtgtccaaaacggagaaaactaacttt
256           L F L D T P V S K T E K T N F
                                          EXON 4
      877 aaaactctgtcttccatggaagacttctggaagttcacagaaggc
271           K T L S S M E D F W K F T E G 922 tccttattggatgggctgtactggaagatgcagcccagcaaccag
286           S L L D G L Y W K M Q P S N Q 967 actgaagctgacaaccgaagtttcatcttctatgagaacctgctg
301           T E A D N R S F I F Y E N L L 1012 ttaggggttccacgaatacggcaactccgagtcagaaatggatcc
316           L G V P R I R Q L R V R N G S 1057 tgctctatccccaggacttgagagatgaaattaagagtgctat
331           C S I P Q D L R D E I K E C Y 1102 gatgtctactctgtcagtagtgaagatagggctccctttgggccc
346           D V Y S V S S E D R A P F G P
                              EXON 5
     1147 cgaaatggaacggcttggatctacacaagtgaaaaagacttgaat
361           R N G T A W I Y T S E K D L N 1192 ggtagtagccactggggaatcattgcaacttatagtggagctggc
376           G S S H W G I I A T Y S G A G 1237 tattatctggatttgtcaagaacaagagaggaaacagctgcacaa
391           Y Y L D L S R T R E E T A A Q 1282 gttgctagcctcaagaaaaatgtctggctggaccgaggaaccagg
406           V A S L K K N V W L D R G T R 1327 gcaactttattgacttctcagtgtacaacgccaacattaacctg
421           A T F I D F S V Y N A N I N L
                              EXON 6
     1372 ttctgtgtggtcaggttattggttgaattcccagcaacaggtggt
436           F C V V R L L V E F P A T G G 1417 gtgattccatcttggcaatttcagcctttaaagctgatccgatat
451           V I P S W Q F Q P L K L I R Y 1462 gtcacaactttgatttcttcctggcagcctgtgagattatcttt
466           V T T F D F L L A A C E I I F 1507 tgtttctttatctttactatgtggtggaagagatattggaaat
481           C F F I F Y Y V V E E I L E I
```

FIG. 4B

```
496   1552 cgcattcacaaactacactatttcaggagtttctggaattgtctg
           R  I  H  K  L  H  Y  F  R  S  F  W  N  C  L
                                    EXON 7
511   1597 gatgttgtgatcgttgt cgtgtcagtggtagctataggaattaac
           D  V  V  I  V  V  L  S  V  V  A  I  G  I  N 526   1642 atatacagaacatcaaatgtggaggtgctactacagtttctggaa
           I  Y  R  T  S  N  V  E  V  L  L  Q  F  L  E 541   1687 gatcaaaatactttccccaactttgagcatctggcatattggcag
           D  Q  N  T  F  P  N  F  E  H  L  A  Y  W  Q 556   1732 atacagttcaacaatatagctgctgtcacagtattttttgtctgg
           I  Q  F  N  N  I  A  A  V  T  V  F  F  V  W
                          EXON 8
571   1777 attaac ctcttcaaattcatcaattttaacaggaccatgagccag
           I  K  L  F  K  F  I  N  F  N  R  T  M  S  Q 586   1822 ctctcgacaaccatgtctcgatgtgccaaagacctgtttggcttt
           L  S  T  T  M  S  R  C  A  K  D  L  F  G  F 601   1867 gctattatgttcttcattatttttcctagcgtatgctcagttggca
           A  I  M  F  F  I  I  F  L  A  Y  A  Q  L  A 616   1912 tacttgtctttcgcactcaggtccatgacttcagtactttccaa
           Y  L  V  F  G  T  Q  V  D  D  F  S  T  F  Q
                          EXON 9
631   1957 gagtgta cttcactcaattccgtatcatttgggcgatatcaac
           E  C  I  F  T  Q  F  R  I  I  L  G  D  I  N 646   2002 tttgcagagattgaggaagctaatcgagttttgggaccaatttat
           F  A  E  I  E  E  A  N  R  V  L  G  P  I  Y
                                                  EXON 10
661   2047 ttcactacatttgtgttctttatgttcttcattctttttc aatatg
           F  T  T  F  V  F  F  M  F  F  I  L  L  N  M 676   2092 tttttggctatcatcaatgatacttactctgaagtgaaatctgac
           F  L  A  I  I  N  D  T  Y  S  E  V  K  S  D 691   2137 ttggcacagcagaaaagctgaaatggaactctcagatcttatcaga
           L  A  Q  Q  K  A  E  M  E  L  S  D  L  I  R
                    EXON 11
706   2182 aag ggctaccataaagctttggtcaaactaaaactgaaaaaaaat
           K  G  Y  H  K  A  L  V  K  L  K  L  K  K  N 721   2227 accgtggatgacatttcagagagtctgcggcaaggaggaggcaag
           E  V  D  D  I  S  E  S  L  R  Q  G  G  G  K EXON 12
      2272 ttaaactttgacgaacttcgacaagatctcaaagg gaagggccat
```

FIG. 4C

```
736                   L  N  F  D  E  L  R  Q  D  L  K  G  K  G  R
       2317 actgatgcagagattgaggcaatattcacaaagtacgaccaagat
751          T  D  A  E  I  E  A  I  F  T  K  Y  D  Q  D
       2362 ggagaccaagaactgactgaacatgaacatcagcagatgagagac
766          G  D  Q  E  L  T  E  H  E  H  Q  Q  M  R  D
                                      EXON 13
       2407 gacttggagaaagagaggaggacctggatttggatcacagttct
781          D  L  E  K  E  R  E  D  L  D  L  D  H  S  S
       2452 ttaccacgtcccatgagcagccgaagtttccctcgaagcctggat
796          L  P  R  P  M  S  S  R  S  F  P  R  S  L  D
       2497 gactctgaggaggatgacgatgaagatagcggacatagctccaga
811          D  S  E  E  D  D  D  E  D  S  G  H  S  S  R
       2542 aggaggggaagcatttctagtggcgtttcttacgaagagtttcaa
826          R  R  G  S  I  S  S  G  V  S  Y  E  E  F  Q
            EXON 14
       2587 gtcctggtgagacgagtggaccggatggagcattccatcggcagc
841          V  L  V  R  R  V  D  R  M  E  H  S  I  G  S
       2632 atagtgtccaagattgacgccgtgatcgtgaagctagagattatg
856          I  V  S  K  I  D  A  V  I  V  K  L  E  I  M
       2677 gagcgagccaaactgaagaggagggaggtgctgggaaggctgttg
871          E  R  A  K  L  K  R  R  E  V  L  G  R  L  L
                              EXON 15
       2722 gatggggtggccgacgatgaaaggctgggtcgtgacagtgaaatc
886          D  G  V  A  E  D  E  R  L  G  R  D  S  E  I
       2767 cataggggaacagatggaacggctagtacgtgaagagttggaacgg
901          H  R  E  Q  M  E  R  L  V  R  E  E  L  E  R
       2812 tgggaatccgatgatgcagcttcccagatcagtcatggtttaggc
916          W  E  S  D  D  A  A  S  Q  I  S  H  G  L  G
       2857 acgccagtggggactaaatggtcaacctcgccccagaagctcccgc
931          T  P  V  G  L  N  G  Q  P  R  P  R  S  S  R
       2902 ccatcttcctcccaatctacagaaggcatggaaggtgcaggtgga
946          P  S  S  S  Q  S  T  E  G  M  E  G  A  G  G
       2947 aatgggagttctaatgtccacgtatga 2973 (SEQ ID NO. 5)
961          N  G  S  S  N  V  H  V  *         (SEQ ID NO. 6)
```

*FIG. 4D*

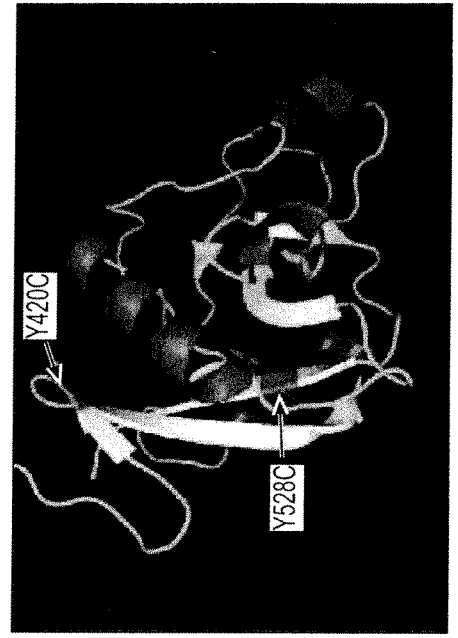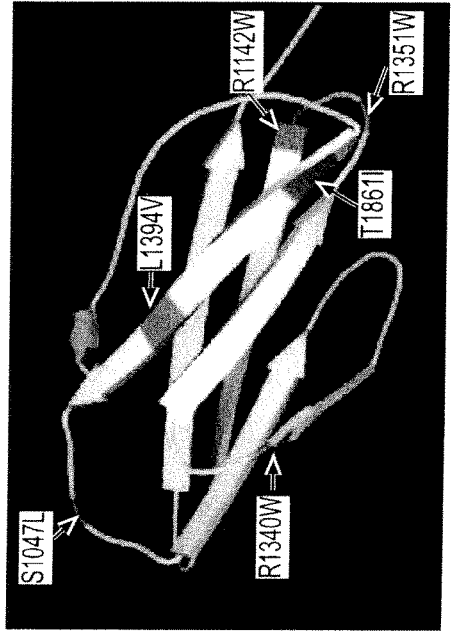
FIGURES 5A-5C

SEQUENCE LISTING

<160> NUMBER OF SEQ ID NOS: 23

<210> SEQ ID NO 1
<211> LENGTH: 14136
<212> TYPE: DNA
<213> ORGANISM: Homo sapiens

<400> SEQUENCE: 1

| | | | | | |
|---|---|---|---|---|---|
| gcactgcagc | gccagcgtcc | gagcgggcgg | ccgagctccc | ggagcggcct | ggccccgagc | 60 |
| cccgagcggg | cgtcgctcag | cagcaggtcg | cggccgcgca | gccccatcca | gccccgcgcc | 120 |
| cgccatgccg | tccgcgggcc | ccgcctgagc | tgcggtctcc | gcgcgcgggc | gggcctgggg | 180 |
| acggcgggc | catgcgcgcg | ctgccctaac | gatgccgccc | gccgcgcccg | cccgcctggc | 240 |
| gctggccctg | ggcctgggcc | tgtggctcgg | ggcgctggcg | gggggccccg | ggcgcggctg | 300 |
| cgggccctgc | gagccccct | gcctctgcgg | cccagcgccc | ggcgccgcct | gccgcgtcaa | 360 |
| ctgctcgggc | cgcgggctgc | ggacgctcgg | tcccgcgctg | cgcatccccg | cggacgccac | 420 |
| agcgctagac | gtctcccaca | acctgctccg | ggcgctggac | gttgggctcc | tggcgaacct | 480 |
| ctcggcgctg | gcagagctgg | atataagcaa | caacaagatt | tctacgttag | aagaaggaat | 540 |
| atttgctaat | ttatttaatt | taagtgaaat | aaacctgagt | gggaacccgt | ttgagtgtga | 600 |
| ctgtggcctg | gcgtggctgc | cgcgatgggc | ggaggagcag | caggtgcggg | tggtgcagcc | 660 |
| cgaggcagcc | acgtgtgctg | ggcctggctc | cctggctggc | cagcctctgc | ttggcatccc | 720 |
| cttgctggac | agtggctgtg | gtgaggagta | tgtcgcctgc | ctccctgaca | acagctcagg | 780 |
| caccgtggca | gcagtgtcct | tttcagctgc | ccacgaaggc | ctgcttcagc | cagaggcctg | 840 |
| cagcgccttc | tgcttctcca | ccggccaggg | cctcgcagcc | ctctcggagc | agggctggtg | 900 |
| cctgtgtggg | gcggcccagc | cctccagtgc | ctcctttgcc | tgcctgtccc | tctgctccgg | 960 |
| cccccgcca | cctcctgccc | ccacctgtag | gggccccacc | ctcctccagc | acgtcttccc | 1020 |
| tgcctcccca | ggggccaccc | tggtggggcc | ccacggacct | ctggcctctg | gccagctagc | 1080 |
| agccttccac | atcgctgccc | cgctcccctgt | cactgccaca | cgctgggact | tcggagacgg | 1140 |
| ctccgccgag | gtggatgccg | ctgggccggc | tgcctcgcat | cgctatgtgc | tgcctgggcg | 1200 |
| ctatcacgtg | acggccgtgc | tggccctggg | ggccggctca | gccctgctgg | ggacagacgt | 1260 |
| gcaggtggaa | gcggcacctg | ccgccctgga | gctcgtgtgc | ccgtcctcgg | tgcagagtga | 1320 |
| cgagagcctt | gacctcagca | tccagaaccg | cggtggttca | ggcctggagg | ccgcctacag | 1380 |
| catcgtggcc | ctgggcgagg | agccggcccg | agcggtgcac | ccgctctgcc | cctcggacac | 1440 |
| ggagatcttc | cctggcaacg | ggcactgcta | ccgcctggtg | gtggagaagg | cggcctggct | 1500 |
| gcaggcgcag | gagcagtgtc | aggcctgggc | cggggccgcc | ctggcaatgg | tggacagtcc | 1560 |
| cgccgtgcag | cgcttcctgg | tctcccgggt | caccaggagc | ctagacgtgt | ggatcggctt | 1620 |
| ctcgactgtg | caggggtgg | aggtgggccc | agcgccgcag | ggcgaggcct | tcagcctgga | 1680 |
| gagctgccag | aactggctgc | ccggggagcc | acacccagcc | acagccgagc | actgcgtccg | 1740 |
| gctcgggccc | accgggtggt | gtaacaccga | cctgtgctca | gcgccgcaca | gctacgtctg | 1800 |
| cgagctgcag | cccggaggcc | cagtgcagga | tgccgagaac | ctcctcgtgg | gagcgcccag | 1860 |
| tggggacctg | cagggacccc | tgacgcctct | ggcacagcag | gacggcctct | cagccccgca | 1920 |
| cgagcccgtg | gaggtcatgg | tattcccggg | cctgcgtctg | agccgtgaag | ccttcctcac | 1980 |
| cacgcccgaa | tttgggaccc | aggagctccg | gcggcccgcc | cagctgcggc | tgcaggtgta | 2040 |
| ccggctcctc | agcacagcag | ggaccccgga | gaacggcagc | gagcctgaga | gcaggtcccc | 2100 |

```
ggacaacagg  acccagctgg  cccccgcgtg  catgccaggg  ggacgctggt  gccctggagc    2160
caacatctgc  ttgccgctgg  acgcctcttg  ccaccccag   gcctgcgcca  atggctgcac    2220
gtcagggcca  gggctacccg  ggcccccta   tgcgctatgg  agagagttcc  tcttctccgt    2280
tgccgcgggg  cccccgcgc   agtactcggt  caccctccac  ggccaggatg  tcctcatgct    2340
ccctggtgac  ctcgttggct  tgcagcacga  cgctggccct  ggcgccctcc  tgcactgctc    2400
gccggctccc  ggccacccctg  gtccccaggc  ccgtacctc   tccgccaacg  cctcgtcatg    2460
gctgccccac  ttgccagccc  agctggaggg  cacttgggcc  tgccctgcct  gtgccctgcg    2520
gctgcttgca  gccacggaac  agctcaccgt  gctgctgggc  ttgaggccca  accctggact    2580
gcggatgcct  gggcgctatg  aggtccgggc  agaggtgggc  aatggcgtgt  ccaggcacaa    2640
cctctcctgc  agctttgacg  tggtctcccc  agtggctggg  ctgcgggtca  tctaccctgc    2700 ccccgcgac   ggccgcctct  acgtgcccac  caacggctca  gccttggtgc  tccaggtgga    2760
ctctggtgcc  aacgccacgg  ccacggctcg  ctggcctggg  ggcagtgtca  gcgcccgctt    2820
tgagaatgtc  tgccctgccc  tggtggccac  cttcgtgccc  ggctgcccct  gggagaccaa    2880 cgatacccctg  ttctcagtgg  tagcactgcc  gtggctcagt  gagggggagc  acgtggtgga    2940
cgtggtggtg  gaaaacagcg  ccagccgggc  caacctcagc  ctgcgggtga  cggcggagga    3000
gcccatctgt  ggcctccgcg  ccacgcccag  ccccgaggcc  cgtgtactgc  agggagtcct    3060
agtgaggtac  agccccgtgg  tggaggccgg  ctcggacatg  gtcttccggt  ggaccatcaa    3120
cgacaagcag  tccctgacct  tccagaacgt  ggtcttcaat  gtcatttatc  agagcgcggc    3180
ggtcttcaag  ctctcactga  cggcctccaa  ccacgtgagc  aacgtcaccg  tgaactacaa    3240
cgtaaccgtg  gagcggatga  acaggatgca  gggtctgcag  gtctccacag  tgccggccgt    3300 gctgtcccc   aatgccacgc  tagcactgac  ggcgggcgtg  ctggtggact  cggccgtgga    3360
ggtggccttc  ctgtggaact  tgggggatgg  ggagcaggcc  ctccaccagt  tccagcctcc    3420
gtacaacgag  tccttcccgg  ttccagaccc  ctcggtggcc  caggtgctgg  tggagcacaa    3480
tgtcatgcac  acctacgctg  ccccaggtga  gtacctcctg  accgtgctgg  catctaatgc    3540
cttcgagaac  ctgacgcagc  aggtgcctgt  gagcgtgcgc  gcctccctgc  cctccgtggc    3600
tgtgggtgtg  agtgacggcg  tcctggtggc  cggccggccc  gtcaccttct  acccgcaccc    3660
gctgccctcg  cctgggggtg  ttctttacac  gtgggacttc  ggggacggct  cccctgtcct    3720
gacccagagc  cagccggctg  ccaaccacac  ctatgcctcg  aggggcacct  accacgtgcg    3780
cctggaggtc  aacaacacgg  tgagcggtgc  ggcggcccag  gcggatgtgc  gcgtctttga    3840
ggagctccgc  ggactcagcg  tggacatgag  cctggccgtg  gagcagggcg  ccccgtggt    3900 ggtcagcgcc  gcggtgcaga  cgggcgacaa  catcacgtgg  accttcgaca  tggggacgg    3960 caccgtgctg  tcgggcccgg  aggcaacagt  ggagcatgtg  tacctgcggg  cacagaactg    4020
cacagtgacc  gtgggtgcgg  ccagccccgc  cggccacctg  gccggagcc   tgcacgtgct    4080 ggtcttcgtc  ctggaggtgc  tgcgcgttga  acccgccgcc  tgcatcccca  cgcagcctga    4140
cgcgcggctc  acggcctacg  tcaccgggaa  cccggcccac  tacctcttcg  actggacctt    4200
cggggatggc  tcctccaaca  cgaccgtgcg  ggggtgcccg  acgtgacac   acaacttcac    4260 gcggagcggc  acgttcccc   tggcgctggt  gctgtccagc  cgcgtgaaca  gggcgcatta    4320
cttcaccagc  atctgcgtgg  agccagaggt  gggcaacgtc  accctgcagc  cagagaggca    4380
gtttgtgcag  ctcggggacg  aggcctggct  ggtggcatgt  gcctggcccc  cgttcccta    4440
```

```
ccgctacacc tgggactttg gcaccgagga agccgccccc acccgtgcca ggggccctga    4500
ggtgacgttc atctaccgag acccaggctc ctatcttgtg acagtcaccg cgtccaacaa    4560
catctctgct gccaatgact cagccctggt ggaggtgcag gagcccgtgc tggtcaccag    4620
catcaaggtc aatggctccc ttgggctgga gctgcagcag ccgtacctgt tctctgctgt    4680
gggccgtggg cgccccgcca gctacctgtg ggatctgggg gacggtgggt ggctcgaggg    4740
tccggaggtc acccacgctt acaacagcac aggtgacttc accgttaggg tggccggctg    4800
gaatgaggtg agccgcagcg aggcctggct caatgtgacg gtgaagcggc gcgtgcgggg    4860
gctcgtcgtc aatgcaagcc gcacggtggt gcccctgaat gggagcgtga gcttcagcac    4920
gtcgctggag gccggcagtg atgtgcgcta ttcctgggtg ctctgtgacc gctgcacgcc    4980
catccctggg ggtcctacca tctcttacac cttccgctcc gtgggcacct tcaatatcat    5040
cgtcacggct gagaacgagg tgggctccgc ccaggacagc atcttcgtct atgtcctgca    5100
gctcatagag gggctgcagg tggtgggcgg tggccgctac ttccccacca accacacggt    5160
acagctgcag gccgtggtta gggatggcac caacgtctcc tacagctgga ctgcctggag    5220
ggacaggggc ccggccctgg ccggcagcgg caaaggcttc tcgctcaccg tgctcgaggc    5280
cggcacctac catgtgcagc tgcgggccac caacatgctg ggcagcgcct gggccgactg    5340
caccatggac ttcgtggagc ctgtgggggtg gctgatggtg accgcctccc cgaacccagc    5400
tgccgtcaac acaagcgtca ccctcagtgc cgagctggct ggtggcagtg gtgtcgtata    5460
cacttggtcc ttggaggagg ggctgagctg ggagacctcc gagccattta ccacccatag    5520
cttccccaca cccggcctgc acttggtcac catgacggca gggaacccgc tgggctcagc    5580
caacgccacc gtggaagtgg atgtgcaggt gcctgtgagt ggcctcagca tcagggccag    5640
cgagcccgga ggcagcttcg tggcggccgg gtcctctgtg cccttttggg ggcagctggc    5700
cacgggcacc aatgtgagct ggtgctgggc tgtgcccggc ggcagcagca agcgtggccc    5760
tcatgtcacc atggtcttcc cggatgctgg caccttctcc atccggctca atgcctccaa    5820
cgcagtcagc tgggtctcag ccacgtacaa cctcacggcg gaggagccca tcgtgggcct    5880
ggtgctgtgg gccagcagca aggtggtggc gcccgggcag ctggtccatt ttcagatcct    5940
gctggctgcc ggctcagctg tcaccttccg cctgcaggtc ggcggggcca accccgaggt    6000
gctccccggg ccccgtttct cccacagctt ccccgcgtc ggagaccacg tggtgagcgt    6060
gcggggcaaa aaccacgtga gctgggccca ggcgcaggtg cgcatcgtgg tgctggaggc    6120
cgtgagtggg ctgcagatgc ccaactgctg cgagcctggc atcgccacgg gcactgagag    6180
gaacttcaca gcccgcgtgc agcgcggctc tcgggtcgcc tacgcctggt acttctcgct    6240
gcagaaggtc cagggcgact cgctggtcat cctgtcgggc cgcgacgtca cctacacgcc    6300
cgtggccgcg ggctgttgg agatccaggt gcgcgccttc aacgccctgg gcagtgagaa    6360
ccgcacgctg gtgctggagg ttcaggacgc cgtccagtat gtggccctgc agagcggccc    6420
ctgcttcacc aaccgctcgg cgcagtttga ggccgccacc agcccagcc ccggcgtgt     6480 ggcctaccac tgggactttg gggatgggtc gccagggcag gacacagatg agcccagggc    6540
cgagcactcc tacctgaggc ctggggacta ccgcgtgcag gtgaacgcct ccaacctggt    6600
gagcttcttc gtggcgcagg ccacggtgac cgtccaggtg ctggcctgcc gggagccgga    6660
ggtggacgtg gtcctgcccc tgcaggtgct gatgcggcga tcacagcgca actacttgga    6720
ggcccacgtt gacctgcgcg actgcgtcac ctaccagact gagtaccgct gggaggtgta    6780
tcgcaccgcc agctgccagc ggccggggcg cccagcgcgt gtggccctgc ccggcgtgga    6840
```

```
cgtgagccgg cctcggctgg tgctgccgcg gctggcgctg cctgtggggc actactgctt   6900
tgtgtttgtc gtgtcatttg gggacacgcc actgacacag agcatccagg ccaatgtgac   6960
ggtggccccc gagcgcctgg tgcccatcat tgagggtggc tcataccgcg tgtggtcaga   7020
cacacgggac ctggtgctgg atgggagcga gtcctacgac cccaacctgg aggacggcga   7080
ccagacgccg ctcagtttcc actgggcctg tgtggcttcg acacagaggg aggctggcgg   7140
gtgtgcgctg aactttgggc cccgcgggag cagcacggtc accattccac gggagcggct   7200
ggcggctggc gtggagtaca ccttcagcct gaccgtgtgg aaggccggcc gcaaggagga   7260
ggccaccaac cagacggtgc tgatccggag tggccgggtg cccattgtgt ccttggagtg   7320
tgtgtcctgc aaggcacagg ccgtgtacga agtgagccgc agctcctacg tgtacttgga   7380
gggccgctgc ctcaattgca gcagcggctc aagcgagggg cggtgggctg cacgtacgtt   7440
cagcaacaag acgctggtgc tggatgagac caccacatcc acgggcagtg caggcatgcg   7500
actggtgctg cggcggggcg tgctgcggga cggcgaggga tacaccttca cgctcacggt   7560
gctgggccgc tctggcgagg aggagggctg cgcctccatc cgcctgtccc caaccgccc    7620 gccgctgggg ggctcttgcc gcctcttccc actgggcgct gtgcacgccc tcaccaccaa   7680
ggtgcacttc gaatgcacgg gctggcatga cgcggaggat gctggcgccc cgctggtgta   7740
cgccctgctg ctgcggcgct gtcgccaggg ccactgcgag gagttctgtg tctacaaggg   7800
cagcctctcc agctacggag ccgtgctgcc cccgggtttc aggccacact cgaggtgggg   7860
cctggccgtg gtggtgcagg accagctggg agccgctgtg gtcgccctca acaggtcttt   7920
ggccatcacc ctcccagagc ccaacggcag cgcaacgggg ctcacagtct ggctgcacgg   7980
gctcaccgct agtgtgctcc cagggctgct gcggcaggcc gatccccagc acgtcatcga   8040
gtactcgttg gccctggtca ccgtgctgaa cgagtacgag cgggccctgg acgtggcggc   8100
agagcccaag cacgagcggc agcaccgagc ccagatacgc aagaacatca cggagactct   8160
ggtgtccctg agggtccaca ctgtggatga catccagcag atcgctgctg cgctggccca   8220
gtgcatgggg cccagcaggg agctcgtatg ccgtcgtgc ctgaagcaga cgctgcacaa   8280
gctggaggcc atgatgctca tcctgcaggc agagaccacc gcgggcaccg tgacgcccac   8340
cgccatcgga gacagcatcc tcaacatcac aggagacctc atccacctgg ccagctcgga   8400
cgtgcgggca ccacagccct cagagctggg agccgagtca ccatctcgga tggtggcgtc   8460
ccaggcctac aacctgacct ctgccctcat gcgcatcctc atgcgctccc gcgtgctcaa   8520
cgaggagccc ctgacgctgg cgggcgagga gatcgtggcc cagggcaagc gctcggaccc   8580
gcggagcctg ctgtgctatg gcggcgcccc agggcctggc tgccacttct ccatccccga   8640
ggctttcagc ggggccctgg ccaacctcag tgacgtggtg cagctcatct ttctggtgga   8700
ctccaatccc tttcccttg gctatatcag caactacacc gtctccacca aggtggcctc   8760
gatggcattc cagacacagg ccggcgccca gatccccatc gagcggctgg cctcagagcg   8820
cgccatcacc gtgaaggtgc ccaacaactc ggactgggct gccggggcc accgcagctc    8880 cgccaactcc gccaactccg ttgtggtcca gccccaggcc tcgtcggtg ctgtggtcac    8940 cctgacagc agcaacccctg cggccgggct gcatctgcag ctcaactata cgctgctgga   9000
cggccactac ctgtctgagg aacctgagcc ctacctggca gtctacctac actcggagcc   9060
ccggcccaat gagcacaaact gctcggctag caggaggatc cgcccagagt cactccaggg   9120
tgctgaccac cggccctaca ccttcttcat ttccccgggg agcagagacc cagcggggag   9180
```

```
ttaccatctg aacctctcca gccacttccg ctggtcggcg ctgcaggtgt ccgtgggcct    9240
gtacacgtcc ctgtgccagt acttcagcga ggaggacatg gtgtggcgga cagaggggct    9300
gctgcccctg gaggagacct cgccccgcca ggccgtctgc ctcacccgcc acctcaccgc    9360
cttcggcgcc agcctcttcg tgccccaag ccatgtccgc tttgtgtttc ctgagccgac    9420
agcggatgta aactacatcg tcatgctgac atgtgctgtg tgcctggtga cctacatggt    9480
catggccgcc atcctgcaca agctggacca gttggatgcc agccggggcc gcgccatccc    9540
tttctgtggg cagcggggcc gcttcaagta cgagatcctc gtcaagacag gctggggccg    9600
gggctcaggt accacggccc acgtgggcat catgctgtat ggggtggaca gccgagcgg    9660 ccaccggcac ctggacggcg acagagcctt ccaccgcaac agcctggaca tcttccggat    9720
cgccaccccg cacagcctgg gtagcgtgtg gaagatccga gtgtggcacg acaacaaagg    9780
gctcagccct gcctggttcc tgcagcacgt catcgtcagg gacctgcaga cggcacgcag    9840
cgccttcttc ctggtcaatg actggctttc ggtggagacg gaggcaacg ggggcctggt    9900 ggagaaggag gtgctggccg cgagcgacgc agccctttg cgcttccggc gctgctggt    9960 ggctgagctg cagcgtggct tctttgacaa gcacatctgg ctctccatat gggaccggcc   10020
gcctcgtagc cgtttcactc gcatccgagg gccacctgc tgcgttctcc tcatctgcct   10080
cttcctgggc gccaacgccg tgtggtacgg ggctgttggc gactctgcct acagcacggg   10140
gcatgtgtcc aggctgagcc cgctgagcgt cgacacagtc gctgttggcc tggtgtccag   10200
cgtggttgtc tatcccgtct acctggccat ccttttctc ttccggatgt cccggagcaa   10260
ggtggctggg agcccgagcc ccacacctgc cgggcagcag gtgctggaca tcgacagctg   10320
cctggactcg tccgtgctgg acagctcctt cctcacgttc tcaggcctcc acgctgaggc   10380 cttttgttgga cagatgaaga gtgacttgtt tctggatgat tctaagagtc tggtgtgctg   10440
gccctccggc gagggaacgc tcagttggcc ggacctgctc agtgacccgt ccattgtggg   10500
tagcaatctg cggcagctgg cacggggcca ggcgggccat gggctgggcc cagaggagga   10560
cggcttctcc ctggccagcc cctactcgcc tgccaaatcc ttctcagcat cagatgaaga   10620
cctgatccag caggtccttg ccgaggggt cagcagccca gcccctaccc aagacaccca   10680
catggaaacg gacctgctca gcagcctgtc cagcactcct ggggagaaga cagagacgct   10740
ggcgctgcag aggctggggg agctgggcc acccagccca ggcctgaact gggaacagcc   10800
ccaggcagcg aggctgtcca ggacaggact ggtggagggt ctgcggaagc gcctgctgcc   10860
ggcctggtgt gcctccctgg cccacgggct cagcctgctc ctggtggctg tggctgtggc   10920
tgtctcaggg tgggtgggtg cgagcttccc ccgggcgtg agtgttgcgt ggctcctgtc   10980
cagcagcgcc agcttcctgg cctcattcct cggctgggag ccactgaagg tcttgctgga   11040
agccctgtac ttctcactgg tggccaagcg gctgcacccg gatgaagatg acaccctggt   11100
agagagcccg gctgtgacgc ctgtgagcgc acgtgtgccc cgcgtacggc caccccacgg   11160
ctttgcactc ttcctggcca aggaagaagc ccgcaaggtc aagaggctac atggcatgct   11220
gcggagcctc ctggtgtaca tgcttttct gctggtgacc ctgctggcca gctatgggga   11280
tgcctcatgc catgggcacg cctaccgtct gcaaagcgcc atcaagcagg agctgcacag   11340
ccgggccttc ctggccatca gcgggtctga ggagctctgg ccatggatgg cccacgtgct   11400
gctgccctac gtccacgga accagtccag cccagagctg ggccccac ggctgcggca   11460 ggtgcggctg caggaagcac tctacccaga ccctcccggc cccagggtcc acacgtgctc   11520
ggccgcagga ggcttcagca ccagcgatta cgacgttggc tgggagagtc ctcacaatgg   11580
```

```
ctcggggacg tgggcctatt cagcgccgga tctgctgggg gcatggtcct ggggctcctg   11640
tgccgtgtat gacagcgggg gctacgtgca ggagctgggc ctgagcctgg aggagagccg   11700
cgaccggctg cgcttcctgc agctgcacaa ctggctggac aacaggagcc gcgctgtgtt   11760
cctggagctc acgcgctaca gcccggccgt ggggctgcac gccgccgtca cgctgcgcct   11820
cgagttcccg gcggccggcc gcgccctggc cgccctcagc gtccgcccct ttgcgctgcg   11880
ccgcctcagc gcgggcctct cgctgcctct gctcacctcg gtgtgcctgc tgctgttcgc   11940
cgtgcacttc gccgtggccg aggcccgtac ttggcacagg aagggcgct ggcgcgtgct    12000 gcggctcgga gcctgggcgc ggtggctgct ggtggcgctg acggcggcca cggcactggt   12060
acgcctcgcc cagctgggtg ccgctgaccg ccagtggacc cgtttcgtgc gcggccgccc   12120
gcgccgcttc actagcttcg accaggtggc gcagctgagc tccgcagccc gtggcctggc   12180
ggcctcgctg ctcttcctgc ttttggtcaa ggctgcccag cagctacgct tcgtgcgcca   12240
gtggtccgtc tttggcaaga cattatgccg agctctgcca gagctcctgg gggtcacctt   12300
gggcctggtg gtgctcgggg tagcctacgc ccagctggcc atcctgctcg tgtcttcctg   12360
tgtggactcc ctctggagcg tggcccaggc cctgttggtg ctgtgccctg ggactgggct   12420
ctctaccctg tgtcctgccg agtcctggca cctgtcaccc ctgctgtgtg tggggctctg   12480
ggcactgcgg ctgtggggcg ccctacggct gggggctgtt attctccgct ggcgctacca   12540
cgccttgcgt ggagagctgt accggccggc ctgggagccc caggactacg agatggtgga   12600
gttgttcctg cgcaggctgc gcctctggat gggcctcagc aaggtcaagg agttccgcca   12660
caaagtccgc tttgaaggga tggagccgct gccctctcgc tcctccaggg gctccaaggt   12720
atccccggat gtgcccccac ccagcgctgg ctccgatgcc tcgcacccct ccacctcctc   12780
cagccagctg gatgggctga gcgtgagcct gggccggctg gggacaaggt gtgagcctga   12840
gccctcccgc ctccaagccg tgttcgaggc cctgctcacc cagtttgacc gactcaacca   12900
ggccacagag gacgtctacc agctggagca gcagctgcac agcctgcaag gccgcaggag   12960
cagccgggcg cccgccggat cttcccgtgg cccatccccg ggcctgcggc cagcactgcc   13020
cagccgcctt gcccgggcca gtcggggtgt ggacctggac actggcccca gcaggacacc   13080
ccttcgggcc aagaacaagg tccacccccag cagcacttag tcctccttcc tggcgggggt   13140
gggccgtgga gtcggagtgg acaccgctca gtattacttt ctgccgctgt caaggccgag   13200
ggccaggcag aatggctgca cgtaggttcc ccagagagca ggcaggggca tctgtctgtc   13260
tgtgggcttc agcactttaa agaggctgtg tggccaacca ggacccaggg tcccctcccc   13320
agctcccttg ggaaggacac agcagtattg gacggtttct agcctctgag atgctaattt   13380
atttccccga gtcctcaggt acagcgggct gtgcccggcc ccaccccctg ggcagatgtc   13440
ccccactgct aaggctgctg gcttcaggga gggttagcct gcaccgccgc cacccctgccc  13500 ctaagttatt acctctccag ttcctaccgt actccctgca ccgtctcact gtgtgtctcg   13560
tgtcagtaat ttatatggtg ttaaaatgtg tatattttg  tatgtcacta ttttcactag   13620
ggctgagggg cctgcgccca gagctggcct cccccaacac ctgctgcgct tggtaggtgt   13680
ggtggcgtta tggcagcccg gctgctgctt ggatgcgagc ttggccttgg gccggtgctg   13740
ggggcacagc tgtctgccag gcactctcat caccccagag gccttgtcat cctcccttgc   13800
cccaggccag gtagcaagag agcagcgccc aggcctgctg gcatcaggtc tgggcaagta   13860
gcaggactag gcatgtcaga ggaccccagg gtggttagag gaaaagactc ctcctggggg   13920
```

-continued

| | |
|---|---|
| ctggctccca gggtggagga aggtgactgt gtgtgtgtgt gtgtgcgcgc gcgacgcgcg | 13980 |
| agtgtgctgt atggcccagg cagcctcaag gccctcggag ctggctgtgc ctgcttctgt | 14040 |
| gtaccacttc tgtgggcatg gccgcttcta gagcctcgac accccccaa ccccccgcacc | 14100 |
| aagcagacaa agtcaataaa agagctgtct gactgc | 14136 |

<210> SEQ ID NO 2
<211> LENGTH: 12909
<212> TYPE: DNA
<213> ORGANISM: Homo sapiens

<400> SEQUENCE: 2

| | |
|---|---|
| atgccgcccg ccgcgcccgc ccgcctggcg ctggccctgg gctgggcct gtggctcggg | 60 |
| gcgctggcgg ggggccccgg gcgcggctgc gggccctgcg agcccccctg cctctgcggc | 120 |
| ccagcgcccg gcgccgcctg ccgcgtcaac tgctcgggcc gcgggctgcg gacgctcggt | 180 |
| cccgcgctgc gcatccccgc ggacgccaca gcgctagacg tctcccacaa cctgctccgg | 240 |
| gcgctggacg ttgggctcct ggcgaacctc tcggcgctgg cagagctgga tataagcaac | 300 |
| aacaagattt ctacgttaga agaaggaata tttgctaatt tatttaattt aagtgaaata | 360 |
| aacctgagtg ggaacccgtt tgagtgtgac tgtggcctgg cgtggctgcc gcgatgggcg | 420 |
| gaggagcagc aggtgcgggt ggtgcagccc gaggcagcca cgtgtgctgg gcctggctcc | 480 |
| ctggctggcc agcctctgct tggcatcccc ttgctggaca gtggctgtgg tgaggagtat | 540 |
| gtcgcctgcc tccctgacaa cagctcaggc accgtggcag cagtgtcctt ttcagctgcc | 600 |
| cacgaaggcc tgcttcagcc agaggcctgc agcgccttct gcttctccac cggccagggc | 660 |
| ctcgcagccc tctcggagca gggctggtgc ctgtgtgggg cggcccagcc ctccagtgcc | 720 |
| tcctttgcct gcctgtccct ctgctccggc ccccgccac ctcctgcccc cacctgtagg | 780 |
| ggccccaccc tcctccagca cgtcttccct gcctcccag gggccaccct ggtggggccc | 840 |
| cacggacctc tggcctctgg ccagctagca gccttccaca tcgctgcccc gctccctgtc | 900 |
| actgccacac gctgggactt cggagacggc tccgccgagg tggatgccgc tgggccggct | 960 |
| gcctcgcatc gctatgtgct gcctgggcgc tatcacgtga cggccgtgct ggccctgggg | 1020 |
| gccggctcag ccctgctggg gacagacgtg caggtggaag cggcacctgc cgccctggag | 1080 |
| ctcgtgtgcc cgtcctcggt gcagagtgac gagagccttg acctcagcat ccagaaccgc | 1140 |
| ggtggttcag gcctggaggc cgcctacagc atcgtggccc tgggcgagga gccggcccga | 1200 |
| gcggtgcacc cgctctgccc ctcggacacg gagatcttcc ctgcaacgg gcactgctac | 1260 |
| cgcctggtgg tggagaaggc ggcctggctg caggcgcagg agcagtgtca ggcctgggcc | 1320 |
| ggggccgccc tggcaatggt ggacagtccc gccgtgcagc gcttcctggt ctcccgggtc | 1380 |
| accaggagcc tagacgtgtg gatcggcttc tcgactgtgc aggggtgga ggtgggccca | 1440 |
| gcgccgcagg gcgaggcctt cagcctggag actgccaga actggctgcc cggggagcca | 1500 |
| cacccagcca cagccgagca ctgcgtccgg ctcgggccca ccgggtggtg taacaccgac | 1560 |
| ctgtgctcag cgccgcacag ctacgtctgc gagctgcagc ccggaggccc agtgcaggat | 1620 |
| gccgagaacc tcctcgtggg agcgcccagt ggggacctgc agggacccct gacgcctctg | 1680 |
| gcacagcagg acggcctctc agccccgcac gagcccgtgg aggtcatggt attcccgggc | 1740 |
| ctgcgtctga gccgtgaagc cttcctcacc acggccgaat ttgggaccca ggagctccgg | 1800 |
| cggcccgccc agctgcggct gcaggtgtac cggctcctca gcacagcagg gacccggag | 1860 |
| aacggcagcg agcctgagag caggtccccg gacaacagga cccagctggc cccgcgtgc | 1920 |

```
atgccagggg gacgctggtg ccctggagcc aacatctgct tgccgctgga cgcctcttgc   1980
cacccccagg cctgcgccaa tggctgcacg tcagggccag ggctacccgg gccccctat    2040
gcgctatgga gagagttcct cttctccgtt gccgcggggc cccccgcgca gtactcggtc   2100
accctccacg gccaggatgt cctcatgctc cctggtgacc tcgttggctt gcagcacgac   2160
gctggccctg gcgccctcct gcactgctcg ccggctcccg gccacctgg tccccaggcc    2220
ccgtacctct ccgccaacgc ctcgtcatgg ctgccccact tgccagccca gctggagggc   2280
acttgggcct gccctgcctg tgccctgcgg ctgcttgcag ccacggaaca gctcaccgtg   2340
ctgctgggct tgaggcccaa ccctggactg cggatgcctg ggcgctatga ggtccgggca   2400
gaggtgggca atggcgtgtc caggcacaac ctctcctgca gctttgacgt ggtctcccca   2460
gtggctgggc tgcgggtcat ctaccctgcc ccccgcgacg gccgcctcta cgtgcccacc   2520
aacggctcag ccttggtgct ccaggtggac tctggtgcca cgccacggc cacggctcgc    2580
tggcctgggg gcagtgtcag cgcccgcttt gagaatgtct gccctgccct ggtgccacc    2640
ttcgtgcccg gctgccccctg ggagaccaac gataccctgt tctcagtggt agcactgccg   2700
tggctcagtg agggggagca cgtggtggac gtggtggtgg aaaacagcgc cagccgggcc   2760
aacctcagcc tgcgggtgac ggcggaggag cccatctgtg gcctccgcgc cacgcccagc   2820
cccgaggccc gtgtactgca gggagtccta gtgaggtaca gccccgtggt ggaggccggc   2880
tcggacatgg tcttccggtg gaccatcaac gacaagcagt ccctgacctt ccagaacgtg   2940
gtcttcaatg tcatttatca gagcgcggcg gtcttcaagc tctcactgac ggcctccaac   3000
cacgtgagca acgtcaccgt gaactacaac gtaaccgtgg agcggatgaa caggatgcag   3060
ggtctgcagg tctccacagt gccggccgtg ctgtccccca atgccacgct agcactgacg   3120
gcgggcgtgc tggtggactc ggccgtggag gtggccttcc tgtggaactt tggggatggg   3180
gagcaggccc tccaccagtt ccagcctccg tacaacgagt ccttcccggt tccagacccc   3240
tcggtggccc aggtgctggt ggagcacaat gtcatgcaca cctacgctgc cccaggtgag   3300
tacctcctga ccgtgctggc atctaatgcc ttcgagaacc tgacgcagca ggtgcctgtg   3360
agcgtgcgcg cctccctgcc ctccgtggct gtgggtgtga gtgacggcgt cctggtggcc   3420
ggccggcccg tcaccttcta cccgcacccg ctgccctcgc ctgggggtgt tctttacacg   3480
tgggacttcg gggacggctc ccctgtcctg acccagagcc agccggctgc caaccacacc   3540
tatgcctcga ggggcaccta ccacgtgcgc ctggaggtca caacacggt gagcggtgcg   3600
gcggcccagg cggatgtgcg cgtctttgag gagctccgcg gactcagcgt ggacatgagc   3660
ctggccgtgg agcagggcgc ccccgtggtg gtcagcgccg cggtgcagac gggcgacaac   3720
atcacgtgga ccttcgacat ggggacggc accgtgctgt cgggcccgga ggcaacagtg   3780
gagcatgtgt acctgcgggc acagaactgc acagtgaccg tgggtgcggc cagccccgcc   3840
ggccacctgg cccggagcct gcacgtgctg gtcttcgtcc tggaggtgct gcgcgttgaa   3900
cccgccgcct gcatccccac gcagcctgac gcgcggctca cggcctacgt caccgggaac   3960
ccggcccact acctcttcga ctggaccttc ggggatggct cctccaacac gaccgtgcgg   4020
gggtgcccga cggtgacaca caacttcacg cggagcggca cgttccccct ggcgctggtg   4080
ctgtccagcc gcgtgaacag ggcgcattac ttcaccagca tctgcgtgga gccagaggtg   4140
ggcaacgtca ccctgcagcc agagaggcag tttgtgcagc tcggggacga ggcctggctg   4200
gtggcatgtg cctggccccc gttcccctac cgctacacct gggactttgg caccgaggaa   4260
```

```
gccgccccca cccgtgccag gggccctgag gtgacgttca tctaccgaga cccaggctcc    4320
tatcttgtga cagtcaccgc gtccaacaac atctctgctg ccaatgactc agccctggtg    4380
gaggtgcagg agcccgtgct ggtcaccagc atcaaggtca atggctccct tgggctggag    4440
ctgcagcagc cgtacctgtt ctctgctgtg ggccgtgggc gccccgccag ctacctgtgg    4500
gatctggggg acggtgggtg gctcgagggt ccggaggtca cccacgctta caacagcaca    4560
ggtgacttca ccgttagggt ggccggctgg aatgaggtga gccgcagcga ggcctggctc    4620
aatgtgacgg tgaagcggcg cgtgcggggg ctcgtcgtca atgcaagccg cacggtggtg    4680
cccctgaatg ggagcgtgag cttcagcacg tcgctggagg ccggcagtga tgtgcgctat    4740
tcctgggtgc tctgtgaccg ctgcacgccc atccctgggg gtcctaccat ctcttacacc    4800
ttccgctccg tgggcacctt caatatcatc gtcacggctg agaacgaggt gggctccgcc    4860
caggacagca tcttcgtcta tgtcctgcag ctcatagagg ggctgcaggt ggtgggcggt    4920
ggccgctact tccccaccaa ccacacggta cagctgcagg ccgtggttag ggatggcacc    4980
aacgtctcct acagctggac tgcctggagg acaggggcc cggccctggc cggcagcggc    5040
aaaggcttct cgctcaccgt gctcgaggcc ggcacctacc atgtgcagct gcgggccacc    5100
aacatgctgg gcagcgcctg ggccgactgc accatggact cgtggagcc tgtggggtgg    5160 ctgatggtga ccgcctcccc gaacccagct gccgtcaaca caagcgtcac cctcagtgcc    5220
gagctggctg tgtgcagtgg tgtcgtatac acttggtcct tggaggaggg gctgagctgg    5280
gagacctccg agccatttac cacccatagc ttccccacac ccggcctgca cttggtcacc    5340
atgacggcag ggaacccgct gggctcagcc aacgccaccg tggaagtgga tgtgcaggtg    5400
cctgtgagtg gcctcagcat cagggccagc gagcccggag gcagcttcgt ggcggccggg    5460
tcctctgtgc cctttggggg gcagctggcc acgggcacca atgtgagctg gtgctgggct    5520
gtgcccggcg gcagcagcaa gcgtggccct catgtcacca tggtcttccc ggatgctggc    5580
accttctcca tccggctcaa tgcctccaac gcagtcagct gggtctcagc cacgtacaac    5640
ctcacggcgg aggagcccat cgtgggcctg gtgctgtggg ccagcagcaa ggtggtggcg    5700
cccgggcagc tggtccattt tcagatcctg ctggctgccg gctcagctgt caccttccgc    5760
ctgcaggtcg gcggggccaa ccccgaggtg ctccccgggc ccgtttctc ccacagcttc    5820 ccccgcgtcg gagaccacgt ggtgagcgtg cggggcaaaa accacgtgag ctgggcccag    5880
gcgcaggtgc gcatcgtggt gctggaggcc gtgagtgggc tgcagatgcc caactgctgc    5940
gagcctggca tcgccacggg cactgagagg aacttcacag cccgcgtgca gcgcggctct    6000
cgggtcgcct acgcctggta cttctcgctg cagaaggtcc agggcgactc gctggtcatc    6060
ctgtcgggcc gcgacgtcac ctacacgccc gtggccgcgg ggctgttgga gatccaggtg    6120
cgcgccttca acgccctggg cagtgagaac cgcacgctgg tgctggaggt tcaggacgcc    6180
gtccagtatg tggccctgca gagcggcccc tgcttcacca accgctcggc gcagtttgag    6240
gccgccacca gccccagccc ccggcgtgtg gcctaccact gggactttgg ggatgggtcg    6300
ccagggcagg acacagatga gcccagggcc gagcactcct acctgaggcc tggggactac    6360
cgcgtgcagg tgaacgcctc caacctggtg agcttcttcg tggcgcaggc cacggtgacc    6420
gtccaggtgc tggcctgccg ggagccggag gtggacgtgg tcctgcccct gcaggtgctg    6480
atgcggcgat cacagcgcaa ctacttggag gcccacgttg acctgcgcga ctgcgtcacc    6540
taccagactg agtaccgctg ggaggtgtat cgcaccgcca gctgccagcg gccggggcgc    6600
ccagcgcgtg tggccctgcc cggcgtggac gtgagccggc ctcggctggt gctgccgcgg    6660
```

```
ctggcgctgc ctgtggggca ctactgcttt gtgtttgtcg tgtcatttgg ggacacgcca    6720
ctgacacaga gcatccaggc caatgtgacg gtggcccccg agcgcctggt gcccatcatt    6780
gagggtggct cataccgcgt gtggtcagac acacgggacc tggtgctgga tgggagcgag    6840
tcctacgacc ccaacctgga ggacggcgac cagacgccgc tcagtttcca ctgggcctgt    6900
gtggcttcga cacagaggga ggctggcggg tgtgcgctga actttgggcc ccgcgggagc    6960
agcacggtca ccattccacg ggagcggctg gcggctggcg tggagtacac cttcagcctg    7020
accgtgtgga aggccggccg caaggaggag gccaccaacc agacggtgct gatccggagt    7080
ggccgggtgc ccattgtgtc cttggagtgt gtgtcctgca aggcacaggc cgtgtacgaa    7140
gtgagccgca gctcctacgt gtacttggag ggccgctgcc tcaattgcag cagcggctcc    7200
aagcgagggc ggtgggctgc acgtacgttc agcaacaaga cgctggtgct ggatgagacc    7260
accacatcca cgggcagtgc aggcatgcga ctggtgctgc ggcggggcgt gctgcgggac    7320
ggcgagggat acaccttcac gctcacggtg ctgggccgct ctggcgagga ggagggctgc    7380
gcctccatcc gcctgtcccc caaccgcccg ccgctggggg gctcttgccg cctcttccca    7440
ctgggcgctg tgcacgccct caccaccaag gtgcacttcg aatgcacggg ctggcatgac    7500
gcggaggatg ctggcgcccc gctggtgtac gccctgctgc tgcggcgctg tcgccagggc    7560
cactgcgagg agttctgtgt ctacaagggc agcctctcca gctacggagc cgtgctgccc    7620
ccgggtttca ggccacactt cgaggtgggc ctggccgtgg tggtgcagga ccagctggga    7680
gccgctgtgg tcgccctcaa caggtctttg gccatcaccc tcccagagcc caacggcagc    7740
gcaacggggc tcacagtctg gctgcacggg ctcaccgcta gtgtgctccc agggctgctg    7800
cggcaggccg atccccagca cgtcatcgag tactcgttgg ccctggtcac cgtgctgaac    7860
gagtacgagc gggccctgga cgtggcggca gagcccaagc acgagcggca gcaccgagcc    7920
cagatacgca agaacatcac ggagactctg tgtccctga gggtccacac tgtggatgac    7980
atccagcaga tcgctgctgc gctggcccag tgcatggggc ccagcaggga gctcgtatgc    8040
cgctcgtgcc tgaagcagac gctgcacaag ctggaggcca tgatgctcat cctgcaggca    8100
gagaccaccg cgggcaccgt gacgcccacc gccatcggag acagcatcct caacatcaca    8160
ggagacctca tccacctggc cagctcggac gtgcgggcac cacagccctc agagctggga    8220
gccgagtcac catctcggat ggtggcgtcc caggcctaca acctgacctc tgccctcatg    8280
cgcatcctca tgcgctcccg cgtgctcaac gaggagcccc tgacgctggc gggcgaggag    8340
atcgtggccc agggcaagcg ctcggacccg cggagcctgc tgtgctatgg cggcgcccca    8400
gggcctggct gccacttctc catccccgag gctttcagcg gggccctggc caacctcagt    8460
gacgtggtgc agctcatctt tctggtggac tccaatccct tcccttttgg ctatatcagc    8520
aactacaccg tctccaccaa ggtggcctcg atggcattcc agacacaggc cggcgcccag    8580
atccccatcg agcggctggc ctcagagcgc gccataccg tgaaggtgcc caacaactcg    8640
gactgggctg cccggggcca ccgcagctcc gccaactccg ccaactccgt tgtggtccag    8700
ccccaggcct ccgtcggtgc tgtggtcacc ctgacagca gcaaccctgc ggccgggctg    8760
catctgcagc tcaactatac gctgctggac ggccactacc tgtctgagga acctgagccc    8820
tacctggcag tctacctaca ctcggagccc cggcccaatg agcacaactg ctcggctagc    8880
aggaggatcc gcccagagtc actccagggt gctgaccacc ggcccttacac cttcttcatt    8940 tccccgggga gcagagaccc agcggggagt taccatctga acctctccag ccacttccgc    9000
```

```
tggtcggcgc tgcaggtgtc cgtgggcctg tacacgtccc tgtgccagta cttcagcgag   9060
gaggacatgg tgtggcggac agaggggctg ctgcccctgg aggagacctc gccccgccag   9120
gccgtctgcc tcacccgcca cctcaccgcc ttcggcgcca gcctcttcgt gcccccaagc   9180
catgtccgct ttgtgtttcc tgagccgaca gcggatgtaa actacatcgt catgctgaca   9240
tgtgctgtgt gcctggtgac ctacatggtc atggccgcca tcctgcacaa gctggaccag   9300
ttggatgcca gccggggccg cgccatccct ttctgtgggc agcggggccg cttcaagtac   9360
gagatcctcg tcaagacagg ctggggccgg ggctcaggta ccacggccca cgtgggcatc   9420
atgctgtatg gggtggacag ccggagcggc accggcacc tggacggcga cagagccttc   9480
caccgcaaca gcctggacat cttccggatc gccaccccgc acagcctggg tagcgtgtgg   9540
aagatccgag tgtggcacga caacaaaggg ctcagccctg cctggttcct gcagcacgtc   9600
atcgtcaggg acctgcagac ggcacgcagc gccttcttcc tggtcaatga ctggctttcg   9660
gtggagacgg aggccaacgg gggcctggtg gagaaggagg tgctggccgc gagcgacgca   9720
gcccttttgc gcttccggcg cctgctgtg gctgagctgc agcgtggctt ctttgacaag   9780
cacatctggc tctccatatg ggaccggccg cctcgtagcc gtttcactcg catccagagg   9840
gccacctgct gcgttctcct catctgcctc ttcctgggcg ccaacgccgt gtggtacggg   9900
gctgttggcg actctgccta cagcacgggg catgtgtcca ggctgagccc gctgagcgtc   9960
gacacagtcg ctgttggcct ggtgtccagc gtggttgtct atcccgtcta cctggccatc  10020
ctttttctct tccggatgtc ccggagcaag gtggctggga gcccgagccc cacacctgcc  10080
gggcagcagg tgctggacat cgacagctgc ctggactcgt ccgtgctgga cagctccttc  10140
ctcacgttct caggcctcca cgctgaggcc tttgttggac agatgaagag tgacttgttt  10200
ctggatgatt ctaagagtct ggtgtgctgg ccctccggcg agggaacgct cagttggccg  10260
gacctgctca gtgacccgtc cattgtgggt agcaatctgc ggcagctggc acggggccag  10320
gcgggccatg gctgggccc agaggaggac ggcttctccc tggccagccc ctactcgcct  10380
gccaaatcct tctcagcatc agatgaagac ctgatccagc aggtccttgc cgaggggtc  10440
agcagcccag cccctaccca agacacccac atggaaacgg acctgctcag cagcctgtcc  10500
agcactcctg gggagaagac agagacgctg cgctgcaga ggctggggga ctggggcca  10560
cccagcccag gctgaactg gaacagccc caggcagcga ggctgtccag gacaggactg  10620
gtggagggtc tgcggaagcg cctgctgccg gcctggtgtg cctccctggc ccacgggctc  10680
agcctgctcc tggtggctgt ggctgtggct gtctcagggt gggtgggtgc gagcttcccc  10740
ccgggcgtga gtgttgcgtg gctcctgtcc agcagcgcca gcttcctggc ctcattcctc  10800
ggctgggagc cactgaaggt cttgctggaa gccctgtact tctcactggt ggccaagcgg  10860
ctgcacccgg atgaagatga cacctggta gagagcccgg ctgtgacgcc tgtgagcgca  10920
cgtgtgcccc gcgtacggcc accccacggc tttgcactct tcctggccaa ggaagaagcc  10980
cgcaaggtca agaggctaca tggcatgctg cggagcctcc tggtgtacat gctttttctg  11040
ctggtgaccc tgctggccag ctatggggat gcctcatgcc atgggcacgc ctaccgtctg  11100
caaagcgcca tcaagcagga gctgcacagc cgggccttcc tggccatcac gcggtctgag  11160
gagctctggc catggatggc ccacgtgctg ctgccctacg tccacgggaa ccagtccagc  11220
ccagagctgg gccccccacg gctgcggcag gtgcggctgc aggaagcact ctacccagac  11280
cctcccggcc ccagggtcca cacgtgctcg gccgcaggag gcttcagcac cagcgattac  11340
gacgttggct gggagagtcc tcacaatggc tcggggacgt gggcctattc agcgccggat  11400
```

```
ctgctggggg catggtcctg gggctcctgt gccgtgtatg acagcggggg ctacgtgcag   11460
gagctgggcc tgagcctgga ggagagccgc gaccggctgc gcttcctgca gctgcacaac   11520
tggctggaca acaggagccg cgctgtgttc ctggagctca cgcgctacag cccggccgtg   11580
gggctgcacg ccgccgtcac gctgcgcctc gagttcccgg cggccggccg cgccctggcc   11640
gccctcagcg tccgccccct tgcgctgcgc cgcctcagcg cgggcctctc gctgcctctg   11700
ctcacctcgg tgtgcctgct gctgttcgcc gtgcacttcg ccgtgccgga ggcccgtact   11760
tggcacaggg aagggcgctg gcgcgtgctg cggctcggag cctgggcgcg gtggctgctg   11820
gtggcgctga cggcggccac ggcactggta cgcctcgccc agctgggtgc cgctgaccgc   11880
cagtggaccc gtttcgtgcg cggccgcccg cgccgcttca ctagcttcga ccaggtggcg   11940
cagctgagct ccgcagcccg tggcctggcg gcctcgctgc tcttcctgct tttggtcaag   12000
gctgcccagc agctacgctt cgtgcgccag tggtccgtct ttggcaagac attatgccga   12060
gctctgccag agtcctgggg ggtcaccttg gcctggtgg tgctcggggt agcctacgcc   12120
cagctggcca tcctgctcgt gtcttcctgt gtggactccc tctggagcgt ggcccaggcc   12180
ctgttggtgc tgtgccctgg gactgggctc tctaccctgt gtcctgccga gtcctggcac   12240
ctgtcacccc tgctgtgtgt ggggctctgg gcactgcggc tgtggggcgc cctacggctg   12300
ggggctgtta ttctccgctg gcgctaccac gccttgcgtg gagagctgta ccggccggcc   12360
tgggagcccc aggactacga gatggtggag ttgttcctgc gcaggctgcg cctctggatg   12420
ggcctcagca aggtcaagga gttccgccac aaagtccgct ttgaagggat ggagccgctg   12480
ccctctcgct cctccagggg ctccaaggta tccccggatg tgcccccacc cagcgctggc   12540
tccgatgcct cgcaccccctc cacctcctcc agccagctgg atgggctgag cgtgagcctg   12600
ggccggctgg ggacaaggtg tgagcctgag ccctcccgcc tccaagccgt gttcgaggcc   12660
ctgctcaccc agtttgaccg actcaaccag gccacagagg acgtctacca gctggagcag   12720
cagctgcaca gcctgcaagg ccgcaggagc agccgggcgc ccgccggatc ttcccgtggc   12780
ccatccccgg gcctgcggcc agcactgccc agccgccttg cccgggccag tcggggtgtg   12840
gacctggcca ctggccccag caggacaccc cttcgggcca gaacaaggt ccaccccagc   12900 agcacttag                                                           12909
```

<210> SEQ ID NO 3
<211> LENGTH: 4302
<212> TYPE: PRT
<213> ORGANISM: Homo sapiens

<400> SEQUENCE: 3

Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
            20                  25                  30

Cys Glu Pro Pro Cys Leu Cys Gly Pro Ala Pro Gly Ala Ala Cys Arg
        35                  40                  45

Val Asn Cys Ser Gly Arg Gly Leu Arg Thr Leu Gly Pro Ala Leu Arg
    50                  55                  60

Ile Pro Ala Asp Ala Thr Ala Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

```
Asp Ile Ser Asn Asn Lys Ile Ser Thr Leu Glu Glu Gly Ile Phe Ala
                100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Arg Trp Ala Glu Glu Gln Gln
    130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Ala Thr Arg
    290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
        355                 360                 365

Ser Asp Glu Ser Leu Asp Leu Ser Ile Gln Asn Arg Gly Gly Ser Gly
    370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
            420                 425                 430

Gln Glu Gln Cys Gln Ala Trp Ala Gly Ala Ala Leu Ala Met Val Asp
        435                 440                 445

Ser Pro Ala Val Gln Arg Phe Leu Val Ser Arg Val Thr Arg Ser Leu
    450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
            500                 505                 510

Pro Thr Gly Trp Cys Asn Thr Asp Leu Cys Ser Ala Pro His Ser Tyr
```

```
            515                 520                 525
Val Cys Glu Leu Gln Pro Gly Gly Pro Val Gln Asp Ala Glu Asn Leu
            530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
                565                 570                 575

Val Phe Pro Gly Leu Arg Leu Ser Arg Glu Ala Phe Leu Thr Thr Ala
                580                 585                 590

Glu Phe Gly Thr Gln Glu Leu Arg Arg Pro Ala Gln Leu Arg Leu Gln
                595                 600                 605

Val Tyr Arg Leu Leu Ser Thr Ala Gly Thr Pro Glu Asn Gly Ser Glu
            610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
                645                 650                 655

Asp Ala Ser Cys His Pro Gln Ala Cys Ala Asn Gly Cys Thr Ser Gly
                660                 665                 670

Pro Gly Leu Pro Gly Ala Pro Tyr Ala Leu Trp Arg Glu Phe Leu Phe
            675                 680                 685

Ser Val Ala Ala Gly Pro Pro Ala Gln Tyr Ser Val Thr Leu His Gly
            690                 695                 700

Gln Asp Val Leu Met Leu Pro Gly Asp Leu Val Gly Leu Gln His Asp
705                 710                 715                 720

Ala Gly Pro Gly Ala Leu Leu His Cys Ser Pro Ala Pro Gly His Pro
                725                 730                 735

Gly Pro Gln Ala Pro Tyr Leu Ser Ala Asn Ala Ser Ser Trp Leu Pro
                740                 745                 750

His Leu Pro Ala Gln Leu Glu Gly Thr Trp Ala Cys Pro Ala Cys Ala
                755                 760                 765

Leu Arg Leu Leu Ala Ala Thr Glu Gln Leu Thr Val Leu Leu Gly Leu
            770                 775                 780

Arg Pro Asn Pro Gly Leu Arg Met Pro Gly Arg Tyr Glu Val Arg Ala
785                 790                 795                 800

Glu Val Gly Asn Gly Val Ser Arg His Asn Leu Ser Cys Ser Phe Asp
                805                 810                 815

Val Val Ser Pro Val Ala Gly Leu Arg Val Ile Tyr Pro Ala Pro Arg
                820                 825                 830

Asp Gly Arg Leu Tyr Val Pro Thr Asn Gly Ser Ala Leu Val Leu Gln
            835                 840                 845

Val Asp Ser Gly Ala Asn Ala Thr Ala Thr Ala Arg Trp Pro Gly Gly
            850                 855                 860

Ser Val Ser Ala Arg Phe Glu Asn Val Cys Pro Ala Leu Val Ala Thr
865                 870                 875                 880

Phe Val Pro Gly Cys Pro Trp Glu Thr Asn Asp Thr Leu Phe Ser Val
                885                 890                 895

Val Ala Leu Pro Trp Leu Ser Glu Gly Glu His Val Val Asp Val Val
                900                 905                 910

Val Glu Asn Ser Ala Ser Arg Ala Asn Leu Ser Leu Arg Val Thr Ala
                915                 920                 925

Glu Glu Pro Ile Cys Gly Leu Arg Ala Thr Pro Ser Pro Glu Ala Arg
            930                 935                 940
```

```
Val Leu Gln Gly Val Leu Val Arg Tyr Ser Pro Val Val Glu Ala Gly
945                 950                 955                 960

Ser Asp Met Val Phe Arg Trp Thr Ile Asn Asp Lys Gln Ser Leu Thr
                965                 970                 975

Phe Gln Asn Val Val Phe Asn Val Ile Tyr Gln Ser Ala Ala Val Phe
            980                 985                 990

Lys Leu Ser Leu Thr Ala Ser Asn His Val Ser Asn Val Thr Val Asn
        995                 1000                1005

Tyr Asn Val Thr Val Glu Arg Met Asn Arg Met Gln Gly Leu Gln
    1010                1015                1020

Val Ser Thr Val Pro Ala Val Leu Ser Pro Asn Ala Thr Leu Ala
    1025                1030                1035

Leu Thr Ala Gly Val Leu Val Asp Ser Ala Val Glu Val Ala Phe
    1040                1045                1050

Leu Trp Asn Phe Gly Asp Gly Glu Gln Ala Leu His Gln Phe Gln
    1055                1060                1065

Pro Pro Tyr Asn Glu Ser Phe Pro Val Pro Asp Pro Ser Val Ala
    1070                1075                1080

Gln Val Leu Val Glu His Asn Val Met His Thr Tyr Ala Ala Pro
    1085                1090                1095

Gly Glu Tyr Leu Leu Thr Val Leu Ala Ser Asn Ala Phe Glu Asn
    1100                1105                1110

Leu Thr Gln Gln Val Pro Val Ser Val Arg Ala Ser Leu Pro Ser
    1115                1120                1125

Val Ala Val Gly Val Ser Asp Gly Val Leu Val Ala Gly Arg Pro
    1130                1135                1140

Val Thr Phe Tyr Pro His Pro Leu Pro Ser Pro Gly Gly Val Leu
    1145                1150                1155

Tyr Thr Trp Asp Phe Gly Asp Gly Ser Pro Val Leu Thr Gln Ser
    1160                1165                1170

Gln Pro Ala Ala Asn His Thr Tyr Ala Ser Arg Gly Thr Tyr His
    1175                1180                1185

Val Arg Leu Glu Val Asn Asn Thr Val Ser Gly Ala Ala Ala Gln
    1190                1195                1200

Ala Asp Val Arg Val Phe Glu Leu Arg Gly Leu Ser Val Asp
    1205                1210                1215

Met Ser Leu Ala Val Glu Gln Gly Ala Pro Val Val Ser Ala
    1220                1225                1230

Ala Val Gln Thr Gly Asp Asn Ile Thr Trp Thr Phe Asp Met Gly
    1235                1240                1245

Asp Gly Thr Val Leu Ser Gly Pro Glu Ala Thr Val Glu His Val
    1250                1255                1260

Tyr Leu Arg Ala Gln Asn Cys Thr Val Thr Val Gly Ala Ala Ser
    1265                1270                1275

Pro Ala Gly His Leu Ala Arg Ser Leu His Val Leu Val Phe Val
    1280                1285                1290

Leu Glu Val Leu Arg Val Glu Pro Ala Ala Cys Ile Pro Thr Gln
    1295                1300                1305

Pro Asp Ala Arg Leu Thr Ala Tyr Val Thr Gly Asn Pro Ala His
    1310                1315                1320

Tyr Leu Phe Asp Trp Thr Phe Gly Asp Gly Ser Ser Asn Thr Thr
    1325                1330                1335
```

-continued

```
Val Arg Gly Cys Pro Thr Val Thr His Asn Phe Thr Arg Ser Gly
1340                 1345                 1350

Thr Phe Pro Leu Ala Leu Val Leu Ser Ser Arg Val Asn Arg Ala
1355                 1360                 1365

His Tyr Phe Thr Ser Ile Cys Val Glu Pro Glu Val Gly Asn Val
1370                 1375                 1380

Thr Leu Gln Pro Glu Arg Gln Phe Val Gln Leu Gly Asp Glu Ala
1385                 1390                 1395

Trp Leu Val Ala Cys Ala Trp Pro Pro Phe Pro Tyr Arg Tyr Thr
1400                 1405                 1410

Trp Asp Phe Gly Thr Glu Glu Ala Ala Pro Thr Arg Ala Arg Gly
1415                 1420                 1425

Pro Glu Val Thr Phe Ile Tyr Arg Asp Pro Gly Ser Tyr Leu Val
1430                 1435                 1440

Thr Val Thr Ala Ser Asn Asn Ile Ser Ala Ala Asn Asp Ser Ala
1445                 1450                 1455

Leu Val Glu Val Gln Glu Pro Val Leu Val Thr Ser Ile Lys Val
1460                 1465                 1470

Asn Gly Ser Leu Gly Leu Glu Leu Gln Gln Pro Tyr Leu Phe Ser
1475                 1480                 1485

Ala Val Gly Arg Gly Arg Pro Ala Ser Tyr Leu Trp Asp Leu Gly
1490                 1495                 1500

Asp Gly Gly Trp Leu Glu Gly Pro Glu Val Thr His Ala Tyr Asn
1505                 1510                 1515

Ser Thr Gly Asp Phe Thr Val Arg Val Ala Gly Trp Asn Glu Val
1520                 1525                 1530

Ser Arg Ser Glu Ala Trp Leu Asn Val Thr Val Lys Arg Arg Val
1535                 1540                 1545

Arg Gly Leu Val Val Asn Ala Ser Arg Thr Val Val Pro Leu Asn
1550                 1555                 1560

Gly Ser Val Ser Phe Ser Thr Ser Leu Glu Ala Gly Ser Asp Val
1565                 1570                 1575

Arg Tyr Ser Trp Val Leu Cys Asp Arg Cys Thr Pro Ile Pro Gly
1580                 1585                 1590

Gly Pro Thr Ile Ser Tyr Thr Phe Arg Ser Val Gly Thr Phe Asn
1595                 1600                 1605

Ile Ile Val Thr Ala Glu Asn Glu Val Gly Ser Ala Gln Asp Ser
1610                 1615                 1620

Ile Phe Val Tyr Val Leu Gln Leu Ile Glu Gly Leu Gln Val Val
1625                 1630                 1635

Gly Gly Gly Arg Tyr Phe Pro Thr Asn His Thr Val Gln Leu Gln
1640                 1645                 1650

Ala Val Val Arg Asp Gly Thr Asn Val Ser Tyr Ser Trp Thr Ala
1655                 1660                 1665

Trp Arg Asp Arg Gly Pro Ala Leu Ala Gly Ser Gly Lys Gly Phe
1670                 1675                 1680

Ser Leu Thr Val Leu Glu Ala Gly Thr Tyr His Val Gln Leu Arg
1685                 1690                 1695

Ala Thr Asn Met Leu Gly Ser Ala Trp Ala Asp Cys Thr Met Asp
1700                 1705                 1710

Phe Val Glu Pro Val Gly Trp Leu Met Val Thr Ala Ser Pro Asn
1715                 1720                 1725

Pro Ala Ala Val Asn Thr Ser Val Thr Leu Ser Ala Glu Leu Ala
```

```
                1730                1735                1740
Gly Gly Ser Gly Val Val Tyr Thr Trp Ser Leu Glu Glu Gly Leu
        1745                1750                1755
Ser Trp Glu Thr Ser Glu Pro Phe Thr Thr His Ser Phe Pro Thr
        1760                1765                1770
Pro Gly Leu His Leu Val Thr Met Thr Ala Gly Asn Pro Leu Gly
        1775                1780                1785
Ser Ala Asn Ala Thr Val Glu Val Asp Val Gln Val Pro Val Ser
        1790                1795                1800
Gly Leu Ser Ile Arg Ala Ser Glu Pro Gly Gly Ser Phe Val Ala
        1805                1810                1815
Ala Gly Ser Ser Val Pro Phe Trp Gly Gln Leu Ala Thr Gly Thr
        1820                1825                1830
Asn Val Ser Trp Cys Trp Ala Val Pro Gly Gly Ser Ser Lys Arg
        1835                1840                1845
Gly Pro His Val Thr Met Val Phe Pro Asp Ala Gly Thr Phe Ser
        1850                1855                1860
Ile Arg Leu Asn Ala Ser Asn Ala Val Ser Trp Val Ser Ala Thr
        1865                1870                1875
Tyr Asn Leu Thr Ala Glu Glu Pro Ile Val Gly Leu Val Leu Trp
        1880                1885                1890
Ala Ser Ser Lys Val Val Ala Pro Gly Gln Leu Val His Phe Gln
        1895                1900                1905
Ile Leu Leu Ala Ala Gly Ser Ala Val Thr Phe Arg Leu Gln Val
        1910                1915                1920
Gly Gly Ala Asn Pro Glu Val Leu Pro Gly Pro Arg Phe Ser His
        1925                1930                1935
Ser Phe Pro Arg Val Gly Asp His Val Val Ser Val Arg Gly Lys
        1940                1945                1950
Asn His Val Ser Trp Ala Gln Ala Gln Val Arg Ile Val Val Leu
        1955                1960                1965
Glu Ala Val Ser Gly Leu Gln Met Pro Asn Cys Cys Glu Pro Gly
        1970                1975                1980
Ile Ala Thr Gly Thr Glu Arg Asn Phe Thr Ala Arg Val Gln Arg
        1985                1990                1995
Gly Ser Arg Val Ala Tyr Ala Trp Tyr Phe Ser Leu Gln Lys Val
        2000                2005                2010
Gln Gly Asp Ser Leu Val Ile Leu Ser Gly Arg Asp Val Thr Tyr
        2015                2020                2025
Thr Pro Val Ala Ala Gly Leu Leu Glu Ile Gln Val Arg Ala Phe
        2030                2035                2040
Asn Ala Leu Gly Ser Glu Asn Arg Thr Leu Val Leu Glu Val Gln
        2045                2050                2055
Asp Ala Val Gln Tyr Val Ala Leu Gln Ser Gly Pro Cys Phe Thr
        2060                2065                2070
Asn Arg Ser Ala Gln Phe Glu Ala Ala Thr Ser Pro Ser Pro Arg
        2075                2080                2085
Arg Val Ala Tyr His Trp Asp Phe Gly Asp Gly Ser Pro Gly Gln
        2090                2095                2100
Asp Thr Asp Glu Pro Arg Ala Glu His Ser Tyr Leu Arg Pro Gly
        2105                2110                2115
Asp Tyr Arg Val Gln Val Asn Ala Ser Asn Leu Val Ser Phe Phe
        2120                2125                2130
```

```
Val Ala Gln Ala Thr Val Thr Val Gln Val Leu Ala Cys Arg Glu
    2135            2140            2145

Pro Glu Val Asp Val Val Leu Pro Leu Gln Val Leu Met Arg Arg
    2150            2155            2160

Ser Gln Arg Asn Tyr Leu Glu Ala His Val Asp Leu Arg Asp Cys
    2165            2170            2175

Val Thr Tyr Gln Thr Glu Tyr Arg Trp Glu Val Tyr Arg Thr Ala
    2180            2185            2190

Ser Cys Gln Arg Pro Gly Arg Pro Ala Arg Val Ala Leu Pro Gly
    2195            2200            2205

Val Asp Val Ser Arg Pro Arg Leu Val Leu Pro Arg Leu Ala Leu
    2210            2215            2220

Pro Val Gly His Tyr Cys Phe Val Phe Val Val Ser Phe Gly Asp
    2225            2230            2235

Thr Pro Leu Thr Gln Ser Ile Gln Ala Asn Val Thr Val Ala Pro
    2240            2245            2250

Glu Arg Leu Val Pro Ile Ile Glu Gly Gly Ser Tyr Arg Val Trp
    2255            2260            2265

Ser Asp Thr Arg Asp Leu Val Leu Asp Gly Ser Glu Ser Tyr Asp
    2270            2275            2280

Pro Asn Leu Glu Asp Gly Asp Gln Thr Pro Leu Ser Phe His Trp
    2285            2290            2295

Ala Cys Val Ala Ser Thr Gln Arg Glu Ala Gly Gly Cys Ala Leu
    2300            2305            2310

Asn Phe Gly Pro Arg Gly Ser Ser Thr Val Thr Ile Pro Arg Glu
    2315            2320            2325

Arg Leu Ala Ala Gly Val Glu Tyr Thr Phe Ser Leu Thr Val Trp
    2330            2335            2340

Lys Ala Gly Arg Lys Glu Glu Ala Thr Asn Gln Thr Val Leu Ile
    2345            2350            2355

Arg Ser Gly Arg Val Pro Ile Val Ser Leu Glu Cys Val Ser Cys
    2360            2365            2370

Lys Ala Gln Ala Val Tyr Glu Val Ser Arg Ser Ser Tyr Val Tyr
    2375            2380            2385

Leu Glu Gly Arg Cys Leu Asn Cys Ser Ser Gly Ser Lys Arg Gly
    2390            2395            2400

Arg Trp Ala Ala Arg Thr Phe Ser Asn Lys Thr Leu Val Leu Asp
    2405            2410            2415

Glu Thr Thr Thr Ser Thr Gly Ser Ala Gly Met Arg Leu Val Leu
    2420            2425            2430

Arg Arg Gly Val Leu Arg Asp Gly Glu Gly Tyr Thr Phe Thr Leu
    2435            2440            2445

Thr Val Leu Gly Arg Ser Gly Glu Glu Glu Gly Cys Ala Ser Ile
    2450            2455            2460

Arg Leu Ser Pro Asn Arg Pro Pro Leu Gly Gly Ser Cys Arg Leu
    2465            2470            2475

Phe Pro Leu Gly Ala Val His Ala Leu Thr Thr Lys Val His Phe
    2480            2485            2490

Glu Cys Thr Gly Trp His Asp Ala Glu Asp Ala Gly Ala Pro Leu
    2495            2500            2505

Val Tyr Ala Leu Leu Leu Arg Arg Cys Arg Gln Gly His Cys Glu
    2510            2515            2520
```

```
Glu Phe Cys Val Tyr Lys Gly Ser Leu Ser Ser Tyr Gly Ala Val
2525                2530                2535

Leu Pro Pro Gly Phe Arg Pro His Phe Glu Val Gly Leu Ala Val
2540                2545                2550

Val Val Gln Asp Gln Leu Gly Ala Ala Val Val Ala Leu Asn Arg
2555                2560                2565

Ser Leu Ala Ile Thr Leu Pro Glu Pro Asn Gly Ser Ala Thr Gly
2570                2575                2580

Leu Thr Val Trp Leu His Gly Leu Thr Ala Ser Val Leu Pro Gly
2585                2590                2595

Leu Leu Arg Gln Ala Asp Pro Gln His Val Ile Glu Tyr Ser Leu
2600                2605                2610

Ala Leu Val Thr Val Leu Asn Glu Tyr Glu Arg Ala Leu Asp Val
2615                2620                2625

Ala Ala Glu Pro Lys His Glu Arg Gln His Arg Ala Gln Ile Arg
2630                2635                2640

Lys Asn Ile Thr Glu Thr Leu Val Ser Leu Arg Val His Thr Val
2645                2650                2655

Asp Asp Ile Gln Gln Ile Ala Ala Ala Leu Ala Gln Cys Met Gly
2660                2665                2670

Pro Ser Arg Glu Leu Val Cys Arg Ser Cys Leu Lys Gln Thr Leu
2675                2680                2685

His Lys Leu Glu Ala Met Met Leu Ile Leu Gln Ala Glu Thr Thr
2690                2695                2700

Ala Gly Thr Val Thr Pro Thr Ala Ile Gly Asp Ser Ile Leu Asn
2705                2710                2715

Ile Thr Gly Asp Leu Ile His Leu Ala Ser Ser Asp Val Arg Ala
2720                2725                2730

Pro Gln Pro Ser Glu Leu Gly Ala Glu Ser Pro Ser Arg Met Val
2735                2740                2745

Ala Ser Gln Ala Tyr Asn Leu Thr Ser Ala Leu Met Arg Ile Leu
2750                2755                2760

Met Arg Ser Arg Val Leu Asn Glu Glu Pro Leu Thr Leu Ala Gly
2765                2770                2775

Glu Glu Ile Val Ala Gln Gly Lys Arg Ser Asp Pro Arg Ser Leu
2780                2785                2790

Leu Cys Tyr Gly Gly Ala Pro Gly Pro Gly Cys His Phe Ser Ile
2795                2800                2805

Pro Glu Ala Phe Ser Gly Ala Leu Ala Asn Leu Ser Asp Val Val
2810                2815                2820

Gln Leu Ile Phe Leu Val Asp Ser Asn Pro Phe Pro Phe Gly Tyr
2825                2830                2835

Ile Ser Asn Tyr Thr Val Ser Thr Lys Val Ala Ser Met Ala Phe
2840                2845                2850

Gln Thr Gln Ala Gly Ala Gln Ile Pro Ile Glu Arg Leu Ala Ser
2855                2860                2865

Glu Arg Ala Ile Thr Val Lys Val Pro Asn Asn Ser Asp Trp Ala
2870                2875                2880

Ala Arg Gly His Arg Ser Ser Ala Asn Ser Ala Asn Ser Val Val
2885                2890                2895

Val Gln Pro Gln Ala Ser Val Gly Ala Val Val Thr Leu Asp Ser
2900                2905                2910

Ser Asn Pro Ala Ala Gly Leu His Leu Gln Leu Asn Tyr Thr Leu
```

-continued

```
                 2915                2920                2925

Leu Asp Gly His Tyr Leu Ser Glu Glu Pro Glu Pro Tyr Leu Ala
            2930                2935                2940

Val Tyr Leu His Ser Glu Pro Arg Pro Asn Glu His Asn Cys Ser
            2945                2950                2955

Ala Ser Arg Arg Ile Arg Pro Glu Ser Leu Gln Gly Ala Asp His
            2960                2965                2970

Arg Pro Tyr Thr Phe Phe Ile Ser Pro Gly Ser Arg Asp Pro Ala
            2975                2980                2985

Gly Ser Tyr His Leu Asn Leu Ser Ser His Phe Arg Trp Ser Ala
            2990                2995                3000

Leu Gln Val Ser Val Gly Leu Tyr Thr Ser Leu Cys Gln Tyr Phe
            3005                3010                3015

Ser Glu Glu Asp Met Val Trp Arg Thr Glu Gly Leu Leu Pro Leu
            3020                3025                3030

Glu Glu Thr Ser Pro Arg Gln Ala Val Cys Leu Thr Arg His Leu
            3035                3040                3045

Thr Ala Phe Gly Ala Ser Leu Phe Val Pro Pro Ser His Val Arg
            3050                3055                3060

Phe Val Phe Pro Glu Pro Thr Ala Asp Val Asn Tyr Ile Val Met
            3065                3070                3075

Leu Thr Cys Ala Val Cys Leu Val Thr Tyr Met Val Met Ala Ala
            3080                3085                3090

Ile Leu His Lys Leu Asp Gln Leu Asp Ala Ser Arg Gly Arg Ala
            3095                3100                3105

Ile Pro Phe Cys Gly Gln Arg Gly Arg Phe Lys Tyr Glu Ile Leu
            3110                3115                3120

Val Lys Thr Gly Trp Gly Arg Gly Ser Gly Thr Thr Ala His Val
            3125                3130                3135

Gly Ile Met Leu Tyr Gly Val Asp Ser Arg Ser Gly His Arg His
            3140                3145                3150

Leu Asp Gly Asp Arg Ala Phe His Arg Asn Ser Leu Asp Ile Phe
            3155                3160                3165

Arg Ile Ala Thr Pro His Ser Leu Gly Ser Val Trp Lys Ile Arg
            3170                3175                3180

Val Trp His Asp Asn Lys Gly Leu Ser Pro Ala Trp Phe Leu Gln
            3185                3190                3195

His Val Ile Val Arg Asp Leu Gln Thr Ala Arg Ser Ala Phe Phe
            3200                3205                3210

Leu Val Asn Asp Trp Leu Ser Val Glu Thr Glu Ala Asn Gly Gly
            3215                3220                3225

Leu Val Glu Lys Glu Val Leu Ala Ala Ser Asp Ala Ala Leu Leu
            3230                3235                3240

Arg Phe Arg Arg Leu Leu Val Ala Glu Leu Gln Arg Gly Phe Phe
            3245                3250                3255

Asp Lys His Ile Trp Leu Ser Ile Trp Asp Arg Pro Pro Arg Ser
            3260                3265                3270

Arg Phe Thr Arg Ile Gln Arg Ala Thr Cys Cys Val Leu Leu Ile
            3275                3280                3285

Cys Leu Phe Leu Gly Ala Asn Ala Val Trp Tyr Gly Ala Val Gly
            3290                3295                3300

Asp Ser Ala Tyr Ser Thr Gly His Val Ser Arg Leu Ser Pro Leu
            3305                3310                3315
```

-continued

Ser Val Asp Thr Val Ala Val Gly Leu Val Ser Val Val Val
    3320            3325            3330

Tyr Pro Val Tyr Leu Ala Ile Leu Phe Leu Phe Arg Met Ser Arg
    3335            3340            3345

Ser Lys Val Ala Gly Ser Pro Ser Pro Thr Pro Ala Gly Gln Gln
    3350            3355            3360

Val Leu Asp Ile Asp Ser Cys Leu Asp Ser Ser Val Leu Asp Ser
    3365            3370            3375

Ser Phe Leu Thr Phe Ser Gly Leu His Ala Glu Ala Phe Val Gly
    3380            3385            3390

Gln Met Lys Ser Asp Leu Phe Leu Asp Asp Ser Lys Ser Leu Val
    3395            3400            3405

Cys Trp Pro Ser Gly Glu Gly Thr Leu Ser Trp Pro Asp Leu Leu
    3410            3415            3420

Ser Asp Pro Ser Ile Val Gly Ser Asn Leu Arg Gln Leu Ala Arg
    3425            3430            3435

Gly Gln Ala Gly His Gly Leu Gly Pro Glu Glu Asp Gly Phe Ser
    3440            3445            3450

Leu Ala Ser Pro Tyr Ser Pro Ala Lys Ser Phe Ser Ala Ser Asp
    3455            3460            3465

Glu Asp Leu Ile Gln Gln Val Leu Ala Glu Gly Val Ser Ser Pro
    3470            3475            3480

Ala Pro Thr Gln Asp Thr His Met Glu Thr Asp Leu Leu Ser Ser
    3485            3490            3495

Leu Ser Ser Thr Pro Gly Glu Lys Thr Glu Thr Leu Ala Leu Gln
    3500            3505            3510

Arg Leu Gly Glu Leu Gly Pro Pro Ser Pro Gly Leu Asn Trp Glu
    3515            3520            3525

Gln Pro Gln Ala Ala Arg Leu Ser Arg Thr Gly Leu Val Glu Gly
    3530            3535            3540

Leu Arg Lys Arg Leu Leu Pro Ala Trp Cys Ala Ser Leu Ala His
    3545            3550            3555

Gly Leu Ser Leu Leu Val Ala Val Ala Val Ala Val Ser Gly
    3560            3565            3570

Trp Val Gly Ala Ser Phe Pro Pro Gly Val Ser Val Ala Trp Leu
    3575            3580            3585

Leu Ser Ser Ser Ala Ser Phe Leu Ala Ser Phe Leu Gly Trp Glu
    3590            3595            3600

Pro Leu Lys Val Leu Leu Glu Ala Leu Tyr Phe Ser Leu Val Ala
    3605            3610            3615

Lys Arg Leu His Pro Asp Glu Asp Asp Thr Leu Val Glu Ser Pro
    3620            3625            3630

Ala Val Thr Pro Val Ser Ala Arg Val Pro Arg Val Arg Pro Pro
    3635            3640            3645

His Gly Phe Ala Leu Phe Leu Ala Lys Glu Glu Ala Arg Lys Val
    3650            3655            3660

Lys Arg Leu His Gly Met Leu Arg Ser Leu Leu Val Tyr Met Leu
    3665            3670            3675

Phe Leu Leu Val Thr Leu Leu Ala Ser Tyr Gly Asp Ala Ser Cys
    3680            3685            3690

His Gly His Ala Tyr Arg Leu Gln Ser Ala Ile Lys Gln Glu Leu
    3695            3700            3705

His Ser Arg Ala Phe Leu Ala Ile Thr Arg Ser Glu Glu Leu Trp
3710                3715                3720

Pro Trp Met Ala His Val Leu Leu Pro Tyr Val His Gly Asn Gln
3725                3730                3735

Ser Ser Pro Glu Leu Gly Pro Pro Arg Leu Arg Gln Val Arg Leu
3740                3745                3750

Gln Glu Ala Leu Tyr Pro Asp Pro Pro Gly Pro Arg Val His Thr
3755                3760                3765

Cys Ser Ala Ala Gly Gly Phe Ser Thr Ser Asp Tyr Asp Val Gly
3770                3775                3780

Trp Glu Ser Pro His Asn Gly Ser Gly Thr Trp Ala Tyr Ser Ala
3785                3790                3795

Pro Asp Leu Leu Gly Ala Trp Ser Trp Gly Ser Cys Ala Val Tyr
3800                3805                3810

Asp Ser Gly Gly Tyr Val Gln Glu Leu Gly Leu Ser Leu Glu Glu
3815                3820                3825

Ser Arg Asp Arg Leu Arg Phe Leu Gln Leu His Asn Trp Leu Asp
3830                3835                3840

Asn Arg Ser Arg Ala Val Phe Leu Glu Leu Thr Arg Tyr Ser Pro
3845                3850                3855

Ala Val Gly Leu His Ala Ala Val Thr Leu Arg Leu Glu Phe Pro
3860                3865                3870

Ala Ala Gly Arg Ala Leu Ala Ala Leu Ser Val Arg Pro Phe Ala
3875                3880                3885

Leu Arg Arg Leu Ser Ala Gly Leu Ser Leu Pro Leu Leu Thr Ser
3890                3895                3900

Val Cys Leu Leu Leu Phe Ala Val His Phe Ala Val Ala Glu Ala
3905                3910                3915

Arg Thr Trp His Arg Glu Gly Arg Trp Arg Val Leu Arg Leu Gly
3920                3925                3930

Ala Trp Ala Arg Trp Leu Leu Val Ala Leu Thr Ala Ala Thr Ala
3935                3940                3945

Leu Val Arg Leu Ala Gln Leu Gly Ala Ala Asp Arg Gln Trp Thr
3950                3955                3960

Arg Phe Val Arg Gly Arg Pro Arg Arg Phe Thr Ser Phe Asp Gln
3965                3970                3975

Val Ala Gln Leu Ser Ser Ala Ala Arg Gly Leu Ala Ala Ser Leu
3980                3985                3990

Leu Phe Leu Leu Leu Val Lys Ala Ala Gln Gln Leu Arg Phe Val
3995                4000                4005

Arg Gln Trp Ser Val Phe Gly Lys Thr Leu Cys Arg Ala Leu Pro
4010                4015                4020

Glu Leu Leu Gly Val Thr Leu Gly Leu Val Val Leu Gly Val Ala
4025                4030                4035

Tyr Ala Gln Leu Ala Ile Leu Leu Val Ser Ser Cys Val Asp Ser
4040                4045                4050

Leu Trp Ser Val Ala Gln Ala Leu Leu Val Leu Cys Pro Gly Thr
4055                4060                4065

Gly Leu Ser Thr Leu Cys Pro Ala Glu Ser Trp His Leu Ser Pro
4070                4075                4080

Leu Leu Cys Val Gly Leu Trp Ala Leu Arg Leu Trp Gly Ala Leu
4085                4090                4095

Arg Leu Gly Ala Val Ile Leu Arg Trp Arg Tyr His Ala Leu Arg

Gly Glu Leu Tyr Arg Pro Ala Trp Glu Pro Gln Asp Tyr Glu Met
4115                4120                4125

Val Glu Leu Phe Leu Arg Arg Leu Arg Leu Trp Met Gly Leu Ser
4130                4135                4140

Lys Val Lys Glu Phe Arg His Lys Val Arg Phe Glu Gly Met Glu
4145                4150                4155

Pro Leu Pro Ser Arg Ser Ser Arg Gly Ser Lys Val Ser Pro Asp
4160                4165                4170

Val Pro Pro Pro Ser Ala Gly Ser Asp Ala Ser His Pro Ser Thr
4175                4180                4185

Ser Ser Ser Gln Leu Asp Gly Leu Ser Val Ser Leu Gly Arg Leu
4190                4195                4200

Gly Thr Arg Cys Glu Pro Glu Pro Ser Arg Leu Gln Ala Val Phe
4205                4210                4215

Glu Ala Leu Leu Thr Gln Phe Asp Arg Leu Asn Gln Ala Thr Glu
4220                4225                4230

Asp Val Tyr Gln Leu Glu Gln Gln Leu His Ser Leu Gln Gly Arg
4235                4240                4245

Arg Ser Ser Arg Ala Pro Ala Gly Ser Ser Arg Gly Pro Ser Pro
4250                4255                4260

Gly Leu Arg Pro Ala Leu Pro Ser Arg Leu Ala Arg Ala Ser Arg
4265                4270                4275

Gly Val Asp Leu Ala Thr Gly Pro Ser Arg Thr Pro Leu Arg Ala
4280                4285                4290

Lys Asn Lys Val His Pro Ser Ser Thr
4295                4300

```
<210> SEQ ID NO 4
<211> LENGTH: 6749
<212> TYPE: DNA
<213> ORGANISM: Homo sapiens
<220> FEATURE:
<221> NAME/KEY: modified_base
<222> LOCATION: (719)..(1277)
<223> OTHER INFORMATION: a, c, t or g
<220> FEATURE:
<221> NAME/KEY: modified_base
<222> LOCATION: (1278)..(1280)
<223> OTHER INFORMATION: a, c, t or g
<220> FEATURE:
<221> NAME/KEY: modified_base
<222> LOCATION: (1288)..(1289)
<223> OTHER INFORMATION: a, c, t or g
<220> FEATURE:
<221> NAME/KEY: modified_base
<222> LOCATION: (1638)..(1638)
<223> OTHER INFORMATION: a, c, t or g
<220> FEATURE:
<221> NAME/KEY: modified_base
<222> LOCATION: (1967)..(1967)
<223> OTHER INFORMATION: a, c, t or g
<220> FEATURE:
<221> NAME/KEY: modified_base
<222> LOCATION: (2248)..(2248)
<223> OTHER INFORMATION: a, c, t or g
<220> FEATURE:
<221> NAME/KEY: modified_base
<222> LOCATION: (2251)..(2251)
<223> OTHER INFORMATION: a, c, t or g
<220> FEATURE:
<221> NAME/KEY: modified_base
<222> LOCATION: (2254)..(2254)
<223> OTHER INFORMATION: a, c, t or g
<220> FEATURE:
```

```
<221> NAME/KEY: modified_base
<222> LOCATION: (2283)..(2283)
<223> OTHER INFORMATION: a, c, t or g
<220> FEATURE:
<221> NAME/KEY: modified_base
<222> LOCATION: (2585)..(2586)
<223> OTHER INFORMATION: a, c, t or g
<220> FEATURE:
<221> NAME/KEY: modified_base
<222> LOCATION: (2625)..(2625)
<223> OTHER INFORMATION: a, c, t or g
<220> FEATURE:
<221> NAME/KEY: modified_base
<222> LOCATION: (2932)..(2932)
<223> OTHER INFORMATION: a, c, t or g
<220> FEATURE:
<221> NAME/KEY: modified_base
<222> LOCATION: (2949)..(2949)
<223> OTHER INFORMATION: a, c, t or g
<220> FEATURE:
<221> NAME/KEY: modified_base
<222> LOCATION: (2972)..(2972)
<223> OTHER INFORMATION: a, c, t or g
<220> FEATURE:
<221> NAME/KEY: modified_base
<222> LOCATION: (2978)..(3406)
<223> OTHER INFORMATION: a, c, t or g
<220> FEATURE:
<221> NAME/KEY: modified_base
<222> LOCATION: (3419)..(3419)
<223> OTHER INFORMATION: a, c, t or g
<220> FEATURE:
<221> NAME/KEY: modified_base
<222> LOCATION: (3604)..(3604)
<223> OTHER INFORMATION: a, c, t or g
<220> FEATURE:
<221> NAME/KEY: modified_base
<222> LOCATION: (3675)..(3675)
<223> OTHER INFORMATION: a, c, t or g
<220> FEATURE:
<221> NAME/KEY: modified_base
<222> LOCATION: (3849)..(3849)
<223> OTHER INFORMATION: a, c, t or g
<220> FEATURE:
<221> NAME/KEY: modified_base
<222> LOCATION: (4132)..(4132)
<223> OTHER INFORMATION: a, c, t or g
<220> FEATURE:
<221> NAME/KEY: modified_base
<222> LOCATION: (4337)..(4337)
<223> OTHER INFORMATION: a, c, t or g
<220> FEATURE:
<221> NAME/KEY: modified_base
<222> LOCATION: (4367)..(4369)
<223> OTHER INFORMATION: a, c, t or g
<220> FEATURE:
<221> NAME/KEY: modified_base
<222> LOCATION: (4396)..(4396)
<223> OTHER INFORMATION: a, c, t or g
<220> FEATURE:
<221> NAME/KEY: modified_base
<222> LOCATION: (4404)..(4404)
<223> OTHER INFORMATION: a, c, t or g
<220> FEATURE:
<221> NAME/KEY: modified_base
<222> LOCATION: (5700)..(5702)
<223> OTHER INFORMATION: a, c, t or g
<220> FEATURE:
<221> NAME/KEY: modified_base
<222> LOCATION: (6611)..(6611)
<223> OTHER INFORMATION: a, c, t or g
<220> FEATURE:
<221> NAME/KEY: modified_base
<222> LOCATION: (6628)..(6628)
<223> OTHER INFORMATION: a, c, t or g
<220> FEATURE:
<221> NAME/KEY: modified_base
<222> LOCATION: (6637)..(6637)
<223> OTHER INFORMATION: a, c, t or g
```

<220> FEATURE:
<221> NAME/KEY: modified_base
<222> LOCATION: (6700)..(6733)
<223> OTHER INFORMATION: a, c, t or g

<400> SEQUENCE: 4

```
ggctcctgag gcgcacagcg ccgagcgcgg cgccgcgcac ccgcgcgccg gacgccagtg        60
accgcgatgg tgaactccag tcgcgtgcag cctcagcagc ccggggacgc caagcggccg       120
cccgcgcccc gcgcgccgga cccggggccgg ctgatggctg gctgcgcggc cgtgggcgcc      180
agcctcgccg ccccggggccg cctctgcgag cagcggggcc tggagatcga gatgcagcgc     240
atccggcagg cggccgcgcg ggaccccccg gccggagccg cggcctcccc ttctcctccg       300
ctctcgtcgt gctcccggca ggcgtggagc cgcgataacc ccggcttcga ggccgaggag       360
gaggaggagg aggtggaagg ggaagaaggc ggaatggtgg tggagatgga cgtagagtgg       420
cgcccgggca gccggaggtc ggccgcctcc tcggccgtga gctccgtggg cgcgcggagc       480 cggggggcttg ggggctacca cggcgcgggc caccccgagcg ggaggcggcg ccggcgagag     540
gaccagggcc cgccgtgccc cagcccagtc ggcggcgggg acccgctgca tcgccacctc       600
cccctggaag ggcagccgcc ccgagtggcc tgggcggaga ggctggttcg cgggctgcga       660
ggtgtaagag cgcgcgaccc gcagcggcag atgcacgaac cagaacggcc ggcgccgggng      720 gcttcttaaa taaaatgata tcttttcttt tcttcattat tattttaaag gtctctgggg       780
aacaagactc atggaggaaa gcagcactaa ccgagagaaa taccttaaaa gtgtttttacg      840 ggaactggtc acatacctcc tttttctcat agtcttgtgc atctgtaagt agaatatttc       900
cttgcactaa tgggaaagtt ttgaaacgat gtgaatttgt ccaaaatgtt tatccacagg       960
aacaatccct ttgtgaaggc tgctggtatg tggatgtgtg ccggttccct tggggcgttc      1020
atttggatct ttctgtgttc cagtgaccta cggcatgatg agctccaatg tgtactacta      1080
cacccggatg atgtcacagc tcttcctaga cacccccgtg tccaaaacgg agaaaactaa      1140
ctttaaaact ctgtcttcca tggaagactt ctggaaggta tttggaaata actttgaaag      1200
tacctctcta tcacaagcca atgcttggtt atgcaacgat gcaggcaggg caaagcagcg      1260
gcatgagctt gaacttnnnn agatgttnnc tttcttttag ttcacagaag gctccttatt      1320
ggatgggctg tactggaaga tgcagcccag caaccagact gaagctgaca accgaagttt      1380
catcttctat gagaacctgc tgttagggggt tccacgaata cggcaactcc gagtcagaaa      1440
tggatcctgc tctatccccc aggacttgag agatgaaatt aaagagtgct atgatgtcta      1500
ctctgtcagt agtgaagata gggctcccctt tgggccccga aatggaaccg cgtaagtgtc      1560
tgtgactcat tggcactcgg tgatattcat ccttgtaatt gcctcaagtg ttccactgat      1620
tgtaactgtt tgttttttngg ttttgttttt aatcagttgg atctacacaa gtgaaaaaga    1680
cttgaatggt agtagccact ggggaatcat tgcaacttat agtggagctg ctattatct      1740 ggatttgtca agaacaagag aggaaacagc tgcacaagtt gctagcctca agaaaaatgt      1800
ctggctggac cgaggaacca gggcaacttt tattgacttc tcagtgtaca acgccaacat      1860
taacctgttc tgtgtggtca ggtgtgtgac tgaggacatg catccctcct atttctgtgt      1920
ggttgtacat acatcctatt ctagggttac ccagaaaaac cttttttntgc aggttgttat      1980 tgttttaatt gttcttattt acatgcaggt tattggttga attcccagca acaggtggtg      2040
tgattccatc ttggcaattt cagcctttaa agctgatccg atatgtcaca acttttgatt      2100
tcttcctggc agcctgtgag attatctttt gtttctttat cttttactat gtggtggaag      2160
```

```
agatattgga aattcgcatt cacaaactac actatttcag gagtttctgg aattgtctgg      2220
atgttgtgat cgttgtggta ggtccganca ncancaccaa atttcctatt ctattctaca      2280
agnatgttaa caattaatac attggtgaag aaaaatatac tagtcatatt aaggtaagtt      2340
tcatatttct aaaacactgt aataaaatat aaatattttg cttttcagct gtcagtggta      2400
gctataggaa ttaacatata cagaacatca aatgtggagg tgctactaca gtttctggaa      2460
gatcaaaata ctttccccaa ctttgagcat ctggcatatt ggcagataca gttcaacaat      2520
atagctgctg tcacagtatt ttttgtctgg attaaggtaa tttataaatt tcatgttcta      2580
cattnnaaat aatattttct ttaaaaaaaa tgagttccac aaaancatgc gaaacaatgt      2640
tttattatac acagtcacac catttggttt atccattcat ctattgatgt cttctctctc      2700
ttacagctct tcaaattcat caattttaac aggaccatga gccagctctc gacaaccatg      2760
tctcgatgtg ccaaagacct gtttggcttt gctattatgt tcttcattat tttcctagcg      2820
tatgctcagt tggcatacct tgtctttggc actcaggtcg atgacttcag tactttccaa      2880
gagtgtatgt aagtatatat gaaattaaga agaaaaattt agtcagagta gncactgttg      2940
cgtggacant ctttggtttt gtattgtggt gntttgtntt attttatag cttcactcaa       3000 ttccgtatca ttttgggcga tatcaacttt gcagagatt aggaagctaa tcgagttttg       3060
ggaccaattt atttcactac atttgtgttc tttatgttct tcattctttt ggtatgtaca      3120
tttatattta tagtggaggt tcaatttaaa cttcgtaaat cctgtcttc tcttttttga       3180 ttgataattc caaattatgt ttcttccttt aattttgcc ctcctttcat ttacaaacag       3240
aatatgtttt tggctatcat caatgatact tactctgaag tgaaatctga cttggcacag      3300
cagaaagctg aaatggaact ctcagatctt atcagaaagg taggaaaaac cttaattctc      3360
aaaaattctt ctgtttctga cataaaatga gcattgtttc acccanattt tagaatacnc      3420
taaaccaagt cttttatttt ttctctctct gatagggcta ccataaagct ttggtcaaac      3480
taaaactgaa aaaaaatacc gtggatgaca tttcagagag tctgcggcaa ggaggaggca      3540
agttaaactt tgacgaactt cgacaagatc tcaaagggtg agaatcatgc ttcctgaggt      3600
tctnaaaaat tcctgcttct aaagataaat tcctggtgat aagagtattt ctagcccaag      3660
ggctcatggg aacanaggat gaatgttatc tgtatcctct ctctaatttc aggaagggcc      3720
atactgatgc agagattgag gcaatattca caaagtacga ccaagatgga gaccaagaac      3780
tgaccgaaca tgaacatcag cagatgagag acgacttgga gaaagagagg gtgggtctgg      3840
tttaggagna accggatttg atttggtacc tacaacacca cacttctgtg gggtctcagt      3900
gttctgctcc tcactcagtg accccttgtt cttcaggagg acctggattt ggatcacagt      3960
tctttaccac gtcccatgag cagccgaagt ttccctcgaa gcctggatga ctctgaggag      4020
gatgacgatg aagatagcgg acatagctcc agaaggaggg gaagcatttc tagtggcgtt      4080
tcttacgaag agtttcaagt gtaagtataa aggaattggc agaatttgcg tngacaattt      4140
gtccctctgt actgtgtttt ccttgcagcc tggtgagacg agtggaccgg atggagcatt      4200
ccatcggcag catagtgtcc aagattgacg ccgtgatcgt gaagctagag attatggagc      4260
gagccaaact gaagaggagg gaggtgctgg gaaggctgtt ggatggggtg gccgaggtca      4320
gtagtcatga gctgaanaca ccgctgctga gcatggtgtt attaatnnna atatatgttg      4380
ctgacagttg tatttnaagt attnactgac ccccaacacc agtttctttt tcccttttta      4440
ggatgaaagg ctgggtcgtg acagtgaaat ccataggaa cagatggaac ggctagtacg       4500
tgaagagttg gaacgctggg aatccgatga tgcagcttcc cagatcagtc atggtttagg      4560
```

```
cacgccagtg ggactaaatg gtcaacctcg ccccagaagc tcccgcccat cttcctccca    4620
atctacagaa ggcatggaag gtgcaggtgg aaatgggagt tctaatgtcc acgtatgata    4680
tgtgtgtttc agtatgtgtg tttctaataa gtgaggaagt ggctgtcctg aattgctgta    4740
acaagcacac tatttatatg ccctgaccac cataggatgc tagtctttgt gaccgattgc    4800
taatcttctg cactttaatt tattttatat aaactttacc catggttcaa agatttttt     4860 ttcttttct catataagaa atctaggtgt aaatattgag tacagaaaaa aaatcttcat     4920
gatgtgtatt gagcggtacg cccagttgcc accatgactg agtcttctca gttgacaatg    4980
aagtagcctt ttaaagctag aaaactgtca aagggcttct gagtttcatt tccagtcaca    5040
aaaatcagta ttgttatttt tttccaagag tgtgaaggaa aatggggcaa ttcctttcca    5100
ctctggcata gttcatgagc ttaatacata gctttctttt aagaaaggag ccttttttt     5160 caactagctt cctggggtaa acttttctaa aagataaaat gggaaggaac tccaaactat    5220
gatagaatct gtgtgaatgg ttaagatgaa tgttaaatac tatgcttttt tgtaagttga    5280
tcgtatctga tgtctgtggg actaactgta tcacttaatt tttaccttat tttggctcta    5340
atttgaataa gctgagtaaa accaccaaag atcagttata ggataaaatg gcatctctaa    5400
ccataacaca ggagaattgg aaggagccct aagttgtcac tcagtttaat ttctttaat     5460 ggttagttta gcctaaagat ttatctgcat attctttttc ccatgtggct ctactcattt    5520
gcaactgaat ttaatgttat aactcatcta gtgagaccaa cttactaaat ttttagtatg    5580
cactgaaagt tttatccaa caattatgtt cattttaagc aaaattttaa gaaagttttg     5640
aaattcataa agcatttggt tttaaactat tttaagaata tagtactcgg tcaggtatgn    5700
nncacgcctg taatcccagc actttgggag gccgaaacag gcgaatcact tgagcccagg    5760
agttcaagac caacatgggc aatgtggcga aactccatct ctacaaaaaa tgcaaaaata    5820
aaaaatatag tactcaagta ttcttgatcc tgtgtttcaa aactagaatt tgtaatgcaa    5880
atggagctca gtctaataaa aaagaggttt tggtattaaa agttcataca ttagacagta    5940
tcagccaaaa tttgagttag caacactgtt tctttacga gagggtctca cccaaattta     6000
tggggagaaa tctatttctc aaaaaaaaaa aatcttcttt tacagaaatg ttgagtaagg    6060
tgacattttg agcgctaata agcaaaagag catgcagtgc tgttaataa ccctcacttg      6120 gagaaccaag agaatcctgt cgtttaatgc tatatttaa tttcacaagt tgttcattta      6180
actggtagaa tgtcagtcca atctccaatg agaacatgag caaatagacc tttccaggtt    6240
gaaagtgaaa catactgggt ttctgtaagt ttttcctcat ggcttcatct ctatctttac    6300
tttctcttga atatgctaca caaagttctt tattactaca tactaaagtt tgcattccag    6360
ggatattgac tgtacatatt tatgtatatg taccatgttg ttacatgtaa acaaacttca    6420
atttgaagtg cagctattat gtggtatcca tgtgtatcga ccatgtgcca tatatcaatt    6480
atggtcacta gaaagtctct ttatgatact ttttattgta ctgttttca tttcacttgc     6540 aaaattttgc agaattcctc ctttctaccc ataaattaca tataattttt cttctttagt    6600
catggagaac nccccccat catctcancc ctattanctt tcccatgtgt actggtatta     6660
ttaaaaagac atttacatac gcaagttttt cactgacaan caagaatgtt attaatgtgt    6720
aatactgagc acntttactt cttaataaa                                      6749
```

<210> SEQ ID NO 5
<211> LENGTH: 2907
<212> TYPE: DNA

<213> ORGANISM: Homo sapiens

<400> SEQUENCE: 5

| | | | | | | |
|---|---|---|---|---|---|---|
| atggtgaact | ccagtcgcgt | gcagcctcag | cagcccgggg | acgccaagcg | gccgcccgcg | 60 |
| ccccgcgcgc | cggacccggg | ccggctgatg | gctggctgcg | cggccgtggg | cgccagcctc | 120 |
| gccgccccgg | gcggcctctg | cgagcagcgg | ggcctggaga | tcgagatgca | gcgcatccgg | 180 |
| caggcggccg | cgcgggaccc | cccggccgga | gccgcggcct | ccccttctcc | tccgctctcg | 240 |
| tcgtgctccc | ggcaggcgtg | gagccgcgat | aaccccggct | tcgaggccga | ggaggaggag | 300 |
| gaggaggtgg | aagggaaga | aggcggaatg | gtggtggaga | tggacgtaga | gtggcgcccg | 360 |
| ggcagccgga | ggtcggccgc | ctcctcggcc | gtgagctccg | tgggcgcgcg | gagccggggg | 420 |
| cttgggggct | accacggcgc | gggccacccg | agcgggaggc | ggcgccggcg | agaggaccag | 480 |
| ggcccgccgt | gccccagccc | agtcggcggc | ggggaccccg | tgcatcgcca | cctcccctg | 540 |
| gaagggcagc | cgccccgagt | ggcctgggcg | gagaggctgg | ttcgcgggct | gcgaggtctc | 600 |
| tggggaacaa | gactcatgga | ggaaagcagc | actaaccgag | agaaataccct | taaaagtgtt | 660 |
| ttacgggaac | tggtcacata | cctccttttt | ctcatagtct | tgtgcatctt | gacctacggc | 720 |
| atgatgagct | ccaatgtgta | ctactacacc | cggatgatgt | cacagctctt | cctagacacc | 780 |
| cccgtgtcca | aaacggagaa | aactaacttt | aaaactctgt | cttccatgga | agacttctgg | 840 |
| aagttcacag | aaggctcctt | attggatggg | ctgtactgga | gatgcagcc | cagcaaccag | 900 |
| actgaagctg | acaaccgaag | tttcatcttc | tatgagaacc | tgctgttagg | ggttccacga | 960 |
| atacggcaac | tccgagtcag | aaatggatcc | tgctctatcc | cccaggactt | gagagatgaa | 1020 |
| attaaagagt | gctatgatgt | ctactctgtc | agtagtgaag | atagggctcc | ctttgggccc | 1080 |
| cgaaatggaa | ccgcttggat | ctacacaagt | gaaaaagact | tgaatggtag | tagccactgg | 1140 |
| ggaatcattg | caacttatag | tggagctggc | tattatctgg | atttgtcaag | aacaagagag | 1200 |
| gaaacagctg | cacaagttgc | tagcctcaag | aaaaatgtct | ggctggaccg | aggaaccagg | 1260 |
| gcaacttta | ttgacttctc | agtgtacaac | gccaacatta | acctgttctg | tgtggtcagg | 1320 |
| ttattggtta | aattcccagc | aacaggtggt | gtgattccat | cttggcaatt | tcagcctta | 1380 |
| aagctgatcc | gatatgtcac | aacttttgat | ttcttcctgg | cagcctgtga | gattatcttt | 1440 |
| tgtttcttta | tcttttacta | tgtggtggaa | gagatattgg | aaattcgcat | tcacaaacta | 1500 |
| cactatttca | ggagtttctg | gaattgtctg | gatgttgtga | tcgttgtgct | gtcagtggta | 1560 |
| gctataggaa | ttaacatata | cagaacatca | aatgtggagg | tgctactaca | gtttctggaa | 1620 |
| gatcaaaata | cttccccaa | ctttgagcat | ctggcatatt | ggcagataca | gttcaacaat | 1680 |
| atagctgctg | tcacagtatt | ttttgtctgg | attaagctct | tcaaattcat | caattttaac | 1740 |
| aggaccatga | gccagctctc | gacaaccatg | tctcgatgtg | ccaaagacct | gtttggcttt | 1800 |
| gctattatgt | tcttcattat | tttcctagcg | tatgctcagt | ggcatacct | tgtctttggc | 1860 |
| actcaggtcg | atgacttcag | tactttccaa | gagtgtatct | tcactcaatt | ccgtatcatt | 1920 |
| ttgggcgata | tcaactttgc | agagattgag | gaagctaatc | gagttttggg | accaatttat | 1980 |
| ttcactacat | ttgtgttctt | tatgttcttc | attcttttga | atatgttttt | ggctatcatc | 2040 |
| aatgatactt | actctgaagt | gaaatctgac | ttggcacagc | agaaagctga | aatggaactc | 2100 |
| tcagatctta | tcagaaaggg | ctaccataaa | gctttggtca | aactaaaact | gaaaaaaat | 2160 |
| accgtggatg | catttcaga | gagtctgcgg | caaggaggag | gcaagttaaa | ctttgacgaa | 2220 |
| cttcgacaag | atctcaaagg | gaagggccat | actgatgcag | agattgaggc | aatattcaca | 2280 |

```
aagtacgacc aagatggaga ccaagaactg accgaacatg aacatcagca gatgagagac    2340
gacttggaga aagagaggga ggacctggat ttggatcaca gttctttacc acgtcccatg    2400
agcagccgaa gtttccctcg aagcctggat gactctgagg aggatgacga tgaagatagc    2460
ggacatagct ccagaaggag gggaagcatt tctagtggcg tttcttacga agagtttcaa    2520
gtcctggtga gacgagtgga ccggatggag cattccatcg gcagcatagt gtccaagatt    2580
gacgccgtga tcgtgaagct agagattatg gagcgagcca aactgaagag gagggaggtg    2640
ctgggaaggc tgttggatgg ggtggccgag gatgaaaggc tgggtcgtga cagtgaaatc    2700 cataggggaac agatggaacg gctagtacgt gaagagttgg aacgctggga atccgatgat    2760
gcagcttccc agatcagtca tggtttaggc acgccagtgg gactaaatgg tcaacctcgc    2820
cccagaagct cccgcccatc ttcctcccaa tctacagaag gcatggaagg tgcaggtgga    2880
aatgggagtt ctaatgtcca cgtatga                                        2907
```

<210> SEQ ID NO 6
<211> LENGTH: 968
<212> TYPE: PRT
<213> ORGANISM: Homo sapiens

<400> SEQUENCE: 6

```
Met Val Asn Ser Ser Arg Val Gln Pro Gln Gln Pro Gly Asp Ala Lys
1               5                   10                  15

Arg Pro Pro Ala Pro Arg Ala Pro Asp Pro Gly Arg Leu Met Ala Gly
            20                  25                  30

Cys Ala Val Gly Ala Ser Leu Ala Ala Pro Gly Gly Leu Cys Glu
        35                  40                  45

Gln Arg Gly Leu Glu Ile Glu Met Gln Arg Ile Arg Gln Ala Ala Ala
    50                  55                  60

Arg Asp Pro Pro Ala Gly Ala Ala Ala Ser Pro Ser Pro Pro Leu Ser
65                  70                  75                  80

Ser Cys Ser Arg Gln Ala Trp Ser Arg Asp Asn Pro Gly Phe Glu Ala
                85                  90                  95

Glu Glu Glu Glu Glu Val Glu Gly Glu Gly Gly Met Val Val
            100                 105                 110

Glu Met Asp Val Glu Trp Arg Pro Gly Ser Arg Arg Ser Ala Ala Ser
        115                 120                 125

Ser Ala Val Ser Ser Val Gly Ala Arg Ser Arg Gly Leu Gly Gly Tyr
    130                 135                 140

His Gly Ala Gly His Pro Ser Gly Arg Arg Arg Arg Glu Asp Gln
145                 150                 155                 160

Gly Pro Pro Cys Pro Ser Pro Val Gly Gly Asp Pro Leu His Arg
                165                 170                 175

His Leu Pro Leu Glu Gly Gln Pro Pro Arg Val Ala Trp Ala Glu Arg
            180                 185                 190

Leu Val Arg Gly Leu Arg Gly Leu Trp Gly Thr Arg Leu Met Glu Glu
        195                 200                 205

Ser Ser Thr Asn Arg Glu Lys Tyr Leu Lys Ser Val Leu Arg Glu Leu
    210                 215                 220

Val Thr Tyr Leu Leu Phe Leu Ile Val Leu Cys Ile Leu Thr Tyr Gly
225                 230                 235                 240

Met Met Ser Ser Asn Val Tyr Tyr Tyr Thr Arg Met Met Ser Gln Leu
                245                 250                 255
```

```
Phe Leu Asp Thr Pro Val Ser Lys Thr Glu Lys Thr Asn Phe Lys Thr
            260                 265                 270

Leu Ser Ser Met Glu Asp Phe Trp Lys Phe Thr Glu Gly Ser Leu Leu
        275                 280                 285

Asp Gly Leu Tyr Trp Lys Met Gln Pro Ser Asn Gln Thr Glu Ala Asp
    290                 295                 300

Asn Arg Ser Phe Ile Phe Tyr Glu Asn Leu Leu Leu Gly Val Pro Arg
305                 310                 315                 320

Ile Arg Gln Leu Arg Val Arg Asn Gly Ser Cys Ser Ile Pro Gln Asp
                325                 330                 335

Leu Arg Asp Glu Ile Lys Glu Cys Tyr Asp Val Tyr Ser Val Ser Ser
            340                 345                 350

Glu Asp Arg Ala Pro Phe Gly Pro Arg Asn Gly Thr Ala Trp Ile Tyr
        355                 360                 365

Thr Ser Glu Lys Asp Leu Asn Gly Ser Ser His Trp Gly Ile Ile Ala
    370                 375                 380

Thr Tyr Ser Gly Ala Gly Tyr Tyr Leu Asp Leu Ser Arg Thr Arg Glu
385                 390                 395                 400

Glu Thr Ala Ala Gln Val Ala Ser Leu Lys Lys Asn Val Trp Leu Asp
                405                 410                 415

Arg Gly Thr Arg Ala Thr Phe Ile Asp Phe Ser Val Tyr Asn Ala Asn
            420                 425                 430

Ile Asn Leu Phe Cys Val Val Arg Leu Leu Val Glu Phe Pro Ala Thr
        435                 440                 445

Gly Gly Val Ile Pro Ser Trp Gln Phe Gln Pro Leu Lys Leu Ile Arg
    450                 455                 460

Tyr Val Thr Thr Phe Asp Phe Phe Leu Ala Ala Cys Glu Ile Ile Phe
465                 470                 475                 480

Cys Phe Phe Ile Phe Tyr Tyr Val Val Glu Glu Ile Leu Glu Ile Arg
                485                 490                 495

Ile His Lys Leu His Tyr Phe Arg Ser Phe Trp Asn Cys Leu Asp Val
            500                 505                 510

Val Ile Val Val Leu Ser Val Val Ala Ile Gly Ile Asn Ile Tyr Arg
        515                 520                 525

Thr Ser Asn Val Glu Val Leu Leu Gln Phe Leu Glu Asp Gln Asn Thr
    530                 535                 540

Phe Pro Asn Phe Glu His Leu Ala Tyr Trp Gln Ile Gln Phe Asn Asn
545                 550                 555                 560

Ile Ala Ala Val Thr Val Phe Phe Val Trp Ile Lys Leu Phe Lys Phe
                565                 570                 575

Ile Asn Phe Asn Arg Thr Met Ser Gln Leu Ser Thr Thr Met Ser Arg
            580                 585                 590

Cys Ala Lys Asp Leu Phe Gly Phe Ala Ile Met Phe Phe Ile Ile Phe
        595                 600                 605

Leu Ala Tyr Ala Gln Leu Ala Tyr Leu Val Phe Gly Thr Gln Val Asp
    610                 615                 620

Asp Phe Ser Thr Phe Gln Glu Cys Ile Phe Thr Gln Phe Arg Ile Ile
625                 630                 635                 640

Leu Gly Asp Ile Asn Phe Ala Glu Ile Glu Glu Ala Asn Arg Val Leu
                645                 650                 655

Gly Pro Ile Tyr Phe Thr Thr Phe Val Phe Met Phe Phe Ile Leu
            660                 665                 670

Leu Asn Met Phe Leu Ala Ile Ile Asn Asp Thr Tyr Ser Glu Val Lys
```

|   |   |   | 675 |   |   |   |   | 680 |   |   |   |   | 685 |   |   |
|---|---|---|---|---|---|---|---|---|---|---|---|---|---|---|---|
| Ser | Asp | Leu | Ala | Gln | Gln | Lys | Ala | Glu | Met | Glu | Leu | Ser | Asp | Leu | Ile |
| 690 | | | | | 695 | | | | | 700 | | | | | |

Arg Lys Gly Tyr His Lys Ala Leu Val Lys Leu Lys Leu Lys Lys Asn
705 710 715 720

Thr Val Asp Asp Ile Ser Glu Ser Leu Arg Gln Gly Gly Gly Lys Leu
 725 730 735

Asn Phe Asp Glu Leu Arg Gln Asp Leu Lys Gly Lys Gly His Thr Asp
 740 745 750

Ala Glu Ile Glu Ala Ile Phe Thr Lys Tyr Asp Gln Asp Gly Asp Gln
 755 760 765

Glu Leu Thr Glu His Glu His Gln Gln Met Arg Asp Asp Leu Glu Lys
 770 775 780

Glu Arg Glu Asp Leu Asp Leu Asp His Ser Ser Leu Pro Arg Pro Met
785 790 795 800

Ser Ser Arg Ser Phe Pro Arg Ser Leu Asp Asp Ser Glu Glu Asp Asp
 805 810 815

Asp Glu Asp Ser Gly His Ser Ser Arg Arg Arg Gly Ser Ile Ser Ser
 820 825 830

Gly Val Ser Tyr Glu Glu Phe Gln Val Leu Val Arg Arg Val Asp Arg
 835 840 845

Met Glu His Ser Ile Gly Ser Ile Val Ser Lys Ile Asp Ala Val Ile
850 855 860

Val Lys Leu Glu Ile Met Glu Arg Ala Lys Leu Lys Arg Arg Glu Val
865 870 875 880

Leu Gly Arg Leu Leu Asp Gly Val Ala Glu Asp Glu Arg Leu Gly Arg
 885 890 895

Asp Ser Glu Ile His Arg Glu Gln Met Glu Arg Leu Val Arg Glu Glu
 900 905 910

Leu Glu Arg Trp Glu Ser Asp Asp Ala Ala Ser Gln Ile Ser His Gly
 915 920 925

Leu Gly Thr Pro Val Gly Leu Asn Gly Gln Pro Arg Pro Arg Ser Ser
 930 935 940

Arg Pro Ser Ser Ser Gln Ser Thr Glu Gly Met Glu Gly Ala Gly Gly
945 950 955 960

Asn Gly Ser Ser Asn Val His Val
 965

<210> SEQ ID NO 7
<211> LENGTH: 53522
<212> TYPE: DNA
<213> ORGANISM: Homo sapiens

<400> SEQUENCE: 7

| tgtaaacttt | ttgagacagc | atctcaccct | gttccccagg | ctggagtgca | gtggtgtgat | 60 |
| catggctcac | tgcagcgtca | acctcctggg | tctacttgat | ctgtaaactt | cgagggaagg | 120 |
| tgtaataaac | cctcctgcaa | tgtctttgtt | tttcaaaatc | tttgtatttc | acagtttagc | 180 |
| ttcgtgggtt | gatgttctat | tttgtttttg | tgtgtgtgtg | tgtgtgtttt | tgttttttt | 240 |
| ttgagacaca | gtcttgctct | tgttgcccag | gctggagtgc | aatggtgtga | tcttggctca | 300 |
| ctgcaacttc | cacctcttgg | gttcaagaga | ttctcctgcc | tcagccttcc | gagtagctag | 360 |
| gattacaggc | gccgccacca | cccccgcta | attttgtatt | tttagtagag | atggggtttc | 420 |
| tccatattgg | tcaggctggt | ctcaaactcc | cgacctcagg | tgatccgccc | acctcagcct | 480 |

```
cccaaaatgc tgggattaca ggcgtgagtc accgcacctg gccaatgttc tattttttgag    540 aacacaacag ttcataatat attctacata gaccatacct gttatgtgta gataaacaga    600
ctcttttccc atttaacacc ttttgcctta ggtttatttt tctggtatca atactggcac    660
acttactttg tttgcagttt cctgtctttt tttttttttt ttttttttttt gagacagagt    720 ctcactctgt cacccaggct ggagtgaagt ggcgggatct cggctcactg caacctctac    780
ctcctgggtt catgcgattc tcctgcctca gcttcccgaa tagctgagac acaactgtg    840 tgccaccatg cccagccaat ttttgtattt ttagtagaca cggggtttca ccatactggc    900
caggatggct caatctcttg acctcgtgat ccacctgcct ccgcctccca aagtgctggg    960
attacaggca tgagccactg tgcctggcct ttttttttct ttttgagatg gagtctcact   1020
ctgtcaccca ggctggagtg cagtgggta acctcaggtc actgcgacct ccgcctcccg    1080
ggttccagtg attctcctgc ctcagcctcc cgagtagctg ggattacagg cacccaccac   1140
catgcctggc taattttttgt attttttagta gagacgggggt tttgccacgt tggccaggtt   1200
ggtctcgaac tcttggcctc atgtgacccg cctgccttgg cctcccaaag tgctgggatt   1260
acaggtgtga gccactgtgc ctggcctggc tttcttgttt cttttctcct cttctagttt   1320
ccccctttta ggctaacaat tattcactgt taataaaaaac cctcaggtct gtattttatc   1380
aagaaacatt tccctcacgt cttcttccct gaaccaaaca agatctctgg cacatttttat   1440 ttgctctgtc tcaccacatg gattttgttt ttttgtttct ttgttttttg agatggagtc    1500
tcactcttgt tgcccaggct ggagtgccat ggcacaatct cagctcactg caacctccac   1560
ctcctgggtt caagcgattc tcctgtctca gcctcctgag tagctgggat tacaggcgcg   1620
tggcaccacc cccagctaat ttttgtattt ttagtagaga cgggggtttca ccatgttggt   1680 caggctggtc tcgaactcct gaccttgtga tctgcccacc ttggcctccc aaagtgctgg   1740
gattacaggc atgagccacc acgcccggcc cccatggttt ttcaaatagt ttagaatttc   1800
atttccaggt aactaatttg cttcttttaaa catatgtctt ttctatttaa gaaatccttt   1860
ctaaacaatt gcattttatt ccacaaccgc cttcaaacaa tcattgagac ttggttaatc   1920
tgttttgctc atttggcagc agtttcttgt ggctgtttct tccctccact ggagtccttg   1980
aatcttaagt ctgtcatttg actgcaatta aaagctgggt ttggaataca atcgcagcct   2040
taccatccac ctgctgtgtg acctggtaaa tttcttttttt ttttttttgag acggagtctt   2100 gctctgttgc ccaggctgga gtgcagtggc acaacctctg cctcccaggt tcaagcgatt   2160
ctactgcctc aggctcccta gtagctggga ttataggtgc ctgccaccat gcccagctga   2220 ttttttgtatt tttagtagag atgaggtttc accatgttgg ctaggctggt ctcgaacttc   2280
tgatcttgtg atctgcccgc ctcggcctcc caaagtgctg ggattacagg catgagccac   2340
cactcccagc cagttctttt tttcttttttt ccatttttttt tttttcgag acaggatctt   2400 actcttttgc ccaggcggga gtgcagtggc acaatcacgg ctcagcgcag ccactgccta   2460
ctgggctcac acgctcctcc ggcctcagcc tctcgagtac ctgggactac aagcgtgagc   2520
cagtttggct aattttggct aattttttgta gaaacggggt ctcgccatgt tggccaggct   2580
ggtctccaac tcctggactc aagggatcca ccttcctccc cctctcaaag ttctgggatt   2640
accggagtga gccactgtgc cctgctggca aatttcttaa actgtctgtg cctcagtgac   2700
ctcatttaat aaagggaata attgtagcac acttttttcta gagctgtgaa gattcaatgg   2760
aataaataag gcaataaatg aatggatggg gaatgaagga tgtgggtttc ctccctcttg   2820
```

```
tctttcaata agctctcacc atcaacctcc cattgcctgt tctctctctt cccctctct      2880
ccctctgtct ctctctcagc caggaaacct ggggtaggga ggcttggagc cagcgggtgc      2940
gtcgggaggc tgcgggtact gactcgggcc gcgcacggag atcgcgggag aaggatccac      3000
aaccgcggaa gaaggatcag ggtggagcct gtggctgctg caggaggagg aacccgccgc      3060
ctggcccaca ccacaggaga agggcggagc agatggcacc ctgcccaccg cttcccgccc      3120
acgcacttta gcctgcagcg gggcggagcg tgaaaaatag ctcgtgctcc tcggccgact      3180
ctgcagtgcg acggcggtgc ttccagacgc tccgccccac gtcgcatgcg ccccgggaac      3240
gcgtggggcg gagcttccgg aggccccgcc ctgctgccga ccctgtggag cggagggtga      3300
agcctccgga tgccagtccc tcatcgctgg cccggtcgcg ctgtggcgaa ggggggcggag      3360
cctgcacccg ccccgccccc cctcgccccg tccgccccgc gccgcgcggg gaggaggagg      3420
aggagccgcg gcgggcccg cactgcagcg ccagcgtccg agcgggcggc cgagctcccg       3480
gagcggcctg gccccgagcc ccgagcgggc gtcgctcagc agcaggtcgc ggccgcagcc      3540
ccatccagcc cgcgcccgcc atgccgtccg cgggccccgc ctgagctgcg gcctccgcgc      3600
gcgggcgggc ctggggacgg cggggccatg cgcgcgctgc cctaacgatg ccgcccgccg      3660
cgcccgcccg cctggcgctg gccctgggcc tgggcctgtg gctcggggcg ctggcggggg      3720
gccccgggcg cggctgcggg ccctgcgagc ccccctgcct ctgcggccca gcgcccggcg      3780
ccgcctgccg cgtcaactgc tcgggccgcg ggctgcggac gctcggtccc gcgctgcgca      3840
tccccgcgga cgccacagcg ctgtgagtag cgggcccagc ggcacccggg agaggccgcg      3900
ggacgggcgg gcgtgggcgg gttccctggc ccgggacggg aagcaggacg cgggccagga      3960
cgctcccagg ggcgaggctc cggcgcggca cggcgggccc tgctaaataa ggaacgcctg      4020
gagccgcggt tggcacggcc ccggggagcc gaaaaacccc gggtctggag acagacgtcc      4080
cacccggggg ctctgcagac gccagcgggg gcggggcgcg gaggccgcgc tcagctggga      4140
ggacaaacag tcgctaattg gagaggaatt gggatgcggc ctggggctgc ggggtacccg      4200
gagaggtggg gatggctgta gggggcggca gggaagagtt ccaggaggtg tctggaaaag      4260
gatttgatgg atgtgcaaga attgggctga tgcttaggaa ggggcgatga ggtgggtcca      4320
gaagaagggg ggtgaacggt gtgagcaaag accgtgaggc tggaggctgg ccacgggagg      4380
tgtgaggggt aggggcaggg tgggaggtgg gctcgcgggt gggctggggt catgaagggc      4440
ctcaggcgct ctgctattgg gttccaaggc tatcctgaga acagggggtga ggggggattg      4500
ccgtgggggg ttaaagcctt gtcatgttcg ctttcgggag ataaaaacaa caggtggcct      4560
ttatggagac gctgcccaga gccaggtctg tgccaggctc ctgttggggg tcgtcatgcg      4620
gaatcctgac tctgaccatc cgaggcatag ggaccgtgga gatttgcatt tcacagatga      4680
ggaaacaggt ttggagaggt gacacgacct gtcccaggca tcacagccgg gatgtgcata      4740
gcaggggttt ggaactatga ggtgcccagg acccagggtt ggattgaaaa gggcggaggg      4800
gactaagata agcagacagt tgtccccagc gctggggaga tcttgggac cagtctgatg      4860
ccttgtattt cccaggctcc aggctcctcg ccgggacagt gtctccttgg gtgcgtgctg      4920
gatccctggg ggacgtggca catccccagg cttgctaaac attgggtggg ttctggcatt      4980
tggttttgta acgtttctgg gtcactcccg cctgtggcca cccttcctta ggggagccgt      5040
gtgtcctttgg ggctttgctg ggtggtctcg agggtgggag aagaatgggt tctcctggac      5100
caatggagcc cgtgccctc ggggccacat tgctcctgcg ctccctgact gcggacgcgt       5160
gtgtctcgcg gctgtctctg tggagatggc ctcctcctgc ctggcaacag cacccacaga      5220
```

```
attgcatcag acctacccca cccgttgttt gtgatgctgt agctgagggc tcctctgtct   5280
gccaggccgg tcactgggga ctctgtccag ggcctggtgg ttcctgcttc ccagcacctg   5340
atggtgtcca tgagagcagc ccctcaggag ctgtccggga gagaagggcg ctggtggctg   5400
ctgagcggag agcaaggccc gtgttctcca ggcccttggc acagcagtgg agccccgcc   5460
cctgccttgt gttgtcctct taggctctgg tcctggggtt tggaggaggg ggaccctggg   5520
agttggtggc ctgtcccagc ctgagctggc aagattccga atgccaggcc cccaagtgt   5580
gcaacagggc acagggtgac ctcatgtggg caggtgggtg ctgttctgta cacacctggg   5640
gccgccgctg ggagagttct ggaaggtggg gtgaggggac ccatggcaaa ctagggcctt   5700
aggaaggatg tgaaggccct ggctggcccc ccaggccacc ctctgtgctg tggggcagcc   5760
cagccatttt gctgtctacc ctgcaaactc ctcctcgggg agacggctgg gttttcccca   5820
gggaagaggg gtcaagctgg gagaggtgaa ggacacagat cacagctgct ggcaggtgtt   5880
caagggtcca agagcgttgc tgtctgggtg tcaccagtag ccttcctggg gggctcacgc   5940
aggtgcctct ccacttgtgg ctccctggct gctgaagctc agcagggaca gctgtgtcca   6000
gttccaggtg gaggacagcc ggggcttctg aggccacagc ctgccttggg ttaatgatgc   6060
tgccgagagg tggtggcttt tggaaaagat ggcgtactgc aaaacgtgct gctctgcgtg   6120
gctcgaagct tcgtggggag acgtgggcag agccgtggct gactcacaga ccccccaccc   6180
cagagcctgc cctgccctcc ctgccccgac ccttctccct cctgacccat gtgttttttt   6240
tttttttttt tttttttgag acagagttca ctcttgttgc caaggctgga gtgcaatggc   6300
acgatctcgg ctcatggcaa cctccgcctc ctgggttcaa gcgcttttc ctgcctcagc   6360
ctcccgagta gctgggatta caggcgtgca ccaccatgcc tggctaattt tgtattttta   6420
gtagagacag ggtttctcca tattggtcag gctggtcttg aactcctgac ctcagatgat   6480
ccgcccgcct cggcctccca aagtgctggg attacaggca tgagccacca cgcccagccc   6540
tgacccatgt tttgaaccaa attccagcca ccctttttatc tgcaagcatt ttggagggca   6600
tcgcaatact gcagacccac ctaacacaac agacagttcc ttcatgccac cgaaggcctg   6660
gtgtgttcac attttggtt taatagtttg aattaagagc caaataaggt ccacacactg   6720
caattagttg atgtcttttt ttttttcttt ttttttttt ttttgagacg gagtcttgct   6780
cttgtctcca ggccgcagtg cagtggcatg atctcagctc accgcaacct ccgactccct   6840
ggttcaagcg attctcctgc ctcagcctcc cgagtacctg gtagctgggt ttacaggcat   6900
gcaccaccgt gcccagctaa ttttttgtatt tttagtagag acggggtttt actgtgttgg   6960
ccaggatggt ctcgatctcc tgacctcgtg atctgcccac ctcggcctcc caaagtgctg   7020
ggattacagg cgtgagccac cgcacccggc caatgtcttt taaaaatata tactttttt   7080
tttttttga cacggagttt cgctcttgtt gcccaggctg gagtgcagtg gcgcgatctc   7140
acctcacgga aacctccgcc tcccgggttc aagtgattct cctgcctcag cctctccagt   7200
agctgggatt acaggcatgt gccaccatgc ctggctaatt ttgtattttt aggagagacg   7260
gggtttctcc acgttggtca ggctggtctc aaactcctga cctcaggtga tccgcctgcc   7320
ttggcctccc aaagtgttgg gattacaggt gtgagccaac gcgcccagac aaaaatatat   7380
gtgtgtcttt aaggctggtc aagcaaagca gtaggactgg agaaagaatg aagaattcta   7440
cctggctgtg atcaattcgt tgtgaacacc actgtgcttg gaccagctag ctgatgtctt   7500
ttgttttgtt ttgtttgaga cggagtctgg ctctgtcacc caggctggag acaatggtg   7560
```

```
tgatctcggc tcactgcagc ctccatctcc cgggttcaag cgattctcct gcctcagcct    7620
cctgagtagc tgggattaga ggcgcgcgcc accacgcccg gctaattttt aaaaatattt    7680
ttagtagaga tgggtttca ccatgttggt caggctggtc ttgaactctt ggccttaggt    7740
gatctgcttg cctcggcctc ccaaagtgct gggattacag gtgtgagtga tgtattttat    7800
ttatttattt atttatttat ttttattatt tgagatggag tctcactctg ttgcccaggc    7860
tggagtgcag cagtgccatc tcagctcact gcaagctccg cctcctgggt tcacgccatt    7920
ctcctgcctc agcctcctga gtagcctgga ctggtgcccg ccaccatgcc cagctaattt    7980
tttgtatttt tagtagagac ggggtttcac cgtgttagcc aggatggtct ggatctcctg    8040
acctcgtgat cctcccgcct cagcctccca aagtgctggg attacaggct tgagccaccg    8100
cctgtctttt aaatgtccga tgatgtctag gagcttccct tcctctcttt ttccttgtgc    8160
aatttgttga agaaactggc tcctgcagcc tggatttctc gctgtgtctt gggggtgcca    8220
cctccatggt gtcacctccg tggtgctgtg agtgtgtgct ttgtgtttct tgtaaattgg    8280
tcgttggagc cgacatccca ttgtcccaga ggttgtcctg gctggcactg gcctaggtgt    8340
agatgtcatc agctcagggc cccctgctct aaaggccact tctggtgctg gttgccactc    8400
accctggctg ggggtcacct gggtctgctg ctgtctcgca aatgctgggg tccaggactg    8460
ggcacatcga gggacttggt aggtgcttgg ttcactgatg taaaatatag gagcacccgg    8520
ggccttgccc tttcccacct gcatccctga atgacaggag agtgtgggag agtgtaggga    8580
cagcaggcgc agaccccggg gcccctgcct gggattggcg tcggggaaga caggcattct    8640
ggagcgaccc ctaggcctga tgccttagag cgcaactgcc agagacacag cttccttggg    8700
gggctggcca ggccacggag gggccctggc tcccatttct ggtccctgga tcctgagagc    8760
gaggactagg gattgtcacc aaggcctcca tgagccctca gcagaaggag gccacccctc    8820
gagggctccg ttatcactgg agcccgcgtt caaccaacac gcagatgatt ctccaaggac    8880
agagatggat gatggggagg gggctggcct ggaaggaccc ccagtgcagg tgacattgaa    8940
gccaggtttc aaagctccca cagggagctg cccagagaga gtccccaagg gcaaggtga    9000
ctcgggggca ggggtagggc ctctgtcagg agagcctagg agaggcctgt gtcttctagg    9060
aagagccctg gcagccgagc ggaggcagtg gtgaggacct gcatcctgca tgtccagctg    9120
gcctcacccg gggtccctga gccgggtctt acgtggctcc cgcactcggg cgttcagaac    9180
gtgcctgcgt gagaaacggt agtttcttta ttagacgcgg atgcaaactc gccaaacttg    9240
tggacaaaaa tgtggacaag aagtcacacg ctcactcctg tacgcgattg ccggcagggg    9300
tgggggaagg gatggggagg ctttggttgt gtctgcagca gttgggaatg tggggcaccc    9360
gagctcccac tgcagaggcg actgtggaga cagagagcac ctgcaggtca tccatgcagt    9420
atcggcttgc atccagatca tacagggaac actatgattc aacaacagac agggaccccg    9480
tttaaacatg gacaagggt cactcacgcc tggaatccca gcagtttggg aggcagggt    9540
gggtggatcg cttgagccca ggagtttgac accagcctgg gcaacagggt gagacccgg    9600
tctctaaaaa ataaaagaac attggccggg cgtggtggta tgcatctgtg gtcccagcta    9660
ttcaggagac tgaggtggga catcacttga gccgaggagg tcaaggctgc agtgagctgt    9720
gatcacacca ctgcactcca ggctgggtca cagagcaaga ccctgtctca aaaaaaaaaa    9780
aaaaaaaaa aaaaaatcac aggatctgaa cagagatttc tccaaagaag acgcacagat    9840
ggccaacagc gtgtgagaag atggtcgcc tcattagtca tgagggaaac gtaaatcaaa    9900
accactgtcc agccgggcgc ggtgcctcac gcctgtaatc ccagcacttt aggagagcag    9960
```

```
atggcttgag gccaggagtt tgaggccagc ctgggcaaca tagcgagacc aataaataga   10020
tattagtggt ggcgcctgta gtcccagcta gttgggaggc tgagggggga ggattccctg   10080
agtctatgag gttgagactg cagttagctg tgatggtgcc actgcactcc agcctgggcg   10140
actaggaaac ggtctttaaa aaaaaaaaaa aaaaacaggg tgggcgcggt ggttcacgcc   10200
tgtaatctca gcactttggg aggccaaggt gggggatca caaggtcagg agtttgtgac    10260
cagcctgacc aacatggtga aacccgttc tactaaaaat acaaaaatta gcgaggtgtg    10320
gtcgtgggcg cctgtaatcc cagctaatta ggaggctgag gcaggagaat cacttgaacc   10380
cgggaggcgg aggttgcagt gagccaatat cacaccactg cactctagcc tggtcaacag   10440
agcgagactc tgtctcaaaa aaaaaaaatg ctgagcgtgg tggcgcatgc ctgtagtctc   10500
agctactttg ggggctgagg caggagaatc gcttgaacct gggaggcaga ggtcgcagtg   10560
aggcaagatt gcaccattgc actccagcct gggagacaga gtgaaactct gtctcaaaaa   10620
gaaaaggtct aggaagagtc cgcaccctct ccccgcggtg ccacgccgg gctccgcgct    10680
gagccctctg tgttcttgtc tctccatacc tcatcacggc accgcagggt tgcagccact   10740
cctggtctca ttttacacac caggaaattg aggctctttg agaagccgtg gtgatgattt   10800
catcagcatg ctctggggca gaccctgca gccgcacagg gtgcctgggg cccacactag    10860
tgccctggtt tatagacaga cagaggtggc agtggcgctt ccgagtcggg ctgcgatgtg   10920
cttgcactcc ccgagggget gaggggccct gcgcccaggt gcagctgctt gggtgctgcc   10980
agccctccc acctctccct ccctgccagc cctcccacc tctccctccc tgccagcccc     11040
tcccacctct ccctccctgc cagcccctcc cacctctccc tccctgccag ccctcccac    11100
ctctccctcc ctgccagccc ctcccacctc tccctccctg cagccctc ccacctctcc    11160
ctccctgcca gccctcca cctctccctc cctccagccc ctcccacctc tccctccctg    11220
ccagcccctc ccacctctcc ctccctgcca gccctcca cctctccctc cctgccagcc    11280
cctcccacct ctccctccct gccagcccct cccacctctc cctccctgcc agcccctccc   11340
acctctccct ccctgccagc cctcccacc tctccctccc tggctcatcc ctgctgtgtc    11400
ccttctctct agtttcctgt tcagtttcag gaaggaggct gggaacccag atgtagggaa   11460
tttgcgccct ggagtcagac ctgggttcac gtcccagcgc ctccacctct ggtgtgacct   11520
tggtccagtc tctcagcctc agtttcctca cctgtaaagt gggctccatg attagatgca   11580
ccctgcaggg cagtgtagca gtgacctggc tcagccactg cagcccaa caatcatacc     11640
ttgttaaagt agctctgtcg gttccctcag gggttccggg ggcccattcc cctgtcctcc   11700
atgcactgtg agacctgccc tgccacagag cagagtgtaa cagcctgagg gtgagagcca   11760
gacactgtgc ctgtgcttag accagacact ggacgacggg agccagtgca gcctgggcgg   11820
gtggactcct atggacccct cagcacccag cctcggtgcc ttcagcgcag ggccgcgtgg   11880
ctgtgggggc tcacaagacc cggcccactc ctgcttgtgc ctacatctgg gtgtttgccc   11940
attggtgcct tttgacgcgt tctggtgtgt gtgagacgtg cggggctggg aagtgttggc   12000
agagccgcga gtaccgtcct cactccttt gttcttttga cgtaagctgg cgagtggcac    12060
tgcctgagtt ccgctcagtg cccgcctga tgtgcggacc ccgctgcatt cttgctgtta   12120
ggtggtggcg gtgtgcgctg tcgctggtgg gcaccgagag tctttgggag ctttggggag   12180
gttgtgccaa gcctgagcct cgacgtcccc cttcccggct ttctgttggc tcttctgagg   12240
ccagggcatc tctatgaggg cctcctgctg gagccgtctc tgtggatctc ctctgccatc   12300
```

```
ctggcccatg agtgggtgat gcgctggcca ccatctggtg acagtggccg ggcaccgctg    12360
ccaaatgtgg gtcccgcatc tgcaagcccc tccctgggtc ccctagggta tggggtggtt    12420
ctgccactgc cctcgctccc ccaccttggg gtgcctctcc ccctgctcgt gggggagacc    12480
ctgcctggga tctgctttcc agcaaggaat atactttgga gggagacaca catgttcttt    12540
tctggagctc tgcagtggcc acggcagccc agcccgccaa gcaccctgga atgaaaacat    12600
cccgctgctg tctgggcctg gcctgcactc tgctgcctgc gctccagctg gctgaggccg    12660
ggcacgtctg cgggcacagc agcggggggcg ccacagtctc cctgcagagt gagcgcagct    12720
ggaaaatgca gctcacgccc tttcccagaa cacctcgctc ttcatggctt ggcagctgtc    12780
cttgcctagg ggccagggtg cccaggcact ggtggcagga aagggctac atctgggct      12840 gaggcgggct gggtccttt ctccctgcag ctcccgaggc ccagcctgg cccagcctgg      12900 cattcctgac cttagcagcg ccatgatctg aagacaggct ggcttctgtg aggccacctc    12960
agaaagggct ttgtgcccag gcagaggcgg aagccagctc ttccttctgg ttgaggcagg    13020
aatgaggcca gcgctgggca agcccatgcc cagggaacgt cacagctgtg ggagtacagg    13080
ggctccgggt tctgagcccg tccactgtgc atcgtggccc tggcctcagg atggctcgta    13140
ccatcattgg ctgtgcccac agccgagtgg gtgatgggat tccggctgcc ccgctggatc    13200
tgtgctgctg ccctctccag ggcactgctg tgcccgcaca gccgggcgca gatggccagt    13260
ttgcttgccc ccccccccac catcctcttc ctaccttggc ttcctccatt gacacactgg    13320
accctgctgg ctgcccgggg aggtgtttgg gggatggtgt tgggggagga ggagggcccc    13380
ttgagcctca gtgtgcccat caggagcgta aggtcagtgc agcacctgcc cacacaggct    13440
gtgaagggtg ggagtggaga gggatgcaag ggggtcacaa cgcctggctc catgtcagct    13500
gcgtgcaggg gcaccaggag ccggcccctca ttctcccctt gaactggaag ggtggccccg    13560
accccagcgg caggtagcat acgtatgaag cgctctcctt cctacacccc acaggtgggc    13620
tcgtctccag acgccctttt tgagctggc tgtgttttc catctgtgta ggcaaggaca     13680
tcgcagactc cccttttctca tctcccctcgt tcagcctccg aggccggagt ctccatccct    13740
gtgcctgcct gtgggtcccg ggaggacctg aggctgccca tgtcacccc ggcatctcat     13800 cctggggaca gttcagccgt gggagggatc tgtaaggaca gaatgccgct gagcctgggg    13860
ctccccagct agtctcacac cccgtgtctg ggacccagag accctcgtgc agggctctgt    13920
tgcttggggc ctggcagcct cgtcctgtat cagaggctgc cacccccacc cctcgtgggg    13980
ccagggttgt ggccggcctc cctggccctc cccatggaag tggtaggcgg agccagcagc    14040
catctgccca gcccgggggct gcactgtttt ttttcaaatg agcaccgtcc caaactgcag    14100
cccgttaatt taaacaggat catttccggc cctggaagcc gcctcactct ccttaaaatag   14160 aaaggagcac agcgcagagg gaaacagatg aggtcatggc tcggctggcc cagcgaggaa    14220
ggggccgcag tggggggtggc actgccgcct gtccctgtc ctctccagcg cccacactgc    14280
agcccatttc ctcaccctgg gcctgctctc ggaagggacg ggcctggggg tcctcttgct    14340
gggcggaggg gaaccagctc ctccaggaga ggacggggcc tggcaggggg catgggcct    14400 ccctgggtct ggcgtcctgt cctgcccctg ccgaggagg agcggttaca taagctccgc    14460
aggcggcccc tccgagccgg tcccccagc ccagtttcca gtgaggcggc cagcgcgggc    14520
gggggtgccg ggcctggcgc acaccgctg ctgaccacac gtgtctggaa tgtgcagatg     14580
tttctttggg ggctccgtcc ggcccccaga ccccactcag catctggtct ggggagtggg    14640
cgcctggggc actcagctct gagtgtgaga ctctgaggca ggtctggttt gtctggggcc    14700
```

```
attccctctg ctgtggattg ggagggcccc gggagctgcc ccacacccag ggaagttctc   14760
ctcagtccca ctgttgcatt ccccgacccc ggctccccg gcccaggagc gcctgtgggg    14820
cagaaggccc agccccaaga cttcccggcc ctgccagcct caggcttcac ccaccctcgc   14880
gccaactgtg ggcagagccc aggggaggg caggagagcc agcgcctggc tgggaacacc    14940 cctgagggc cgaggctcca gggcgagggg gcccgacctg ggttcacac gcccgggtgg    15000 cgggcagacc cgctgcagca tgagacacgt gtcagctacc tcgggccggc aggctggccc   15060
tgctgcccac agccctggga cgtggcccca cctgtgacgg gtgtggaggg gcagcctcca   15120
ggcctggcca caccctctgc tgttgctgct cctgctccag gattggcaag ggtgctggga   15180
aggggtgaag accgtactg tggccacaca cctgggactt ccttctccac ccagtggtgc    15240
cccagcagcc gctaaggagc ccgctgggtc ccacgctagg atggtcctaa ctcctcccgc   15300
cttccagatc ggacgctcgg cgctggggac cccttgtgtc ccggggctgg ggcaccgtcc   15360
tgcccccatg ggggtgtact cctcccgaca agcttggctt cagcttccct gggagcacat   15420 cctggcccctc gggcacccat caggctgtcc ctgtgcacct ggctcccacc cttccagctc   15480
atagcaggaa ctggggtgag gagtgcgtgg ggcagcaagg gcctgggacc ccagaggacc   15540
ctgcactctg ctctgtgctc ttgcctgggc ttagggccgc tcggtggtcc tgctgccaga   15600
tgcctgggcc ctgctgtgtc ccccatcctt gcagggaacc agaacgtggg ggcagggcat   15660
cagacagcgg cgatgatgtc acctggcggg tgcagaggaa gcccgagggg cggggtgggg   15720
gggctggcgc gaggctgcct ggctaggcct tggcgttccc ccagaacggc gatggcaaaa   15780
gcagatggag acgtgaaaaa gtacgggagc aagcgaggtg aggactccac ggggacccct   15840
gtgctgttcc ctgtccctga agcccacacc tgagtcctgc ccagggcaga tgcttccaca   15900
cccagggggc acctgagtcc tacccagggc agacgcttcc acaccctggg ggctggggga   15960
ctgcacctgg ctcctgtctg ggccccagct tcattccact gccctgggcc ctgggagctc   16020
ggccgagcgg ggtccccaag accttgctgc atttctgggc cttgggctgg ggtgagggcc   16080
gggagaagga gccagcctgg agcctggcac gcagggagtg catggccaga accggtgaca   16140
ggcagggctg cctgctggcg tggaagaagt gtccatggca ccccccaggcc tggttcacag   16200 tgggatgggc ggggagccgg ggggctctgg ggtcctcggc tgacctgccc ccacccctgc   16260
cctggcttgt cagctcccag cagcagccac tcttgatgga ttttccagaa aatgaggtgt   16320
ggccaaacat cttcaggctt ttccttcttt cctttctccc gtggcctggg tgggagctgc   16380
tccccatgcc tggggcagg tgcgagagcc tgtgcccctc cctggggcag tttcacagct    16440
gtgtccctcc cagggggcct gcctgtgttc accgtggcct ctgcagcacc tctcgcccct   16500
tagggctcct gcgcctcggg tcccggtgcc tcatttctcc ctaaagcatt ggttctgctg   16560
ccgccgcagc cgctggaaag tccctcctca ggtctaactg cagttcctca cggcacagtg   16620
ttccccctcg ggcatggtgc ttgggcagtg gtgtgagtc cagctgcctc accctgtctc    16680
gagaatggcc tcttgctggt ctcccagcca ccaccctgtc ccaccccacg gcggggatgg   16740
tgtggatgcc tagcagcgcg gctgtgggcc cacccatcct tatgggcagt ggggagcacc   16800
tcagcccgtg tccctacctt ggtgtagagg aggggacggc agagaagcag ggttcagtta   16860 gggggggaagt ggtggccctg ccggaggggc cgttccctgt gtgcctggcc cccagatcct   16920
ctcccctccc ggagcccagg gcacaggcat aggctctctg agtgtcccac agcccctggg   16980
ggaagggaac tgcaccccca accgtgccct ccatccgcag atggaacgag aagctccggg   17040
```

```
agccagtgcc cagcgtctca tctgtctggg cacccagccc aggtgagggc ctggctccac   17100
cgtccgtggc tggtgctgct tcctggcacg gagaaggcct cggctgctct gtcccctcag   17160
ctggggtggc ctctggtccc cttctttgtt ggttcccttc tcaagctctt gccctggccc   17220
cgggccccac cgggcagcct gtgtgtgcgt ctctcctgcg ccgggtaggc tcctgtggga   17280
gcggagctcc ggtgggagga gcagggctgg aggctggcag gggctgggcg ggtgttcagg   17340
gatggaggcc gccccggctt ggggctggct gccgggtggt cattgctggg aagagcaagt   17400
ctaggcggag gcacctgctg ggtcactcgt ggggagggtg acacctgggg aagtagaggc   17460
ccgtggcagg aggtgaggcc tcggggtcct ggggagcagg ggggtggtgt gcagacctgc   17520
ggagccatag tcctgtgcca ggagcactac tgggagtgcg tgggaccagg aggggtgccc   17580
agggtgggcg gcagagtgac ccccgaggtg cttgaggccg aggggaggtg gagttctcgg   17640
tttgccccag ctctctgtct actcacctcc gcatcaccag ctccaggacc tggtttgtaa   17700
ctcgggcagc tctgaaaaga gagacatgct gccgccctgt ggtttctgtt gcttttcctt   17760
cactgactac tgacatggga tgttttcct acggctgtga ccaattgtgc ttcttctaat   17820
tgcctggttt ttcttttttt gttttggag ttttctcttt cttcctccc tccctctcac   17880 cctccatcct tttttttttt attttattt tttgagatgg agcttcactc ttgcaggatg   17940
gggtgctgga gtgcagggt gcgatctcag ctcactgcaa cctctgcctc gcgggttcaa   18000
gtgattctcc tgcctaagcc tcctgagtag ctggaattac aggtgcttgc caccacgccc   18060
gactaattct gtagttttgg tagagacagg gtgtctccgt gttggtcggt ctggtcttga   18120
actcctgacc tcaggtgatg cgcccgcctc agcctcccaa agtgctggga ttacaggcag   18180
gagccattgc acccggctct ttcccttct cctttcttc tctctctcct ccctttcttt   18240
cttttctttt cttttttttt tcttttgaga tggagtctcg ctctgtcacc aggctggatt   18300
gcagtggcgt gatcttggct cactgcaacc ttcgcctccc gggttcacgt gattctcctg   18360
cctcagcctc ctgagtggct ggcactacag gctcccgccg ccatgcccgg ctaattttg   18420 cattttagt agagacaggg tttcaccctg ttggccagga tggtctcgat ctcttgatct   18480
catgatccac ccaccttggc ctcccaaagt tctggcatta caggagtgag ccaccgtgcc   18540
cggccatctt tctttccttg ctttctcttt gttttcttc gagaccgggt cttgctctgt   18600
cgcccaggct ggactgcagt ggcacaatca tagctcactg cagcctcgac ttccctggct   18660
caagcgatcc ttcctcctca gccccccgag tagctggaac tacagttaca cactaccatg   18720
cctggctgat tcttttttc cttgtagaga tggggtcttg ctatgctgtc catcctggtc   18780
tcaaactcct ggccttccca aagcactggg tttacaggca taagccacca cacccagttt   18840
ccttttcttc tttttaactg gaatagttga cgttttcttt attagctgtg tgtcaggagg   18900
gtatttttgg cctttagtat gtcgtgtaag ttgctagtgc ttttctgaga ttgtagtttg   18960
ttttctaatt ttatttatat tttgcgtaga agttgtgtat tttagatgga gttaggtcgg   19020
ctggtctttg atgttttatt tattaattat gtatgtattt atttattttt gaggtagagt   19080
ctcgccgttt cacccaggct ggagtacagt gatgcgatct cagctccctg tagccttgac   19140
ctctctgggc tcaagtgatt tttctctcct ctacctcccg agtacttggg acccaggcg   19200 catgccgcca tgcctggcta atgtgtattt tttgtagata cggggtctca ctgtgttgcc   19260
cagggtggtt tcaaaatcct gggcccaggc gatccttccg tctcagctcc cacggtgctg   19320
tgttaccggc gtgtgcccag tgcctggccg tcttggaggt cttgtttctc tgggtttatg   19380
cctcgaggtg gcgcctgctc ccctgtgctc cctggtagcc tggtagtgag cctgcttctc   19440
```

| | |
|---|---|
| acacagtcat acctggttgt ggtcccacag tgggaccacc ctgttgggtt cagaacagga | 19500 |
| gatggggggcc cctcgagtct gtgtgggggc tgtggacagg gttgggagac cttggctctg | 19560 |
| tgggggactg tggacagggg atgggggggcc ttggccctgc gtgggatggg ttgggggtcc | 19620 |
| gtgcccttcc tggccctggg tggacaggtc catgtggcac tcggcatagg gctgagatgg | 19680 |
| gtgcagaggg ctgaggcccc caggcctctc ctggcttggt ttccccagat gagtgttcat | 19740 |
| ttgggtcttc catcagaaag tcccctcctg acctctggga gtggggagct caagggtggg | 19800 |
| aggccatagc ttggggatgc tggcaatgtg tgggatgggc ccagggaagg cctctggcct | 19860 |
| actaggggct ctggccctga cccacggcca ctcactcctc agagacgtct cccacaacct | 19920 |
| gctccgggcg ctggacgttg ggctcctggc gaacctctcg gcgctggcag agctgtgagt | 19980 |
| gtcccccagt cgtgccagca tgcggggctc actccgggtg ggctggcggc accgcctctt | 20040 |
| gctgctcagc tgtgggggct tccatcagct ttgccgaatc cccgtctct tccagggata | 20100 |
| taagcaacaa caagatttct acgttagaag aaggaatatt tgctaattta tttaatttaa | 20160 |
| gtgaaatgta agttgtggtt cttggggtgg ggtcctggct ggaccccagg cccccaatat | 20220 |
| cccttctgcc ctcccagttg gtccgtgtcc ccttccaggc ttgagaccag atcctggggg | 20280 |
| cagttcactg cctgcttgga gcccccagt gccggcttgg ttggggcagg ggaggcggtg | 20340 |
| ctgtcagggt ggctccaggg cctggttgcc agtggggggc tggcatagac ccttcccacc | 20400 |
| agacctggtc cccaacacct gcccctgccc tgcagaaacc tgagtgggaa cccgtttgag | 20460 |
| tgtgactgtg gctggcgtg gctgccgcga tgggcggagg agcagcaggt gcgggtggtg | 20520 |
| cagcccgagg cagccacgtg tgctgggcct ggctccctgg ctggccagcc tctgcttggc | 20580 |
| atcccccttgc tggacagtgg ctgtggtgag tgccggtggg tggggccagc tctgtccttc | 20640 |
| ccagccaggt gggacctggg ccctgcagac actgggcagg gctcaggaag gcctctctgg | 20700 |
| gggggggcctc cggccaagg gaacagcatg ggagcctgtg agtgcggcgg gcggatgtgg | 20760 |
| gggcgtgggg tggagccagg aggagcagaa cccggggtcc agtggctgcc tcttctaggt | 20820 |
| gaggagtatg tcgcctgcct ccctgacaac agctcaggca ccgtggcagc agtgtccttt | 20880 |
| tcagctgccc acgaaggcct gcttcagcca gaggcctgca gcgccttctg cttctccacc | 20940 |
| ggccagggcc tcgcagccct ctcggagcag ggctggtgcc tgtgtggggc ggcccagccc | 21000 |
| tccagtgcct cctttgcctg cctgtccctc tgctccggcc cccgccacc tctgcccccc | 21060 |
| acctgtaggg gccccaccct cctccagcac gtcttccctg cctcccagg ggccaccctg | 21120 |
| gtggggcccc acgacctct ggcctctggc cagctagcag ccttccacat cgctgccccg | 21180 |
| ctccctgtca ctgccacacg ctgggacttc ggagacggct ccgccgaggt ggatgccgct | 21240 |
| gggcggctg cctcgcatcg ctatgtgctg cctgggcgct atcacgtgac ggccgtgctg | 21300 |
| gccctggggg ccggctcagc cctgctgggg acagacgtgc aggtggaagc ggcacctgcc | 21360 |
| gccctggagc tcgtgtgccc gtcctcggtg cagagtgacg agagcctcga cctcagcatc | 21420 |
| cagaaccgcg gtggttcagg cctggaggcc gcctacagca tcgtggccct gggcgaggag | 21480 |
| ccggcccgag gtgagtgtct gctgcccact ccccttcctc cccagggcca tccagatggg | 21540 |
| gcagagcctg gtaccccgt cttgggccca cactgaccgt tgacaccctc gttcccaccg | 21600 |
| gtctccagcg gtgcacccgc tctgcccctc ggacacggag atcttccctg caacgggca | 21660 |
| ctgctaccgc ctggtggtgg agaaggcgg ctggctgcag gcgcaggagc agtgtcaggc | 21720 |
| ctgggccggg gccgccctgg caatggtgga cagtcccgcc gtgcagcgct tcctggtctc | 21780 |

-continued

```
ccgggtcacc aggtgcctgc ccccaccccc cgaggggcca taggttggga gatctctgaa   21840 gcactgggc agagactgcg gctggggagt ctcaggagga aggaggtggg agctgggccg    21900
gccctggtga gcaggtggcg ccggccggtg gggccgttcc tgtcagctct gcagatgcag   21960
aggtggacat gagctggggg cagcctccgg acactcctgg gcacgccata cgggaggtgg   22020
cctgcacggg gatccctgcc ggtacccaca ggccccgtgg gtgggtgctg ctgtgagcct   22080
gggctggtgg gccctggtct ccgggctctg agcctcagtt tccccatctg gaaagggggga  22140 cagtgatggg gctcccagcg ggctgctgtg agggtgggag gatggaggag tgccctgagc   22200
cccctgccat cccacacccg cccccaggag cctagacgtg tggatcggct tctcgactgt   22260 gcaggggtg gaggtgggcc cagcgccgca gggcgaggcc ttcagcctgg agagctgcca   22320
gaactggctg cccggggagc cacacccagc cacagccgag cactgcgtcc ggctcgggcc   22380
caccgggtgg tgtaacaccg acctgtgctc agcgccgcac agctacgtct gcgagctgca   22440 gccccggaggt gtgcgggggg ccaggcaggg gcctgagacg ctggctgtgg ttaggggcct   22500
gccgagcgcc cgcggtggag cctgggctga ggaggagggg ctggtggggg ggttttcggg   22560
cggctcggtc cccagtctgt tcgtcctggt gtcctgggcc ctggcccggc gcctcactgt   22620
gcactcgcca ccccaggccc agtgcaggat gccgagaacc tcctcgtggg agcgcccagt   22680
ggggacctgc agggacccct gacgcctctg gcacagcagg acggcctctc agccccgcac   22740
gagcccgtgg aggtagtcgg cccccccacgt tctacaacct gccctcctgc ctgccctgg   22800 aggccttgcc tgccctgccc actgtgggtc tcgccaaaaa acttgggggc cttaatgttg   22860
cttgtgccca gtgaagatgg ttgggaaaat ccagagtgca gagaggaaag cgtttactca   22920
cattacctcc aggcctttttc tctgagcgtg tgtgagttat tcctgaaagg caggtcaggg   22980
gtcctgcccc ccatggacag tttccaccgg agtcttcctc tcgagcgaca ggagccaggc   23040
ctgtgggggt ctgatggctc gctctccttc cctcccctct tcctgggaag ttcgggtagg   23100
gggagtctgg gcttcaggct gggatggggt ctgtggagct gaggcggccc cctgcccacc   23160
aggtcatggt attcccgggc ctgcgtctga gccgtgaagc cttcctcacc acggccgaat   23220
ttgggaccca ggagctccgg cggcccgccc agctgcggct gcaggtgtac cggctcctca   23280
gcacagcagg tgggactctg ggtggtgggt ggtgggtggt gggcgccgca ggactcgggg   23340
tggcctctct gagcttttcac gtctgctggt cctgtggcca ccagagtggt tcccagtctt   23400
aggtggacag agcagggggtt ccagagacac cagctcattc caggtgtcct gggggtggat   23460
tgggtggggc ctgcctgggg gccggcctgg gtcagtcggc tggccggaga cggacgcagc   23520
actgggctgg gagtgctgcc caggtgggga gacctgtcct cacagcaagg ccaggattgc   23580
tggtgcaggc agttgggcat ctctgacggt ggcctgtggg caaatcaggg ccccaacacc   23640
ctcccctcct cacagggacc ccggagaacg gcagcgagcc tgagagcagg tccccggaca   23700
acaggaccca gctggccccc gcgtgcatgc caggggacg ctggtgccct ggagccaaca   23760
tctgcttgcc gctggacgcc tcctgccacc cccaggcctg cgccaatggc tgcacgtcag   23820
ggccagggct acccgggggcc ccctatgcgc tatggagaga gttcctcttc tccgttcccg   23880
cggggccccc cgcgcagtac tcggtgtgtg gccctgacct gggtctgttc cctgcatctc   23940
ctcaggccac cttcctgtct gctgcccagg gtctgggtct gtgcaccaga cacacccagc   24000
ctgcaggccc ctcccacgtc cttgccacct ctgacctccg acctctgcag tgccctcggc   24060
cctctcccag tgggagaagc tctcgcctgg gcccttggca cgagctgtgc ctcctcttcc   24120
tctctcccag cacagctgct ccttcctgtc tgccaggtct tggcctgtgt cctctcccg    24180
```

```
tgtgtccccc ggtctgcaac tgtcctgcct gtccttgtca cgagcactgt ggggaggctc   24240
cttgaggtgt ggctgacgaa gcggggagcc ctgcgtgtcc accctcatcc gtcgtgcggg   24300
ggtccacggg ccatgaccgt gaggacgtga tgcagccctg cctccctctc cacaggtcac   24360
cctcacggca caggatgtcc tcatgctccc tggtgacctc gttggcttgc agcacgacgc   24420
tggccctggc gccctcctgc actgctcgcc ggctcccggc caccctggtc cccgggcccc   24480
gtacctctcc gccaacgcct cgtcatggct gccccacttg ccagcccagc tggagggcac   24540
ttgggcctgc cctgcctgtg ccctgcggct gcttgcagcc acggaacagc tcaccgtgct   24600
gctgggcttg aggcccaacc ctggactgcg gctgcctggg cgctatgagg tccgggcaga   24660
ggtgggcaat ggcgtgtcca ggcacaacct ctcctgcagc tttgacgtgg tctccccagt   24720
ggctgggctg cgggtcatct accctgcccc ccgcgacggc cgcctctacg tgcccaccaa   24780
cggctcagcc ttggtgctcc aggtggactc tggtgccaac gccacggcca cggctcgctg   24840
gcctggggga gtgtcagcg cccgctttga gaatgtctgc cctgccctgg tggccacctt   24900
cgtgcccggc tgcccctggg agaccaacga taccctgttc tcagtggtag cactgccgtg   24960
gctcagtgag ggggagcacg tggtggacgt ggtggtggaa aacagcgcca gccgggccaa   25020
cctcagcctg cgggtgacgg cggaggagcc catctgtggc ctccgcgcca cgcccagccc   25080
cgaggcccgt gtactgcagg gagtcctagt ggtgagtatg gccgaggctc caccaccagc   25140
ccccaggcag gtgcctgcag acagggtgct cacacagggc gtgaggcctg gcttcccagt   25200
gagggcagca gcccagttac tggggacgtc ggccccgggc aggtcctgct ggctggctcc   25260
tcgggctacc tggtgggctt taaattcctg gaaagtcacg gctctgacag tggctccgct   25320
aactcattcc actgtctcat ttcacaaaat gaatttaaaa ctctgctccc tgacctcaca   25380 cgagccccg tgagtctctc acgccctctg ctgtgttctc gcctggctaa agcgagtggc   25440
ttttgaggtg gagtctgaac ccctgatggg aaactgcggg ctgccgcgg tgccaccatg   25500 ctgggtacat ggggacagg gctgtctcca tcttgcgggt acctgcctct tcaccagggg   25560
ccttgggagg ggccatcaga aatggcgtga cctgtgcagc ctgtcctggg ttctgtaagc   25620
cagtgtaggt gcctcccctc actgctccga gctctctggg tgaggagctg gggcaagagc   25680
gccgggaggg tctgagaaga ctcagagaga ggtggactct ttgtagctgg tactaggttt   25740
gctttacaga tggggaaact gaggcacaga gaggttgagg cattagtagt actacatggc   25800
tggctggaga gccggacagt gagtgtccca gcccgggctt ggctcccatg gcatgcagag   25860
ccccgggcac ctcctctcct ctgtgcccg cgtgggactc tccagcccga cgggaggtgt   25920
gtccaggagg cgacaggcta agggcagagt cctccacaga gcccaggctg acaccattcc   25980
ccccgcagag gtacagcccc gtggtggagg ccggctcgga catggtcttc cggtggacca   26040
tcaacgacaa gcagtccctg accttccaga acgtggtctt caatgtcatt tatcagagcg   26100
cggcggtctt caagctctca gtaggtgggc ggggtgggg agggaggggg atggggcggg   26160
gcagggcggg ggcgggctcc accttcacct ctgccttctg ctctgcttca tgctgcccga   26220
ggacgctgcc atggctgtgg gtgagtggag ggagggacgc caatcagggc caggcctctc   26280
acctgccacc tgggctcact gacgcctgtc cctgcagctg acggcctcca accacgtgag   26340
caacgtcacc gtgaactaca acgtaaccgt ggagcggatg aacaggatgc agggtctgca   26400
ggtctccaca gtgccggccg tgctgtcccc caatgccacg ctagcactga cggcgggcgt   26460
gctggtggac tcggccgtgg aggtggcctt cctgtgagtg actcggggc cggtttgggg   26520
```

| | |
|---|---|
| tgggcaccag gctcttgtcc cagccccagc ctcagccgag ggaccccac atcacgggt | 26580 |
| tgcttttctg agcctcggtt tccctgtctg ttgggaggta actgggtgca caggagccct | 26640 |
| gaggctgcac gggagccggg agaggcctca gcacagccgg gtgggccctg aatggaggcc | 26700 |
| cggggcgtga ctgcagagtg gagcctcggc tgggtcccaa gcaccccctg ccccgccacc | 26760 |
| gcccacccct gtcccggttc actcactgcg tcccaccgcc ccggcaggtg gacctttggg | 26820 |
| gatggggagc aggccctcca ccagttccag cctccgtaca acgagtcctt cccgttcca | 26880 |
| gaccctcgg tggcccaggt gctggtggag cacaatgtca tgcacaccta cgctgcccca | 26940 |
| ggtgagggat gaggggtga gggggccact gcctttcagg ctctgagcac gggtccccc | 27000 |
| agctccccag tcaagctgcc cccttcctc cccaacagcc ctcactgtga cctcacctgg | 27060 |
| gctgatggct taggccctac tggggtgagg gaggggccag gcgtggggg agtggacagg | 27120 |
| gaagctgggc ccctgaactg cgccccccgc cctccccggg cctggctctt gctgctctgc | 27180 |
| tgccccgagt gcagctgcac ttggaggcgg tgcgtcctcg ccaggcagcc ctcagtgctg | 27240 |
| ctacacctgt gctccgtccc gcacgtggct gggagcctg gaccctaa ggctgggccg | 27300 |
| caggtgcagc cgttcacccc gggctcctca ggcggggggc ttctgccgag cgggtgggga | 27360 |
| gcaggtgggg gtgccgcggc tgcccactc gggcctgtcc ccacaggtga gtacctcctg | 27420 |
| accgtgctgg catctaatgc cttcgagaac cggacgcagc aggtgcctgt gagcgtgcgc | 27480 |
| gcctccctgc cctccgtggc tgtgggtgtg agtgacggcg tcctggtggc cggccggccc | 27540 |
| gtcaccttct acccgcaccc gctgccctcg cctgggggtg ttctttacac gtgggacttc | 27600 |
| ggggacggct cccctgtcct gacccagagc cagccggctg ccaaccacac ctatgcctcg | 27660 |
| aggggcacct accacgtgcg cctggaggtc aacaacacgg tgagcggtgc ggcggcccag | 27720 |
| gcggatgtgc gcgtctttga ggagctccgc ggactcagcg tggacatgag cctgccgtg | 27780 |
| gagcagggcg ccccgtggt ggtcagcgcc gcggtgcaga cgggcgacaa catcacgtgg | 27840 |
| accttcgaca tggggacgg caccgtgctg tcgggcccgg aggcaacagt ggagcatgtg | 27900 |
| tacctgcggg cacagaactg cacagtgacc gtgggtgcgg ccagccccgc cggccacctg | 27960 |
| gcccggagcc tgcacgtgct ggtcttcgtc ctggaggtgc tgcgcgttga acccgccgcc | 28020 |
| tgcatcccca cgcagcctga cgcgcggctc acggcctacg tcaccgggaa cccggcccac | 28080 |
| tacctcttcg actggacctt cggggatggc tcctccaaca cgaccgtgcg ggggtgcccg | 28140 |
| acggtgacac acaacttcac gcggagcggc acgttccccc tggcgctggt gctgtccagc | 28200 |
| cgcgtgaaca gggcgcatta cttcaccagc atctgcgtgg agccagaggt gggcaacgtc | 28260 |
| accctgcagc cagagaggca gtttgtgcag ctcggggacg aggcctggct ggtggcatgt | 28320 |
| gcctggcccc cgttcccta ccgctacacc tgggactttg gcaccgagga agccgccccc | 28380 |
| acccgtgcca ggggccctga ggtgacgttc atctaccgag acccaggctc ctatcttgtg | 28440 |
| acagtcaccg cgtccaacaa catctctgct gccaatgact cagccctggt ggaggtgcag | 28500 |
| gagcccgtgc tggtcaccag catcaaggtc aatggctccc ttgggctgga gctgcagcag | 28560 |
| ccgtacctgt tctctgctgt gggccgtggg cgccccgcca gctacctgtg ggatctgggg | 28620 |
| gacggtgggg ggctcgaggg tccggaggtc acccacgctt acaacagcac aggtgacttc | 28680 |
| accgttaggt ggccggctgg aatgaggtga gccgcagcga ggcctggctc aatgtgacgg | 28740 |
| tgaagcggcg cgtgcggggg ctcgtcgtca atgcaagccc cacggtggtg ccctgaatg | 28800 |
| ggagcgtgag cttcagcacg tcgctggagg ccggcagtga tgtgcgctat tcctgggtgc | 28860 |
| tctgtgaccg ctgcacgccc atccctgggg gtcctaccat ctcttacacc ttccgctccg | 28920 |

```
tgggcacctt caatatcatc gtcacggctg agaacgaggt gggctccgcc caggacagca   28980
tcttcgtcta tgtcctgcag ctcatagagg ggctgcaggt ggtgggcggt ggccgctact   29040
tccccaccaa ccacacggta cagctgcagg ccgtggttag ggatggcacc aacgtctcct   29100
acagctggac tgcctggagg gacaggggcc cggccctggc cggcagcggc aaaggcttct   29160
cgctcaccgt ctcgaggccg gcacctacca tgtgcagctg cgggccacca acatgctggg   29220
cagcgcctgg gccgactgca ccatggactt cgtggagcct gtggggtggc tgatggtggc   29280
cgcctccccg aacccagctg ccgtcaacaa aagcgtcacc ctcagtgccg agctggctgg   29340
tggcagtggt gtcgtataca cttggtcctt ggaggagggg ctgagctggg agacctccga   29400
gccatttacc acccatagct tccccacacc cggcctgcac ttggtcacca tgacggcagg   29460
gaacccgctg ggctcagcca acgccaccgt ggaagtggat gtgcaggtgc ctgtgagtgg   29520
cctcagcatc agggccagcg agcccggagg cagcttcgtg gcggccgggt cctctgtgcc   29580
cttttggggg cagctggcca cgggcaccaa tgtgagctgg tgctgggctg tgcccggcgg   29640
cagcagcaag cgtggccctc atgtcaccat ggtcttcccg gatgctggca ccttctccat   29700
ccggctcaat gcctccaacg cagtcagctg ggtctcagcc acgtacaacc tcacggcgga   29760
ggagcccatc gtgggcctgg tgctgtgggc cagcagcaag gtggtggcgc ccgggcagct   29820
ggtccatttt cagatcctgc tggctgccgg ctcagctgtc accttccgcc tgcaggtcgg   29880
cggggccaac cccgaggtgc tccccgggcc ccgtttctcc cacagcttcc cccgcgtcgg   29940
agaccacgtg gtgagcgtgc ggggcaaaaa ccacgtgagc tgggcccagg cgcaggtgcg   30000
catcgtggtg ctgaggccg tgagtgggct gcaggtgccc aactgctgcg agcctggcat   30060
cgccacgggc actgagagga acttcacagc ccgcgtgcag cgcggctctc gggtcgccta   30120
cgcctggtac ttctcgctgc agaaggtcca gggcgactcg ctggtcatcc tgtcgggccg   30180
cgacgtcacc tacacgcccg tggccgcggg gctgttggag atccaggtgc gcgccttcaa   30240
cgccctgggc agtgagaacc gcacgctggt gctggaggtt caggacgccg tccagtatgt   30300
ggccctgcag agcggcccct gcttcaccaa ccgctcggcg cagtttgagg ccgccaccag   30360
ccccagcccc cggcgtgtgg cctaccactg ggactttggg gatgggtcgc cagggcagga   30420
cacagatgag cccagggccg agcactccta cctgaggcct ggggactacc gcgtgcaggt   30480
gaacgcctcc aacctggtga gcttcttcgt ggcgcaggcc acggtgaccg tccaggtgct   30540
ggcctgccgg gagccggagg tggacgtggt cctgccctg caggtgctga tgcggcgatc   30600
acagcgcaac tacttggagg cccacgttga cctgcgcgac tgcgtcacct accagactga   30660
gtaccgctgg gaggtgtatc gcaccgccag ctgccagcgg ccggggcgcc cagcgcgtgt   30720
ggccctgccc ggcgtggacg tgagccgcc tcggctggtg ctgccgcggc tggcgctgcc   30780
tgtgggcgcac tactgctttg tgtttgtcgt gtcatttggg gacacgccac tgacacagag   30840
catccaggcc aatgtgacgg tggccccga gcgcctggtg cccatcattg agggtggctc   30900
ataccgcgtg tggtcagaca cacgggacct ggtgctggat gggagcgagt cctacgaccc   30960
caacctggag gacggcgacc agacgccgct cagtttccac tgggcctgtg tggcttcgac   31020
acaggtcagt gcgtggcagg gccgtcctcc atgcccctca cccgtccaca cccatgagcc   31080
cagagaacac ccagcttgcc accagggctg gcccgtcctc agtgcctggt gggccccgtc   31140
ccagcatggg gaggggtct cccgcgctgt ctcctgggcc gggctctgct ttaaaactgg   31200
atggggctct caggccacgt cgcccccttgt tctcggcctg cagagggagg ctggcgggtg   31260
```

```
tgcgctgaac tttgggcccc gcgggagcag cacggtcacc attccacggg agcggctggc    31320
ggctggcgtg gagtacacct tcagcctgac cgtgtggaag gccggccgca aggaggaggc    31380
caccaaccag acggtgggtg ccgcccgccc ctcggccact tgccttggac agcccagcct    31440
ccctggtcat ctactgtttt ccgtgtttta gtgctggtgg aggccgcacg ctctcccctc    31500
tctgtttctg atgcaaattc tatgtaacac gacagcctgc ttcagctttg cttccttcca    31560
aacctgccac agttccacgt acagtcttca agccacatat gctctagtgg caaaagctac    31620
acagtcccct agcaatacca acagtgagga agagcccctt cccacccag aggtagccac     31680 tgtccccagc ccatgtccct gttgctggat gtggtgggcc ggttctcacc ctcacgctcc    31740
cctctctgga ccggccagga ggcttggtga ccctgagccc gtggtggctg ctcctgctgc    31800
tgtcaggcgg ggcctgctgg tgccccagag tgggcgtctg ttccccagtc cctgctttcc    31860
tcagctggcc tgattggggg tcttcccaga ggggtcgtct gaggggaggg tgtgggagca    31920
ggttccatcc cagctcagcc tcctgaccca ggccctggct aagggctgca ggagtctgtg    31980
agtcaggcct acgtggcagc tgcggtcctc acacccacac atacgtctct tctcacacgc    32040
atccccccag gggccctcag tgagcattgc ctgcctcctg ctagggtcca gctgggtcca    32100
gtacaccaga acgcacactc cagtgtcctc tgccctgtgt atgcccttcc gccgtccaag    32160
ttggaaggtg gcaaaccgga tgagtatcct gggagggagt gagctcaccg gcagtggcca    32220
ggcccctggg aaacctggag tttgggagca gcatcctcca tgggtccccc agtccttcca    32280
gcaggccaaa tagacctgtg ttggaggtaa ccccactccc acgccaggtg ctgatccgga    32340
gtggccgggt gcccattgtg tccttggagt gtgtgtcctg caaggcacag gccgtgtacg    32400
aagtgagccg cagctcctac gtgtacttgg agggccgctg cctcaattgc agcagcggct    32460
ccaagcgagg ggtgagtgtt gagcggggtg tgggcgggct ggggatgggt cccatggccg    32520
aggggacggg gcctgcaggc agaagtgggg ctgacagggc agagggttgc gccccctcac    32580 cacccttct gcctgcagcg gtgggctgca cgtacgttca gcaacaagac gctggtgctg     32640
gatgagacca ccacatccac gggcagtgca ggcatgcgac tggtgctgcg gcggggcgtg    32700
ctgcgggacg gcgagggata caccttcacg ctcacggtgc tgggccgctc tggcgaggag    32760
gagggctgcg cctccatccg cctgtccccc aaccgcccgc cgctgggggg ctcttgccgc    32820
ctcttcccac tggcgctgt gcacgccctc accaccaagg tgcacttcga atgcacgggt     32880
gagtgcaggc ctgcgtgggg ggagcagcgg gatcccccga ctctgtgacg tcacggagcc    32940
ctcccgtgat gccgtgggga ccgtccctca ggctggcatg acgcggagga tgctggcgcc    33000
ccgctggtgt acgccctgct gctgcggcgc tgtcgccagg gccactgcga ggagttctgt    33060
gtctacaagg gcagcctctc cagctacgga gccgtgctgc cccgggttt caggccacac     33120 ttcgaggtgg gcctggccgt ggtggtgcag gaccagctgg gagccgctgt ggtcgccctc    33180
aacaggtgag ccaggccgtg ggagggcgcc cccgagactg ccacctgctc accacccct    33240 ctgctcgtag gtctttggcc atcaccctcc cagagcccaa cggcagcgca acggggctca    33300
cagtctggct gcacgggctc accgctagtg tgctcccagg gctgctgcgg caggccgatc    33360
cccagcacgt catcgagtac tcgttggccc tggtcaccgt gctgaacgag gtgagtcag    33420 cctgggaggg gacgtcacat ctgctgcatg cgtgcttggg accaagacct gtaccctgc    33480 ctggagcttt gcagagggct catcccgggc cccagagata atcccagtg acccctgaagc    33540 agcacccga ccttccgctc ccagcagcca cacccaccgg gccctctccg gcgtctgctt     33600
tccacaatgc agccccgcc caggagggcc catgtgctta ccctgttttg cccatgaaga    33660
```

```
aacagctcag tgttgtgggt cagtgcccgc atcacacagc gtctagcacg taactgcacc  33720
ccgggagtcg tgggcatctg ctggcctcct gccggcctcc tgcgctgctg acagcttgct  33780
gtgccccctg cctgccccag tacgagcggg ccctggacgt ggcgcagagc ccaagcacga  33840
gcggcagcac cgagcccaga tacgcaagaa catcacggag actctggtgt ccctgagggt  33900
ccacactgtg gatgacatcc agcagatcgc tgctgcgctg cccagtgca tggtaggatg  33960
gccccacctg ctcaccctgc ccgcatgcc tgccagggca ctgggttcag ccccccaggg  34020
cagacgggca gcttggccga ggagctgagc ctccagcctg ggctccttcc tgccatggcg  34080
ttcctcggtc tctgacctgc ttcagtagcc tcagccgttc tgtcctgtgt gaacgcaggg  34140
tgcctctcgg gggacccagg gtgtaaagag gggcccagat gtggggaggg actaagaaga  34200
tgctgctctg tgccctccac tctcccctcc cctccctcc ccttccctc cctagcccc    34260
tccctcctc cctccccta gcccttcccc tcctccctc cctagccct ttcccttctt    34320
cccccagc cttccccctc ctccctccc ctagcctc ccctcctcc ctccctacc       34380
ccttccctc ctccccctccc ctagacctc cctcacctc ctccgctga gccctccac    34440
tcgtccccca gccctccct ccctagccc ctccctccc ccttcctcc ctcctcccc     34500
tccctcctc ccctccctc ttcctccc tccctcctc ccttcctc cctctcctc       34560
cccctcccct cctgtccccc ctcctccct cctccctct ccctcctcc ccctcctcc    34620
tcccctcct ccctcctccc tcctcccct cctcctctc cctcctccc tcctccctc    34680
ctccctccc ctcctccccc tccccctcc cttcctccc ctcccctc cctcctccc     34740
cctctcctcc tcccatccct cctcccatcc ctcctcccg ttcccattct ctcccctccc  34800
ccttccattt ctccctcctc ccctgccct ctctcctcc tcacctcccc ttctccgctc   34860
ctttcttctc ctccctcct ttctctcct cctccccttc tccccttctc ctcttctccc   34920
cttctcctct cttttcatcc ttcccttctt ccctcctttc ctcctcttt ccctcttctc  34980
ccccctcctc ccctccttcc tcctcccatt cccctcctc ccccctccca ttccccctcc  35040
tcccctcctt cctcctcca ttaccccctc tctcctcccc tcctcccacc ccctctcct   35100
cccggctcct ctcctcccct cctcatcccc ctcctctcct tccctcctaa ccccctcct   35160
ctcctcccct cctcatcccc ctcctctcct tccctcctcc tatccccct cctctcctcc  35220
cctcctccta ttcccctcc tctcctcccc tccttcctcc tcctcctc ccatgccccc    35280
tcctcccctc ctcccatccc cctcctcccc tcctccctcc tcccatccca tcccctcct   35340
ctcctcccct tctctccct cctcctcc ctcctctcc tctcctcctc tcctccctc     35400
ctcccatccc ccctcctccc atccccct ctctcctccc cactcctctc ctccccactc    35460
ctctcctccc ctcatccccc tcctctccc tccctcccc ctctctcct tccctcctcc    35520
tttcctcccc tcccctcct tccccctcct ccccctcctt ctccccatcc ccttcccct    35580
tctcctcctc tccctcccc cttctctttt tccctcctcc tccttcctc ctccctctt    35640
ctccccttt cccttttctc ttcctctcct ccccttctc cctcctgtcc tccctccctt    35700
tctctcttc tttcctccct ttccttctcc cctgttctcc tccctcccct ttctcccttt   35760
tcttccctcc tcctttcctc ccctcctcct tttctctgtt tctcttcctt tccctccac   35820
tttcccttc cttccccctc tcttttctct ttcctttcct ctcccttct cttccttttc    35880
ctctctcccc ttctttttccc tcttccctc ccctcctctt ccctccct cctcttcccc   35940
tccctcctc ttccctccc ctcctcttcc cctctcctcc tcttccctc cctcctctt     36000
```

```
tccctcccct cttctcctcc cctcctctcc cctcttcccc tccctcctc ttccctcccc    36060
ttccctcccc ctcctcttcc ctcccttcc cctccctcc tcttccctcc ccttccctc    36120
ctcttccttc ctctcttccc ctcccctcct cttccctccc ctcttccct ccccttctct    36180
tctcctcccc ttctcttccc ctcccctttt cttccctctc cttgtcttcc ctgcccctcct    36240
cttccctccc ctcctcttcc ctcccctctt ccctctcct cctcttccct ccctcttcc    36300
tctttcctct tccctcccc tcctcctccc tcccctttcc cctcttcccc tccctccgc    36360
ttccctcccc tttctccccc ttctctcccc tccctctcc cccttctct ccctcccct    36420
ctccccttc tctcccctcc cctctccccc ttctctcccc tctcctctcc cccttctctc    36480
cccttctct ccccttctc tctcccttc tctcccctt ctctcccctc cccccttctc    36540
tccctcccc tctcccctt ctctccctc ccctctccc tgtcctctcc tctccaccct    36600
tctctcccct cccctctcct ctcccccttc cctctcctct cccccttctc tccctcccc    36660
tctcctctcc cccctttct ccactccct ctcctctctc cctcctcct ccgtctcat    36720
gtgaagaggt gccttgtgtg gtcggtgggc tgcatcacgt ggtccccagg tggaggccct    36780
gggtcatgca gagccacaga aaatgcttag tgaggaggct gtgggggtcc agtcaagtgg    36840
gctctccagc tgcagggctg ggggtgggag ccaggtgagg acccgtgtag agaggagggc    36900
gtgtgcaagg agtggggcca ggagcggggc tggacactgc tggctccaca caggggccca    36960
gcagggagct cgtatgccgc tcgtgcctga agcagacgct gcacaagctg gaggccatga    37020
tgctcatcct gcaggcagag accaccgcgg gcaccgtgac gcccaccgcc atcggagaca    37080
gcatcctcaa catcacaggt gccgcggccc gtgccccatg ccacccgccc gccccgtgcg    37140
gccctttcct ctgcctcccct cctcccccca accgcgtcgc ctttgcccca tcccatcttc    37200
gtccccctcc cctcccccca attcccatcc tcatccccct cccccaattc ccattctcct    37260
ccccctcccc cttccctatt accatcccctt ttctccatct ctctcccctt ttctccattt    37320
cccccccccgt cctcccgtc cttttgtcca ttccctcat cttcctcatc ccctcatcc    37380
cccttcccct cccttatccc ccttcccctc ccttccccc tgctcctctt cttctcccctt    37440
ctcttttctc taccctttc cttccttttt cctccctctc cccatcatcc ccctcatctt    37500
cgtcctcatc cccatcacct tccccctccc cctccacca ctctctctcc agcttccccc    37560
ttccttctgc ctgcacctcg ctctctgccc cctcaggttc ccccttcctc ccagccccca    37620
ccctccggct ccccctttt gcctgccccc acctccctc tacctccctg tctctgcact    37680
gacctcacgc atgtctgcag gagacctcat ccacctggcc agctcggacg tgcgggcacc    37740
acagccctca gagctgggag ccgagtcacc atctcggatg gtggcgtccc aggcctacaa    37800
cctgacctct gccctcatgc gcatcctcat gcgctcccgc gtgctcaacg aggagcccct    37860
gacgctggcg ggcgaggaga tcgtggccca gggcaagcgc tcggaccccgc ggagcctgct    37920
gtgctatggc ggcgccccag ggcctggctg ccacttctcc atccccgagg ctttcagcgg    37980
ggccctggcc aacctcagtg acgtggtgca gctcatcttt ctggtggact ccaatcccctt    38040
tcccttttggc tatatcagca actacaccgt ctccaccaag gtggcctcga tggcattcca    38100
gacacaggcc ggcgcccaga tccccatcga gcggctggcc tcagagcgcg ccatcaccgt    38160
gaaggtgccc aacaactcgg actgggctgc ccggggccac cgcagctccg ccaactccgc    38220
caactccgtt gtggtccagc cccaggcctc cgtcggtgct gtggtcaccc tggacagcag    38280
caaccctgcg gccgggctgc atctgcagct caactatacg ctgctggacg gtgcgtgcag    38340
cgggtggggc acacgcggcc ccctggcctt gttcttgggg ggaaggcgtt tctcgtaggg    38400
```

```
cttccatggg tgtctctggt gaaatttgct ttctgtttca tgggctgctg ggggcctggc    38460
cagagaggag ctgggggcca cggagaagca ggtgccagct ctggtgcaga ggctcctatg    38520
ctttcaggcc cgtggcagag ggtgggctca ggagggccat cgtgggtgtc ccccgggtgg    38580
ttgagcttcc cggcaggcgt gtgacctgcg cgttctgccc caggccacta cctgtctgag    38640
gaacctgagc cctacctggc agtctaccta cactcggagc cccggcccaa tgagcacaac    38700
tgctcggcta gcaggaggat ccgcccagag tcactccagg gtgctgacca ccggccctac    38760
accttcttca tttccccggg gtgagctctg cgggccagcc tggcagggca gggcagggca    38820
tcatgggtca gcattgcctg ggttactggc cccatgggga cggcaggcag cgaggggact    38880
ggaccgggta tgggctctga gactgcgaca tccaacctgg cggagcctgg gctcacgtcc    38940
gctacccctt ccctgcccag gagcagagac ccagcgggga gttaccatct gaacctctcc    39000
agccacttcc gctggtcggc gctgcaggtg tccgtgggcc tgtacacgtc cctgtgccag    39060
tacttcagcg aggaggacat ggtgtggcgg acagaggggc tgctgcccct ggaggagacc    39120
tcgccccgcc aggccgtctg cctcacccgc cacctcaccg ccttcggcgc cagcctcttc    39180
gtgcccccaa gccatgtccg cttttgtgttt cctgtgagtg accctgtgct cctgggagcc    39240
tctgcagagt cgaggagggc ctgggtgggc tcggctctat cctgagaagg cacagcttgc    39300
acgtgacctc ctgggcccgg cggctgtgtc ctcacaggag ccgacagcgg atgtaaacta    39360
catcgtcatg ctgacatgtg ctgtgtgcct ggtgacctac atggtcatgg ccgccatcct    39420
gcacaagctg gaccagttgg atgccagccg gggccgcgcc atccctttct gtgggcagcg    39480
gggccgcttc aagtacgaga tcctcgtcaa gacaggctgg ggccggggct caggtgaggg    39540
gcgcagcggg gtggcagggc ctcccctgct ctcactggct gtgctggttg caccctctgg    39600
gagtgagtct cgtcgcaggc gtcagaacaa ggcagttttt gcagtgctgt gtgaagggct    39660
cgtgtgttca tcctgggaat gacctcgtga gcactcactg tccctgagga ctaggacagc    39720
tcctagctgg aagtaggtgc cagtcagtca gggtgggcag cccacgttct gcacagtagc    39780
gtggccccac aagtgacgtg agcatcgcta ccactgtggg agactgtgca tccaccgcg    39840
atcctgactg catagctcgt ctctcagacg gaggcgccag caccctcccc gtggctgttt    39900
cttcagtacc tccatttcc tttcattgga attgcccttc tggcattccc ttttgttt     39960
cgttttctt tttttagaga cggagtctca ctctgttgcc caggctggag tgcaatggca    40020
tgatcttggc tcacagcaac ttccagctcc cgggtttaag ccattcccct taagcgattc    40080
tcctgagtag ctgggagtac aggtgcacac caccaccc agttaatttt tcaccatgtc    40140
agccaggcga actcctgacc tcaggtgatc cgcctgcctc ggcctgccag agtgctggga    40200
tgacaggtgt gagccaccac acctggctgt gttcccattt tttatctctg tgctgctttc    40260
ctcttcattg cccagttctt tcttttgatt acctacttt aaaaactgtc ggccgggcgc    40320
ggtggctcac acctgtaatc cgagcacttt gggaggccag gcaggcaaat cacgggtca    40380
ggagatcgag accatcctgg ctaacggtga aaccctgtct ctaataaaaa gtacaaaaaa    40440
attagcccgg cgtagtggca ggcgcctgta gtcccagctc cttgggagac tgaggcagga    40500
gaatggcgtg aacccgggag gcggagcttg cagtgagctg agattgcgcc actgcactcc    40560
agcctgggtg acacagcaag actccatctc aaaaaaaaaa gaaaaaaat actgtcacct    40620
gggtctgtca ctgggagagg aggtgacaca gcttcacgct ttgcagtctg tgcatgaact    40680
gagggacggg tgtgtggtgc gggtcaccgg ttgtggcatg actgaggcgt ggacaggtgt    40740
```

```
gcagtgcggg tcactggttg tggtgtggac tgaggcgtgt gcagccatgt ttgcatgtca   40800
caagttacag ttcttcccat gtaacttaat catgtccttg aggtcctgct gttaattgga   40860
caaattgcag taaccgcagc tccttgtgta tggcagagcc gtgcaaagcc gggactgcct   40920
gtgtggctcc ttgagtgcgc acaggccaaa gctgagatga cttgcctggg atgccacacg   40980
tgttgggcag cagaccgagc ctcccacccc tccctcttgc ctcccaggta ccacggccca   41040
cgtgggcatc atgctgtatg gggtggacag ccggagcggc caccggcacc tggacggcga   41100
cagagccttc caccgcaaca gcctggacat cttccggatc gccaccccgc acagcctggg   41160
tagcgtgtgg aagatccgag tgtggcacga caacaaaggt ttgtgcggac cctgccaagc   41220
tctgcccctc tgccccgca ttggggcgcc ctgcgagcct gacctccctc ctgcgcctct   41280
gcagggctca gccctgcctg gttcctgcag cacgtcatcg tcaggacct gcagacggca   41340 cgcagcgcct tcttcctggt caatgactgg ctttcggtgg agacggaggc caacgggggc   41400
ctggtggaga aggaggtgct ggccgcgagt aaggcctcgt tccatggtcc cactccgtgg   41460
gaggttgggc agggtggtcc tgccccgtgg cctcctgcag tgcggccctc cctgccttct   41520
aggcgacgca gccctttgc gcttccggcg cctgctggtg gctgagctgc agcgtggctt   41580 cttttgacaag cacatctggc tctccatatg ggaccggccg cctcgtagcc gtttcactcg   41640
catccagagg gccacctgct gcgttctcct catctgcctc ttcctgggcg ccaacgccgt   41700
gtggtacggg gctgttggcg actctgccta caggtgggtg ccgtagggt cggggcagcc   41760 tcttcctgcc cagcccttcc tgccctcag cctcacctgt gtggcctcct ctcctccaca   41820
cagcacgggg catgtgtcca ggctgagccc gctgagcgtc gacacagtcg ctgttggcct   41880
ggtgtccagc gtggttgtct atcccgtcta cctggccatc cttttttctct tccggatgtc   41940 ccggagcaag gtgggctggg gctggggacc cgggagtact gggaatggag cctgggcctc   42000
ggcaccatgc ctagggccgc cactttccag tgctgcagcc agagggaaag gcgtccacca   42060
aaggctgctc gggaagggtc aacacacttg agcagcctta gctagactga ccaggggaaa   42120
agagagaaga ctcagaagcc agaatggtga agaacgagg gcactttgct aagcagacgc   42180
cacggacgac tgcacagcag cacgccagat aactcagaag aagcaagcac gcggctgtgc   42240
acgcttccga aatgcactcc agaagaaaat ctcagtacat ctataggaag tgaagaggct   42300
gagttagtcc cttagaaacg tcccagtggc cgggccgggt gtggtggctc acgcctgtaa   42360
tcccaacact tcaggtggcc gaggtgggcg gatctgagtc caggagtttg agaccagcct   42420
gggcaacata gcaagacccc atctatataa aacattaaaa agggccaggc gcggtggctc   42480
acgcctgtaa tcccagcact ttgggaggcc gaggcgggca gatcacttga ggtcaggagt   42540
tcgagaccag cctggccaac acaatgaaac cccgactcta ctacaaatac aaaaacttag   42600
ctgggcatgg tggcgggcgc ctgtagtccc agctactcga gaggctgagg caggagaatg   42660
gcatgaaccc aggaggcgga gcttgcagtg agccgagatt gcgccactgc actccatcct   42720
gggcaacgga gcaagactcc atctccaaaa aaaaaaaaaa aaatcccac aaagaaaagc   42780 tcaggctcag agccttcacg atagaatttt tctaagcagt taaggaagaa ttaacaccaa   42840
tccttcacag actctttcca agaatacagc aggtgggaac gcttcccatt catacgaaa   42900 cgggaggccg caccccttag gaatgcacac gtggggtcct caagaggtta catgcaaact   42960
aaccccagca gcacacagag aaggcgcata agccgcgacc aggaggggtt gctcccgagt   43020
ccgtggcagg aaccagaggc cacatgtggc tgctcgtatt taagttaatt aaaatgaac   43080 gatggccggg tgtggtggct cacacctgta atcccagcac tttgggaggc ggaggcgggc   43140
```

```
agatcacttg aggtcaggag ttccaagacc agcctggcca acacagtgaa accccgtctc   43200
tactaaaaat acaaaaaatt agctgggcat ggtggcaggc acctgtaatc ccagctactc   43260
aggaggctga gccaggacaa tcgcctgaac gcgggaggtg gaggttgcag tgagctgaga   43320
ttgcgccatt gcactccagc ctgggtgaca gcgagactcc atctaaaaaa gaaaatatga   43380
aatttaaaac tctgttcctt agctgcacca gtctgctgtc aagtgttcag tggcacacgt   43440
cgcgaggggc tgccatcacg gacggtgcag atgtcccata tatccagcat tctaggacat   43500
tctgtcagat ggcaccgggc tctgtcctgt ctgctgagga ggtggcttct catccctgtc   43560
ctgagcaggt ctgagctgcc gcccgctgac cactgccctc gtcctgcagg tggctgggag   43620
cccgagcccc acacctgccg ggcagcaggt gctggacatc gacagctgcc tggactcgtc   43680
cgtgctggac agctccttcc tcacgttctc aggcctccac gctgaggtga ggactctact   43740
gggggtcctg ggctgggctg ggggtcctgc cgccttggcg cagcttggac tcaagacact   43800
gtgcacctct cagcaggcct tgttggaca gatgaagagt gacttgtttc tggatgattc   43860
taagaggtgg gttccctaga gaaacctcga gccctggtgc aggtcactgt gtctggggtg   43920 ccggggggtgt gcgggctgcg tgtccttgct gggtgtctgt ggctccatgt ggtcacacca   43980
cccgggagca ggtttgctcg gaagcccagg gtgtccgtgc gtgactggac ggggtgggc   44040 tgtgtgtgtg acacatcccc tggtaccttg ctgacccgcg ccacctgcag tctggtgtgc   44100
tggccctccg gcgagggaac gctcagttgg ccggacctgc tcagtgaccc gtccattgtg   44160
ggtagcaatc tgcggcagct ggcacggggc caggcgggcc atgggctggg cccagaggag   44220
gacggcttct ccctggccag ccccctactcg cctgccaaat ccttctcagc atcaggtgag   44280 ctgggggtgag aggaggggc tctgaagctc acccttgcag ctgggcccac cctatgcctc   44340
ctgtacctct agatgaagac ctgatccagc aggtccttgc cgagggggtc agcagcccag   44400
ccctacccca agacacccac atggaaacgg acctgctcag cagcctgtga gtgtccggct   44460
ctcgggggag gggggattgc cagaggaggg gccgggactc aggccaggca gccgtggttc   44520
ccgcctgggg tagggtgggg tggggtgcca gggcagggct gtggctgcac cacttcactt   44580
ctctgaacct ctgttgtctg tggaaagagc ctcatgggat ccccagggcc ccagaaccct   44640
ccctctaggg agggagcagg ctcatggggc tttgtaggag cagaaaggct cctgtgtgag   44700
gctggccggg gccacgtttt tatcttggtc tcagagcagt gagaaattat gggcgggttt   44760
ttaaataccc cattttttggc cgggcgcggt ggctcacacg tgtaatccca gcactttggg   44820
aggccgaggt gggcagatga cctgaggtca gcagttcgag accagcctgg ccaacatggc   44880
gaaaccccgt ctctactaaa aatacaaaaa attagccggg catgctggca ggcgcctgta   44940
gtcccagtta ctcgggagac tgaggtagga gaatcgattg aacctggtag gtgaaggttg   45000
tagtgagccg agatcgcgcc actgcactcc agcctgggca acaagagcga aactccgtct   45060
caaaaacaaa aaaattcctc aatttcttgg ttgttttgta acttatcaac aaatggtcat   45120
atagaggtta ccttgtatgt agtcacgcac atagtcacgc acatggcagc cggcggcgga   45180
gcgcacccac ggcgtgttcc cacgcgtgtg accccgggct ctgccatgcc tcctatgct   45240 caggtgtgct gaggtccaca cggccctgcc gttgcactgc agctgcctgc aggattcagt   45300
gcagtggcat gcagtgcagg tgcggtgccc cggagccaca ggccacacca cagggcctgc   45360
atgcacaggg gctgcggtgt ctgggtttgg gtaactacgc cctgtgacat ttgcacagca   45420
acagaattac ctaatgacgc atttctcaga acacatccct ggcactaagt ggtgcgtgac   45480
```

```
tgctgctttt gcatccacat ctagtttgat ttgtgtgtta ttcctttgag tgcttctcat    45540
tgttaagcaa ccaagaacta aagaggtatg aactgcccct ggactcaaac aaaaaggaaa    45600
acttcctgat ttacaaaagg cagataacca tcacatgagg gcatctttat gaataaattg    45660
ctggttggtt ttaaaaatac agagtatggg gaaatccagg ggtagtcact acatgctgac    45720
cagccccagg tatctccggc ccaaagctct gtgaaatcca gattcagtgc ttccgcgggg    45780
atttctgacg gcagctcaga ctccgcatcc acacagagcg cgtggccctc accctcccgg    45840
cttcctcaac ccttggccgt cccttgctcg gacagtgctt cgggctgacc aggtcggagg    45900
cttgggtttg tcctggaccc ctctgcgtcc ttcctcactg cagcctccag cgcgtcccgt    45960
ggctcctttc ccaacgcaga gcacggcctt ccctgcgcct gagcctgcac cctccgtcct    46020
ggcggcgcct ctgccctggc attccctgcc actccatgcc tccctattgg ccattctccg    46080
tctctgccag cgagagcctg ctccctgagt cagaccctga gtcatttgtg ttgctataaa    46140
ggaatagttg aggctgggtt atttttttatt tttatttatt tttttgagat ggagtctctg    46200
ttgcccagac tggagtgcag tcgcatgatc tcggctcact gcaaagtctg cctcccacgt    46260
tcaagcagtt atctgcctca gcctcccaag tagctaagat tacaggcgcc cgccgccaca    46320
gccggctaat ttttttgtgtg tgtgttttag tagagaggag gtttcaccat cttagccagg    46380
ctggtcttga actcctgacc tcgtgatcca cccatctcag cctcccaaaa tgctgagatt    46440
acaggcgtga gccaccacgc ctgaccaagt tgaggctagg tcattttttta attttttgta    46500 aagacagggt ctcactgtct ccaactcctg agctcaagtg atcctcctgc ctcagcctcc    46560
tgaagtgctg ggattacagg cttgagacac tgcgcccagc caagagtgtc ttttatcctc    46620
cgagagacag caaaacagga agcattcagt gcagtgtgac cctgggtcag gccgttcttt    46680
cggtgatggc ctgacgaggg cgcaggtacg ggagagcgtc ctgagagccc gggactcggc    46740
gtctcgcagt tggtctcgtc ctcccccctca acgtgtcttc gctgcctctg tacctcttct    46800
ctagcagctc tgggaccggg catatcagca tggtggcccg atgcagtggc acagcctcgg    46860
tggtcactgg ctcctggaga cacaagcaga tctctggcct cagggagccc tacacactgt    46920
tgggatttga aaggcattca tatgtttcct tgtccagaag ttaattttag gccataaacc    46980
tgcatgggac agacacactg gcgtctctag attgtagaga tgcttgttgg atggttgaga    47040
cccaatcata gtttgcaggg ttgaaggggg gctcattgca ccctgagaga ctgtgcactg    47100
ctgtaagggc agctggtcag gctgtgggcg atgggtttat cagcagcaag cgggcgggag    47160
agggacgcag gcggacgcct gacttcggtg cctggagtgg ctcttggttc cctggctccc    47220
agcaccactc ccactctcgt ttgggggtagg gtcttccggc tttttgtcgg ggggacccctg    47280 tgacccaaga ggctcaagaa actgcccgcc caggttaaca tgggcttggc tgcaactgcc    47340
tcctggaggc cgggatgaat tcacagccta ccatgtccct caggtccagc actcctgggg    47400
agaagacaga gacgctggcg ctgcagaggc tgggggagct ggggccaccc agcccaggcc    47460
tgaactggga acagccccag gcagcgaggc tgtccaggac aggtgtgctt gcgtagcccc    47520
gggatgcccc tagcccctcc ctgtgagctg cctctcacag gtctgtctct gcttccccag    47580
gactggtgga gggtctgcgg aagcgcctgc tgccggcctg gtgtgcctcc ctggcccacg    47640
ggctcagcct gctcctggtg gctgtggctg tggctgtctc agggtgggtg ggtgcgagct    47700
tcccccgggg cgtgagtgtt gcgtggctcc tgtccagcag cgccagcttc ctggcctcat    47760
tcctcggctg ggagccactg aaggtgaggg ggctgccagg ggtaggctac aggcctccat    47820
cacgggggac ccctctgaag ccacccccttc cccaggtctt gctggaagcc ctgtacttct    47880
```

```
cactggtggc caagcggctg cacccggatg aagatgacac cctggtagag agcccggctg    47940
tgacgcctgt gagcgcacgt gtgccccgcg tacggccacc ccacggcttt gcactcttcc    48000
tggccaagga agaagcccgc aaggtcaaga ggctacatgg catgctgcgg gtgagcctgg    48060
gtgcggcctg tgccctgcc acctccgtct cttgtctccc acctcccacc catgcacgca     48120
ggacactcct gtccccttt cctcacctca gaaggccctt aggggttcaa tgctctgcag     48180
cctttgcccg gtctccctcc taccccacgc cccccacttg ctgccccagt ccctgccagg    48240
gcccagctcc aatgcccact cctgcctggc cctgaaggcc cctaagcacc actgcagtgg    48300
cctgtgtgtc tgcccccagg tggggttccg ggcagggtgt gtgctgccat taccctggcc    48360
aggtagagtc ttggggcgcc ccctgccagc tcaccttcct gcagccacac ctgccgcagc    48420
catggctcca gccgttgcca aagccctgct gtcactgtgg gctggggcca ggctgaccac    48480
agggcccccc cgtccaccag agcctcctgg tgtacatgct ttttctgctg gtgaccctgc    48540
tggccagcta tggggatgcc tcatgccatg ggcacgccta ccgtctgcaa agcgccatca    48600
agcaggagct gcacagccgg gccttcctgg ccatcacgcg gtacgggcat ccggtgcact    48660
ggtctgtctt ctgggcttta gttttgcctt tagtccagcc agaccctagg ggacatgtgg    48720
acatgtgtag ataccttttgt ggctgctaga actggaggta ggtgctgctg gcatcagtag    48780
gcagagggga gggacacagg tccgtgtctt gcagtgcaca ggacgggccc atgacagaca    48840
actgtctgcc ccagaacatc cccaggataa ggctgagaag cccaggtcta gccgtggcca    48900
gcagggcagt gggagccatg ttccctgggt ctctggtggc cgctcactcg aggcgggcat    48960
ggggcagtag gggctggagc gtgtgactga tgctgtggca ggtctgagga gctctggcca    49020
tggatggccc acgtgctgct gccctacgtc cacgggaacc agtccagccc agagctgggg    49080
cccccacggc tgcggcaggt gcggctgcag gaaggtgagc tggcagggcg tgccccaaga    49140
cttaaatcgt tcctcttgtt gagagagcag ccttttagcgg agctctggca tcagccctgc    49200
tccctagctg tgtgacccttt gccctcttaa caccgccgtt tccttctctg tatatgagag    49260
atggtaacgt tgtctaattg atggctgctg ggagggttcc ctggggtggc gccgaaccag    49320
agctcaggcg agctggccag caggaaacac tcctgttggg ttttgatgag gccctggccc    49380
cggcctgggg ctctgtgtgt ttcagcactc tacccagacc ctcccggccc cagggtccac    49440
acgtgctcgg ccgcaggagg cttcagcacc agcgattacg acgttggctg ggagagtcct    49500
cacaatggct cggggacgtg ggcctattca gcgccggatc tgctggggtg agcagagcga    49560 gggcccccggg cgtctacgcc aaggacaagg gagtagttct ccaggagtgc gcggcctcc    49620 tgaccagcct ggctccgggg tgccggaagg gctggggtgc ggcacccacg ccaccctct    49680 ccggcagggc atggtcctgg ggctcctgtg ccgtgtatga cagcggggc tacgtgcagg     49740 agctgggcct gagcctggag gagagccgcg accggctgcg cttcctgcag ctgcacaact    49800
ggctggacaa caggtgggag ctccctcccc tgccctctcc ggggtggccg cagtcaccag    49860
ccaggagccc accctcactc ctccggcccc cgctggccta ggcggcttcc acagcccctc    49920
agccacgcct gcactgcgcg gtcccgcag ctcccgccct gccacccgct cctactgacc     49980
cgcaccctct gcgcaggagc cgcgctgtgt tcctggagct cacgcgctac agcccggccg    50040
tggggctgca cgccgccgtc acgctgcgcc tcgagttccc ggcggccggc cgcgccctgg    50100
ccgccctcag cgtccgcccc tttgcgctgc gccgcctcag cgcgggcctc tgctgcctc     50160 tgctcacctc ggtacgcccg tccccggcca gaccccgcgc ctcccaccgg cagcgtcccg    50220
```

```
ccccctcgcg gggccccgcc cggcagcgtc tcacccctcg cagcgccccg ccccctcgca    50280
gcgtcccgcc ccctcgcagg gcccgcccc  ggcagcgtcc cgcccctcg  tagggccccg    50340 ccccggcagc gtcccgcccc ctcgcagggc cccgccccgg cagcgtccct cccgccctcc    50400
tgaccgcgcc ccccacaggt gtgcctgctg ctgttcgccg tgcacttcgc cgtgccgag     50460 gcccgtactt ggcacaggga agggcgctgg cgcgtgctgc ggctcggagc ctgggcgcgg    50520
tggctgctgg tggcgctgac ggcggccacg gcactggtac gcctcgccca gctgggtgcc    50580
gctgaccgcc agtggacccg tttcgtgcgc ggccgcccgc gccgcttcac tagcttcgac    50640
caggtggcgc agctgagctc cgcagcccgt ggcctggcgg cctcgctgct cttcctgctt    50700
ttggtcaagg tgagggctgg gccggtgggc gcggggctgg gcgcacaccc cagggctgca    50760
agcagacaga tttctcgtcc gcaggctgcc cagcagctac gcttcgtgcg ccagtggtcc    50820
gtctttggca agacattatg ccgagctctg ccagagctcc tgggggtcac cttgggcctg    50880
gtggtgctcg gggtagccta cgcccagctg gccatcctgg taggtgactg cgcggccggg    50940
gagggcgtct tagctcagct cagctcagct gtacgccctc actggtgtcg ccttccccgc    51000
agctcgtgtc ttcctgtgtg gactccctct ggagcgtggc ccaggccctg ttggtgctgt    51060
gccctgggac tgggctctct accctgtgtc ctgccgagtc ctggcacctg tcaccccgtc    51120
tgtgtgtggg gctctgggca ctgcggctgt ggggcgccct acggctgggg gctgttattc    51180
tccgctggcg ctaccacgcc ttgcgtggag agctgtaccg gccggcctgg gagccccagg    51240
actacgagat ggtggagttg ttcctgcgca ggctgcgcct ctggatgggc ctcagcaagg    51300
tcaaggaggt gggtacggcc cagtgggggg gagagggaca cgccctgggc tctgcccagg    51360
gtgcagccgg actgactgag cccctgtgcc gccccagtt  ccgccacaaa gtccgctttg    51420
aagggatgga gccgctgccc tctcgctcct ccagggctc  caaggtatcc ccggatgtgc    51480
ccccacccag cgctggctcc gatgcctcgc accctccac  ctcctccagc cagctggatg    51540
ggctgagcgt gagcctgggc cggctgggga caaggtgtga gcctgagccc tcccgcctcc    51600
aagccgtgtt cgaggccctg ctcacccagt ttgaccgact caaccaggcc acagaggacg    51660
tctaccagct ggagcagcag ctgcacagcc tgcaaggccg caggagcagc cgggcgcccg    51720
ccggatcttc ccgtggccca tccccgggcc tgcggccagc actgcccagc cgccttgccc    51780
gggccagtcg gggtgtggac ctggccactg gccccagcag gacacccctt cgggccaaga    51840
acaaggtcca ccccagcagc acttagtcct ccttcctggc gggggtgggc cgtggagtcg    51900
gagtggacac cgctcagtat tactttctgc cgctgtcaag gccagagggcc aggcagaatg    51960 gctgcacgta ggttccccag agagcaggca ggggcatctg tctgtctgtg ggcttcagca    52020
ctttaaagag gctgtgtggc caaccaggac ccagggtccc ctcccagct  cccttgggaa    52080 ggacacagca gtattggacg gtttctagcc tctgagatgc taatttattt ccccgagtcc    52140
tcaggtacag cgggctgtgc ccggccccac cccctgggca gatgtccccc actgctaagg    52200
ctgctggctt cagggagggt tagcctgcac cgccgccacc ctgcccctaa gttattacct    52260
ctccagttcc taccgtactc cctgcaccgt ctcactgtgt gtctcgtgtc agtaatttat    52320
atggtgttaa aatgtgtata ttttttgtatg tcactatttt cactaggct  gaggggcctg    52380 cgcccagagc tggcctcccc caacacctgc tgcgcttggt aggtgtggtg gcgttatggc    52440
agcccggctg ctgcttggat gcgagcttgg ccttgggccg gtgctggggg cacagctgtc    52500
tgccaggcac tctcatcacc ccagaggcct tgtcatcctc ccttgcccca ggccaggtag    52560
caagagagca gcgcccaggc ctgctggcat caggtctggg caagtagcag gactaggcat    52620
```

```
gtcagaggac cccagggtgg ttagaggaaa agactcctcc tgggggctgg ctcccagggt    52680
ggaggaaggt gactgtgtgt gtgtgtgtgt gcgcgcgcgc acgcgcgagt gtgctgtatg    52740
gcccaggcag cctcaaggcc ctcggagctg gctgtgcctg cttctgtgta ccacttctgt    52800
gggcatggcc gcttctagag cctcgacacc cccccaaccc ccgcaccaag cagacaaagt    52860
caataaaaga gctgtctgac tgcaatctgt gcctctatgt ctgtgcactg gggtcaggac    52920
tttatttatt tcactgacag gcaataccgt ccaaggccag tgcaggaggg agggccccgg    52980
cctcacacaa actcggtgaa gtcctccacc gaggagatga ggcgcttccg ctggcccacc    53040
tcatagccag gtgtgggctc ggctggagtc tgtgcagggg cttgctatg ggacggaggg     53100 tgcaccagag gtaggctggg gttggagtag gcggcttcct cgcagatctg aaggcagagg    53160
cggcttgggc agtaagtctg ggaggcgtgg caaccgctct gcccacacac ccgccccaca    53220
gcttgggcag ccagcacacc ccgctgaggg agccccatat tccctacccg ctggcggagc    53280
gcttgatgtg gcggagcggg caatccactt ggaggggtag atatcggtgg ggttggagcg    53340
gctatgatgc acctgtgagg ccatctgggg acgtaggcag ggggtgagct cactatcagg    53400
tggcacctgg gcctgtccca ccagctcacg cctggaccca cccccactca catttgcgtg    53460
cagggccatc tggcgggcca cgaagggcag gttgcggtca gacacgatct tggccacgct    53520
gg                                                                   53522
```

<210> SEQ ID NO 8
<211> LENGTH: 23
<212> TYPE: PRT
<213> ORGANISM: Homo sapiens

<400> SEQUENCE: 8

Leu Ser Pro Asn Ala Thr Leu Ala Leu Thr Ala Gly Val Leu Val Asp
1               5                   10                  15

Ser Ala Val Glu Val Ala Phe
            20

<210> SEQ ID NO 9
<211> LENGTH: 48
<212> TYPE: PRT
<213> ORGANISM: Homo sapiens
<220> FEATURE:
<221> NAME/KEY: MOD_RES
<222> LOCATION: (4)..(23)
<223> OTHER INFORMATION: Any amino acid

<400> SEQUENCE: 9

Asp Gly Glu Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Val Ala Gln Val Leu Val Glu His Asn
            20                  25                  30

Val Met His Thr Tyr Ala Ala Pro Gly Glu Tyr Leu Leu Thr Val Leu
        35                  40                  45

<210> SEQ ID NO 10
<211> LENGTH: 22
<212> TYPE: PRT
<213> ORGANISM: Homo sapiens

<400> SEQUENCE: 10

Leu Val Ala Gly Arg Pro Val Thr Phe Tyr Pro His Pro Leu Pro Ser
1               5                   10                  15

```
Pro Gly Gly Val Leu Tyr
            20

<210> SEQ ID NO 11
<211> LENGTH: 28
<212> TYPE: PRT
<213> ORGANISM: Homo sapiens

<400> SEQUENCE: 11

Asp Gly Ser Pro Val Leu Thr Gln Ser Gln Pro Ala Ala Asn His Thr
1               5                   10                  15

Tyr Ala Ser Arg Gly Thr Tyr His Val Arg Leu Glu
            20                  25

<210> SEQ ID NO 12
<211> LENGTH: 21
<212> TYPE: PRT
<213> ORGANISM: Homo sapiens

<400> SEQUENCE: 12

Pro Thr Gln Pro Asp Ala Arg Leu Thr Ala Tyr Val Thr Gly Asn Pro
1               5                   10                  15

Ala His Tyr Leu Phe
            20

<210> SEQ ID NO 13
<211> LENGTH: 29
<212> TYPE: PRT
<213> ORGANISM: Homo sapiens

<400> SEQUENCE: 13

Asp Gly Ser Ser Asn Thr Thr Val Arg Gly Cys Pro Thr Val Thr His
1               5                   10                  15

Asn Phe Thr Arg Ser Gly Thr Phe Pro Leu Ala Leu Val
            20                  25

<210> SEQ ID NO 14
<211> LENGTH: 23
<212> TYPE: PRT
<213> ORGANISM: Homo sapiens

<400> SEQUENCE: 14

Gln Phe Val Gln Leu Gly Asp Glu Ala Trp Leu Val Ala Cys Ala Trp
1               5                   10                  15

Pro Pro Phe Pro Tyr Arg Tyr
            20

<210> SEQ ID NO 15
<211> LENGTH: 29
<212> TYPE: PRT
<213> ORGANISM: Homo sapiens

<400> SEQUENCE: 15

Thr Glu Glu Ala Ala Pro Thr Arg Ala Arg Gly Pro Glu Val Thr Phe
1               5                   10                  15

Ile Tyr Arg Asp Pro Gly Ser Tyr Leu Val Thr Val Thr
            20                  25

<210> SEQ ID NO 16
<211> LENGTH: 21
<212> TYPE: PRT
<213> ORGANISM: Homo sapiens
```

```
<400> SEQUENCE: 16

Gly Leu Glu Leu Gln Gln Pro Tyr Leu Phe Ser Ala Val Gly Arg Gly
1               5                   10                  15

Arg Pro Ala Ser Tyr
            20

<210> SEQ ID NO 17
<211> LENGTH: 25
<212> TYPE: PRT
<213> ORGANISM: Homo sapiens

<400> SEQUENCE: 17

Asp Gly Gly Trp Leu Glu Gly Pro Glu Val Thr His Ala Tyr Asn Ser
1               5                   10                  15

Thr Gly Asp Phe Thr Val Arg Val Ala
            20                  25

<210> SEQ ID NO 18
<211> LENGTH: 26
<212> TYPE: PRT
<213> ORGANISM: Homo sapiens
<220> FEATURE:
<221> NAME/KEY: MOD_RES
<222> LOCATION: (3)..(7)
<223> OTHER INFORMATION: Any amino acid

<400> SEQUENCE: 18

Pro Gly Xaa Xaa Xaa Xaa Xaa Ala Gly Ser Ser Val Pro Phe Trp Gly
1               5                   10                  15

Gln Leu Ala Thr Gly Thr Asn Val Ser Trp
            20                  25

<210> SEQ ID NO 19
<211> LENGTH: 25
<212> TYPE: PRT
<213> ORGANISM: Homo sapiens

<400> SEQUENCE: 19

Gly Gly Ser Ser Lys Arg Gly Pro His Val Thr Met Val Phe Pro Asp
1               5                   10                  15

Ala Gly Thr Phe Ser Ile Arg Leu Asn
            20                  25

<210> SEQ ID NO 20
<211> LENGTH: 22
<212> TYPE: PRT
<213> ORGANISM: Homo sapiens

<400> SEQUENCE: 20

Val Val Ala Pro Gly Gln Leu Val His Phe Gln Ile Leu Leu Ala Ala
1               5                   10                  15

Gly Ser Ala Val Thr Phe
            20

<210> SEQ ID NO 21
<211> LENGTH: 27
<212> TYPE: PRT
<213> ORGANISM: Homo sapiens

<400> SEQUENCE: 21

Gly Ala Asn Pro Glu Val Leu Pro Gly Pro Arg Phe Ser His Ser Phe
1               5                   10                  15
```

```
Pro Arg Val Gly Asp His Val Val Ser Val Arg
            20                  25

<210> SEQ ID NO 22
<211> LENGTH: 30
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any amino acid

<400> SEQUENCE: 22

Cys Xaa Pro Ser Asp Thr Glu Ile Phe Pro Gly Asn Gly His Cys Tyr
1               5                   10                  15

Arg Leu Val Val Glu Lys Ala Ala Trp Leu Gln Ala Gln Glu
            20                  25                  30

<210> SEQ ID NO 23
<211> LENGTH: 16
<212> TYPE: PRT
<213> ORGANISM: Homo sapiens

<400> SEQUENCE: 23

Trp Cys Asn Thr Asp Leu Cys Ser Ala Pro His Ser Tyr Val Cys Glu
1               5                   10                  15
```

PKD MUTATIONS AND EVALUATION OF SAME

RELATED APPLICATION

This application is a continuation of U.S. patent application Ser. No. 12/309,337, filed Sep. 2, 2009, now U.S. Pat. No. 8,771,946, which is a National Phase of International Patent Application No. PCT/US2007/16705, filed Jul. 24, 2007, which claims priority from U.S. Provisional Patent Application No. 60/832,780, filed on Jul. 24, 2006. The entire teachings of the above applications are incorporated herein by reference in their entirety.

GOVERNMENT SUPPORT

The invention was supported in part by Becas FPI de investigacion from Ministerio de Ciencia y Technologia (Spain) and grants R01DK70617, P50-DK57325 and R37DK48006 from the National Institutes of Health. The Governments have certain rights in the invention.

SEQUENCE LISTING

The instant application contains a Sequence Listing which has been submitted electronically in ASCII format and is hereby incorporated by reference in its entirety. The ASCII copy, created on Jan. 28, 2014, is named 103779-0367_SL.txt and is 171,496 bytes in size.

BACKGROUND OF THE INVENTION

Autosomal dominant polycystic kidney disease (ADPKD) is an exceptionally common inherited disorder in humans, affecting approximately one in every 600 to 1000 individuals (Gabow P. A., *N Engl J Med* 329(5):332-342, 1993). The disease is characterized by age dependent growth of renal cysts such that end-stage renal disease (ESRD) typically ensues during mid-adulthood. ADPKD may alternatively, or in addition, involve cysts in other organs including liver and spleen, as well as gastrointestinal, cardiovascular, and musculoskeletal abnormalities (Gabow P. A., *N Engl J Med* 329(5):332-342, 1993; Gabow P et al., *Adv Nephrol* 18:19-32, 1989). Both ADPKD type 1 and type 2 share the entire range of renal and extrarenal manifestations, but type 2 appears to have a delayed onset relative to type 1. The common phenotypic complications observed for ADPKD which include hypertension, hematuria and urinary tract infection, seem to be clinically milder in type 2 patients.

Approximately 85 percent of ADPKD cases are caused by mutations in the PKD1 gene [MIM 601313], which is located on chromosome 16, while the remainder are due to mutations in the PKD2 gene [MIM 173910] located on chromosome 4 (Peters et al., *Contrib Nephrol* 97:128-139, 1992; European Polycystic Kidney Disease Consortium, *Cell,* 77(6):881-894, 1994; International Polycystic Kidney Disease Consortium, *Cell* 81(2):289-298, 1995; Hughes J. et al, *Nat Genet* 10(2):151-160, 1995; Mochizuki T. et al., *Science* 272(5266):1339-1342, 1996). However, genetic testing for ADPKD has posed a unique set of challenges in terms of DNA diagnostics. PKD1 analysis in particular has been complicated because the 5' portion of the gene (exons 1-34) is replicated in at least five highly homologous copies (with less than 2% divergence) elsewhere on chromosome 16 (Hughes J. et al, *Nat Genet* 10(2):151-160, 1995). Further complicating PKD1 mutant analysis, PKD1 has a high rate of potentially non-pathogenic DNA variation; thus the nature of each change detected must be verified. Several techniques have been used to detect mutations in the PKD1 gene including using gene-specific primers to amplify large products screened via nested PCR techniques, denaturing high-performance liquid chromatography (DHPLC) to screen nested PCR products for mutations and direct sequencing of the entire PKD1 coding sequence (Watnick T J et al., *Hum Mol Genet* 6(9):1473-1481, 1997; Watnick T J et al., *Mol Cell* 2(2):247-251, 1998; Watnick T. et al., *Am J Hum Genet* 65(6):1561-1571, 1999; Phakdeekitcharoen B. et al., *Kidney Int* 58(4):1400-1412, 2000; Phakdeekitcharoen B. et al., *J Am Soc Nephrol* 12:955-963, 2001; Thomas R. et al., *Am J Hum Genet* 65(1):39-49, 1999; Perichot R. A., *Hum Genet* 105(3):231-239, 1999; Perichot R. et al., *Eur J Hum Genet* 8(5):353-359, 2000; Afzal A. R. et al., *Genet* 4(4): 365-370; Rossetti S. et al., *Lancet* 361(9376):2196-2201, 2003; Rossetti S. et al., *Kidney Int* 61:1588-1599, 2002; Rossetti S. et al., *Am J Hum Genet* 68(1):46-63, 2001, Inoue S. et al., *Hum Mutat* 19(6):622-628, 2002; Burtey S. et al., *J Med Genet* 39(6):422-429, 2002; Mizoguchi M. et al., *J Hum Genet* 46(9):511-517, 2001; Zhang D. Y. et al., *Zhonghua Yi Xue Yi Chuan Xue Za Zhi* 21(3):211-214, 2004). However, some of these strategies may not be cost effective for routine clinical sample analysis and/or their mutation detection rate has not been established or is inadequate. For example, direct DNA sequencing of the entire coding regions of PKD1 and PKD2 is considered necessary because no mutational hot spots have been identified in either PKD1 or PKD2. Although several pathogenic mutations in PKD1 and PKD2 have been identified, the known mutations do not account for all those individuals with ADPKD. Thus, to accurately diagnose and treat the disease, there remains a need to identify other mutations of PKD1 or PKD2 which are linked to ADPKD.

SUMMARY OF THE INVENTION

Several novel nucleotide sequence alterations in the PKD1 and PKD2 genes have been identified that are associated with ADPKD. The mutations in PKD1 and PKD2 were found by direct sequencing of the genes and the pathogenicity of the mutations determined using a combination of various analyses and algorithms. The mutations in the PKD1 and PKD2 genes identified as pathogenic can be used to detect and/or predict the occurrence of ADPKD in an individual. This is important clinically in diagnostic and prognostic analysis of the genes for ADPKD.

Accordingly, the invention relates to methods of detecting or predicting the occurrence of ADPKD in an individual. In one aspect, the present invention relates to a method of detecting or predicting the occurrence of autosomal dominant polycystic kidney disease (ADPKD) in an individual comprising detecting the presence of one or more nucleotide sequence alterations in a PKD1 gene having the nucleotide sequence of SEQ ID NO:1 or SEQ ID NO:7 in a nucleic acid sample obtained from said individual, wherein said one or more alterations are selected from the group consisting of: a deletion of TTTAA at nucleotide positions 559 to 563 of SEQ ID NO:1, an insertion of CT at nucleotide position 1124 of SEQ ID NO:1, an insertion of an A, T, G, or C at nucleotide position 2291 of SEQ ID NO:1, an insertion of an A, T, G, or C at nucleotide position 2297 of SEQ ID NO:1, an insertion a T at nucleotide position 5365 of SEQ ID NO:1, an insertion of a G at nucleotide position 6666 of SEQ ID NO:1, an insertion of an A at nucleotide position 6881 of SEQ ID NO:1, a deletion of a T at nucleotide position 8713 of SEQ ID NO:1, an insertion of an A, T, G, or C at nucleotide position 9134 of SEQ ID NO:1, an insertion of 5 nucleotides at nucleotide position 9536 of SEQ ID NO:1, a deletion of a T at nucleotide position 10239 of SEQ ID NO:1, a change of a C to an A at nucleotide position 483 of SEQ ID NO:1, a change of a C to a T at nucleotide position 4517 of SEQ ID NO:1, a change of a C to an A at nucleotide position 7006 of SEQ ID NO:1, a change of a C to T at nucleotide position 8267 of SEQ ID NO:1, a change of a G to a T at nucleotide position 8639 of SEQ ID NO:1, a change of a G to an A at nucleotide position 20168 of SEQ ID NO:7, a change of a G to a T at nucleotide position 31025 of SEQ ID NO:7, a change of a G to a C at nucleotide position 33415 of SEQ ID NO:7, a deletion of CAA between nucleotide positions 508 to 516 of SEQ ID NO:1, a deletion of TGG at nucleotide positions 1848 to 1850 of SEQ ID NO:1, a deletion of CCAACTCCG at nucleotide positions 8892 to 8900 of SEQ ID NO:1, a deletion of AAG at nucleotide positions 9905 to 9907 of SEQ ID NO:1, a deletion of CTC at nucleotide positions 10070 to 10072 of SEQ ID NO:1, a deletion of TGG at nucleotide positions 12597 to 12599 of SEQ ID NO:1, a change of a C to an A at nucleotide position 1023 of SEQ ID NO:1, a change of a G to an A at nucleotide position 385 of SEQ ID NO:1, a change of an A to a G at nucleotide position 1470 of SEQ ID NO:1, a change of a C to a T at nucleotide position 4262 of SEQ ID NO:1, a change of a T to an A at nucleotide position 8855 of SEQ ID NO:1, a change of an A to a G at nucleotide position 1794 of SEQ ID NO:1, a change of a G to an A at nucleotide position 6036 of SEQ ID NO:1, a change of a C to a T at nucleotide position 2042 of SEQ ID NO:1, a change of a C to a T at nucleotide position 3351 of SEQ ID NO:1, a change of an A to a G at nucleotide position 6756 of SEQ ID NO:1, a change of a C to a T at nucleotide position 5793 of SEQ ID NO:1, a change of a C to a T at nucleotide position 6707 of SEQ ID NO:1, a change of a G to a C at nucleotide position 10187 of SEQ ID NO:1, a change of a C to a G at nucleotide position 7116 of SEQ ID NO:1, a change of an A to a G at nucleotide position 10311 of SEQ ID NO:1, a change of a T to a C at nucleotide position 7554 of SEQ ID NO:1, a change of a C to a T at nucleotide position 7757 of SEQ ID NO:1, a change of a T to a C at nucleotide position 8067 of SEQ ID NO:1, a change of a C to a T at nucleotide position 8138 of SEQ ID NO:1, a change of a C to a T at nucleotide position 8509 of SEQ ID NO:1, a change of a C to an A at nucleotide position 10096 of SEQ ID NO:1 and a change of a C to a T at nucleotide position 12658 of SEQ ID NO:1. The detection of one or more of the listed nucleotide sequence alterations indicates that the individual has ADPKD or will develop ADPKD. In one embodiment, at least one nucleotide sequence alteration other than the one or more nucleotide sequence alterations listed above is also detected in SEQ ID NO:1 and/or SEQ ID NO:4, wherein the at least one nucleotide sequence alteration which is also detected is associated with ADPKD. In another aspect, the one or more nucleotide sequence alterations are detected by sequencing, polymerase chain reaction (PCR), DHPLC or combinations of the foregoing.

The present invention also relates to a method of detecting or predicting the occurrence of autosomal dominant polycystic kidney disease (ADPKD) in an individual comprising detecting the presence of one or more nucleotide sequence alterations in a PKD2 gene having the nucleotide sequence of SEQ ID NO:4 in a nucleic acid sample obtained from said individual, wherein said one or more alterations are selected from the group consisting of: an insertion of an A at nucleotide position 2226 of SEQ ID NO:4, a deletion of AG at nucleotide positions 2422 to 2423 of SEQ ID NO:4, a change of a C to a T at nucleotide position 2680 of SEQ ID NO:4, IVS7-1G>A, IVS8+5G>A, a deletion of TGG at nucleotide positions 374-376 of SEQ ID NO:4 and a deletion of TTC between nucleotide positions 1876-1881 of SEQ ID NO:4, wherein detection of the one or more nucleotide sequence alterations indicates that the individual has ADPKD or will develop ADPKD. In one embodiment, at least one nucleotide sequence alteration other than the one or more nucleotide sequence alterations listed above is also detected in SEQ ID NO:1 and/or SEQ ID NO:4, wherein the at least one nucleotide sequence alteration also detected is associated with ADPKD. In yet another embodiment, the one or more nucleotide sequence alterations are detected by sequencing, PCR, DHPLC or combinations thereof.

The present invention further relates to a method for detecting in an individual the presence or absence of a mutant PKD gene comprising obtaining a nucleic acid sample from the individual and detecting the presence or absence of one or more nucleotide sequence alterations in a PKD1 or PKD2 gene of the individual, wherein the one or more alterations are selected from the group consisting of: a deletion of TTTAA at nucleotide positions 559 to 563 of SEQ ID NO: 1, an insertion of CT at nucleotide position 1124 of SEQ ID NO:1, an insertion of an A, T, G, or C at nucleotide position 2291 of SEQ ID NO:1, an insertion of an A, T, G, or C at nucleotide position 2297 of SEQ ID NO:1, an insertion of a T at nucleotide position 5365 of SEQ ID NO:1, an insertion of a G at nucleotide position 6666 of SEQ ID NO:1, an insertion of an A at nucleotide position 6881 of SEQ ID NO:1, a deletion of a T at nucleotide position 8713 of SEQ ID NO:1, an insertion of an A, T, G, or C at nucleotide position 9134 of SEQ ID NO:1, an insertion of 5 nucleotides at nucleotide position 9536 of SEQ ID NO:1, a deletion of a T at nucleotide position 10239 of SEQ ID NO:1, a change of a C to an A at nucleotide position 483 of SEQ ID NO:1, a change of a C to a T at nucleotide position 4517 of SEQ ID NO:1, a change of a C to an A at nucleotide position 7006 of SEQ ID NO:1, a change of a C to T at nucleotide position 8267 of SEQ ID NO:1, a change of a G to a T at nucleotide position 8639 of SEQ ID NO:1, a change of a G to an A at nucleotide position 20168 of SEQ ID NO:7, a change of a G to a T at nucleotide position 31025 of SEQ ID NO:7, a change of a G to a C at nucleotide position 33415 of SEQ ID NO:7, a deletion of CAA between nucleotide positions 508 to 516 of SEQ ID NO:1, a deletion of TGG at nucleotide positions 1848 to 1850 of SEQ ID NO:1, a deletion of CCAACTCCG at nucleotide positions 8892 to 8900 of SEQ ID NO:1, a deletion of AAG at nucleotide positions 9905 to 9907 of SEQ ID NO:1, a deletion of CTC at nucleotide positions 10070 to 10072 of SEQ ID NO:1, a deletion of TGG at nucleotide positions 12597 to 12599 of SEQ ID NO:1, a change of a C to an A at nucleotide position 1023 of SEQ ID NO:1, a change of a G to an A at nucleotide position 385 of SEQ ID NO:1, a change of an A to a G at nucleotide position 1470 of SEQ ID NO:1, a change of a C to a T at nucleotide position 4262 of SEQ ID NO:1, a change of a T to an A at nucleotide position 8855 of SEQ ID NO:1, a change of an A to a G at nucleotide position 1794 of SEQ ID NO:1, a change of a G to an A at nucleotide position 6036 of SEQ ID NO:1, a change of a C to a T at nucleotide position 2042 of SEQ ID NO:1, a change of a C to a T at nucleotide position 3351 of SEQ ID NO:1, a change of an A to a G at nucleotide position 6756 of SEQ ID NO:1, a change of a C to a T at nucleotide position 5793 of SEQ ID NO:1, a change of a C to a T at nucleotide position 6707 of SEQ ID NO:1, a change of a G to a C at nucleotide position 10187 of SEQ ID NO:1, a change of a C to a G at nucleotide position 7116 of SEQ ID NO:1, a change of an A to a G at nucleotide position 10311 of SEQ ID NO:1, a change of a T to a C at nucleotide position 7554 of SEQ ID NO:1, a change of a C to a Tat nucleotide position 7757 of SEQ ID NO:1, a change of a T to a C at nucleotide position 8067 of SEQ ID NO:1, a change of a C to a Tat nucleotide position 8138 of SEQ ID NO:1, a change of a C to a Tat nucleotide position 8509 of SEQ ID NO:1, a change of a C to an A at nucleotide position 10096 of SEQ ID NO:1, a change of a C to a Tat nucleotide position 12658 of SEQ ID NO:1, a change of a C to an A at nucleotide position 7476 of SEQ ID NO:1, a change of a C to a G at nucleotide position 3527 of SEQ ID NO:1, a change of a C to an A at nucleotide position 1947 of SEQ ID NO:1, a change of an A to a G at nucleotide position 3312 of SEQ ID NO:1, a change of a C to a G at nucleotide position 4391 of SEQ ID NO:1, a change of a T to an A at nucleotide position 11040 of SEQ ID NO:1, a change of a G to a Tat nucleotide position 840 of SEQ ID NO:1, a change of a G to an A at nucleotide position 7197 of SEQ ID NO:1, a change of a G to a C at nucleotide position 351 of SEQ ID NO:1, a change of a G to an A at nucleotide position 4757 of SEQ ID NO:1, a change of an A to a C at nucleotide position 1023 of SEQ ID NO:1, an insertion of: an A at nucleotide position 2226 of SEQ ID NO:4, a deletion of AG at nucleotide positions 2422 to 2423 of SEQ ID NO:4, a change of a C to a T at nucleotide position 2680 of SEQ ID NO:4, IVS7-1G>A, IVS8+5G>A, a deletion of TGG at nucleotide positions 374-376 of SEQ ID NO:4, a deletion of TTC between nucleotide positions 1876-1881 of SEQ ID NO:4 and a change of a G to an A at nucleotide position 634 of SEQ ID NO:4, wherein detection of the one or more nucleotide sequence alterations is indicative of a mutant PKD gene. In one embodiment, the presence or absence of the one or more nucleotide sequence alterations in the PKD1 or PKD2 gene of the individual indicates that the individual has ADPKD. In another embodiment, the presence or absence of one or more nucleotide sequence alterations in the PKD1 or PKD2 nucleic acid sequence is detected by sequencing, PCR and/or DHPLC.

The identification of mutations associated with ADPKD provides conclusive diagnostic information, allows the blood relatives of an individual to be pre-symptomatically and inexpensively evaluated for counseling and planning using targeted PKD gene analysis and allows prospective living-related kidney donors to be tested and subsequently accepted or rejected for donation with greater certainty. Pre-symptomatic testing for ADPKD may be particularly relevant not only in the evaluation of living kidney donors from ADPKD families, but also in the early detection for treatment with new agents that may be indicated for use early in the course of the disease (e.g., before cystic disease is apparent), family planning, the detection of ADPKD in young individuals (e.g., those under 30) for whom ultrasound imaging may not be accurate and/or adequate or in those families with PKD2-associated ADPKD, a clinically milder disease. In addition, clinicians may encounter patients with atypical cystic disease in whom the diagnosis is not obvious. Thus, using the novel, pathogenic mutations identified in the PKD1 and PKD2 genes, the methods of the invention help to better assist in the diagnosis and management of existing ADPKD and/or predict the likelihood of the occurrence of ADPKD in an individual.

BRIEF DESCRIPTION OF THE DRAWINGS

FIGS. 1A-1E depict the PKD1 coding sequence (GenBank Accession No. L33243) (SEQ ID NO:1).

FIGS. 2A-2B depict the PKD2 coding sequence (GenBank Accession Nos. AF004859-AF004873) (SEQ ID NO:4).

FIGS. 3A-3T depict wild-type PKD1 cDNA coding sequence according to one embodiment of the invention. Exon and PCR product junctions are depicted above the nucleotide sequence and amino acids are positioned under the center of each codon.

FIGS. 4A-4D depict wild-type PKD2 cDNA coding sequence according to one embodiment of the invention. Exon and PCR product junctions are depicted above the nucleotide sequence and amino acids are positioned under the center of each codon.

FIG. 5A illustrates missense mutations affecting the PKD1 repeats and C-lectin domain. Changes that disrupt the consensus sequence are red (dark-shaded) those that do not are yellow (light-shaded). Consensus sequence code: 1 (aliphatic), a (aromatic), c (charged), s (small residue), p (polar residue), b (big residue), h (hydrophobic), capital letters represent the corresponding amino acid codon. FIG. 5A discloses SEQ ID NOS 8-23, respectively, in order of appearance.

FIGS. 5B and 5C illustrate ribbon diagrams of the PKD repeat (5B) and C-lectin domain (5C) with potential pathogenic missense changes indicated.

DETAILED DESCRIPTION OF THE INVENTION

Figure 6:
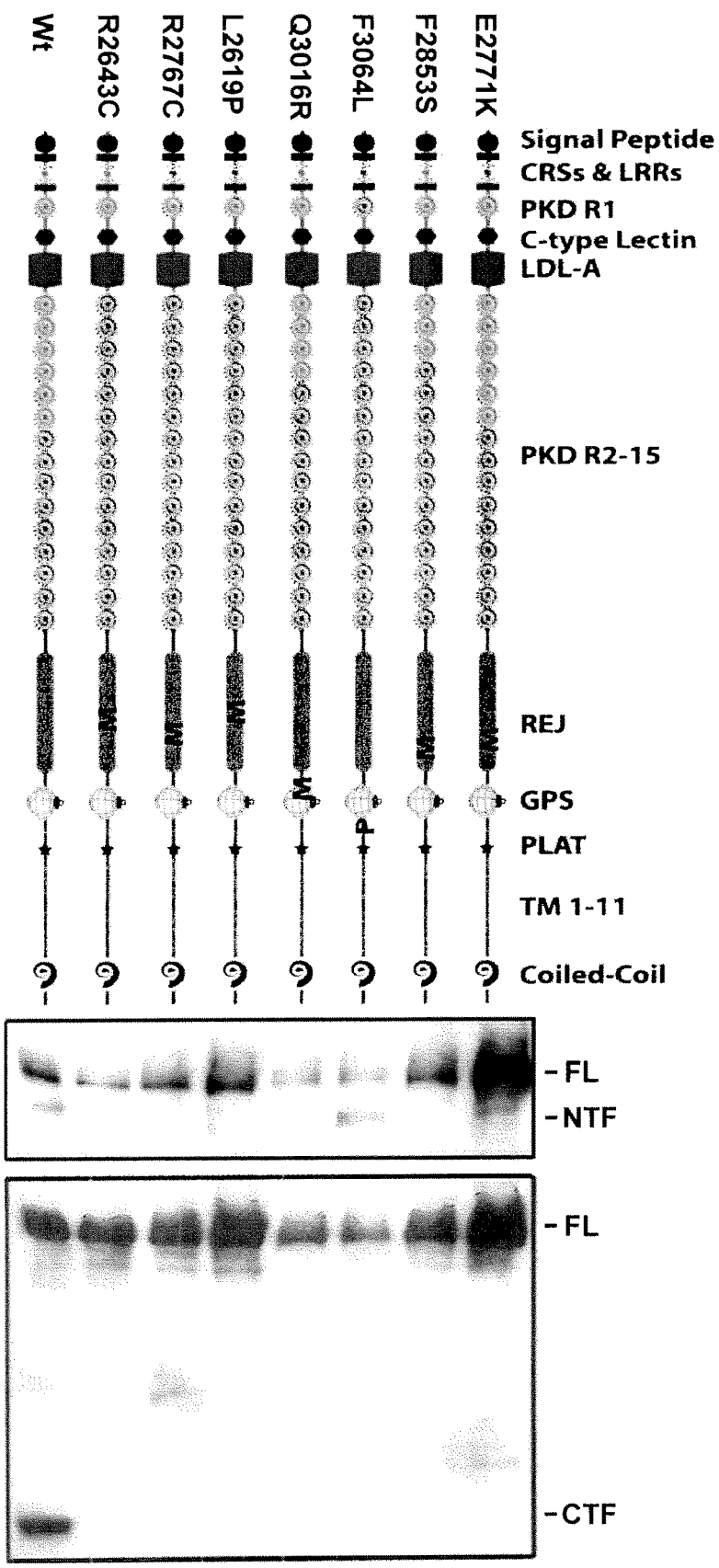
FIG. 6 illustrates a schematic of PKD1 mutant polypeptides with the location of each amino acid substitution indicated, M (missense) or P (polymorphism) and a photograph of a western blot of the full-length, flagged-tagged PKD1 constructs for each mutant protein and any cleavage products. FL: full-length, NTF: PKD1 N-terminal cleavage fragment, CTF; PKD1 C-terminal cleavage fragment.

The PKD genes are genomic DNA sequences that map to chromosomal position 16p13.3 (PKD1) or chromosomal position 4q21-23 (PKD2) and give rise to messenger RNA molecules encoding PKD1 and PKD2 proteins. The PKD1 and PKD2 genes comprise the sequences of SEQ ID NO:1 and SEQ ID NO:4, respectively, which include introns and putative regulatory sequences. Like many other genes, PKD1 and PKD2 gene sequences, when compared among individuals, show sequence variations that do not affect gene expression or expression and/or function of the gene product.

The PKD1 gene (e.g., GenBank Accession Number L39891, SEQ ID NO:7) spans about 54 kb of genomic DNA on chromosome 16 (16p13.3) and contains a 12,906 basepair coding sequence divided into 46 exons from which a 14 kb mRNA is transcribed. The protein product of PKD1, polycystin-1 (PC-1) (GeneBank Accession No. AAC37576, SEQ ID NO:3), is a 4303 amino acid protein with a predicted mass of 460 kDa which forms multiprotein complexes at the cell membrane and is thought to function in cell-cell and cell-matrix signal regulation. (Arnould T et al., *J Biol. Chem* 273:6013-6018, 1992; Parnell S. C. et al., *J Biol Chem*, 277:19566-19572, 2002; Bhunia A. K. et al., *Cell*, 109:157-168, 2002; Nauli S. M. et al., *Nat Genet* 33:129-137, 2003).

Approximately 75% of the PKD1 gene is duplicated and shares about 97% identity with its homologous copies. The reiterated region encompasses a 50 kb (5') portion of the gene containing the first 34 exons. Only the most 3', 5.7 kb of the gene, containing exons 35-46, is unique to PKD1. Another notable feature of the PKD1 gene is a polypyrimidine tract in intron 21 that is 2.5 kb long, the longest described in the human genome.

The PKD2 gene (see e.g., GenBank Accession Numbers AF004859 (exon1)-AF004873 (exon 15), SEQ ID NO:4) (see also GenBank Accession Number V50928) spans 68 kb of genomic DNA and is located on chromosome 4 (4q21-23). PKD2 contains 15 exons and encodes a 5.4 kb transcript (see e.g., GenBank Accession Number NM000297) from which a 968-amino acid protein product, polycystin-2 (PC-2) of approximately 110 kDa is generated (SEQ ID NO:6) (see also GenBank Accession Number NP00288). Polycystin-2 has been shown to interact with the carboxy-terminus of PC-1 and functions as a cation channel in complex with PC-1. (Gonzalez-Perrett S. et al., *Proc Natl Acad Sci USA* 98:1182-1187, 2000; Vassilev P. M. et al, *Biochem Biophys Res Commun* 282:341-350, 2001; Koulen P. et al., *Nat Cell Biol* 4:191-197, 2002; Hanaoka K. et al., *Nature* 408:990-994, 2000). Unlike PKD1, PKD2 is a single copy gene, making its analysis much more straight-forward. See Table 1 for a summary of the PKD genes. Further discussion of PKD1 and PKD2 genes, gene and protein alterations and methods of detecting the same can be found in US 2006/0246504, US 2003/0008288, WO 2002/006529, US 2005/017399, U.S. Pat. Nos. 7,083,915, 6,031,088, 6,228,591, US 2007/0166755, US 2005/0100898, U.S. Pat. Nos. 6,916,619, 6,656,681, 6,485,960, 6,380,360 and WO 1995/018225, which are all herein incorporated by reference.

TABLE 1

PKD gene description

|  | PKD1 | PKD2 | Total |
|---|---|---|---|
| Gene Description |  |  |  |
| Chromosome | 16p13.3 | 4q21-23 |  |
| Genomic length | 54 kb | 68 kb |  |
| Exons | 46 | 15 |  |
| Base pairs | 12,909 | 2,904 |  |
| Codons | 4,303 | 968 |  |
| Protein | Polycystin-1 | Polycystin-2 |  |
| Analysis: |  |  |  |
| Long Range PCRs | 8 | — | 8 |
| Amplicons | 54 | 17 | 71 |
| Base Pairs evaluated (including adjacent intronic sequence) | 13,830 | 3,204 | 17,034 |

PKD Gene Analysis

Genomic DNA obtained from a sample from a subject can be used as the template for generating one or more PKD-specific amplification products (e.g., long-range PKD amplification products). DNA testing is advantageous as it has the potential to provide genetic information to an isolated individual (e.g., when family members are unavailable for linkage studies. Both copies of the PKD genes in an individual should be analyzed/sequenced to identify bona fide gene mutations, as mutations have been detected on a normal haplotype and/or in combination with other amino acid truncating mutations.

A sample can be a biological material which is isolated from its natural environment containing target nucleic acid (e.g., a nucleic acid comprising a PKD gene), and may consist of purified or isolated nucleic acid, or may comprise a biological sample such as a tissue sample, a biological fluid sample, or a cell sample comprising the target nucleic acid. Collecting a tissue sample also includes in vitro harvest of cultured human cells derived from an individual's tissue or any means of in vivo sampling directly from a subject, for example, by blood draw, spinal tap, tissue smear or tissue biopsy. Optionally, tissue samples can be stored before analysis by well known storage means that preserve a sample's nucleic acid(s) in an analyzable condition, such as quick freezing, or a controlled freezing regime, in the presence of a cryoprotectant, for example, dimethyl sulfoxide (DMSO), glycerol, or propanediol-sucrose. Tissue samples can also be pooled before or after storage for purposes of amplifying them for analysis. In some embodiments, the sample contains DNA, tissue or cells from two or more different individuals. In another embodiment, the amount of sample necessary to analyze a PKD gene is dependent on the type of sample (e.g., more than 5 milliliters of blood) and this amount is best assessed by one of skill in the art. Preferably, aseptic techniques are used to obtain these samples to avoid their contamination.

Methods of isolating genomic DNA from a particular sample are well known and routine (see Sambrook et al., supra, 1989). In a particular embodiment, amplification of the genomic PKD DNA has advantages over the cDNA amplification process, including, for example, the allowance of the analysis of exons and introns of the PKD gene. As such, a target sequence of interest associated with either an intron or exon sequence of a PKD gene can be amplified and characterized. A target sequence of interest is any sequence or locus of a PKD gene that contains or is thought to contain a nucleotide sequence alteration, including those alterations that correlate with a PKD-associated disorder or disease (e.g., ADPKD).

Mutations in a PKD gene can be detected by amplification, including, for example, by polymerase chain reaction (PCR), ligase chain reaction, self sustained sequence replication, a transcriptional amplification system, Q-Beta Replicase, or any other nucleic acid amplification method, followed by the detection of the amplification products. Accordingly, in one embodiment, genomic DNA extracted from whole blood serves as a template for highly specific PKD1 gene amplification by long-range amplification of 8 segments encompassing the entire PKD1 duplicated region. The specific long-range amplification prevents the spurious amplification of PKD1 homologs that would otherwise confound the analysis. These PKD1 homologs are sequences which are closely related to PKD1, but which do not encode an expressed PKD1 gene product. In fact, analysis of the PKD1 gene had not been amenable to genetic analysis largely because of the presence of at least three highly homologous copies of the gene that map proximal to PKD1 along chromosome 16 (16p13.1). The sequence of these PKD1 gene homologs are contained in GenBank Accession Nos. AC002039, AC010488, AC040158, AF320593 AND AF320594 (each of which is incorporated herein by reference). Several examples of such homologs that map to chromosomal location 16p13.1 or 4q21-23 have been identified and sequenced. A PKD1 homologue may share more than 95% sequence identity to an authentic PKD gene.

In some embodiments of the invention, a nested amplification is performed using amplified products in a preceding amplification reaction as templates. Preferably, the nested amplification reaction is a nested PCR using PCR amplified products from a preceding PCR reaction as templates. In addition to optimizing the annealing temperature of the primers, "nested" amplification can be used to increase the specificity and sensitivity of the PKD-specific amplification assay. For example, a method comprising a nested PCR can involve two sequential PCR reactions. After multiple cycles of PCR (e.g., 10 to 40, or 10 to 30 or 10 to 20 cycles) with the first pair of primers comprising at least one PKD-specific primer (e.g., a PKD-specific primer and a control primer or two PKD-specific primers), a small amount aliquot of the first reaction (e.g., 1 µl of a 50 µl reaction) serves as the template for a second round comprising multiple cycles of PCR reaction (e.g., 10 to 40, or 10 to 30 or 10 to 20 cycles) with a new set of primers comprising at least one PKD-specific primer (e.g., a PKD-specific primer and a control primer or two PKD-specific primers) that anneal to sequences internal to, or nested between, the first pair.

In a particular embodiment, the 8 long range PCR products described above serve as template for 43 nested PCR reactions and cover exons 1-34 of the PKD1 gene. The unique region of the PKD1 gene (exons 35-46) and the entire PKD2 gene are amplified from genomic DNA as 28 additional gene segments. Using the nested PCR procedure, the template that is successfully amplified is selected twice for PKD-specificity. The use of nested PCR can also greatly enhance the yield of the species-specific product and, therefore, the sensitivity of the assay, when a single primer pair fails by itself.

Methods for designing primers and for performing PCR are known in the art (see *Current Protocols in Molecular Biology*, supra). The general criteria for selecting primers applies to primers for both the long-range PCR and nested PCR. With regard to primer for the nested PCR, both nested primers should anneal to sequences internal to (e.g., within) the first pair of primers and at least one of the nested primers. Some PKD1-specific primers which eliminate unintended amplification of PKD1 homologs have been developed (see, e.g., U.S. 2003/0008288, which is incorporated herein by reference). Other such primers can be designed, where a "PKD-specific" primer would be a nucleic acid sequence which anneals to a sequence within a PKD gene (including introns and exons) under specific stringent conditions. A PKD-specific primer, anneals to a unique site present in the authentic expressed PKD1 gene, and not to PKD1 homologs or other sequences under specific stringent conditions. Thus, PKD-specific primers can be designed using these unique PKD sites. The length of a unique site may vary from several nucleotides to thousands of nucleotides. Most of unique sites that have been identified comprises less than or equal to 100 nucleotides, e.g., less than or equal to 50 nucleotides, or less than or equal to 30 nucleotides. Amplification using PKD-specific primers increases the specificity of the amplification reaction and reduces the amount of by-products amplified from PKD homologs. The primers may be 10 to 60 nucleotides in length, for example, 18-52 nucleotides in length.

The 71 PCR products are bi-directionally sequenced to detect nucleotide sequence alterations. In a particular embodiment, all PCR primers comprise a tag (e.g., M13 forward and reverse primer sequences) to permit bi-directional sequencing of all fragments with the same primers. Methods of sequencing DNA are well-known in the art and are dependent on the primer position and/or fragment length. For example, in one embodiment, sequencing is performed using ABI Big Dye terminator chemistry followed by electrophoresis on an ABI 3730 capillary sequencer. Nucleotide alterations of the invention can be detected in a PKD sequence to assess existing or potential ADPKD. Novel alterations identified can be clinically interpreted as disease-associated mutations, for example, frameshift or nonsense mutations or invariant splice site changes. Benign polymorphisms would include silent or conservative missense mutations, intronic variants and synonymous codon changes.

Sequence alterations in a PKD gene can also be detected using denaturing high performance liquid chromatography (DHPLC). DHPLC has been used to detect sequence variants by separating a heteroduplex (resulting from the presence of a mutation) and a homoduplex having the same basepair length. This separation is based on the fact that a heteroduplex has a lower melting temperature (Tm) than a homoduplex. DHPLC can separate heteroduplexes that differ by as little as one base pair under certain conditions. The "heteroduplex site separation temperature" or "midpoint temperature" or "Tm" is defined herein to mean, the temperature at which one or more base pairs denature, i.e., separate, at the site of base pair mismatch in a heteroduplex DNA fragment. When DHPLC is carried out at a partially denaturing temperature, i.e., a temperature sufficient to denature a heteroduplex at the site of a base pair mismatch, homoduplexes can be separated from heteroduplexes having the same base pair length and detected by various methods (e.g., gel electrophoresis). DHPLC can also be used to separate duplexes having different basepairs in length.

Evaluation of Identified PKD Nucleotide Alterations

Numerous novel nucleotide alterations in PKD have been identified (see Tables 4-7). These sequence alterations were then evaluated to determine whether they were pathogenic, this is, resulted in an altered PKD gene product (e.g., protein, polypeptide). A "nucleotide sequence alteration" or "nucleotide alteration" or "mutation" refers to a nucleotide sequence modification including one or more substitutions (transitions or transversions), deletions (including loss of locus), insertions (including duplications), translocations, inversions and/or other modifications relative to a normal PKD gene (e.g., SEQ ID NO:1, SEQ ID NO:7 or SEQ ID NO:4). Thus, a nucleotide alteration/change in a PKD1 or PKD2 nucleotide sequence (e.g., DNA or mRNA) can be a deletion, insertion, substitution or inversion, or can be silent such that there is no change in the reading frame of a polypeptide encoded by the PKD polynucleotide. Pathogenic mutations are those nucleic acid alterations that result in an amino acid change (e.g., a non-silent or non-conservative change) and/or introduces a STOP codon into the nucleotide sequence, or changes nucleotide sequence involved in transcription or translation of the PKD1 or PKD2 nucleotide sequence; for example, a change that results in altered splicing of a PKD1 or PKD2 gene transcript into an mRNA (see FIGS. 7A and 7B). An "amino acid alteration" refers to an amino acid modification including a substitution, a frameshift, a deletion, a truncation and an insertion, and/or other modifications relative to the normal PKD amino acid sequence (e.g., SEQ ID NO:3 or SEQ ID NO:6). Thus, a mutation in a PKD gene sequence can result in the expression of a truncated PKD polypeptide, or even a complete loss of expression of the PKD polypeptide.

In contrast, polymorphic mutations or variants are those nucleic acid alterations that do not alter and/or are not expected to alter a PKD protein/polypeptide in the above-described manner and/or do not correlate with the signs or symptoms of a PKD-associated disorder such as ADPKD (see Tables 8 and 9). These mutations include, for example, nucleotide substitutions that do not result in a change in the encoded amino acid, i.e., silent mutations, in which the wild type (see, e.g., SEQ ID NOs:1, 7 or 4) and mutant codons both encode the same amino acid; those that do not segregate with the disease or those that are found in a panel of unaffected individuals. Nucleic acid alterations that cause conservative amino acid substitutions in which a wild-type amino acid (see, e.g., SEQ ID NOs:3 or 6) is substituted for another amino acid with similar properties, may also be non-pathogenic polymorphic mutations, as it would be expected that the secondary structure and hydropathic nature of the PKD polypeptide would be substantially unchanged by these mutations. In general, the following groups of amino acid substitutions are thought to be conservative: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. With respect to PKD mutations, polymorphisms are then defined as: (i) sequence variants not predicted to alter an amino acid; (ii) missense changes found in homozygosity in at least one individual; (iii) intronic sequences of unknown significance; or (iv) changes in the 3' UTR of unknown significance. Accordingly, polymorphic mutations would be expected to result in a PKD protein/polypeptide that is still properly expressed and/or fully functional; that is, these variants would not be expected to be associated with ADPKD.

Nucleotide sequence alterations identified in PKD1 and PKD2 genes can be evaluated for pathogenicity in a number of ways. Mutant PKD nucleotide sequence can be compared to wild-type PKD sequence (SEQ ID NOs:1 and 4) and the effect of the nucleic acid sequence alterations on amino acid codon(s) assessed. For example, a change in nucleotide sequence that produces a stop codon (e.g., UGA, UAA, UAG) or a frameshift, which generally results in a nonsensical polypeptide and/or also produces a stop codon, or that alters a consensus donor/acceptor splice site would result in a non-functional PKD protein, a truncated PKD protein, or obliterate its expression altogether. These mutations would be expected to be pathogenic and thus correlates with ADPKD.

PKD nucleic acid sequence alterations that do not result in the production of a stop codon, frameshift or splice site mutation can also be assessed by comparing the mutant PKD amino acid sequence to the wild-type PKD amino acid sequence from various species to determine if the alteration affects an amino acid residue that is conserved across several species. In particular, an amino acid change (i.e., a missense mutation) or a deletion of several adjacent nucleotide residues (e.g., a deletion of 3, 6 or 9 nucleotides) which would cause a complete deletion of one or more amino acid residues (i.e., an in-frame deletion; see also Table 5) would result in a PKD polypeptide that is still expressed. The change or loss of an amino acid residue conserved across several species (e.g., human, canine, mouse, fish, fruit fly, nematode, etc), where a "conserved" amino acid residue is one that is identical or has similar properties (e.g., ala, pro, gly, glu, asp, gln asn, ser, thr), would strongly indicate that the amino acid residue is important/critical to PKD protein function. Accordingly, such PKD mutations might also be expected to be associated with and/or predictive of ADPKD.

Furthermore, there are also several algorithms that can be used to predict/evaluate alterations to a PKD nucleic acid sequence, particularly those that result in a missense mutation. These algorithms include, for example, the Miller/Kumar matrix (Miller M. P. and Kumar S., *Hum Mol Genet* 10(21):2319-2328, 2001); Grantham's chemical difference matrix; Online Mendelian Inheritance in Man (OMIM), //www.ncbi.nlm.nih.gov/Omim/; Splice Site Prediction by Neural Network (SSPNN) (see also Reese M. G. et al., *J Comput Biol* 4(3):311-323, 1997), fruitfly.org.seqtools/splice.html; Automated Splice Site Analyses (ASSA) (see also, Nalla V. K. et al., *Hum Mutat* 25(4):334-342, 2005 and Rogan P. K. et al., *Hum Mutat* 12(3)153-171, 1998), //splice.cmh.edu/; Simple Modular Architecture Research Tool (SMART), //smart.embl.de; Pfam, www.sanger.ac.uk/Software/Pfam/; MDRD equation: //nephron.com/cgi-bin/MDRDSI.cgi; Prediction of Protein Sorting Signals and Localization Sites in Amino Acid Sequences II (PSORT II) (see also Krogh A. et al., *J Mol Biol* 305:567-580, 2001), //psortims.u-tokyo.ac.jp/form2.html; and Transmembrane Helices Prediction (TMHMM), (see also Grimm D. H. et al, *J Biol Chem* 278:36786-36793, 2003), //www.cbs.dtu.dk-.services/TMHMM/. By predicting mRNA and/or protein structure, function and motifs, these and other algorithms can help determine the likelihood that a mutation (e.g., a missense mutation) represents a pathogenic change as opposed to a polymorphism.

Further assessment of PKD mutations not clearly pathogenic could also be aided with a dataset comprising complete sequence information from a population of unaffected, ethnically diverse individuals. Normal or wild-type PKD1 and PKD2 sequence information from such a population would be a useful control for comparison to novel PKD mutations identified to both evaluate the presence or absence of a sequence variant in the control population and expand the spectrum of known non-pathogenic sequence variants. Having such a dataset to compare to PKD mutations that have been identified would be advantageous diagnostically and prognostically, especially in the analysis of individuals having less than a 50% probability of having ADPKD (e.g., individuals not the progeny and/or siblings of an individual with ADPKD).

The effect of mutations in a PKD gene on a PKD gene product can be assessed and/or confirmed by expressing a polynucleotide having or constructed (e.g., a recombinant polynucleotide) to have the identified mutation(s). The polynucleotide can comprise the mutant PKD polypeptide or a portion of a recombinant nucleic acid molecule, which, for example, can encode a fusion PKD protein (e.g., a tagged PKD protein). The mutant polynucleotide or recombinant nucleic acid molecule can be inserted into a vector, which can be an expression vector, and can be derived from a plasmid, a virus or the like. The expression vector generally contains an origin of replication, a promoter, and one or more genes that allow phenotypic selection of transformed cells containing the vector. Expression vectors suitable for use are well-known in the art e.g., a T7-based expression vector for expression in bacteria, a pMSXND expression vector for expression in mammalian cells or baculovirus-derived vectors for expression in insect cells and the like. The choice of a vector will depend on the size of the polynucleotide sequence and the host cell to be employed. Thus, the vector used in the methods of the invention can be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides. Cosmids and phagemids are particularly suited for the expression or manipulation of a PKD polynucleotide (e.g., SEQ ID NO:1) or a mutant PKD1 polynucleotide.

A variety of host-expression vector systems can be utilized to express wildtype PKD polynucleotide sequence (e.g., SEQ ID NO:1 or SEQ ID NO:4), the PKD coding sequence (e.g., SEQ ID NO:2 or SEQ ID NO:5) and a variant or mutant PKD1 or PKD2 polynucleotide. In a particular embodiment, the PKD polynucleotide(s) is tagged (e.g., FLAG, Myc, biotin, streptavadin, avadin and the like) to aid in purification and/or visualization of the PKD polypeptide after it has been exposed. Such host-expression systems represent vehicles by which the nucleotide sequences of interest can be produced and subsequently purified, and also represent cells that, when transformed or transfected with the appropriate nucleotide coding sequences, can express a PKD protein, including a PKD variant or mutant polypeptide or peptide portion thereof in situ. Such cells include, but are not limited to, microorganisms such as bacteria (e.g., *E. coli, B. subtilis*) transformed with recombinant bacteriophage DNA, plasmid DNA or cosmid DNA expression vectors containing a PKD1 polynucleotide, or oligonucleotide portion thereof (wild type, variant or other mutant); yeast (e.g., *Saccharomyces, Pichia*) transformed with recombinant yeast expression vectors containing a PKD polynucleotide, or oligonucleotide portions thereof (wild type, variant or other PKD mutant); insect cell systems infected with recombinant virus expression vectors (e.g., baculovirus) containing a PKD polynucleotide, or oligonucleotide portion thereof (wild type, PKD variant or other mutant); plant cell systems infected with recombinant virus expression vectors (e.g., cauliflower mosaic virus or tobacco mosaic virus) or transformed with recombinant plasmid expression vectors (e.g., Ti plasmid) containing a mutant PKD polynucleotide, or oligonucleotide portion thereof; or mammalian cell systems (e.g., HEK293, COS, CHO, BHK, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter). Further discussion of vectors and expressions systems for PKD polynucleotides can be found, for example, in US 2003/0008288.

Figure 8A:
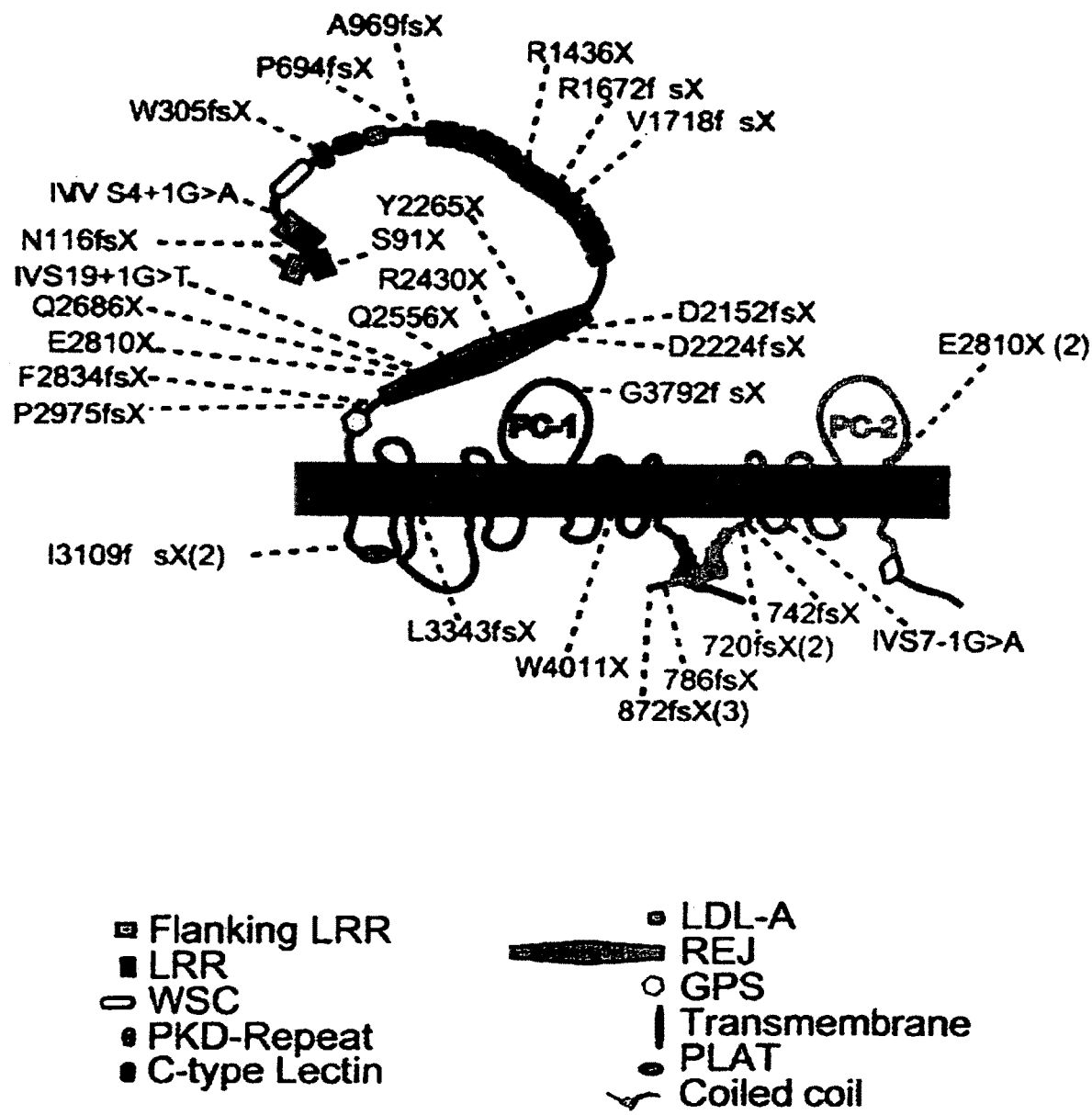
FIGS. 8A and 8B are schematic representations of polycystin-1 (PC-1) (8A) and polycystin-2 (PC-2) (8B). The location of pathogenic (Class I and Class II, see Example) mutations are indicated.

For instance, the PKD1 gene product, polycystin-1 (PC-1), which is believed to function as a cell surface signaling receptor at cell-cell and cell-matrix junctions and as a mechano-sensor in renal cells, is an 11-transmembrane glycoprotein with a long N-terminal extracellular region and short cytoplasmic tail (Boletta A. and Germino G. G., *Trends Cell Biol* 13(9):484-492, 2003; Harris P. C. and Torres V. E., *Curr Opin Nephrol Hypentens* 15(4):456-463, 2006; Nauli S. M. et al., *Nat Genet* 33(2):129-137, 2003; Hughes J. et al., *Nat Genet* 10(2):151-160, 1995) (see also FIG. 8A). PC1 has several amino acid sequence motifs of interest (e.g., receptor for egg jelly (REJ) domain, G-protein coupled receptor proteolytic site (GPS), C-type lectin domain, leucine rich repeat (LRR), polycystic kidney disease repeat (PKD-R), transmembrane domain (TM), coiled-coil domain (CC)) (see also FIG. 4). A site useful for evaluation of PC-1 function/activity is the GPS domain, a site at which the PC-1 protein undergoes cleavage (Qian F. et al., *Proc Natl Acad Sci USA* 99(26):16981-16986, 2002). Cleavage of PC1 at this site produces an N-terminal fragment (NTF) and a C-terminal fragment (CTF) and this cleavage is critical for normal PC-1 function (Qian F. et al., *Proc Natl Acad Sci USA* 24:99(26):16981-16986). Thus, expression and cleavage of the PKD1 gene product can be used to assess the pathogenicity of identified PKD1 mutations, particularly missense mutations. PKD1 mutants can be constructed (e.g., in an expression vector) and expressed (as, e.g., a recombinantly tagged fusion protein) in the above-described manner and the cleavage of the PKD1 mutant gene products assayed (e.g., by immunoprecipitation and/or western blot, fluoresence of a tag, radioactivity or the like).

One or more of the above-described methods to assess/evaluate PKD mutations can be used to determine whether PKD1 or PKD2 gene mutations that have been identified are benign polymorphisms or pathogenic, such that the mutations can be associated with ADPKD and, subsequently used to diagnose or predict ADPKD in, for instance, the methods of the invention.

Methods of the Invention

The PKD mutations identified and determined to be pathogenic are listed in Tables 4-7. These mutations are used in the methods of the invention to detect or predict the occurrence of ADPKD in an individual or detect the presence or absence of a mutant PKD gene in an individual. Specifically, ADPKD is detected or the occurrence of ADPKD is predicted by detecting the presence of one or more of the identified nucleotide sequence alterations in a PKD1 gene having the nucleotide sequence of SEQ ID NO:1 or SEQ ID NO:7 in a nucleic acid sample obtained from an individual. Similarly, ADPKD can be detected or predicted in an individual using the methods of the invention by detecting the presence of one or more of the identified nucleotide sequence alterations in a PKD2 gene having the nucleotide sequence of SEQ ID NO:4 in a nucleic acid sample obtained from an individual. As several mutations in the PKD genes that are associated with ADPKD have been detected in just a single individual/family (see e.g., Table 7), these other nucleotide sequence alterations in a PKD1 gene (e.g., SEQ ID NO:1 or 7) and/or PKD2 gene (SEQ ID NO:4) not listed above (see Summary of Invention and Tables 4-7) can also be detected in the methods of the invention. The methods can be performed by obtaining a sample (e.g., biological fluid, tissue, cell) from an individual by one or more procedures (e.g., DNA isolation method/kit) and/or one or more methods (e.g., sequencing, PCR, DHPLC) as described above.

In addition, the invention relates to methods of detecting the presence or absence of a mutant PKD gene in an individual by obtaining a nucleic acid sample from the individual (e.g., biological fluid, tissue or cell sample), by the above-described methods (e.g., DNA isolation method/kit) and detecting the presence or absence of one or more of the identified nucleotide sequence alterations in a PKD1 or PKD2 gene, by using one or more of the above-described processes (e.g., sequencing, PCR, DHPLC or the like). In a particular embodiment, detection of one or more of the identified PKD nucleotide sequence alterations indicates that the individual has ADPKD or may develop ADPKD.

EXEMPLIFICATION

Patient Recruitment and Clinical Evaluation

Eighty-two unrelated ADPKD patients were recruited from outpatient nephrology clinics. The Johns Hopkins Institutional Review board approved the study and informed consent was obtained from each patient. A diagnosis of ADPKD was based on established ultrasound criteria described (Ravine et al., *Lancet* 2:343(8901):824-7, 1994). A detailed medical history was obtained from each participant at the time of entry into the study. A coded blood sample was collected from each proband and sent to Athena Diagnostics, Inc. for mutation analysis. In most cases routine laboratory data were obtained as part of the standard medical evaluation.

Baseline characteristics of the study population are summarized in Table 2. The average age of the study participants was 46.5 years of age. Only 22% had reached ESRD at the time that mutation analysis was performed. The average glomerular filtration rate (GFR) for those that had not reached ESRD was 68 ml/min. Family history was either unknown or was negative for ADPKD in 34% of the patients.

Mutation Analysis

DNA sequence analysis of patient samples was performed using methods described in detail previously and optimized at Athena Diagnostics, Inc (Watnick T J et al., *Hum Mol Genet* 6(9):1473-1481, 1997; Watnick T J et al., *Mol Cell* 2(2):247-251, 1998; Watnick T. et al., *Am J Hum Genet* 65(6):1561-1571, 1999; Phakdeekitcharoen B. et al., *Kidney Int* 58(4):1400-1412, 2000; Phakdeekitcharoen B. et al., *J Am Soc Nephrol* 12:955-963, 2001), which references are incorporated in entirety herein. For example, genomic DNA is derived from whole blood using a Puregene® DNA extraction kit (Gentra Systems, Inc. Minneapolis, Minn.) or other suitable extraction method. Amplified DNA product served as a template for highly specific long-range PCR amplification of the 8 segments encompassing the entire PKD1 duplicated region, to prevent the amplification of PKD1 homologs that would confound the analysis. The 8 long range PCR products served as template for 43 nested PCR reactions while the unique region of the PKD1 gene and the entire PKD2 gene were amplified from genomic DNA as 28 additional gene segments. PCR primers were tagged with M13 forward and reverse primer sequences to permit bi-directional sequencing of all fragments with the same primers.

PCR products were then bi-directionally sequenced, for example, using ABI Big Dye™ terminator chemistry (versions 3.1 and 1.1 depending upon primer position and/or fragment length) followed by electrophoresis on an ABI 3730 capillary sequencer (Applera Corporation, Norwalk, Conn.). This process provides sequence data for the entire coding region of the PKD1 and PKD2 genes including the highly conserved exon-intron splice junctions.

Analysis of Normal Samples

A normal population was selected from anonymized samples, older than 65, submitted to Athena Diagnostics, Inc for ataxia testing. PCR products from a minimum of 171 individuals were sequenced to determine the frequency of certain common variants in either PKD1 or PKD2. Complete DNA analysis was not performed for these samples.

Generation of PC-1 Variant Constructs for Cleavage Testing

Missense variants were generated, for example using the QuickChange™ Site-Directed Mutagenesis Kit (Stratagene). The full-length wild type PKD1 cDNA construct and three of the constructs have been previously described (Q3016R, F3064L, F2853S) (Hanaoka K. et al., *Nature* 408:990-994, 2000; Qian F. et al., *Proc Natl Acad Sci USA* 24:99(26):16981-16986, 2002), incorporated in entirety herein.

Cleavage Assay

Constructs were transfected into HEK293 cells using Lipofectamine Plus™ (Life Technologies, Rockville, Md.). After transfection, the cells were lysed in buffer [20 mM sodium phosphate, pH 7.2, 150 mM NaCl, 1 mM EDTA, 10% (vol/vol) glycerol, 0.5% Triton X-100] for 1 hr on ice in the presence of protease inhibitor (Roche Molecular Biochemicals). The cell lysates were immunoprecipitated (IP) using ANTI-FLAG® M2 beads Affinity Gel Freezer-Safe (SIGMA) and then resolved on a NuPAGE® 3-8% Tris-Acetate Gel (Invitrogen). The IP products were electro-blotted onto an Immobilon™ transfer membrane (MILLIPORE) and probed with α-Leucine-rich-repeat (LRR) and α-C-terminus (CT) antibodies for PC1. These antibodies have been previously described (Boletta A. et al., *Mol Cell* 6:1267-1273, 2000; Qian F. et al., *Proc Natl Acad Sci USA* 24:99(26):16981-16986, 2002).

Results

DNA sequence variance analysis identified three categories of variants. Class I variants were defined as those having definitive pathogenic sequence variants, including stop codons, frameshift and splice site alterations, that are diagnostic without additional information (Tables 3, 4). Class II variants included those demonstrating in-frame deletions or amino acid substitutions determined likely to be pathogenic based on various algorithms, as described in detail below. Class III variants included those where no pathogenic changes were confirmed.

Class I Variants

Forty-two percent (N=34) of the study population had stop codons, frameshift or splice site alterations (Tables 3, 4). Twenty-four of these alterations occurred in PKD1 (29% of total sample) and 10 in PKD2 (12% of total sample). The mutations found in Class I variants were expected to result in premature truncation of a PKD1 or PKD2 protein and therefore segregate with ADPKD.

Class II Variants

Thirty participants had either an in-frame deletion or at least one amino acid substitution deemed likely to be pathogenic (Tables 5 and 6). A total of 8 unique in-frame deletions (6 in the PKD1 gene and 2 in PKD2 gene) were detected (Table 5). In each case, the deletion affected one or more residues fully or highly conserved between *Fugu rubripes* (Fugu fish) and *Mus musculus* (mouse) polycystin proteins.

There were 10 individuals with no other truncating PKD mutations who had unique intronic variants. Two of the predicted splice site mutations did not directly affect a consensus splice donor/acceptor site; JHU573 and JHU595 had an intronic change at the $5^{th}$ base pair from the intron 24 splice donor site (IVS24+5 G>C) that affected a residue that is highly conserved as a guanine in 84% of donor splice sites. Both the Neural Network Splice Site prediction program (SSPN) and Automated Splice Site Analyses (ASSA) predicted that these variants resulted in improper splicing, as such an alteration would severely disrupt the architecture of the splice donor site at the exon 24/intron 24 boundary. JHU105 had a similar alteration (IVS8+5,G>A) at the $5^{th}$ basepair from the end of PKD2 exon 8 splice donor site (i.e., the $5^{th}$ nucleotide base counted from left to right after nucleotide residue 1964 of SEQ ID NO:5 into the following intron (intron 8)), in which the highly conserved guanine residue was replaced by an adenine. In addition, IVS37-10C>A (JHU 604), was previously reported to segregate with ADPKD in a European family (Bogdanova, M. et al., *Hum Mutat* 16(2):166-174, 2000). JHU562 also had a PKD2 pathogenic mutation that affected a splice site, IVS7-1G>A (i.e., a change from a guanine to an adenine at the $1^{st}$ nucleotide residue counted right to left from the beginning of exon 8 (e.g., nucleotide residue 1783 of SEQ ID NO:5) into the previous intron (intron 7)), which resulted in the loss of the acceptor site for exon 7.

Most of the remaining participants had a combination of amino acid substitutions, primarily in PKD1. Three major criteria were used to judge the pathogenicity of each missense variant. Conservation of the altered residue between human polycystin-1 and Fugu fish and mouse proteins was examined. Amino acids that were considered "fully conserved" were those that were identical in all three species, while amino acids with similar properties (i.e. belonging to the same class) were deemed to be "highly conserved" residues. In addition, a pathogenicity score for each missense variant was assigned using the matrix of Miller and Kumar (Miller M. P. and Kumar S., *Hum Mol Genet* 12(21):2319-2328, 2001), which defines the relative likelihood that a missense change represents a pathogenic alteration versus a polymorphism. This algorithm was developed by using interspecies sequence comparisons coupled with Grantham's chemical difference matrix to determine the common attributes of amino acid replacement mutations across 7 disease genes (including tuberous sclerosis and cystic fibrosis). Other investigators have used this strategy to assist in characterizing amino acid substitutions (Sharp A. M. et al., *J Med Genet* 42(4):336-349, 2005). Finally, literature was reviewed to determine whether any of the variants had been reported by others to occur in unaffected individuals. Several amino acid substitutions (N=13, Table 9), detected in homozygosity in one or more individuals, were classified as polymorphisms. Since germ line ADPKD mutations are heterozygous, one of these changes would have to be associated with a wild type allele, presumably inherited from an unaffected parent.

Analysis of individual amino acid substitutions, grouped by patient, is summarized in Table 6. An amino acid substitution was deemed to be pathogenic, if it occurred at a fully or highly conserved amino acid residue and if it was also predicted to have a higher pathogenic potential using the matrix of Miller and Kumar (Table 6, shaded in Gray). Using these strict criteria, 24 of 30 patients had one or more pathogenic amino acid substitutions. Six of these missense changes were predicted to disrupt structural determinants of either the C-type lectin (Y420C, Y528C) or one of the PKD repeats (S1047L, R1340W, R1351W, T1861I) (FIGS. 5A and 5B). Three of the missense changes (Q3016R, E2771K, F2853S) were previously shown to disrupt polycystin-1 cleavage, a property that is critical for normal polycystin-1 function (see FIG. 6) (Qian F. et al., *Proc Natl Acad Sci USA* 24:99(26):16981-16986, 2002).

Recurrent PKD1 variants (R2200C, Q739R, G2814R, Q2182R, G2309R, R1340W) that met the criteria for pathogenicity were observed in 7 individuals and were also present in other individuals who harbored either chain terminating mutations or other predicted pathogenic amino acid substitutions (Tables 4, 6 and 7). For example, R2200C was present in 4 patients, JHU584, JHU606, JHU111 and JHU573. The latter two individuals had a PKD1 frame shift mutation and a splice site mutation, respectively. This association suggested that these changes represented polymorphisms. To further characterize the missense mutations, 342 normal chromosomes were sequenced to identify polymorphisms and the R2200C sequence alteration was seen in a small (1.4%) fraction but greater than the polymorphism threshold of 1%. Likewise Q739R (this study 6.4%) and G2814R (Rossetti et al., 0.9%) have also been reported in a small percentage of the unaffected population and are or may be polymorphisms, respectively (Thomas T. et al., *Am J Hum Genet* 65(1):39-49, 1999 and Rossetti S. et al., *Kidney Int* 61(5):1588-1599, 2002).

If patients with only these pathogenic recurrent variants (without additional chain terminating mutations or other pathogenic amino acid substitution) were eliminated, then approximately 21% of the sample (N=17/82 patients) would be predicted to harbor a pathogenic PKD1 missense mutation.

Five participants JHU 602 (N=2), JHU100 (N=3), JHU588 (N=2), JHU411 (N=2), JHU114 (N=2) had more than one PKD1 amino acid variant that met the criteria for pathogenicity. This observation raises the possibility that a combination of missense changes in cis might cooperatively result in a diminished level of functional PKD1 protein (Reiterova J. et al., *Hum Mutat* 19(5):573, 2002).

In contrast with PKD1, only two PKD2 amino acid substitutions were detected among the 37 patients lacking chain-terminating mutations. One change (M800L in JI-IU559, Table 6), was not considered pathogenic by the criteria of the present system and did not segregate with disease in a PKD2 family. A second PKD2 substitution, A190T, was found in 3 patients and, likewise, did not meet the criteria for pathogenicity as it was identified in 3.2% of normal chromosomes (Table 6).

In assessing Class II variants, detection of in-frame deletions was a useful predictor of pathogenicity. Also amino acid substitutions resulting in loss of polycystin-1 cleavage were predictive of pathogenicity.

Figure 8B:
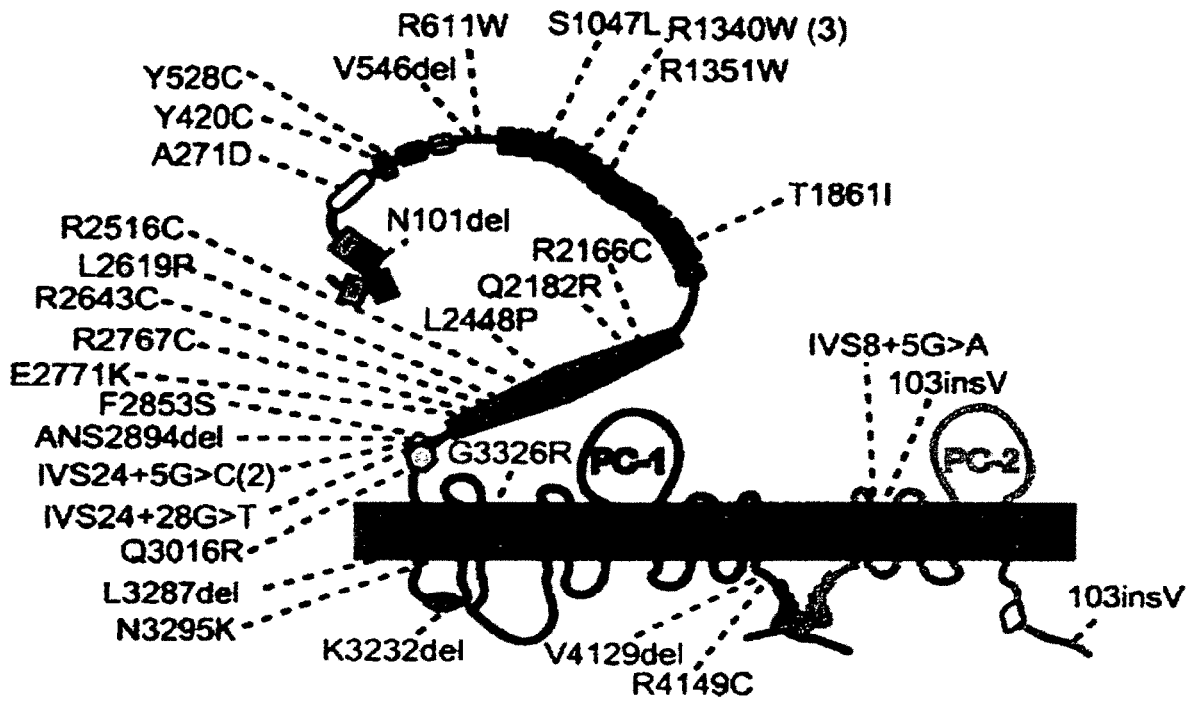

Class I and Class II amino acid changes in the PKD-1 protein (polycystin-1) and PKD-2 protein (polycystin-2) are depicted in a schematic in FIG. 8.

Class III Variants

Eighteen subjects in the study lacked definitive pathogenic sequence alterations (Tables 6 and 9). Of these, 9 had clear and extensive family history of polycystic kidney disease (Table 9). The other 9 had enlarged kidneys with cysts, with 4 of these individuals suffering from significant renal dysfunction (GFR<40) at the time of DNA testing.

Failure to detect pathogenic or potentially pathogenic changes in a subset of individuals with polycystic kidney disease may be due to several reasons. Mutational events in individuals with Class III tests could involve introns or other regulatory regions that were not assayed by the methodology that was used. Direct sequencing might also miss deletions or duplications, which would appear as an area of homozygous normal sequence. Alternatively, the stringent criteria used may have identified some missense changes as benign when they are in fact pathogenic. For example, JHU617, with an extensive family history of ADPKD, was found to have a unique leucine to valine change in PKD repeat 4 that was judged more likely to be a polymorphism by the matrix of Miller/Kumar. Nevertheless, this change does disrupt the structure of PKD repeat 4 and could be pathogenic (see FIGS. 5A and 5B). In addition, as reported by Reynolds, missense variants may unexpectedly activate cryptic splice sites, thereby reducing the level of normal transcript (Reynolds D. M. et al., *J Am Soc Nephrol* 10(10:2342-2351, 1999).

Functional Analysis of Missense Changes

To confirm that a subset of PKD1 amino acid substitutions predicted to be pathogenic disrupted the functional properties of the protein, full-length mutant constructs were generated and transiently expressed in HEK293 cells. FIG. 6 demonstrates that E2771K, Q3016R and F2853S disrupt cleavage, as do three additional missense changes, R2643C, R2767C and L2619P.

Polymorphism and Variability in PKD Genes

Figure 7A:
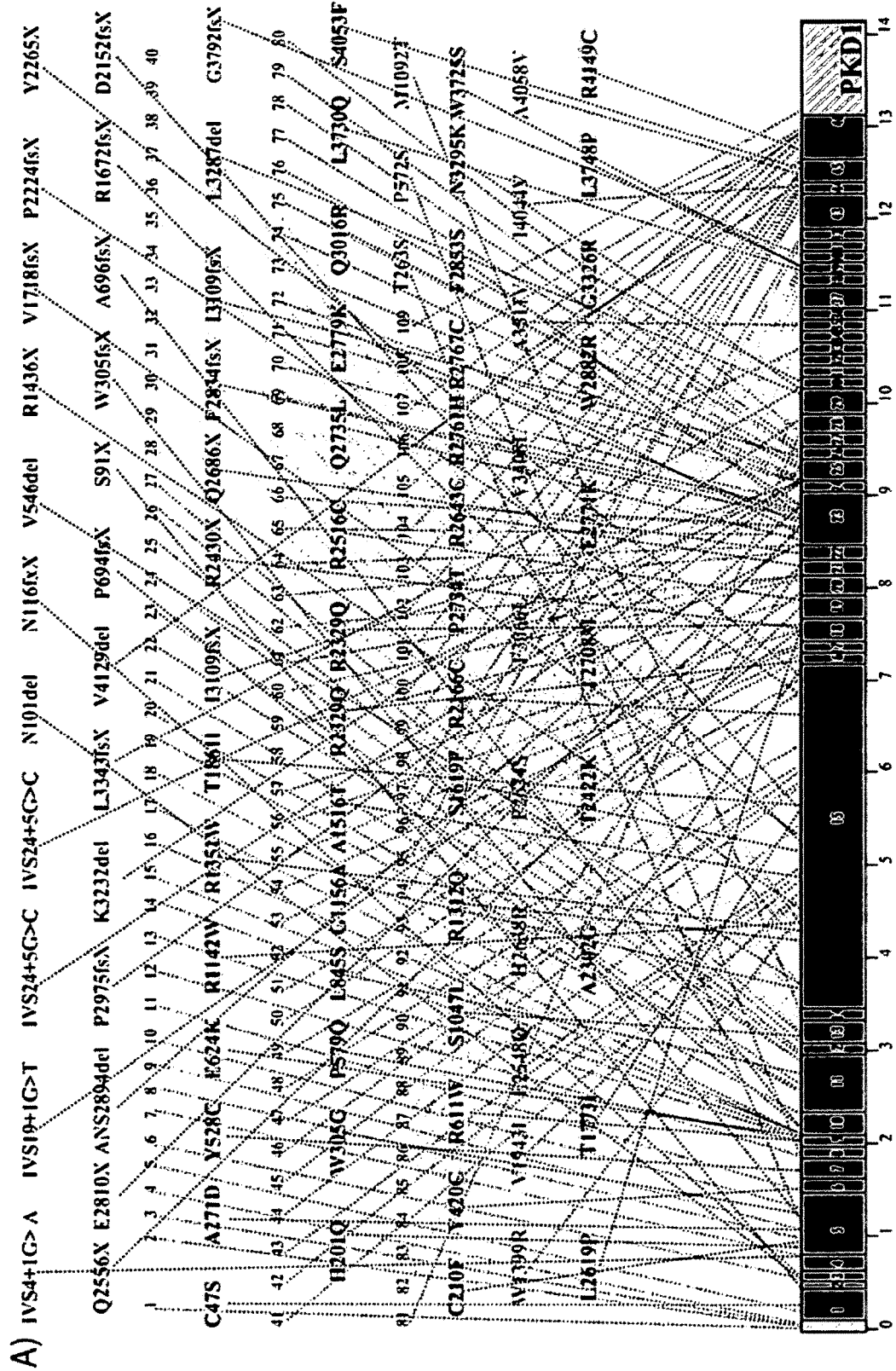
FIGS. 7A-7B are schematics illustrating all the PKD1 (5A) and PKD2 (5B) mutations identified. Numbers 1-113 refer to identifiers of the mutations in Table 8.
Figure 7B:
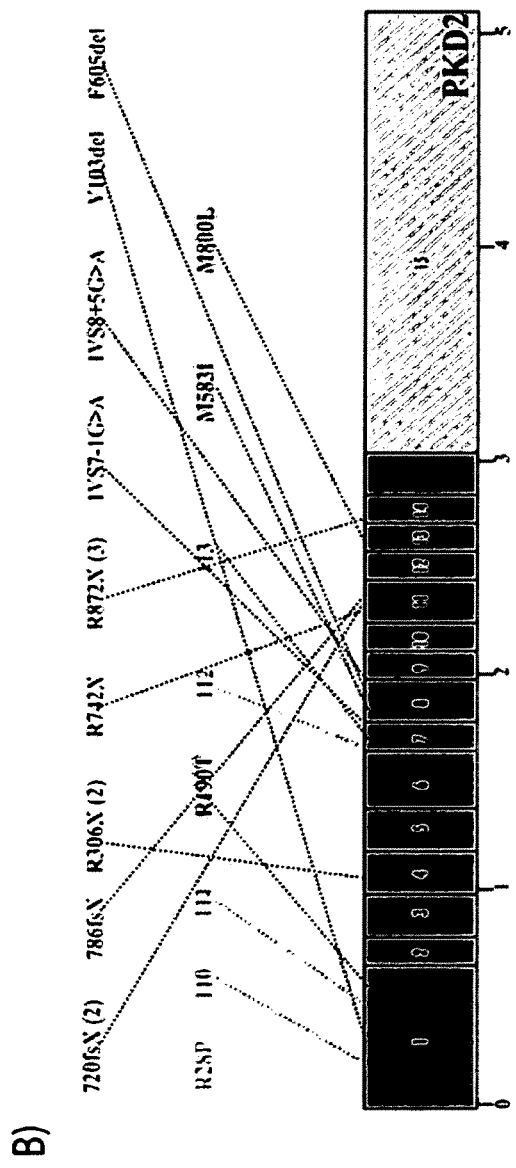

In addition to the sequence alterations described in Tables 4-7, a large number of polymorphisms were detected (Table 9) (see also FIGS. 7A and 7B). Polymorphisms are defined as: (i) sequence variants not predicted to alter an amino acid; (ii) missense changes found in homozygosity in at least one patient; (iii) intronic sequences of unknown significance; or (iv) changes in the 3' UTR of unknown significance.

Further discussion of the above example can be found in M. A. Garcia-Gonzalez et al., Evaluating the clinical utility of a molecular genetic test for polycystic kidney disease, Mol. Genet. Metab (2007) in press, doi:10.1016/j.ymgme.2007.05.004, which is herein incorporated by reference.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

TABLE 2

Cohort characteristics. *N = 82 subjects. $^{\epsilon}$ESRD defined as transplant, dialysis or MDRD GFR <10 ml/minute. $^{¥}$N = 80 patients.

| | |
|---|---|
| % Female* | 50% |
| Average Age at time of Test* | 46.5 (range 1-73 y) |
| % ESRD$^{\epsilon,*}$ | 20.7% |
| Average GFR (ml/min)$^{¥}$ | 68.7 (range 14-126) |

TABLE 2-continued

Cohort characteristics. *N = 82 subjects. $^{\epsilon}$ESRD defined as transplant, dialysis or MDRD GFR <10 ml/minute. $^{¥}$N = 80 patients.

| | |
|---|---|
| % Liver cysts* | 74.3% |
| % Vascular complications* | 9.8% |
| % Unknown or no Family history* | 30.5% |

TABLE 3

PKD mutations definitively pathogenic.

| | Truncation and Splicing | | | |
|---|---|---|---|---|
| Gene | Stop Codon | Frameshift | Splicing | Total % |
| PKD1 | 8 (9.8%) | 14 (17.1%) | 4 (4.9%) | 31.7% |
| PKD2 | (7.3%) | 3 (3.7%) | 2 (2.4%) | 13.4% |
| Total % | 17.1% | 20.8% | 7.3% | 45.1% |

TABLE 4

Truncating and Splice site mutations. Leucine Rich Repeat (LRR), Polycystic Kidney Disease Repeat (PKD-R), Receptor for Egg Jelly domain (REJ), Transmembrane (TM), Coiled Coil (CC), Novel change (N). See *Full Reference List* for mutation references.

| | Mutation | | Mutation Effect | | | | | |
|---|---|---|---|---|---|---|---|---|
| ID | cDNA | Protein | Stop Codon | Splice Site | Exon | Domain | Rate | Ref. |
| PKD1 gene | | | | | | | | |
| Frameshift: | | | | | | | | |
| JHU111 | 559delTTTAA | N116fsX | 117 | | 3 | LRR2 | 1/164 | N. |
| JHU568 | 1124insCT | W305 fsX | 334 | | 5 | PKDR1 | 1/164 | N. |
| JHU582 | 2291ins1 | P694 fsX | 713 | | 10 | | 1/164 | N. |
| JHU585 | 2297ins1 | A696 fsX | 713 | | 10 | | 1/164 | N. |
| JHU15 | 5225delAG | R1672 fsX | 1721 | | 15 | PKDR11 | 1/164 | 1, 8, 23 |
| JHU508 | 5365insT | V1718 fsX | 1770 | | 15 | PKDR12 | 1/164 | N. |
| JHU613 | 6666insG | D2152 fsX | 2174 | | 15 | REJ | 1/164 | N. |
| JHU611 | 6881insA | P2224 fsX | 2261 | | 15 | REJ | 1/164 | N. |
| JHU577 | 8713delT | F2834 fsX | 2874 | | 23 | | 1/164 | N. |
| JHU600 | 9134ins1 | P2975 fsX | 3068 | | 24 | | 1/164 | N. |
| JHU579 | 9536ins5 | I3109 fsX | 3317 | | 26 | | 2/164 | N. |
| JHU609 | 9536ins5 | I3109 fsX | 3317 | | 26 | | 2/164 | N. |
| JHU599 | 10239delT | L3343 fsX | 3395 | | 30 | TM3 | 1/164 | N. |
| JHU104 | 11587delG | G3792 fsX | 3824 | | 40 | | 1/164 | 26 |
| Nonsense: | | | | | | | | |
| JHU605 | 483 C > A | S91X | 91 | | 2 | LRR1 | 1/164 | N. |
| JHU567 | 4517 C > T | R1436X | 1436 | | 15 | PKDR8 | 1/164 | N. |
| JHU108 | 7006 C > A | Y2265X | 2265 | | 15 | REJ | 1/164 | N. |
| JHU563 | 7499 C > T | R2430X | 2430 | | 18 | REJ | 1/164 | 2, 3 |
| JHU593 | 7877 C > T | Q2556X | 2556 | | 19 | REJ | 1/164 | N. |
| JHU083 | 8267 C > T | Q2686X | 2686 | | 22 | REJ | 1/164 | N. |
| JHU574 | 8639 G > T | E2810X | 2810 | | 23 | REJ | 1/164 | N. |
| JHU620 | 12243 G > A | W4011X | 4011 | | 44 | TM9 | 1/164 | N. |
| Splicing: | | | | | | | | |
| JHU572 | | IVS4 + 1G > A. | | Loss of donor site | 4 | | 1/164 | N. |
| JHU580 | | IVS19 + 1G > T. | | Loss of donor site | 19 | REJ | 1/164 | N. |
| JHU573 | | IVS24 + 5G > C. | | Loss of donor site | 24 | | 2/164 | N. |
| JHU595 | | IVS24 + 5G > C. | | Loss of donor site | 24 | | 2/164 | N. |
| PKD2 gene | | | | | | | | |
| Frameshift: | | | | | | | | |
| JHU586 | 2226insA | 720fsX | | | 11 | | 2/164 | N. |
| JHU116 | 2226insA | 720fsX | | | 11 | | 2/164 | N. |
| JHU591 | 2422delAG | 786fsX | | | 12 | CC | 1/164 | N. |

TABLE 4-continued

Truncating and Splice site mutations. Leucine Rich Repeat (LRR),
Polycystic Kidney Disease Repeat (PKD-R), Receptor for Egg Jelly domain (REJ),
Transmembrane (TM), Coiled Coil (CC), Novel change (N). See *Full Reference List*
for mutation references.

| ID | Mutation cDNA | Protein | Mutation Effect Stop Codon | Splice Site | Exon | Domain | Rate | Ref. |
|---|---|---|---|---|---|---|---|---|
| Nonsense: | | | | | | | | |
| JHU578 | 982 C > T | R306X | | | 4 | TM1 | 2/164 | 5 |
| JHU583 | 982 C > T | R306X | | | 4 | TM1 | 2/164 | 5 |
| JHU607 | 2224 C > T | R742X | | | 11 | | 1/164 | 6 |
| JHU594 | 2680C > T | R872X | | | 14 | | 3/164 | N. |
| JHU566 | 2680C > T | R872X | | | 14 | | 3/164 | N. |
| JHU608 | 2680C > T | R872X | | | 14 | | 3/164 | N. |
| Splicing: | | | | | | | | |
| JHU562 | | IVS7 − 1G > A | | Loss of acceptor site | 7 | | 1/164 | N. |
| JHU105[L2] | | IVS8 + 5G > A | | Loss of donor site | 8 | | 1/164 | N. |

TABLE 5

In-Frame Deletions. Leucine rich repeat-2 (LRR2), polycystic kidney
disease repeat (PKD-R), receptor for egg jelly domain (REJ), Transmembrane (TM),
coiled coil (CC), Novel change (N), * Disrupts the Consensus sequence for the
Domain.

| ID | Mutation cDNA | Protein | Exon | Domain | Conservation Fugu | Mouse | Level | Variant | Ref. |
|---|---|---|---|---|---|---|---|---|---|
| PKD1 gene | | | | | | | | | |
| JHU115 | 514-551delCAA | N101del | 3 | LRR2 | N | N | Fully | 1/164 | N. |
| JHU107[L1] | 1848-1851delTGG | V546del | 8 | | V | V | Fully | 1/164 | N. |
| JHU560 | 8892-8898delCCAACTCCG | ANS2894del | 23 | | AGA | VGS | Highly | 1/164 | N. |
| JHU592 | 9905-9909delAAG | K3232del | 28 | PLAT | I | K | Highly | 1/164 | N. |
| JHU571 | 10070-10074delCTC | L3287del | 29 | TM2 | L | L | Fully | 1/164 | N. |
| JHU112 | 12597-12600delTGG | V4129del | 45 | | V | V | Fully | 1/164 | N. |
| PKD2 gene | | | | | | | | | |
| JHU 596 | 374-378delTGG | V103del | 1 | Poly-Glu | — | V | Highly | 1/164 | N. |
| JHU416[L2] | 1879-1882delTTC | F605del | 8 | TM5 | — | F | Highly | 1/164 | N. |

TABLE 6

Families with One or More Amino Acid Changes.

| ID | Mutation Gene | cDNA | Protein | Exon | Domain | Conservation Graham | Fugu | Mouse | Level | Rate | Ref. | Total #of variants. PKD 1 | PKD 2 |
|---|---|---|---|---|---|---|---|---|---|---|---|---|---|
| JHU612 | PKD1 | 1023C > A | A271D | 5 | WSC | Path.H. | A | A | Fully | 1/164 | N. | 4 | 0 |
| | PKD1 | 385G > A | A92T | 2 | | Equal | E | A | Highly | 1/164 | N. | | |
| JHU602 | PKD1 | 1470A > G | T420C | 6 | C-LECT* | Path.H. | F | Y | Highly | 1/164 | N. | 25 | 1 |
| | PKD1 | 4262C > T | R1351W | 15 | PKDR7* | Path.H. | R | R | Fully | 1/164 | N. | | |
| | PKD1 | 8855T > A | W2882R | 23 | | Path.H. | G | Q | No | 1/164 | N. | | |
| | PKD1 | 9109G > C | E2966D[Fp] | 24 | | Poly. H. | G | E | Highly | 1/164 | 10, 3, 24, 27 | | |
| JHU103 | PKD1 | 1794A > G | Y528C | 7 | C-LECT* | Path.H. | Y | Y | Fully | 1/164 | N. | 28 | 1 |
| | PKD1 | 6036G > A | R1942H | 15 | PKDR14 | Equal | R | R | Fully | 1/164 | N. | | |
| JHU001 | PKD1 | 2042C > T | R611W | 9 | | Path.H. | R | R | Fully | 1/164 | N. | 6 | 0 |
| | PKD1 | 8651G > A | G2814R | 23 | REJ | Path.H. | A | G | Highly | 6/164 | 8, 9 | | |
| JHU411 | PKD1 | 3351C > T | S1047L | 13 | PKDR4* | Path.H. | M | S | Highly | 1/164 | N. | 60 | 1 |
| | PKD1 | 6756A > G | Q2182R | 15 | REJ | Path.H. | G | Q | Highly | 2/164 | N. | | |
| | PKD2 | 634G > A | A190T | 1 | | Equal | — | A | Highly | 3/164 | N. | | |
| JHU100 | PKD1 | 5793C > T | T1861I | 15 | PKDR13* | Path.H. | T | S | Highly | 1/164 | N. | 8 | 1 |
| | PKD1 | 6707C > T | R2166C | 15 | REJ | Path.H. | P | R | Highly | 1/164 | N. | | |
| | PKD1 | 4229C > T | R13340W | 15 | PKDR6* | Path.H. | H | H | Fully | 3/164 | 8 | | |

TABLE 6-continued

Families with One or More Amino Acid Changes.

| ID | Gene | cDNA | Protein | Exon | Domain | Graham | Fugu | Mouse | Level | Rate | Ref. | PKD 1 | PKD 2 |
|---|---|---|---|---|---|---|---|---|---|---|---|---|---|
| JHU564 | PKD1 | 10187G > C | G3326R | 30 | TM3 | Path.H. | G | G | Fully | 1/164 | N. | 4 | 1 |
| | PKD1 | 7116C > G | A2302G | 15 | REJ | Equal | S | A | Highly | 1/164 | N. | | |
| | PKD1 | 10311A > G | I3367V | 31 | | Poly. H. | I | V | Highly | 1/164 | N. | | |
| JHU588 | PKD1 | 7554T > C | L2448P | 18 | REJ | Path.H. | L | L | Fully | 1/164 | N. | 39 | 0 |
| | PKD1 | 4229C > T | R1340W | 15 | PKDR6* | Path.H. | H | H | Highly | 3/164 | 8 | | |
| JHU603 | PKD1 | 7757T > T | R2516C | 19 | REJ | Path.H. | R | R | Fully | 1/164 | N. | 4 | 0 |
| JHU569 | PKD1 | 8067T > C | L2619P | 20 | REJ | Path.H. | L | L | Fully | 1/164 | N. | 22 | 2 |
| | PKD1 | 8411C > A | P2734T | 23 | REJ | Equal | P | P | Fully | 1/164 | 3 | | |
| | PKD1 | 8415A > T | Q2735L | 23 | REJ | Equal | S | Q | Highly | 1/164 | 3 | | |
| JHU597 | PKD1 | 8138C > T | R2643C | 21 | REJ | Path.H. | R | R | Fully | 1/164 | N | 3 | 1 |
| JHU101 | PKD1 | 8509C > T | R2767C | 23 | REJ | Path H. | R | R | Fully | 1/164 | N | 4 | 2 |
| JHU109 | PKD1 | 8522G > A | E2771KFm | 23 | REJ | Path H. | E | E | Fully | 1/164 | 3, 24, 23 | 3 | 0 |
| JHU589 | PKD1 | 8769T > C | F2853SFm | 23 | | Path. H. | F | F | Fully | 1/164 | 4, 24 | 22 | 2 |
| JHU576 | PKD1 | 10096C > A | N3295K | 29 | TM2 | Path.H. | N | N | Fully | 1/164 | N | 3 | 0 |
| JHU114 | PKD1 | 12658C > T | R4149C | 46 | | Path.H. | R | R | Fully | 1/164 | N | 22 | 1 |
| | PKD1 | 4229C > T | R1340W | 15 | PKDR6* | Path.H. | H | H | Highly | 3/164 | 8 | | |
| JHU601B | PKD1 | 9258A > G | Q3016RFm | 25 | GPS | Path. H | Q | Q | Fully | 1/164 | 4, 3, 27, 24 | 43 | 1 |
| | PKD1 | 2427A > G | Q739R | 11 | | Path.H. | R | Q | Highly | 11/164 | 21 | | |
| JHU565 | PKD1 | 7476C > A | T2422K | 18 | REJ | Equal | T | T | Fully | 1/164 | N. | 24 | 0 |
| | PKD1 | 3527C > G | L1106V | 15 | PKDR4 | Poly. H. | S | V | No | 1/164 | N. | | |
| | PKD1 | 3713C > T | P1168S | 15 | PKDR5 | Equal | — | P | Highly | 2/164 | 8 | | |
| JHU570 | PKD1 | 1947C > A | P579Q | 9 | | Equal | P | P | Fully | 1/164 | N. | 5 | 1 |
| | PKD1 | 2427A > G | Q739R | 11 | | Path.H. | R | Q | Highly | 11/164 | 21 | | |
| JHU575 | PKD1 | 3312A > G | N1034S | 13 | PKDR4 | Poly.H. | G | S | No | 1/164 | N. | 17 | 1 |
| JHU178 | PKD1 | 3713C > T | P1168S | 15 | PKDR5 | Equal | — | P | Highly | 2/164 | 8 | 2 | 1 |
| | PKD2 | 634G > A | A190T | 1 | | Equal | — | A | Highly | 3/164 | N. | | |
| JHU610 | PKD2 | 634G > A | A190T | 1 | | Equal | — | A | Highly | 3/164 | N. | 40 | 2 |
| JHU617 | PKD1 | 4391C > G | L1394V | 15 | PKDR8* | Poly. H. | V | L | Highly | 1/164 | N. | 5 | 1 |
| | PKD1 | 11040T > A | L3730Q | 39 | | Equal | F | L | Highly | 1/164 | N. | | |
| JHU587 | PKD1 | 840G > T | C210F | 5 | | Equal | C | C | Fully | 1/164 | N. | 6 | 2 |
| | PKD1 | 7197G > A | R2329Q | 16 | REJ | Equal | E | R | Highly | 1/164 | N. | | |
| | PKD1 | 2427A > G | Q739R | 11 | | Path.H. | R | Q | Highly | 11/164 | 21 | | |
| JHU559 | PKD1 | 351G > C | C47S | 1 | LRR-N | Poly.H. | W | C | Highly | 1/164 | N. | 24 | 3 |
| | PKD2 | 2464A > C | M800L | 13 | | Poly.H. | — | M | Highly | 1/164 | 11 | | |
| JHU606 | PKD1 | 6809C > T | R2200C | 15 | REJ | Path.H. | R | R | Fully | 4/164 | 23 | 5 | 2 |
| JHU584 | PKD1 | 6809C > T | R2200C | 15 | REJ | Path.H. | R | R | Fully | 4/164 | 23 | 20 | 1 |
| JHU106 | PKD1 | 8651G > A | G2814R | 23 | REJ | Path.H. | A | G | Highly | 6/164 | 3, 8 | 4 | 1 |
| JHU614 | PKD1 | 4757G > A | A1516T | 15 | PKDR9 | Equal | T | L | No | 2/164 | N. | 10 | 0 |
| | PKD1 | 1973A > C | E586D | 9 | | Equal | A | E | Highly | 1/164 | N. | | |
| | PKD1 | 2427A > G | Q739R | 11 | | Path.H. | R | Q | Highly | 11/164 | 21 | | |

Families underlined are those with one or more amino acid change that meets criteria of pathogenicity (bold font) and not found in patients with definitive pathogenic sequence variants.
Fp = do not disrupt cleavage;
Fm = disrupt cleavege. See Full Reference List for mutation references.

TABLE 7

Families with multiple PKD mutations associated with ADPKD.
Occasionally, families with a mutation associated to the disease had other change that could be classified also as associated to the disease by meeting our criteria or disrupting the consensus sequence of the Domain*.

| | Mutations Disease Associated | | Amino acid changes highly pathogenic | | # of Changes per patient | |
|---|---|---|---|---|---|---|
| Pedigree | PKD1 | PKD2 | PKD1 | PKD2 | PKD1 | PKD2 |
| JHU605 | S91X | | | | 4 | 0 |
| JHU 567 | R1436X | | | | 24 | 0 |
| JHU108 | Y2265X | | Q739R | | 5 | 1 |
| JHU563 | R2430X | | Q739R | R807Q | 19 | 1 |
| JHU593 | Q2556X | | | | 3 | 2 |
| JHU083 | Q2686X | | | | 5 | 0 |
| JHU574 | E2810X | | G2814R | | 4 | 0 |
| JHU620 | W4011X | | | | 22 | 0 |
| JHU568 | W305 fsX | | W305C* | | 4 | 1 |
| JHU582 | P694 fsX | | | | 1 | 0 |
| JHU585 | A696 fsX | | | | 6 | 2 |
| JHU508 | V1718 fsX | | | | 5 | 2 |
| JHU613 | D2152 fsX | | E624K | | 21 | 0 |

TABLE 7-continued

Families with multiple PKD mutations associated with ADPKD.
Occasionally, families with a mutation associated to the disease had other change
that could be classified also as associated to the disease by meeting our criteria or
disrupting the consensus sequence of the Domain*.

| Pedigree | Mutations Disease Associated | | Amino acid changes highly pathogenic | | # of Changes per patient | |
|---|---|---|---|---|---|---|
| | PKD1 | PKD2 | PKD1 | PKD2 | PKD1 | PKD2 |
| JHU611 | P2224 fsX | | | | 29 | 1 |
| JHU600 | P2975 fsX | | Q739R | | 25 | 2 |
| JHU609 | I3109 fsX | | | | 41 | 1 |
| JHU579 | I3109 fsX | | G2814R | | 23 | 2 |
| JHU577 | F2834fsX | | Q739R | | 4 | 1 |
| JHU111 | N116 fsX | | R2200C S1619F | | 7 | 1 |
| JHU15 | R1672 fsX | | | | 5 | 1 |
| JHU599 | L3343 fsX | | R1312Q | | 20 | 1 |
| JHU104 | G3792 fsX | | | | 4 | 2 |
| JHU115 | N101del | | | | 20 | 0 |
| JHU107 | V546del | | R1142W | | 25 | 1 |
| JHU560 | ANS2894del | | | | 21 | 1 |
| JHU592 | K3232del | | | | 3 | 1 |
| JHU571 | L3287del | | | | 10 | 0 |
| JHU112 | V4129del | | S4053F | | 19 | 2 |
| JHU580 | IVS19 + 1G > T. | | G2814R | | 5 | 1 |
| JHU573 | IVS24 + 5G > C | | R2200C | | 5 | 0 |
| JHU595 | IVS24 + 5G > C | | | | 16 | 2 |
| JHU572 | IVS4 + 1G > A | | | | 17 | 1 |
| JHU578 | | R306X | | | 3 | 3 |
| JHU583 | | R306X | | | 5 | 1 |
| JHU607 | | R742X | | | 21 | 1 |
| JHU594 | | R872X | | | 22 | 3 |
| JHU566 | | R872X | | | 1 | 3 |
| JHU608 | | R872X | | G2814R | 4 | 2 |
| JHU596 | | V103del | | Q2182R | 35 | 1 |
| JHU416 | | F605del | | | 2 | 3 |
| JHU591 | | 786fsX | | | 4 | 2 |
| JHU562 | | IVS7 − 1G > A | | | 3 | 2 |
| JHU105 | | IVS8 + 5G > A | | T1773I* | 3 | 2 |
| JHU116 | | 720 fsX | | Q739R | 3 | 2 |
| JHU586 | | 720 fsX | | T1773I* | 22 | 1 |

TABLE 8

Families without disease-associated PKD mutations. *disrupts the
consensus sequence. ^^predicted to generate a new splice site.

| ID | Non-pathogenic missense | | Intronic Changes | | Family history | # of Changes | |
|---|---|---|---|---|---|---|---|
| | PKD1 | PKD2 | PKD1 | PKD2 | | PKD1 | PKD2 |
| JHU565 | L1106V P1168S T2422K | | | | Yes | 24 | 0 |
| JHU570 | Q739R P579Q | | | | Yes | 5 | 1 |
| JHU575 | N1034S | | | | No | 17 | 1 |
| JHU178 | P1168S | A190T | | | Yes | 2 | 1 |
| JHU610 | | A190T | | | No | 40 | 2 |
| JHU617 | L1394V* L3730Q | | | | Yes | 5 | 1 |
| JHU587 | C210F Q739R R2329Q | | | | No | 6 | 2 |
| JHU559 | C47S | M800L | | | Yes | 24 | 3 |
| JHU604 | Q739R | | IVS37 − 10C > A^^ | | Yes | 2 | 0 |
| JHU606 | R2200C | | | | No | 5 | 2 |
| JHU584 | R2200C | | | | No | 20 | 1 |
| JHU590 | | | IVS24 + 28G > T^^ | | Yes | 3 | 1 |
| JHU106 | G2814R | | | | Yes | 4 | 1 |

TABLE 8-continued

Families without disease-associated PKD mutations. *disrupts the consensus sequence. ˆpredicted to generate a new splice site.

| ID | Non-pathogenic missense PKD1 | Non-pathogenic missense PKD2 | Intronic Changes PKD1 | Intronic Changes PKD2 | Family history | # of Changes PKD1 | # of Changes PKD2 |
|---|---|---|---|---|---|---|---|
| JHU614 | E586D<br>Q739R<br>A1516T | | | | No | 10 | 0 |
| JHU102[L1] | | | | | Yes | 21 | 0 |
| JHU616 | | | | | Yes | 17 | 0 |
| JHU615 | | | | | No | 0 | 1 |
| JHU110[L3] | | | | | Yes | 3 | 0 |
| JHU113 | | | | | No | 2 | 1 |
| JHU598 | | | | | No | 19 | 0 |

TABLE 9

Polymorphisms Identified. See *Full Reference List* for mutation references.

| ID# | Designation | cDNA Change (s) | Location | Domain | Frequency | Ref. |
|---|---|---|---|---|---|---|
| | | | PKD1 Polymorphisms. | | | |
| — | T263S(H) | 1004C > T | Exon 5 | | 2/164 | N. |
| — | P572S(H) | 1925C > T | Exon 8 | | 4/164 | 8 |
| — | M1092T(H) | 3486T > C | Exon 14 | PKD R4 | 30/164 | 8 |
| — | W1399R(H) | 4406T > G | Exon 15 | PKD R8 | 22/164 | 1, 8, 16 |
| — | V1943I(H) | 6038G > A | Exon 15 | PKD R14 | 5/164 | 8 |
| — | E2548Q(H) | 7853G > C | Exon 19 | REJ | 4/164 | 1 |
| — | H2638R(H) | 8124A > G | Exon 21 | REJ | 32/164 | 1 |
| — | P2674S(H) | 8231C > T | Exon 21 | REJ | 2/164 | 3, 8 |
| — | F3066L (H) | 9407T > C | Exon 25 | | 38/164 | 3, 17, 34 |
| — | V3408L(H) | 10433G > C | Exon 33 | | 5/164 | N. |
| — | A3511V(H) | 10743C > T | Exon 35 | | 13/164 | 3, 8 |
| — | I4044V(H) | 12341A > G | Exon 44 | TM10 | 42/164 | 3, 8, 17, 18, 14, 10 |
| — | A4058V(H) | 12386C > T | Exon 45 | | 12/164 | 8, 10 |
| 1 | | 104C > T | Exon 1 | 5'UTR | 1/164 | N. |
| 2 | | 145C > T | Exon 1 | 5'UTR | 2/164 | N. |
| 3 | | 160C > T | Exon 1 | 5'UTR | 1/164 | N. |
| 4 | | 210C > T | Exon 1 | 5'UTR | 1/164 | N. |
| 5 | L72L | 425C > T | Exon 1 | LRR1 | 2/164 | N. |
| 6 | G109G | 538A > T | Exon 3 | LRR2 | 1/164 | N. |
| 7 | IVS4 + 1G > A(H) | | Intron 4 | | 1/164 | N. |
| 8 | S196S | 799C > T | Exon 5 | | 2/164 | N. |
| 9 | A341A | 1234C > T | Exon 5 | PKD R1 | 5/164 | 3 |
| 10 | L373L(H) | 1330T > C | Exon 5 | | 36/164 | 3, 8, 15 |
| 11 | G441G | 1534G > A | Exon 6 | C-LECT | 1/164 | N. |
| 12 | H570H | 1921C > T | Exon 8 | | 1/164 | 3, 8 |
| 13 | IVS9 + 2del7 | | Intron 9 | | 12/164 | N. |
| 14 | IVS9 + 2 T > A | | Intron 9 | | 1/164 | N. |
| 15 | IVS9 + 28del7 (H) | | Intron 9 | | 4/164 | 8 |
| 16 | ISV9-44G > C | | Intron 9 | | 1/164 | 8 |
| 17 | IVS9-4A > G | | Intron 9 | | 42/164 | 8 |
| 18 | IVS10-4 G > A | | Intron 10 | | 1/164 | N. |
| 19 | P738P(H) | 2425C > G | Exon 11 | | 4/164 | N. |
| 20 | A745A | 2448C > G | Exon 11 | | 1/164 | N. |
| 21 | A898A | 2905A > C | Exon 11 | PKD R2 | 4/164 | 8, 9 |
| 22 | P900P | 2911G > A | Exon 11 | PKD R2 | 10/164 | 8, 16, 9 |
| 23 | D910D | 2941C > T | Exon 11 | PKD R2 | 10/164 | 8, 16, 9 |
| 24 | IVS11-5C > T | | Intron 11 | | 2/164 | 8 |
| 25 | IVS11 + 23C > T(H) | | Intron 11 | | 4/164 | N. |
| 26 | IVS12-15C > T | | Intron 12 | | 5/164 | N. |
| 27 | G1021G(H) | 3274T > C | Exon 13 | PKD R4 | 30/164 | 8, 16, 9 |
| 28 | L1037L | 3392A > G | Exon 13 | PKD R4 | 15/164 | 9 |
| 29 | E1061E | 3394G > A | Exon 14 | PKD R4 | 1/164 | N. |
| 30 | P1076P | 3439G > A | Exon 14 | PKD R4 | 1/164 | N. |
| 31 | A1124A | 3583C > T | Exon 15 | PKD R4 | 25/164 | 8, 9 |
| 32 | S1125S | 3586C > T | Exon 15 | PKD R5 | 25/164 | 8, 9 |
| 33 | F1163F | 3700C > T | Exon 15 | PKD R5 | 1/164 | N. |
| 34 | T1171T | 3724C > G | Exon 15 | PKD R5 | 1/164 | N. |
| 35 | D1310D | 4141C > T | Exon 15 | PKD R7 | 1/164 | N. |
| 36 | L1357L | 4282G > T | Exon 15 | PKD R7 | 1/164 | N. |
| 37 | S1373S | 4330C > T | Exon 15 | PKD R7 | 1/164 | N. |
| 38 | S1452S | 4567T > C | Exon 15 | PKD R8 | 1/164 | N. |

TABLE 9-continued

Polymorphisms Identified. See *Full Reference List* for mutation references.

| ID# | Designation | cDNA Change (s) | Location | Domain | Frequency | Ref. |
|---|---|---|---|---|---|---|
| 39 | P1511P | 4744G > A | Exon 15 | PKD R9 | 1/164 | N. |
| 40 | A1555A(H) | 4876A > C | Exon 15 | Extracellular | 42/164 | 16, 1, 9 |
| 41 | T1558T | 4885G > A | Exon 15 | Extracellular | 9/164 | 2 |
| 42 | S1603S | 5020C > T | Exon 15 | Extracellular | 1/164 | N. |
| 43 | T1724T(H) | 5383C > T | Exon 15 | PKD R12 | 40/164 | 8, 9, 21 |
| 44 | A1818A(H) | 5665G > A | Exon 15 | PKD R13 | 5/164 | 8, 9 |
| 45 | G1860G | 5791C > A | Exon 15 | PKD R13 | 1/164 | N. |
| 46 | A1894A | 5893C > T | Exon 15 | PKD R14 | 1/164 | 8, 9 |
| 47 | L1921L | 5974G > A | Exon 15 | PKD R14 | 2/164 | 8, 9 |
| 48 | V2026V | 6289C > T | Exon 15 | PKD R15 | 1/164 | N. |
| 49 | R2121R | 6574C > T | Exon 15 | PKD R16 | 1/164 | N. |
| 50 | T2180T | 6751C > T | Exon 15 | REJ | 1/164 | N. |
| 51 | A2202A | 6817G > A | Exon 15 | REJ | 1/164 | N. |
| 52 | V2257V | 6982G > A | Exon 15 | REJ | 1/164 | N. |
| 53 | G2309G | 7138C > T | Exon 16 | REJ | 4/164 | 8, 9 |
| 54 | IVS16 + 10 G > A | | Intron 16 | REJ | 1/164 | N. |
| 55 | R2359R | 7289G > C | Exon 17 | REJ | 3/164 | N. |
| 56 | L2389L(H) | 7376T > C | Exon 17 | REJ | 46/164 | 1, 2, 8, 9. |
| 57 | G2425G | 7486C > T | Exon 18 | REJ | 1/164 | N. |
| 58 | L2481L(H) | 7652C > T | Exon 18 | REJ | 39/164 | 1, 8 |
| 59 | IVS19 + 24 C > A | | Intron 19 | REJ | 2/164 | N. |
| 60 | L2570L(H) | 7919T > C | Exon 20 | REJ | 31/164 | 1, 9 |
| 61 | IVS20 + C > A | | Intron20 | REJ | 1/164 | N. |
| 62 | ISV20-16C > G | | Intron20 | REJ | 2/164 | N. |
| 63 | T2708M | 8334C > T | Exon 22 | REJ | 1/164 | 3, 8 |
| 64 | IVS22 + 8G > A (H) | | Intron 22 | REJ | 1/164 | 1, 8 |
| 65 | S2729S | 8398G > A | Exon 23 | REJ | 2/164 | N. |
| 66 | A2749A | 8458G > A | Exon 23 | REJ | 1/164 | N. |
| 67 | S2766S | 8509C > T | Exon 23 | REJ | 1/164 | 13 |
| 68 | D2789D | 8578C > T | Exon 23 | REJ | 2/164 | N. |
| 69 | S2813S | 8650C > T | Exon 23 | REJ | 2/164 | 3, 8, 24 |
| 70 | S2893S | 8890C > G | Exon 23 | | 2/164 | 3 |
| 71 | A2971A(H) | 9124T > C | Exon 24 | | 2/164 | N. |
| 72 | IVS24-20G > A (H) | | Intron 24 | | 3/164 | N. |
| 73 | IVS24-17A > G(H) | | Intron 24 | | 6/164 | N. |
| 74 | IVS24 + 17A > G | | Intron 24 | | 32/164 | N. |
| 75 | S3007S | 9232C > T | Exon 25 | | 1/164 | N. |
| 76 | V3065V(H) | 9406G > C | Exon 25 | | 38/164 | 24 |
| 77 | V3090V | 9481C > T | Exon 26 | TM1 | 3/164 | N. |
| 78 | P3110P(H) | 9543T > C | Exon 26 | | 37/164 | 6 |
| 79 | IVS26 + 76C > A | | Intron26 | | 1/164 | N. |
| 80 | IVS27-13T > C(H) | | Intron27 | | 15/164 | 8 |
| 81 | T3223T | 9880G > A | Exon 28 | PLAT | 2/164 | 6, 3, 8 |
| 82 | S3265S | 10006C > T | Exon 29 | | 1/164 | N. |
| 83 | IVS29-4 C > T | | Intron29 | | 1/164 | N. |
| 84 | A3455A | 10576C > T | Exon 34 | | 1/164 | N. |
| 85 | L3589L | 10976C > T | Exon 36 | TM5 | 5/164 | N. |
| 86 | IVS37-4C > T | | Intron 37 | | 1/164 | N. |
| 87 | IVS38 + 11G > A | | Intron 38 | | 4/164 | N. |
| 88 | R3752R | 11385C > A | Exon 39 | Polycystin motif | 1/164 | N. |
| 89 | L3753L | 11465G > C | Exon 39 | Polycystin motif | 1/164 | N. |
| 90 | IVS39-25del72bp | | Intron 39 | | 1/164 | 7, 3 |
| 91 | IVS41 + C > T | | Intron 41 | | 1/164 | N. |
| 92 | IVS41 + 5insGGG | | Intron 41 | | 2/164 | 8 |
| 93 | IVS41-11C > T | C > T | Intron 41 | | 2/164 | N. |
| 94 | S3893S(H) | 11890C > T | Exon 42 | | 3/164 | 8 |
| 95 | IVS43 + 42C > A | | Intron 43 | | 6/164 | N. |
| 96 | R3971R | 12124C > T | Exon 43 | | 3/164 | N. |
| 97 | L4025L | 12286C > T | Exon 44 | | 1/164 | N. |
| 98 | L4035L | 12316C > T | Exon 44 | TM10 | 1/164 | N. |
| 99 | IVS44 + 22delG | | Intron44 | | 4/164 | N. |
| 100 | L4089L | 12478C > G | Exon 45 | TM11 | 1/164 | N. |
| 101 | A4091A(H) | 12484A > G | Exon 45 | TM11 | 43/164 | 8, 3, 17, 18, 7 |
| 102 | L4136L(H) | 12617C > T | Exon 45 | | 13/164 | 8, 14 |
| 103 | V4152V | 12667C > T | Exon 46 | | 2/164 | N. |
| 104 | P4161P | 12696C > A | Exon 46 | | 1/164 | N. |
| 105 | S4189S | 12778C > T | Exon 46 | | 1/164 | 6 |
| 106 | P4209P(H) | 12838T > C | Exon 46 | | 40/164 | 8, 6, 3 |
| 107 | L4221L | 12874C > T | Exon 46 | COILED COIL | 1/164 | N. |
| 108 | A4255A | 12978C > T | Exon 46 | | 1/164 | N. |
| 109 | | 13135G > A | 3'UTR | | 2/164 | 8 |

TABLE 9-continued

Polymorphisms Identified. See *Full Reference List* for mutation references.

| ID# | Designation | cDNA Change (s) | Location | Domain | Frequency | Ref. |
|---|---|---|---|---|---|---|
| | | PKD2 Polymorphisms. | | | | |
| — | R28P(H) | 149C > T | Exon 1 | | 50/164 | 8, 10, 22 |
| 110 | R60R | 246G > A | Exon 1 | | 1/164 | N. |
| 111 | G140G(H) | 486G > A | Exon 1 | | 22/164 | N. |
| 112 | IVS6-4C > T | | Intron 6 | | 1/164 | N. |
| 113 | L539L | 1683G > C | Exon 7 | | 1/164 | N. |

FULL REFERENCE LIST

1. Watnick T, Phakdeekitcharoen B, Johnson A, et al. Mutation detection of PKD1 identifies a novel mutation common to three families with aneurysms and/or very-early-onset disease. *Am J Hum Genet* 65(6):1561-71, 1999.
2. Phakdeekitcharoen B, Watnick T J, Ahn C, et al. Thirteen novel mutations of the replicated region of PKD1 in an Asian population. *Kidney Int* 58(4): 1400-12, 2000.
3. Rossetti S, Strmecki L, Gamble V, et al. Mutation analysis of the entire PKD1 gene: genetic and diagnostic implications. *Am J Hum Genet* 68(1):46-63, 2001.
4. Peral B, Gamble V, Strong C, et al. Identification of mutations in the duplicated region of the polycystic kidney disease 1 gene (PKD1) by a novel approach. *Am J Hum Genet* 60(6):1399-410, 1997.
5. Veldhuisen B, Saris J J, de Haij S, et al. A spectrum of mutations in the second gene for autosomal dominant polycystic kidney disease (PKD2). *Am J Hum Genet* 61(3):547-55, 1997.
6. Peral B, Ong A C, San Millan J L, et al. A stable, nonsense mutation associated with a case of infantile onset polycystic kidney disease 1 (PKD1). *Hum Mol Genet* 5(4): 539-42, 1996.
7. Peral B, San Millan J L, Ong A, et al. Screening the 3' region of the polycystic kidney disease 1 (PKD1) gene reveals six novel mutations. *Am J Hum Genet* 58(1):86-96, 1996.
8. Rossetti S, Chauveau D, Walker D, et al. A complete mutation screen of the ADPKD genes by DHPLC. *Kidney Int* 61, 1588-1599, 2002.
9. Thomas R, McConnell R, Whittaker J, et al. Identification of mutations in the repeated part of the autosomal dominant polycystic kidney disease type 1 gene, PKD1, by long-range PCR. *Am J Hum Genet* 65(1):39-49, 1999.
10. Rossetti S, Bresin E, Restagno G, et al. Autosomal dominant polycystic kidney disease (ADPKD) in an Italian family carrying a novel nonsense mutation and two missense changes in exons 44 and 45 of the PKD1 Gene. *Am J Med Genet* 16; 65(2): 155-9, 1996.
11. Reiterova J, Stekrova J, Peters D J, et al. Four novel mutations of the PKD2 gene in Czech families with autosomal dominant polycystic kidney disease. *Hum Mutat* 19(5): 573, 2002.
12. Hanaoka K, Qian F, Boletta A, et al. Co-assembly of polycystin-1 and -2 produces unique cation-permeable currents. *Nature* 408, 990-994, 2000.
13. Inoue S, Inoue K, Utsunomiya M, et al. Mutation analysis in PKD1 of Japanese autosomal dominant polycystic kidney disease patients. *Hum Mutat* 19(6):622-8, 2002.
14. Perrichot R A, Mercier B, Simon P M, et al. DGGE screening of PKD1 gene reveals novel mutations in a large cohort of 146 unrelated patients. *Hum Genet* 105 (3):231-9, 1999.
15. Bogdanova N, McCluskey M, Sikmann K, et al. Screening the 3' region of the polycystic kidney disease 1 (PKD1) gene in 41 Bulgarian and Australian kindreds reveals a prevalence of protein truncating mutations. *Hum Mutat* 16(2): 166-74, 2000.
16. Watnick T J, Torres V E, Gandolph M A, et al. Somatic mutation in individual liver cysts supports a two-hit model of cystogenesis in autosomal dominant polycystic kidney disease. *Mol Cell* 2(2):247-51, 1998.
17. Perrichot R, Mercier B, Quere I, et al. Novel mutations in the duplicated region of PKD1 gene. *Eur J Hum Genet* 8(5): 353-9, 2000.
18. Boletta, A., Qian, F., Onuchic, L. F., et al. Polycystin-1, the gene product of PKD1, induces resistance to apoptosis and spontaneous tubulogenesis in MDCK cells. *Mol. Cell* 6, 1267-1273, 2000.
19. Aguiari G, Savelli S, Garbo M, et al. Novel splicing and missense mutations in autosomal dominant polycystic kidney disease 1 (PKD1) gene: expression of mutated genes. *Hum Mutat* 16(5):444-5, 2000.
20. Bycroft M, Bateman A, Clarke J, et al. The structure of a PKD domain from polycystin-1: implications for polycystic kidney disease. *EMBO J.* 15; 18(2):297-305, 1999.
21. Torra R, Viribay M, Telleria D, et al. Seven novel mutations of the PKD2 gene in families with autosomal dominant polycystic kidney disease. *Kidney Int* 56(1):28-33, 1999.
22. Rossetti S, Chauveau D, Kubly V, et al. Association of mutation position in polycystic kidney disease 1 (PKD1) gene and development of a vascular phenotype. *Lancet* 28; 361(9376):2196-201, 2003.
23. Afzal A R, Florencio R N, Taylor R, et al. Novel mutations in the duplicated region of the polycystic kidney disease 1 (PKD1) gene provides supporting evidence for gene conversion. *Genet* 4(4):365-70, 2000.
24. Roelfsema J H, Spruit L, Saris J J, et al. Mutation detection in the repeated part of the PKD1 gene. *Am J Hum Genet* 61(5): 1044-52, 1997.
25. Bogdanova N, McCluskey M, Sikmann K, et al. Screening the 3' region of the polycystic kidney disease 1 (PKD1) gene in 41 Bulgarian and Australian kindreds reveals a prevalence of protein truncating mutations. *Hum Mutat* 16(2): 166-74, 2000.
26. Qian F, Boletta A, Bhunia A K, Xu H, et al. Cleavage of polycystin-1 requires the receptor for egg jelly domain and is disrupted by human autosomal-dominant polycystic kidney disease 1-associated mutations. *Proc Natl Acad Sci USA* 24; 99(26): 16981-6, 2002.
27. Gabow P A. Autosomal dominant polycystic kidney disease. *N Engl J Med* 29; 329(5): 332-42, 1993.

What is claimed is:

1. A method for detecting a mutant PKD1 gene in a human subject, comprising: a) generating a PKD1 nucleic acid by (i) performing a first amplification reaction comprising a long range amplification of a PKD1 gene in a sample from a human subject suspected of having an autosomal dominant polycystic kidney disease (ADPKD); and (ii) performing a second amplification reaction and a third amplification reaction which form a nested PCR; b) contacting the PKD1 nucleic acid generated in step a) with an oligonucleotide that specifically hybridizes to a mutation, wherein the mutation is a change of a T to an A at a PKD1 nucleic acid nucleotide position corresponding to position 8855 of SEQ ID NO:1, wherein the oligonucleotide is detectably labeled and comprises a sequence of less than 100 nucleotides that is fully complementary to a portion of the PKD1 nucleic acid that comprises the mutation; c) detecting hybridization of the oligonucleotide with the PKD1 nucleic acid under stringent conditions, wherein detection of hybridization is indicative of a mutant PKD1 gene in the human subject; and d) diagnosing or predicting occurrence of autosomal dominant polycystic kidney disease (ADPKD) in the human subject when the mutant PKD1 gene is detected.

2. The method of claim 1, wherein the method further comprises use of a technique selected from the group consisting of sequencing, one or more additional polymerase chain reactions (PCR), denaturing high performance liquid chromatography and a combination thereof.

3. The method of claim 1, wherein the oligonucleotide is detectably labelled with a radiolabel, an enzymatic label or a fluorescent label.

4. The method of claim 1, wherein the nested PCR uses different PKD-specific primers.

5. The method of claim 4, wherein the method further comprises use of a primer that specifically amplifies a PKD1 nucleic acid, but does not specifically amplify a PKD1 homolog.

6. The method of claim 1, wherein the human subject suspected of having an autosomal dominant polycystic kidney disease (ADPKD) is a blood relative of an individual with ADPKD.

* * * * *